US012799516B2

(12) United States Patent
Lemke et al.

(10) Patent No.: US 12,799,516 B2
(45) Date of Patent: Nov. 17, 2026

(54) ARCHAEAL PYRROLYSYL tRNA SYNTHETASES FOR ORTHOGONAL USE

(71) Applicant: European Molecular Biology Laboratory, Heidelberg (DE)

(72) Inventors: Edward Lemke, Mainz (DE); Christine Köhler, Forst (DE); Gemma Estrada Girona, London (GB); Florence Müller, Heidelberg (DE)

(73) Assignee: EUROPEAN MOLECULAR BIOLOGY LABORATORY, Heidelberg (DE)

( * ) Notice: Subject to any disclaimer, the term of this patent is extended or adjusted under 35 U.S.C. 154(b) by 1123 days.

(21) Appl. No.: 17/800,806

(22) PCT Filed: Feb. 18, 2021

(86) PCT No.: PCT/EP2021/054049
§ 371 (c)(1),
(2) Date: Aug. 18, 2022

(87) PCT Pub. No.: WO2021/165410
PCT Pub. Date: Aug. 26, 2021

(65) Prior Publication Data
US 2025/0277249 A1 Sep. 4, 2025

(30) Foreign Application Priority Data
Feb. 21, 2020 (EP) .................................... 20158737

(51) Int. Cl.
*C12P 21/02* (2006.01)
*C12N 9/12* (2006.01)
(Continued)

(52) U.S. Cl.
CPC ............ *C12P 21/02* (2013.01); *C12N 9/1247* (2013.01); *C12N 15/113* (2013.01); *C12N 15/85* (2013.01);
(Continued)

(58) Field of Classification Search
CPC ................ C12N 2310/12; C12N 15/79; C12N 2310/3519; C12N 15/11; C12N 15/85; C12P 21/02
See application file for complete search history.

(56) References Cited

U.S. PATENT DOCUMENTS 5,500,357 A * 3/1996 Taira .................... C12N 15/113 435/325
11,492,608 B2 11/2022 Lemke et al.
(Continued)

FOREIGN PATENT DOCUMENTS

EP 0596901 B1 * 8/2000 ......... C12N 15/1132
EP 2192185 A1 6/2010
(Continued)

OTHER PUBLICATIONS

Jackson Laboratory, Retrieved from the Internet: <URL: https://www.jax.org/news-and-insights/2015/april/introduction-to-tet-expression-systems on Feb. 6, 2025, 4 pgs (Year: 2015).*
(Continued)

*Primary Examiner* — Catherine Konopka
*Assistant Examiner* — Shabana S Meyering
(74) *Attorney, Agent, or Firm* — Viksnins Harris Padys Malen LLP

(57) ABSTRACT

The present invention is concerned with efficient orthogonal translation systems for eukaryotic cells. Specifically, the invention relates to eukaryotic cells comprising polynucleotides encoding a prokaryotic tRNA synthetase (pRS) and an RNA molecule comprising a prokaryotic tRNA (ptRNA) and
(Continued)

one or more than one ribozyme (termed "ptRNA-ribozyme" herein). It also relates to a method for expressing a polypeptide of interest (POI) comprising one or more non-canonical amino acid (ncAA) residues by such eukaryotic cells, and to kits useful in such method. The invention further relates to polynucleotides encoding the ptRNA-ribozyme.

9 Claims, 9 Drawing Sheets

Specification includes a Sequence Listing.

(51) Int. Cl.
*C12N 15/113* (2010.01)
*C12N 15/85* (2006.01)

(52) U.S. Cl.
CPC .. *C12Y 207/07006* (2013.01); *C12N 2310/12* (2013.01); *C12N 2800/107* (2013.01); *C12N 2830/003* (2013.01); *C12N 2830/60* (2013.01)

(56) References Cited

U.S. PATENT DOCUMENTS

2009/0293148 A1* 11/2009 Ren .................... C12N 15/8216
800/278
2010/0267087 A1* 10/2010 Yokoyama .............. C12P 21/00
435/325

FOREIGN PATENT DOCUMENTS

| | | | |
|---|---|---|---|
| EP | 3309260 | A1 | 4/2018 |
| NO | 2017124034 | A1 | 7/2017 |
| WO | 2011009624 | A1 | 1/2011 |
| WO | 2017093254 | A1 | 6/2017 |
| WO | 2018069481 | A1 | 4/2018 |

OTHER PUBLICATIONS

Dunn (Gene, vol. 68, Issue 2, Sep. 7, 1988, pp. 259-266). (Year: 1988).*

Barber, et al., "Mutants of the RNA-Dependent Protein Kinase (PKR) Lacking Double-Stranded RNA Binding Domain I can act as Transdominant Inhibitors and Induce Malignant Transformation", Molecular and Cellular Biology 15 (6), 3138-3146 (1995).

Huot, et al., "Inducible orthogonal aminoacylation demonstrates that charging is required for mitochondrial tRNA import in Trypanosoma brucei", Scientific Reports 9, 10836, 8 pages (2019).

Baier, G , et al., "Construction and characterization of Ick- and fyn-specific tRNA: Ribozyme chimeras", Molecular Immunology 31 (12), 923-932 (1994).

Chin, J , et al., "Addition of p-Azido-L-phenylalanine to the Genetic Code of *Escherichia coli*", J Am Chem Soc 124, 9026-9027 (2002).

Chin, J , et al., "An Expanded Eukaryotic Genetic Code", Science vol. 301, 964-967 (2003).

Chin, J , "Expanding and Reprogramming the Genetic Code of Cells and Animals", Annu Rev Biochem 83, 379-408 (2014).

Fu, S , et al., "ValidNESs: a database of validated leucine-rich nuclear export signals", Nucleic Acids Research 41, D338-D343 (2012).

La Cour, T , et al., "Analysis and prediction of leucine-rich nuclear export signals", Protein Engineering, Design & Selection 17(6), 527-536 (2004).

Lemke, E , "The Exploding Genetic Code", ChemBioChem 15, 1691-1694 (2014).

Mukai, T , et al., "Adding L-lysine derivatives to the genetic code of mammalian cells with engineered pyrrolysyl-tRNA synthetases", Biochemical and Biophysical Research Communications 371, 818-822 (2008).

Neumann, H , et al., "Genetically encoding NE-acetyllysine in recombinant proteins", Nature Chemical Biology vol. 4(4), 232-234 (2008).

Nguyen, D , et al., "Genetic Encoding and Labeling of Aliphatic Azides and Alkynes in Recombinant Proteins via a Pyrrolysyl-tRNA Synthetase/tRNA CUA Pair and Click Chemistry", J Am Chem Soc 131, 8720-8721 (2009).

Patent Cooperation Treaty, International Search Report and Written Opinion for PCT/EP2021/054049, 9 pages, dated Apr. 23, 2021.

Thompson, J., et al., "Improved accumulation and activity of ribozymes expressed from a tRNA-based RNA polymerase III promoter", Nucleic Acids Research 23 (12), 2259-2268 (1995).

Wan, W , et al., "Pyrrolysyl-tRNA Synthetase: an ordinary enzyme but an outstanding genetic code expansion tool", Biochim Biophys Acta 1844 (6), 1059-1070 (2014).

Wang, L , et al., "Expanding the Genetic Code", Annu Rev Biophys Biomol Struct 35, 225-249 (2006).

Willis, J , et al., "Mutually orthogonal pyrrolysyl-tRNA synthetase/tRNA pairs", Nature Chemistry 10, 831-837, doi.org/10.1038/s41557-018-0052-5, 9 pages (2018).

Yanagisawa, T , et al., "Multistep Engineering of Pyrrolysyl-tRNA Synthetase to Genetically Encode Nε-(p-Azidobenzyloxycarbonyl) lysine for Site-Specific Protein Modification", Chemistry and Biology 15, 1187-1197 (2008).

* cited by examiner

T-REx

Tet-On

CMV-NES-PylRS$^{AF}$, CMV-tetO-T7RNAP, T7-tRNA$^{Pyl}$-HDV

ARCHAEAL PYRROLYSYL tRNA SYNTHETASES FOR ORTHOGONAL USE

CROSS-REFERENCE TO RELATED APPLICATION(S)

This application claims the benefit of priority of EP Application No. 20158737.5, filed Feb. 21, 2020.

SEQUENCE LISTING

The instant application contains a Sequence Listing which has been submitted in ASCII format via EFS-Web and is hereby incorporated by reference in its entirety. Said ASCII copy, created on Mar. 9, 2023, is named 05710.057US1_ST25 and is 1,23,137 bytes in size.

FIELD OF THE INVENTION

The present invention is concerned with efficient orthogonal translation systems for eukaryotic cells. Specifically, the invention relates to eukaryotic cells comprising polynucleotides encoding a prokaryotic tRNA synthetase (pRS) and an RNA molecule comprising a prokaryotic tRNA (ptRNA) and one or more than one ribozyme (termed "ptRNA-ribozyme" herein), to a method for expressing a polypeptide of interest (POI) comprising one or more non-canonical amino acid (ncAA) residues by such eukaryotic cells, and to kits useful in such method. The invention further relates to polynucleotides encoding the ptRNA-ribozyme.

BACKGROUND OF THE INVENTION

Genetic code expansion (GCE) is one of the most powerful tools for protein engineering, including site-specific introduction of post-translational modifications or labeling of proteins with specialized dyes to study protein structure or dynamics. Specifically, GCE allows for the translational modification of polypeptides by direct genetic encoding of ncAA residues, in particular using stop codon suppression, by means of a tRNA/aminoacyl tRNA synthetase (tRNA/RS) pair that is orthogonal to the translation machinery of the host cell. Ideal orthogonal tRNA/RS pairs show no cross-reactivity with the host's translation machinery, minimizing their impact on the housekeeping translational activity and normal physiology of the cell. Various prokaryotic (bacterial and archaeal) tRNA/RS pairs have been used to genetically encode a variety of ncAA residues in polypeptides including. e.g., engineered *Methanococcus jannaschii* tRNA/tyrosyl-RS, *E. coli* tRNA/leucyl-RS as well as *Methanosarcina mazei* and *M. barkeri* tRNA/pyrrolysyl-RS pairs. See. e.g., Chin et al., J Am Chem Soc 124:9026, 2002; Chin et al., Science 301:964, 2003; Nguyen et al., J Am Chem Soc 131:8720, 2009; Yanagisawa et al., Chem Biol 15:1187, 2008; Liu et al., Annu Rev Biochem 83:379-408, 2010; Lemke, ChemBioChem 15:1691-1694, 2014; Wan et al., Biochim Biophys Acta 1844:1059-170, 2014.

Over the years, various developments have been made to improve efficiency of GCE. These include, e.g., the use of archaeal RS which lack a nuclear localization signal (NLS) and/or comprise a nuclear export signal (NES) so as to allow for the RS to be localized predominantly in the cytoplasm (rather than in the nucleus) as described in WO 2018/069481. Further approaches for increasing GCE efficiency which have been explored include promoter engineering, better evolution of the orthogonal RS, release-factor engineering and multi-chaining of tRNAs, to name a few (for review see, e.g., Chin et al., Annu Rev Biochem 83:379-408, 2014).

Nevertheless, there is still a high demand for strategies which improve efficiency of GCE in eukaryotic cells. With more efficient GCE, the cell can express a higher amount of the POI comprising one or more ncAA residues. A higher amount of POI that is available for labeling and imaging purposes is, e.g., advantageous when polypeptides of low abundance are to be labeled. It was therefore an object of the present invention to (further) increase efficiency of GCE.

SUMMARY OF THE INVENTION

The inventors surprisingly found that expression of the orthogonal tRNA as an RNA molecule that comprises the tRNA together with a ribozyme and the co-expression of a double-stranded RNA-(dsRNA-)binding polypeptide can increase the amount of POI expressed by GCE in eukaryotic cells. Without wishing to be bound by theory it is assumed that the dsRNA-binding polypeptide inhibits the phosphorylation of the alpha subunit of eukaryotic initiation factor 2α (eIF-2α) by protein kinase R (PKR) and thus alleviates the impairment of eIF-2α activity and protein synthesis associated with said PKR activity. Without wishing to be bound by theory, it is further assumed that the ribozyme improves tRNA processing which can be difficult in eukaryotic cells, and thus increases the amount of processed functional orthogonal tRNA that is available for GCE. An ample supply of processed functional orthogonal tRNA is essential for GCE (such as, e.g., amber suppression), in particular considering that orthogonal tRNAs may also interact with non-translational components inside the cells, like tRNA processing machinery and elongation factors.

Thus, in a first aspect, the present invention relates to a eukaryotic cell comprising:

(a) a polynucleotide encoding a prokaryotic aminoacyl tRNA synthetase (pRS), and (b) a polynucleotide encoding a prokaryotic tRNA (ptRNA) and one or more than one ribozyme.

In a further aspect, the present invention relates to a eukaryotic cells comprising:

(a) a polynucleotide encoding a prokaryotic aminoacyl tRNA synthetase (pRS), (b) a polynucleotide encoding a prokaryotic tRNA (ptRNA), and (c) a polynucleotide encoding a polypeptide capable of binding to dsRNA (dsRNA-binding polypeptide) as described herein.

In the eukaryotic cells of the present invention, the pRS encoded by the polynucleotide of item (a) is capable of acylating the ptRNA, in particular acylating the ptRNA with non-canonical amino acid (ncAA), and the sequences encoding the ptRNA and the ribozyme(s) comprised by the polynucleotide of item (b) are linked such that transcription produces an RNA molecule comprising both the ptRNA and the ribozyme(s) (ptRNA-ribozyme).

The dsRNA-binding polypeptide used (such as, e.g., encoded by a polynucleotide used, or expressed) in the context of the present invention, comprises an amino acid sequence having at least 80%, at least 85%, at least 90%, at least 93%, at least 95%, at least 96%, at least 97%, at least 98%, at least 99% or 100% identity to the sequence set forth in any one of SEQ ID NOs:37, and 57-59.

In a further aspect, the present invention relates to a polynucleotide encoding an RNA molecule comprising a ptRNA and a ribozyme (ptRNA-ribozyme) as described herein.

In a further aspect, the present invention relates to a polynucleotide, or combination of two or more polynucleotides, comprising a nucleotide sequence encoding an RNA molecule comprising a ptRNA and a ribozyme (ptRNA-ribozyme) as described herein, and:

(i) a nucleotide sequence encoding a tetO-binding protein as described herein, or
(ii) a nucleotide sequence encoding a pRS as described herein, or
(ii) both of (i) and (ii).

Said two or three nucleotide sequences can be located on the same polypeptide. Or each of said two or three nucleotide sequences can be located on a separate polynucleotide (thus resulting in a combination of two or three polynucleotides, respectively). Or two of said three nucleotide sequences can be located on the same polynucleotide, while the third nucleotide sequence (i.e., the ptRNA-ribozyme-encoding sequence or the pRS-encoding sequence or the tetO-binding protein-encoding sequence) is located on a separate polynucleotide (thus resulting in combination of two polynucleotides).

In a further aspect, the present invention relates to a method for preparing a polypeptide of interest (POI) having one or more than one non-canonical amino acid (ncAA) residue in its amino acid sequence, wherein the method comprises:

(a) expressing, in a eukaryotic cell:
 a pRS and
 an RNA molecule comprising a ptRNA and a ribozyme (ptRNA-ribozyme) as described herein;
(b) expressing the POI in the eukaryotic cell in the presence of one or more than one ncAA or salt thereof corresponding to the one or more than one ncAA residue of the POI; and
(c) optionally recovering the expressed POI.

In a further aspect, the present invention relates to a method for preparing a polypeptide of interest (POI) having one or more than one non-canonical amino acid (ncAA) residue in its amino acid sequence, wherein the method comprises:

(a) expressing, in a eukaryotic cell:
 a pRS,
 a prokaryotic tRNA (ptRNA) and
 a polypeptide capable of binding to dsRNA (dsRNA-binding polypeptide) as described herein;
 and
(b) expressing the POI in the eukaryotic cell in the presence of one or more than one ncAA or salt thereof corresponding to the one or more than one ncAA residue of the POI; and
(c) optionally recovering the expressed POI.

In the methods for preparing a polypeptide of interest (POI) according to the present invention, the pRS is capable of acylating the ptRNA with the ncAA or the salt thereof, and the POI is encoded by a nucleotide sequence that comprises one or more than one selector codon encoding the one or more than one ncAA residue. Said selector codon is the reverse complement of the anticodon of the ptRNA.

Steps (a) and (b) of said methods can be carried out concomitantly or sequentially. For example, expression step (a) can be carried out first followed by expression step (b). When starting with the expression of pRS and the RNA molecule (ptRNA-ribozyme or ptRNA, respectively) according to step (a), said expression may continue when starting the expression of the POI according to step (b).

In a further aspect, the present invention relates to a kit for preparing a POI having one or more than one ncAA residue in its amino acid sequence, wherein the kit comprises one or more than one ncAA, or salt thereof, corresponding to the one or more than one ncAA residue of the POI, and:

(a) a polynucleotide, or combination of two or more polynucleotides, of the invention as described herein, or
(b) a polynucleotide encoding a dsRNA-binding polypeptide as described herein, or
(c) a eukaryotic cell of the invention as described herein.

In GCE, uncontrolled expression of the orthogonal tRNA/RS pair can lead to unwanted side effects. For example, over-excess of unused RS and/or unused tRNA might impair cell viability. The present invention solves this problem by further providing eukaryotic cells, polynucleotides, methods and kits for GCE wherein (i) the transcription of nucleotide sequence(s) encoding the tRNA (ptRNA or ptRNA-ribozyme), the pRS or both is controlled by a tetracycline-responsive promoter element (TRE), or (ii) the transcription of said nucleotide sequence(s) is catalyzed by an RNA polymerase (e.g., a T7 RNA polymerase), wherein expression of said RNA polymerase is controlled by a TRE. Thus, expression of said tRNA and/or pRS becomes inducible by the co-expression of proteins binding to (tetracycline operator (tetO) sequences within) the TRE, such as, e.g., a tetracycline repressor (tetR), a tetracycline-controlled transcriptional activator (tTA) or a reverse tTA (rtTA) and the presence (or absence) of tetracycline or a tetracycline derivative such as, e.g., doxycycline.

Samples include controls where cells were not fed with the ncAA SCO ("–SCO", bottom row). The numbers in the quadrants indicate the percentage of cells in the respective population calculated based on the total number of measured cells: cells without reporter gene expression (bottom left. "double negatives"), cells showing only GFP fluorescence (bottom right, "GFP only"), cells expressing only iRFP without amber suppression (top left, "iRFP only"), cells expressing the full reporter due to amber suppression (top right, "double positives"). See example 1. Experiment with plasmid pCAGGS (containing CMV enhancer with chicken actin promoter and intron).

Figure 4A:
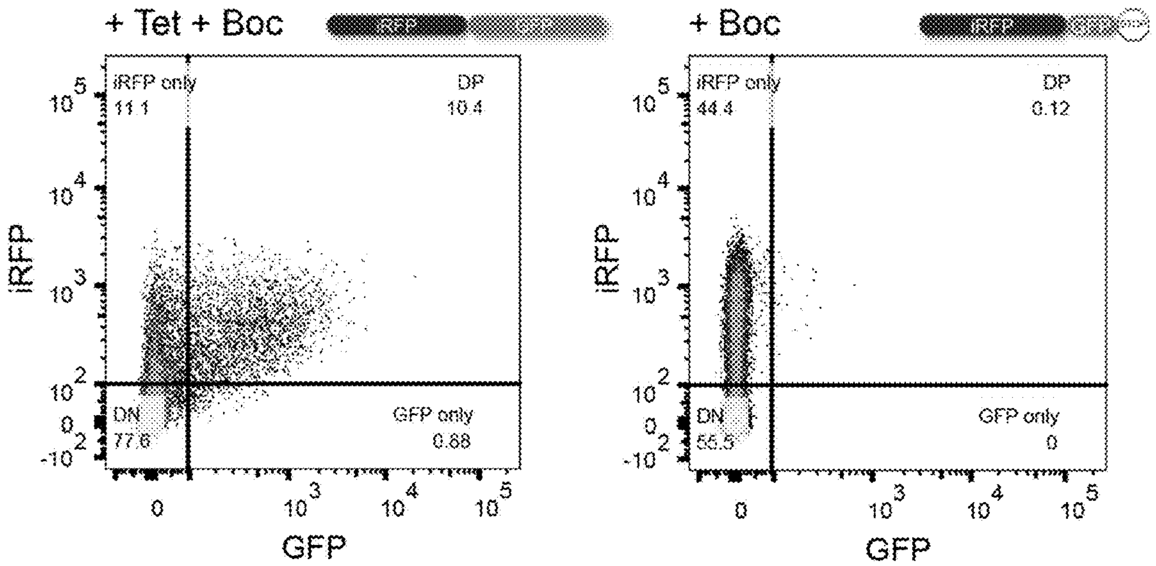

FIG. 4*a* shows the results of a flow cytometry analysis of HEK Flp-In T-REx 293 cells carrying expression cassettes for the NLS-iRFP-Flag-GFP$^{Y39\rightarrow TAG}$-6His amber suppression reporter, NES-T7RNAP, and the amber suppression pair tRNA$^{Pyl}$/NES-PylRS$^{AF}$, wherein the tRNA$^{Pyl}$ was expressed together with a HDV ribozyme ("tRNA$^{Pyl}$-HDV rib.") or without such ribozyme ("tRNA$^{Pyl}$"), and NES-PylRS$^{AF}$ and NES-T7RNAP were inducibly expressed using the T-REx system (ThermoFisher Scientific). Cells were fed with the ncAA BOC ("+Boc"), and expression of NES-PylRS$^{AF}$ and NES-T7RNAP was either induced with tetracycline ("+Tet", left chart) or was not induced (control, right chart). The numbers in the quadrants indicate the percentage of cells in the respective population calculated based on the total number of measured cells: cells without reporter gene expression (bottom left. "DN"=double negatives), cells showing only GFP fluorescence (bottom right, "GFP only"), cells expressing only iRFP without amber suppression (top left, "iRFP only"), cells expressing the full reporter due to amber suppression (top right, "DP"=double positives). See example 2.

Figure 4B:
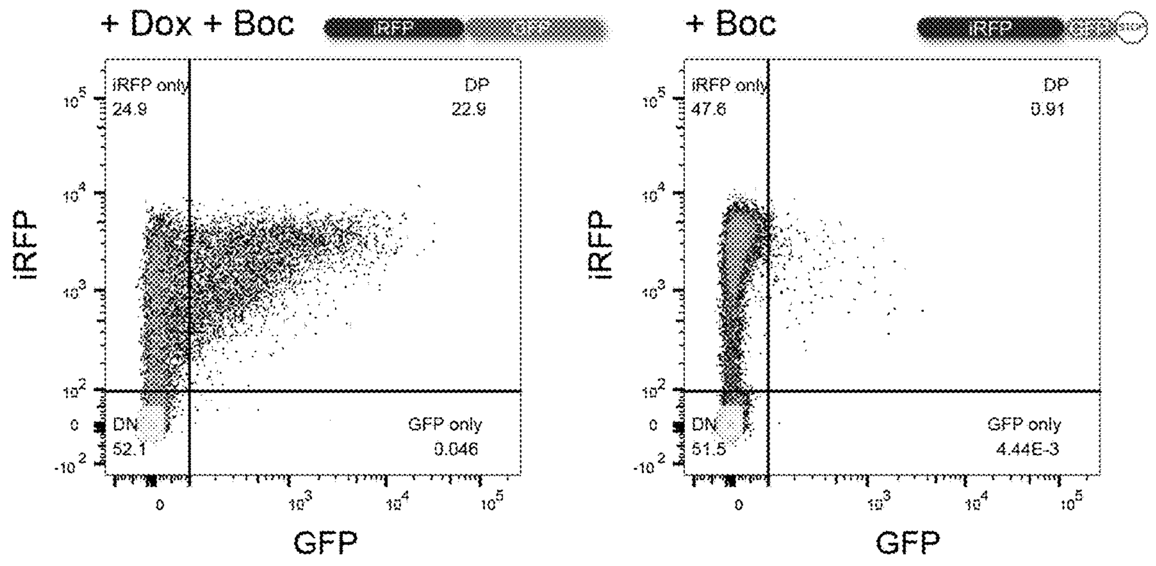

FIG. 4*b* shows the results of a flow cytometry analysis of HEK293T cells carrying expression cassettes for the NLS-iRFP-Flag-GFP$^{Y39\rightarrow TAG}$-6His amber suppression reporter, NES-T7RNAP, and the amber suppression pair tRNA$^{Pyl}$/NES-PylRS$^{AF}$, wherein the tRNA$^{Pyl}$ was expressed together with a HDV ribozyme ("tRNA$^{Pyl}$-HDV rib.") or without such ribozyme ("tRNA$^{Pyl}$"), and NES-PylRS$^{AF}$ and NES-T7RNAP were inducibly expressed using the Tet-On system. Cells were fed with the ncAA BOC ("+Boc"), and expression of NES-PylRS$^{AF}$ and NES-T7RNAP was either induced with doxycycline ("+Dox", left chart) or was not induced (control, right chart). The numbers in the quadrants indicate the percentage of cells in the respective population calculated based on the total number of measured cells: cells without reporter gene expression (bottom left, "DN"=double negatives), cells showing only GFP fluorescence (bottom right, "GFP only"), cells expressing only iRFP without amber suppression (top left, "iRFP only"), cells expressing the full reporter due to amber suppression (top right, "DP"=double positives). See example 2.

Figure 5A:
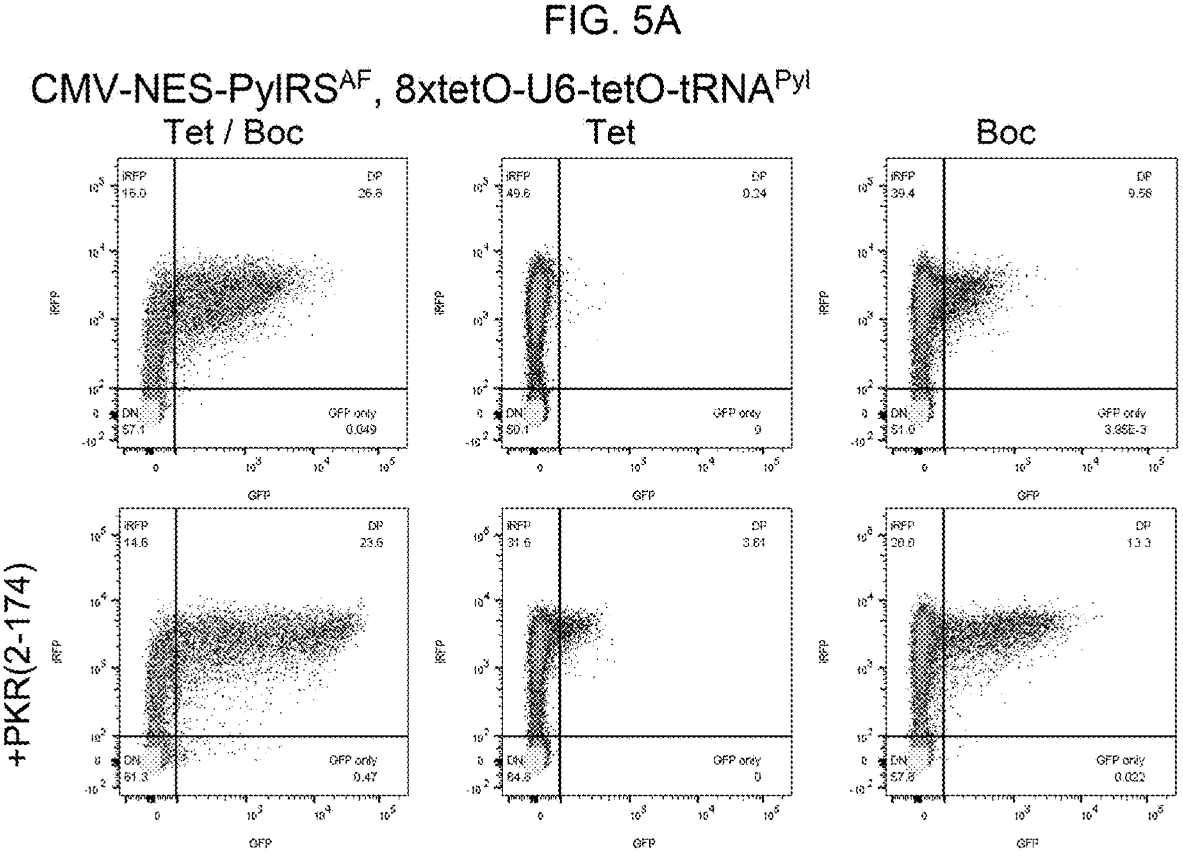
Figure 5B:
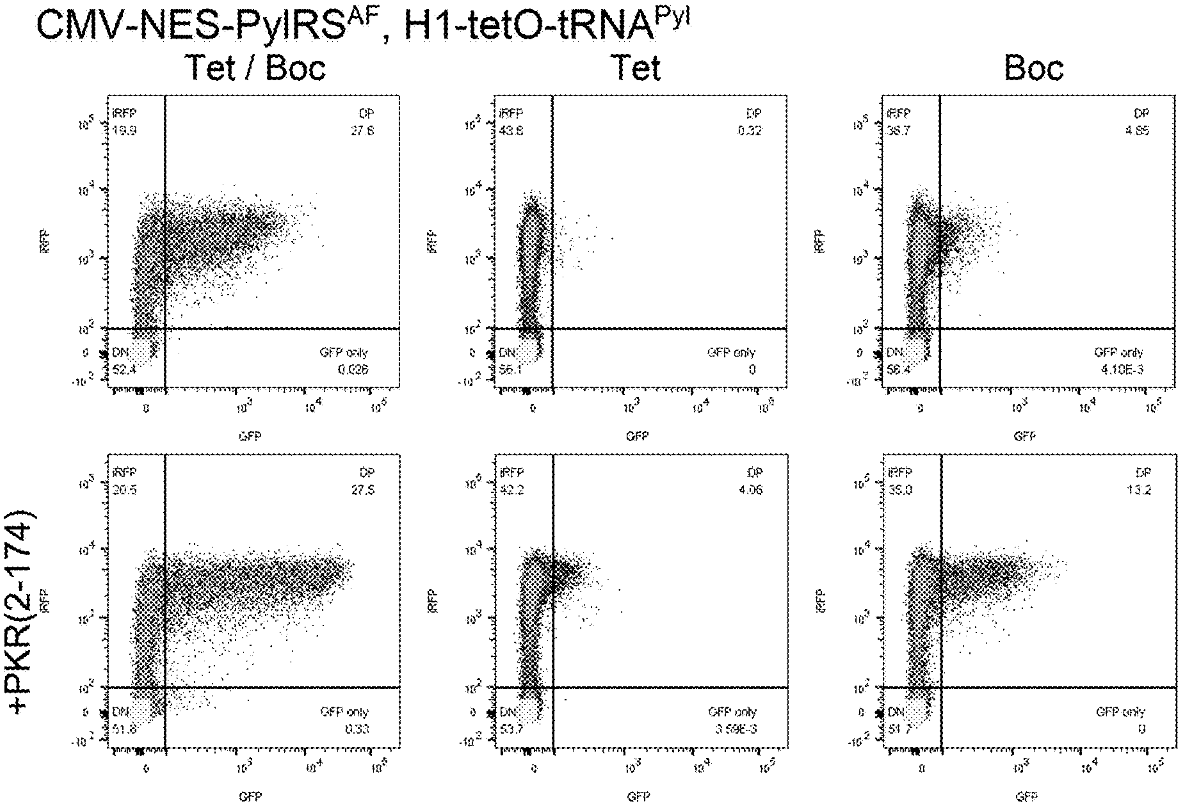
Figure 5C:
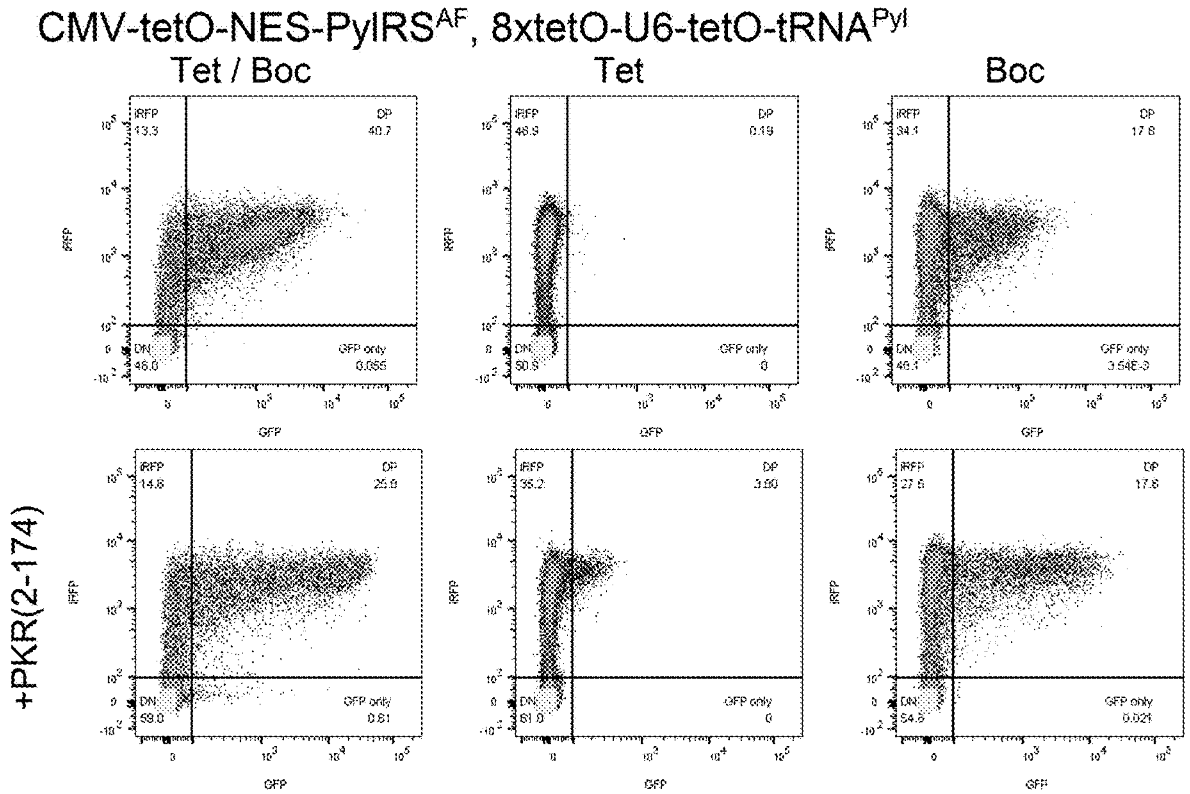
Figure 5D:
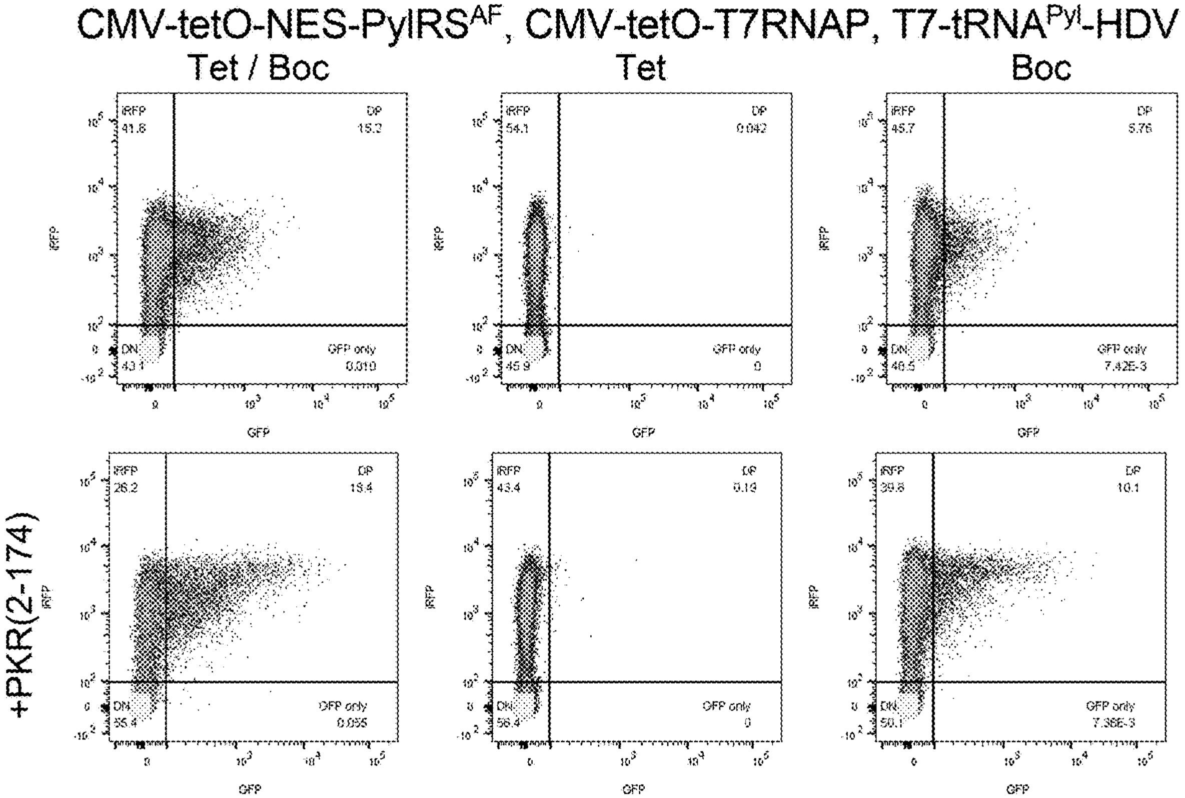
Figure 5E:
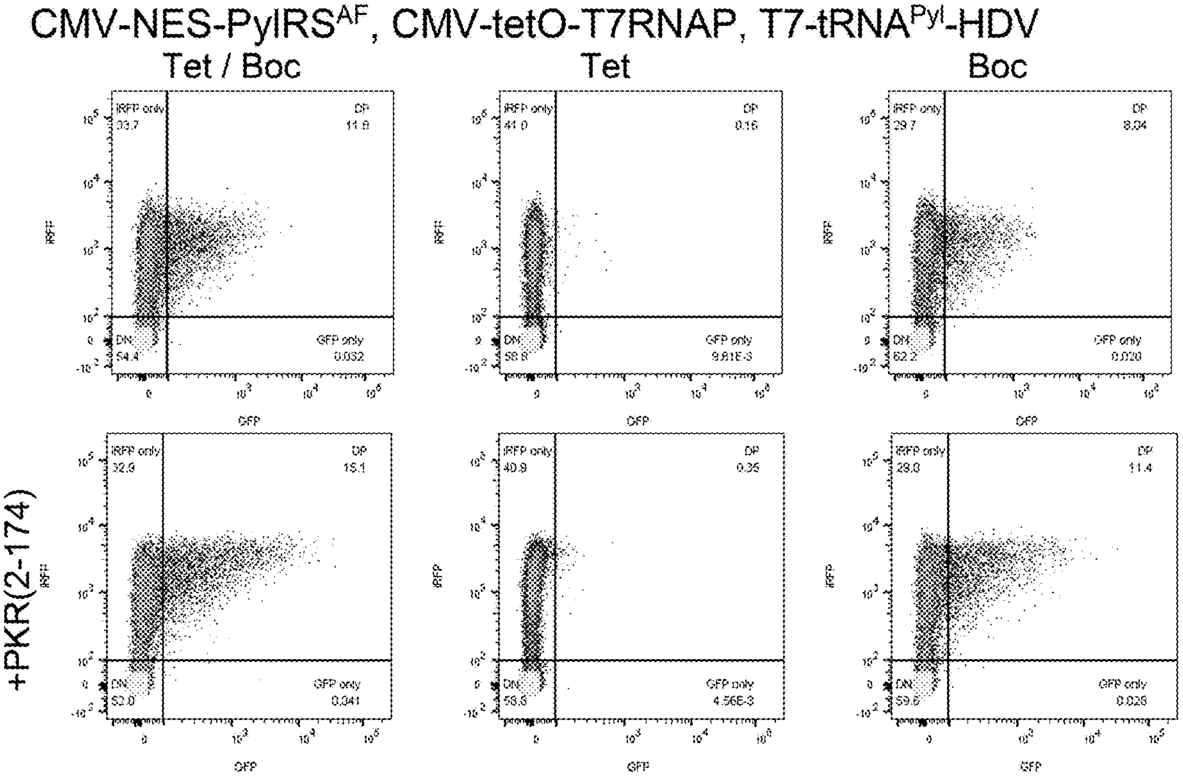
Figure 5F:
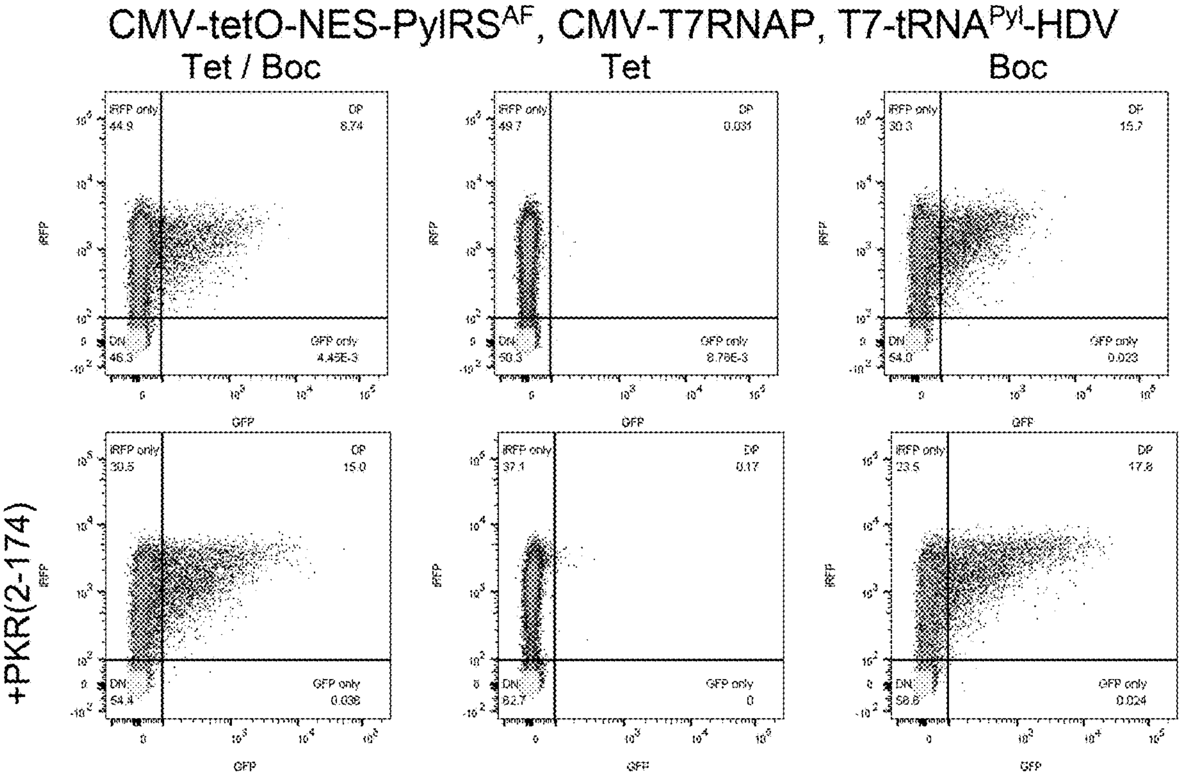

FIG. 5 shows the results of a flow cytometry analysis of HEK293T cells carrying expression cassettes for:

FIG. 5*a*: NLS-iRFP-Flag-GFP$^{Y39\rightarrow TAG}$-6His amber suppression reporter, tetR, and the amber suppression pair tRNA$^{Pyl}$/NES-PylRS$^{AF}$ wherein the expression of tRNA$^{Pyl}$ was controlled by a tetracycline-inducible variant of the human U6 promoter comprising eight tetO sequences before the U6 promoter and two tetO sequences after the U6 promoter and expression of NES-PylRS$^{AF}$ was controlled by the (constitutive) CMV promoter;

FIG. 5*b*: NLS-iRFP-Flag-GFP$^{Y39\rightarrow TAG}$-6His amber suppression reporter, tetR, and the amber suppression pair tRNA$^{Pyl}$/NES-PylRS$^{AF}$ wherein the expression of tRNA$^{Pyl}$ was controlled by a tetracycline-inducible variant of the human H1 promoter comprising two tetO sequences and expression of NES-PylRS$^{AF}$ was controlled by the (constitutive) CMV promoter;

FIG. 5*c*: NLS-iRFP-Flag-GFP$^{Y39\rightarrow TAG}$-6His amber suppression reporter, tetR, and the amber suppression pair tRNA$^{Pyl}$/NES-PylRS$^{AF}$ wherein the expression of tRNA$^{Pyl}$ was controlled by a tetracycline-inducible variant of the human U6 promoter comprising eight tetO sequences before the U6 promoter and two tetO sequences after the U6 promoter and expression of NES-PylRS$^{AF}$ was controlled by a tetracycline-inducible variant of the CMV promoter comprising two tetO sequences;

FIG. 5*d*: NLS-iRFP-Flag-GFP$^{Y39\rightarrow TAG}$-6His amber suppression reporter, tetR, NES-T7RNAP expressed under the control of a tetracycline-inducible variant of the CMV promoter comprising two tetO sequences, and the amber suppression pair tRNA$^{Pyl}$/NES-PylRS$^{AF}$ wherein tRNA$^{Pyl}$ was expressed together with a HDV ribozyme under the control of the T7 promoter and expression of NES-PylRS$^{AF}$ was controlled by a tetracycline-inducible variant of the CMV promoter comprising two tetO sequences;

FIG. 5*e*: NLS-iRFP-Flag-GFP$^{Y39\rightarrow TAG}$-6His amber suppression reporter, tetR. NES-T7RNAP expressed under the control of a tetracycline-inducible variant of the CMV promoter comprising two tetO sequences, and the amber suppression pair tRNA$^{Pyl}$/NES-PylRS$^{AF}$ wherein tRNA$^{Pyl}$ was expressed together with a HDV ribozyme under the control of the T7 promoter and expression of NES-PylRS$^{AF}$ was controlled by the (constitutive) CMV promoter;

FIG. 5*f*: NLS-iRFP-Flag-GFP$^{Y39\rightarrow TAG}$-6His amber suppression reporter, tetR, NES-T7RNAP expressed under the control of the (constitutive) CMV promoter, and the amber suppression pair tRNA$^{Pyl}$O/NES-PylRS$^{AF}$ wherein tRNA$^{Pyl}$ was expressed together with a HDV ribozyme under the control of the T7 promoter and expression of NES-PylRS$^{AF}$ was controlled by a tetracycline-inducible variant of the CMV promoter comprising two tetO sequences.

The HEK293T cells further carried an expression cassette for HA-tagged human PKR(2-174) ("+PKR(2-174)", histograms in the bottom row of each of FIGS. 5*a-f*) or lacked said expression cassette (=control, histograms in the top row of each of FIGS. 5*a-f*). The cells were fed with the ncAA BOC ("Boc", histograms in the left and right column of each of FIGS. 5*a-f*) or not (histograms in the middle column), and expression of the inducible elements (tRNA$^{Pyl}$, NES-PylRS$^{AF}$ and/or NES-T7RNAP) was induced with tetracycline ("Tet" histograms in the left and middle column of each of FIGS. 5*a-f*) or was not induced (histograms in the right column). The numbers in the quadrants indicate the percentage of cells in the respective population calculated based on the total number of measured cells: cells without reporter gene expression (bottom left, "DN"=double negatives), cells showing only GFP fluorescence (bottom right, "GFP only"), cells expressing only iRFP without amber suppression (top left, "iRFP only"), cells expressing the full reporter due to amber suppression (top right, "DP"=double positives). See example 3.

DETAILED DESCRIPTION OF THE INVENTION

Unless otherwise stated or required by context, singular terms shall include pluralities and plural terms shall include the singular. Thus, for example, eukaryotic cells defined as comprising "a polynucleotide encoding a pRS" include eukaryotic cells comprising one or more than one of such polynucleotide as well as eukaryotic cells wherein said polynucleotide(s) encode(s) one or more than one pRS.

If not otherwise stated, nucleotide sequences are depicted herein in the 5' to 3' direction. If not otherwise stated, amino acid sequences are depicted herein in the direction from N-terminus to C-terminus.

1. Prokaryotic Aminoacyl tRNA Synthetase/Prokaryotic tRNA (pRS/ptRNA)

The eukaryotic cells of the invention comprise a polynucleotide encoding a prokaryotic RS/tRNA (pRS/ptRNA) pair, wherein the pRS is capable of acylating the ptRNA. In particular, the pRS is capable of acylating the tRNA with an amino acid or amino acid analog (such as, e.g., compounds which differ from amino acids such that the α-amino group is replaced by a hydroxyl group and/or the carboxylic acid function forms an ester), and preferably with a non-canonical amino acid (ncAA).

The ptRNA and the pRS used in the context of the present invention are orthogonal to the translation machinery of the eukaryotic (host) cell (recombinantly) expressing said ptRNA and pRS. The term "orthogonal" as used herein indicates that the thus specified molecule (e.g., an orthogonal tRNA (O-tRNA) and/or an orthogonal RS (O-RS)) is used with reduced efficiency by the translation system (e.g., the host cell) of interest.

The term "translation system" generally refers to a set of components necessary to incorporate a naturally occurring amino acid in a growing polypeptide chain (protein). Components of a translation system include, e.g., ribosomes, tRNAs, aminoacyl tRNA synthetases, mRNA and the like. Translations systems used in the context of the present invention are preferably eukaryotic cells.

Specifically, "orthogonal" refers to the inability or reduced efficiency (such as, e.g., less than 20% efficient less than 10% efficient, less than 5% efficient, or less than 1% efficient) of an O-tRNA or an O-RS to function with the endogenous RSs or endogenous tRNAs, respectively, of the translation system of interest (wherein said orthogonal RS or orthogonal tRNA is used). For example, an O-tRNA in a translation system of interest is (amino-)acylated by any endogenous RS of the translation system with reduced or even zero efficiency, when compared to (amino-)acylation of an endogenous tRNA by the endogenous RS. For example, an O-RS (amino-)acylates any endogenous tRNA in the translation system of interest with reduced or even zero efficiency, as compared to (amino-)acylation of the endogenous tRNA by an endogenous RS. An "orthogonal translation system" is used herein to refer to a translation system using an RS/O-tRNA$^{ncAA}$ pair that allows for introducing ncAA residues into a growing polypeptide chain.

Unless indicated differently, the terms "endogenous tRNA" and "endogenous aminoacyl tRNA synthetase" ("endogenous RS") used therein refer to a tRNA and an RS, respectively, that was present in the cell ultimately used as translation system prior to introducing the pRS and the ptRNA, respectively, used in the context of the present invention.

The ptRNAs and pRSs used in the methods and/or fusion proteins of the invention can be naturally occurring (i.e. are ptRNAs and pRSs as found in prokaryotic organisms in nature) or can be derived by mutation of a naturally occurring ptRNA or pRS, respectively. In various embodiments, the ptRNA and pRS are derived from a prokaryote, e.g., from an eubacterium or an archaebacterium (e.g., *E. coli*; a *Methanococcus* species such as *M. jannaschii*; a *Methanosarcina* species such as *M. mazei, M. barkeri. M. acetivorans, M. thermophile*; a *Methanococcoides* species such as *M. burtonii*; a *Desulfitobacterium* species such as *D. hafniense*). In another embodiment, the ptRNA is a naturally occurring, or a mutant of a naturally occurring, ptRNA from a first prokaryote and the RS is derived from naturally occurring, or a mutant of a naturally occurring, pRS from a second prokaryote.

Suitable (orthogonal) ptRNA/pRS pairs can be selected from libraries of mutant ptRNAs and pRSs, e.g. based on the results of a library screening. Methods for evolving tRNA/RS pairs are described, e.g., in WO 02/085923 and WO 02/06075.

Several prokaryotic RSs have been used for genetic code expansion including the *Methanococcus* jannaschii tyrosyl-tRNA synthetase, *E. coli* tyrosyl-tRNA synthetase, *E. coli* leucyl-tRNA synthetase, and pyrrolysyl-tRNA synthetases from certain *Methanosarcina* species (such as *M. mazei, M. barkeri, M. acetivorans, M. thermophila*), *Methanococcoides* species (such as *M. burtonii*). *Desulfitobacterium* species (such as *D. hafniense*) or *Methanomethylophilus* species (such as *M. alvus*). Corresponding orthogonal pRS/ptRNA pairs have been used to genetically encode a variety of functionalities in polypeptides (Chin, Annu Rev Biochem 2014, 83:379-408; Chin et al., J Am Chem Soc 2001, 124:9026; Chin et al., Science 2003, 301:964; Nguyen et al., J Am Chem Soc 2009, 131:8720; Willis and Chin, Nat Chem 2018, 10:831-837); Yanagisawa et al., Chem Biol 2008, 15:1187). Such pRSs and ptRNAs can be used in the present invention.

Pyrrolysyl tRNA synthetases (PylRSs) which can be used as pRSs in the context of the present invention may be wildtype or genetically engineered PylRSs. Examples for wildtype PylRSs include, but are not limited to. PylRSs from archaebacteria and eubacteria such as *Methanosarcina* maize, *Methanosarcina barkeri, Methanococcoides burtonii, Methanosarcina acetivorans, Methanosarcina thermophila, Methanomethylophilus alvus* and *Desulfitobacterium hafniense*. Genetically engineered PylRSs have been described, for example, by Neumann et al. (Nat Chem Biol 2008, 4:232), by Yanagisawa et al. (Chem Biol 2008, 15:1187), and in EP2192185A1. The efficiency of genetic code expansion using PylRS can be increased by modifying the amino acid sequence of the PylRS such that it is not directed to the nucleus. To this end, the nuclear localization signal (NLS) can be removed from the PylRS or can be overridden by introducing a suitable nuclear export signal (NES). Thus, in particular embodiments of the invention, the pRS is a PylRS, or a functional fragment or mutant, as described herein that lacks the NLS and/or comprises a NES as described, e.g., in WO 2018/069481. For example, such PylRS may carry a NES, preferably inserted between (the methionine residue at) amino acid position 1 of the pRS and the amino acid position 2 of the pRS.

The term "nuclear export signal" (abbreviated as "NES") refers to an amino acid sequence which can direct a polypeptide containing it (such as a NES-containing pRS of the invention or a NES-T7RNAP as used herein) to be exported from the nucleus of a eukaryotic cell. Said export is believed to be mostly mediated by Crm1 (chromosomal region maintenance 1, also known as karyopherin exportin 1). NESs are known in the art. For example, the database ValidNESs (validness.ym.edu.tw/) provides sequence information of experimentally validated NES-containing proteins. Further, NES databases like, e.g., NESbase 1.0 (www.cbs.dtu.dk/databased/NESbase-1.0/; see Le Cour et al., Nucl Acids Res 31 (1), 2003) as well as tools for NES prediction like NetNES (www.cbs.dtu.dk/services/NetNES/; see La Cour et al., La Cour et al., Protein Eng Des Sel 17 (6): 527-536, 2004), NESpredictor (NetNES, www.cbs.dtu.dk/; see Fu et al., Nucl Acids Res 41: D338-D343, 2013; La Cour et al., Protein Eng Des Sel 17 (6): 527-536, 2004)) and NESsential (a web interface combined with ValidNESs) are available to the public. Hydrophobic leucine-rich NESs are most common and represent the best characterized group of NESs to date. A hydrophobic leucine-rich NES is a non-conservative motif having 3 or 4 hydrophobic residues. Many of these NESs comprise the conserved amino acid sequence pattern LxxLxL (SEQ ID NO:28) or LxxxLxL (SEQ ID NO:29), wherein each L is independently selected from leucine, isoleucine, valine, phenylalanine and methionine amino acid residues, and each x is independently selected from any amino acid (see La Cour et al., Protein Eng Des Sel 17 (6): 527-536, 2004).

Particular NESs which are suitable as signal peptide for the pRS (in particular the PylRS) used in the present invention are known in the art (e.g., from NES databases) and described, e.g., in WO 2018/069481. In specific embodiments, the pRS used in the invention comprises a hydrophobic leucine-rich NES, in particular a NES comprising the amino acid sequence LxxLxL (SEQ ID NO:28) or LxxxLxL (SEQ ID NO:29), wherein each L is independently selected from leucine, isoleucine, valine, phenylalanine and methionine, and each x is independently selected from any amino acid; more particularly a NES comprising an amino acid sequence selected from $L^1xxL^2xxL^1xL^3$ (SEQ ID NO:30), $L^1xxxL^2xxL^1xL^3$ (SEQ ID NO:31). $L^1xxL^2xxxL^1xL^3$ (SEQ ID NO:32) and $L^1xxxL^2xxxL^1xL^3$ (SEQ ID NO:33), wherein $L^1$ is leucine, $L^2$ is selected from leucine, isoleucine, valine, phenylalanine and methionine, $L^3$ is selected from leucine and isoleucine, and each x is independently selected from any amino acid. Preferably, the NES comprises the amino acid sequence LPPLERLTL (SEQ ID NO:34) which is found in the HIV-1 Rev protein or, more preferably, the amino acid sequence ACPVPLQLPPLERLTLD (SEQ ID NO:35).

A "nuclear localization signal" (abbreviated as "NLS", also referred to in the art as "nuclear localization sequence") is an amino acid sequence that "tags" (i.e. can direct) a polypeptide containing it (e.g., NLS-iRFP-Flag-$GFP^{Y39\rightarrow TAG}$-6His) to be imported into the nucleus of a eukaryotic cell. Said export is believed to be mediated by binding of the NLS-containing polypeptide to importin (also known as karyopherin) so as to form a complex that moves through a nuclear pore. NLSs are known in the art. A multitude of NLS databases and tools for NLS prediction are available to the public, such as NLSdb (see Nair et al., Nucl Acids Res 31(1), 2003), cNLS Mapper (www.nls-mapper-.aib.keio.ac.jp; see Kosugi et al., Proc Natl Acad Sci USA. 106(25):10171-10176, 2009; Kosugi et al., J Biol Chem 284(1):478-485, 2009), SeqNLS (see Lin et al., PLoS One 8(10):e76864, 2013), and NucPred (www.sbc.su.se/~maccallr/nucpred/; see Branmeier et al., Bioinformatics 23(9): 1159-60, 2007). Classical NLSs can be monopartite or bipartite. Bipartite NLSs consist of two basic amino acid clusters and a spacer of about 10 amino acids linking said dusters. A typical core sequence comprised by monopartite NLSs is $KX^1X^2X^3$ (SEQ ID NO:20), wherein $X^1$ and $X^3$ are independently selected from K and R, and $X^2$ is any amino acid. Exemplary NLS include the NLSs comprising the amino acid sequence PKKKRKV (SEQ ID NO:21).

Examples of specific pRSs which can be used in the context of the present invention include, but are not limited to:

*Methanococcus jannaschii* tyrosyl-tRNA synthetase;
*Escherichia coli* tyrosyl-tRNA synthetase;
*Escherichia coli* leucyl-tRNA synthetase;
*Methanosarcina mazei* pyrrolysyl-tRNA synthetase;
*Methanosarcina barkeri* pyrrolysyl-tRNA synthetase;
*Methanosarcina acetivorans* pyrrolysyl-tRNA synthetase;
*Methanosarcina thermophila* pyrrolysyl-tRNA synthetase;
*Methanococcoides burtonii* pyrrolysyl-tRNA synthetase;
*Desulfitobacterium hafniense* pyrrolysyl-tRNA synthetase;
*Methanomethylophilus alvus* pyrrolysyl-tRNA synthetase;

as well as functional (i.e., enzymatically active) fragments and mutants of these polypeptides. Said functional fragments and mutants may comprise at least 60%, at least 70%, at least 80%, at least 90%, at least 95%, at least 96%, at least 97%, at least 98% or at least 99% amino acid sequence identity to the aminoacyl tRNA synthetase they are derived from.

Particular examples of pRSs useful as in the present invention which are *M. mazei* PylRSs include, but are not limited to:

$PylRS^{AF}$ (*Methanosarcina mazei* pyrrolysyl tRNA synthetase double mutant: Y306A, Y384F; Uniprot Q8PWY1; SEQ ID NO:22);
$PylRS^{AA}$ (*Methanosarcina mazei* pyrrolysyl tRNA synthetase double mutant: N346A, C348A; Uniprot Q8PWY1; SEQ ID NO:23);
$PylRS^{AAAF}$ (*Methanosarcina mazei* pyrrolysyl tRNA synthetase quadruple mutant: Y306A, N346A, C348A, Y384F; Uniprot Q8PWY1; SEQ ID NO:24);

as well as functional (i.e., enzymatically active) fragments and mutants of these polypeptide segments. Said functional fragments and mutants may comprise at least 60%, at least 70%, at least 80%, at least 90%, at least 95%, at least 96%, at least 97%, at least 98% or at least 99% amino acid sequence identity to the PylRSs they are derived from.

According to particular embodiments, wild-type and mutant *M. mazei* PylRSs as described herein are used for aminoacylation of tRNA with ncAAs as described in WO2012/104422 or WO2015/107064. Exemplary ncAAs for this purpose include, but are not limited to, 2-amino-6-(tert-butoxycarbonylamino)hexanoic acid (BOC), 2-amino-6-(cyclooct-2-yn-1-yloxycarbonylamino)hexanoic acid (SCO), 2-amino-6-(cyclooct-2-yn-1-yloxyethoxycarbonylamino)hexanoid acid, 2-amino-6[(4E-cyclooct-4-en-1-yl)oxycarbonylamino]hexanoic acid (TCO), 2-amino-6 [(2E-cyclooct-2-en-1-yl)oxycarbonylamino]hexanoic acid (TCO*), 2-amino-6-(prop-2-ynoxycarbonylamino)hexanoic acid (PrK), 2-amino-6-(9-biocyclo[6.1.0]non-4-ynyl-methoxycarbonylamino)hexanoid acid (BCN) and particularly the 2S-(L-) enantiomer of these amino acids.

Functional fragments and mutants of pRS described herein are functional in that they have the acylating enzymatic activity of the parent pRS, wherein the degree of said enzymatic activity of the fragment or mutant may be higher or less than, or about the same as, that of the parent pRS. Such fragments and mutants can be characterized by a minimum degree of sequence identity as described herein.

Amino acid or nucleotide sequence identity as used herein means identity over the entire length of the thus characterized amino acid or nucleotide sequence, respectively. The percentage identity values can be determined as known in the art on the basis of BLAST alignments, blastp algorithms (protein-protein BLAST), or using the Clustal method (Higgins et al., Comput Appl. Biosci. 1989, 5(2):151-1).

Functional fragments and mutants of particular pRSs which are useful in the present invention can be obtained, e.g., by conservative amino acid substitution, i.e. the replacement of an amino acid residue with different amino acid residues having similar biochemical properties (e.g. charge, hydrophobicity and size) as known in the art. Typical examples are substitution of Leu by lie or vice versa, substitution of Asp by Glu or vice versa, substitution of Asn by Gin or vice verse, and others.

ptRNAs which can be used in the context of the present invention include, but are not limited to, pyrrolysyl tRNA of *M. mazei* and functional mutants thereof. Expediently, the anticodon of the ptRNA is the anticodon to a selector codon such as, e.g., the CUA anticodon to the Amber stop codon TAG, the anticodon UCA to the Opal stop codon TGA, or the anticodon UUA to the Ochre stop codon TAA. Examples for such pyrrolysyl tRNAs include, but are not limited to, those encoded by the nucleotide sequence of SEQ ID NO:25 ($tRNA^{Pyl,CUA}$), SEQ ID NO:26 ($tRNA^{Pyl,UCA}$) or SEQ ID NO:27 ($tRNA^{Pyl,UUA}$).

A ptRNA used in the context of the present invention can act as a suppressor tRNA which alters the reading of a messenger RNA (mRNA) in a given translation system (e.g., a eukaryotic cell of the present invention). A suppressor tRNA can read through, e.g., a stop codon, a four base codon, or a rare codon.

O-RS/O-tRNA (pRS/ptRNA) pairs used in the invention preferably have the following properties: the O-tRNA is preferentially acylated (with an ncAA) by the O-RS. In addition, the orthogonal pair functions in the translation system of interest (e.g. the eukaryotic cell of the invention) such that the O-tRNA (that has been acylated with the ncAA) is used to incorporate said amino acid or ncAA residue into the growing polypeptide chain of a POI. Incorporation occurs in a site specific manner. Specifically, the O-tRNA recognizes (specifically binds via its anticodon to) a selector codon (e.g., an Amber, Ochre or Opal stop codon) in the mRNA coding for the POI.

The term "preferentially acylates" refers to an efficiency of, e.g., about 50% efficient, about 70% efficient, about 75% efficient, about 85% efficient, about 90% efficient, about 95% efficient, or about 99% or more efficient, at which an O-RS acylates an O-tRNA with a ncAA compared to an endogenous tRNA or amino acid of a translation system of interest. The ncAA residue is then incorporated into a growing polypeptide chain with high fidelity, e.g., at greater than about 75% efficiency for a given selector codon, at greater than about 80% efficiency for a given selector codon, at greater than about 90% efficiency for a given selector codon, at greater than about 95% efficiency for a given selector codon, or at greater than about 99% or more efficiency for a given selector codon.

2. Ribozymes and ptRNA-Ribozyme

In one aspect of the present invention, the ptRNA is expressed in the form of an RNA molecule comprising the ptRNA sequence and one or more than one ribozyme (ptRNA-ribozyme).

The term "ribozyme" as used herein refers to an RNA molecule, or a part thereof, that is capable of site-specific self-cleavage. Specifically, a ribozyme is capable of catalyzing the site-specific cleavage of the phosphodiester bond between two ribonucleotides within the ribonucleotide sequence of (same) the ribozyme.

Ribozymes are well known in the art. Examples of ribozymes which can be used in the ptRNA-ribozyme of the present invention include, but are not limited to, a hammerhead ribozyme (e.g., a hammerhead ribozyme of SEQ ID NO:4), a hairpin ribozyme (e.g., the hairpin ribozyme of SEQ ID NO:5), a Varkud satellite (VS) ribozyme (e.g., the VS ribozyme of SEQ ID NO:6), a glucosamine-6-phosphate synthetase (glmS) riboswitch (e.g., the glmS riboswitch of SEQ ID NO:7) and a hepatitis delta virus (HDV) ribozyme (e.g., a HDV ribozyme of SEQ ID NO:1, 2 or 3). Information on these ribozymes can be found, e.g., in Ferré-D'Amaré et al. (Cold Spring Harb Perspect Biol 2010, 2:a003574), Cochrane et al. (Chem Biol 2007, 14(1):97-105) and Schürer et al. (Nucl Acids Res 2002, 30(12):e56). In preferred embodiments of the invention, the ribozyme is a HDV ribozyme of SEQ ID NO:1.

The RNA comprising the ptRNA and the ribozyme used in the present invention comprises one or more than one ribozyme which is/are located relative to the ptRNA such that the ribozyme-catalyzed site-specific (self-)cleavage of the RNA releases the 5'-end and/or the 3'-end of the ptRNA. Thus, said ribozyme-catalyzed (self-)cleavage yields an RNA molecule comprising the ptRNA sequence wherein the 5'-end and/or the 3'-end of the ptRNA sequence coincides with the 5'-end or 3'-end, respectively, of said RNA molecule. In a particular embodiment, ribozyme-catalyzed (self-)cleavage of the RNA comprising the ptRNA and the ribozyme yields an RNA molecule that consists of the ptRNA. In a preferred embodiment, the ribozyme is a HDV ribozyme, in particular a HDV ribozyme of SEQ ID NO:1, that is directly (i.e. without any interjacent ribonucleotides) covalently linked (fused) to the 3'-end of the ptRNA so as to form a continuous ptRNA-ribozyme fusion.

3. Inducible and Constitutive Expression of ptRNA and/or pRS

As a further aspect, the present invention provides eukaryotic cells, methods for preparing a POI and related subject matter as described herein, wherein the expression of the ptRNA (or the ptRNA-ribozyme) or the pRS or both is inducible (in contrast to constitutive). Specifically, said inducibility is achieved in that transcription of the nucleotide sequences encoding the pRS or the ptRNA/ptRNA-ribozyme or both is controlled (directly) by a tetracycline-responsive promoter element or its transcription is catalyzed by an RNA polymerase, wherein expression of said RNA polymerase is controlled by a tetracycline-responsive promoter element.

Suitable systems for TRE-regulated transcription are well known in the art and have become standard tools for inducible gene expression. See, e.g., Gossen and Bujard, Proc Natl Acad Sci USA. 1992, 89(12):5547-5551; Yao et al., Hum Gene Ther. 1998, 9(13):1939-1950; Das et al., Curr Gene Ther, 2016, 16(3):156-167.

The term "tetracycline-responsive promoter element" (abbreviated "tetracycline response element" or "TRE") refers to a promoter sequence comprising one, or more (such as, e.g., two, three, four, five, six, seven or more, for instance two or seven) tetracycline operator (tetO) sequences. A tetO is a polynucleotide segment having the sequence of SEQ ID NO:8 or a functional variant thereof that is capable of binding to a tetO-binding protein such as, e.g., a tetracycline repressor (tetR), tetracycline-controlled transcriptional activator (tTA) or a reverse tTA (rtTA) protein. A TRE may further comprise at least part of the minimal CMV promoter sequence set forth in SEQ ID NO:9.

In the context of the present invention, the transcription of a TRE-controlled sequence is in particular the transcriptional synthesis of a herein described RNA molecule (ptRNA or ptRNA-ribozyme), the transcription of the pRS-encoding sequence, or the transcriptional synthesis of the RNA polymerase (e.g., T7 RNA polymerase) catalyzing the transcriptional synthesis of a herein described ptRNA or ptRNA-ribozyme.

The eukaryotic cells of the invention wherein expression of one or more of the pRS, ptRNA/ptRNA-ribozyme and T7RNAP is controlled by a TRE as described herein expediently further comprise a polynucleotide encoding a tetO-binding protein (tetR, rtTA or tTA) as described herein to allow for inducing the expression said TRE-controlled coding sequences in the presence or absence, respectively, of tetracycline, doxycycline or a functional analogue thereof as described herein.

Figure 2:
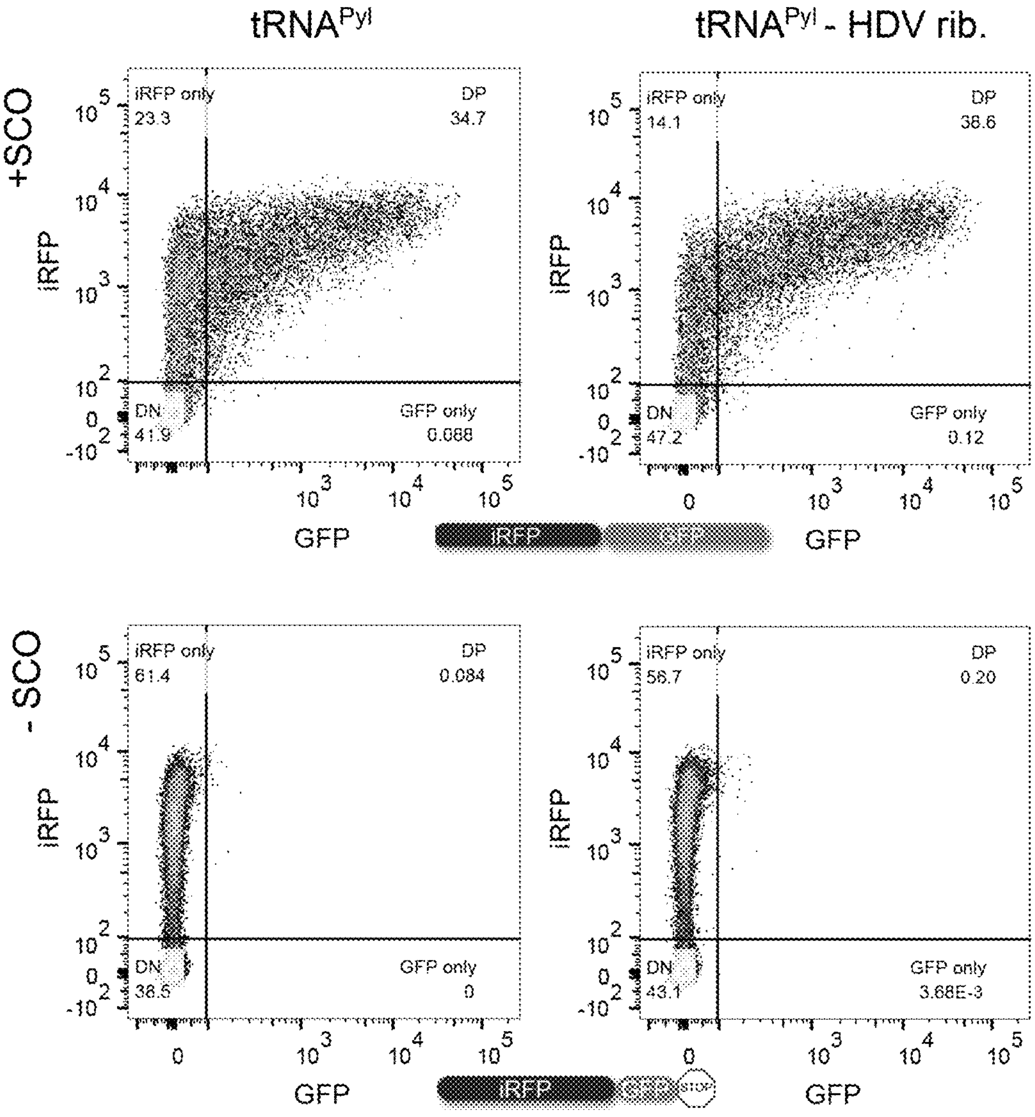
FIG. 2 shows the results of a flow cytometry analysis of HEK293T cells carrying expression cassettes for the NLS-iRFP-Flag-GFP$^{Y39\rightarrow TAG}$-6His amber suppression reporter, T7RNAP and the amber suppression pair tRNA$^{Pyl}$/PylRS$^{AF}$, wherein the tRNA$^{Pyl}$ was either expressed together with a HDV ribozyme ("tRNA$^{Pyl}$-HDV rib.") or without such ribozyme ("tRNA"). The HEK293T cells further carried an expression cassette for HA-tagged human PKR(2-174). Samples include controls where cells were not fed with the ncAA SCO ("−SCO", bottom row). The numbers in the quadrants indicate the percentage of cells in the respective population calculated based on the total number of measured cells: cells without reporter gene expression (bottom left, "DN"=double negatives), cells showing only GFP fluorescence (bottom right, "GFP only"), cells expressing only iRFP without amber suppression (top left, "iRFP only"), cells expressing the full reporter due to amber suppression (top right, "DP"=double positives). See example 1. Experiment with plasmid pcDNA3.1 (containing the CMV promoter).

Particular examples of TREs which can be used in the context of the present invention include those comprising (or having) the sequence of any one of SEQ ID NOs:10-12. A TRE comprising (or having) the sequence of SEQ ID NO:10 or SEQ ID NO:11 is useful in combination with a rtTA, as well as for tTA. A TRE comprising (or having) the sequence of SEQ ID NO:12 is particularly useful in combination with a tetR. The tetO-binding protein and the TRE chosen to control the transcriptional synthesis of a herein described RNA molecule (ptRNA or ptRNA-ribozyme), pRS-mRNA, and/or RNA polymerase mRNA are thus expediently selected to match (bind to) each other so as to allow for inducible transcriptional control.

rtTAs and tTAs are generally known in the art, e.g., from Das et al. (Curr Gene Therapy 2016, 16:156-167) and the references cited therein. Exemplary rtTA proteins may be selected from those listed in FIG. 2B of Das et al. (supra).

rtTAs are fusion proteins comprising a first polypeptide which binds to a tetO sequence in the presence of tetracycline or a tetracycline analogue (in particular in the presence of doxycycline). Said first polypeptide is (operatively) linked to a second polypeptide which activates transcription in eukaryotic cells. The first polypeptide is preferably a mutant of the 207aa TetR selected from, e.g., the list of rtTAs shown in FIG. 2 of Das et al. (supra). The second polypeptide is preferably the 127aa transcription activation domain of the herpes simplex virus VP16 protein. The first and second polypeptide are preferably covalently linked so as to form a fusion protein, such as a fusion protein comprising the sequence of SEQ ID NO:14 and functional equivalents thereof.

An rtTA binds to (tetO sequences of) the TRE in the presence of a doxycycline or a functional analogue thereof. Said binding of the rtTA facilitates or enhances the binding of RNA polymerase and thereby the transcription of the TRE-controlled sequence. In such so-called "Tet-On" system, transcription of the TRE-controlled sequence is thus induced in the presence of an rtTA by adding doxycycline, or a functional analogue thereof. Accordingly, methods of the present invention, wherein transcription (and thus expression) of one or more of the pRS, ptRNA/ptRNA-ribozyme and T7RNAP is controlled by such Tet-On system, expediently further comprise the steps of:

- expressing an rtTA in the eukaryotic cell and
- contacting said cell with doxycycline, or a functional analogue thereof (thereby inducing transcription of the TRE-controlled sequence).

The rtTA is expressed in the cell at least concomitantly with (i.e., prior to and/or concomitantly with) the expression of the TRE-controlled sequence.

tTAs are fusion proteins comprising a first polypeptide which binds to a tetO sequence in the absence of tetracycline, doxycycline or a functional analogue thereof. Said first polypeptide is (operatively) linked to a second polypeptide which activates transcription in eukaryotic cells. The first polypeptide is preferably the 207aa TetR or a functional derivative thereof. The second polypeptide is preferably the 127aa transcription activation domain of the herpes simplex virus VP16 protein. The first and second polypeptides are preferably covalently linked so as to form a fusion protein.

A tTA binds to (tetO sequences of) the TRE in the absence (or at reduced concentrations) of a tetracycline, doxycycline or a functional analogue thereof. Said binding of the tTA facilitates or enhances the binding of RNA polymerase and thereby the transcription of the TRE-controlled sequence. In such so-called "Tet-Off" system, transcription of the TRE-controlled sequence is thus induced in the presence of a tTA by removing (or reducing the concentration of) previously present tetracycline, doxycycline, or a functional analogue thereof. Accordingly, methods of the present invention, wherein transcription (and thus expression) of one or more of the pRS, ptRNA/ptRNA-ribozyme and T7RNAP is controlled by such Tet-Off system, expediently further comprise the steps of:

- expressing an tTA in the eukaryotic cell and
- keeping said cell prior to the expression of the TRE-controlled sequence in contact with tetracycline, doxycycline, or a functional analogue thereof (thereby suppressing the binding of tTA to the TRE and thus the (trans-)activation of the transcriptional synthesis of said TRE-controlled sequence) and then reducing the concentration of, or preferably removing, said tetracycline, doxycycline, or analogue thereof so as to induce transcription of the TRE-controlled sequence.

The tTA is expressed in the cell at least concomitantly with (i.e., prior to and/or concomitantly with) the expression of the TRE-controlled sequence.

Tetracycline repressor (tetR) proteins are generally known in the art. See, e.g., Hillen and Berens, Annu Rev Microbiol 1994, 48:345-369. Exemplary tetR proteins which can be suitably used in the context of the present invention include polypeptides comprising (or having) the amino acid sequence set forth in SEQ ID NO:13 and functional equivalents thereof.

A tetR binds to (tetO sequences of) the TRE in the absence (or at reduced concentrations) of a doxycycline or a functional analogue thereof. Said binding of the tetR inhibits or prevents the binding of RNA polymerase and thereby the transcription of the TRE-controlled sequence. In such so-called "T-REx" system, transcription of the TRE-controlled sequence is thus induced in the presence of a tetR by adding tetracycline, doxycycline, or a functional analogue thereof. Accordingly, methods of the present invention, wherein transcription (and thus expression) of one or more of the pRS, ptRNA/ptRNA-ribozyme and T7RNAP is controlled by such T-REx system, expediently further comprise the steps of:

- expressing a tetR in the eukaryotic cell and
- contacting said cell with tetracycline, doxycycline, or a functional analogue thereof (thereby inducing transcription of the TRE-controlled sequence).

The tetR is expressed in the cell at least prior to (i.e., prior to, or prior to both prior to and concomitantly with) the expression of the TRE-controlled sequence.

The transcription of a herein described RNA molecule (ptRNA or ptRNA-ribozyme) and/or the transcription of the pRS-encoding sequence can be controlled by a constitutive promoter. Constitutive promoters and the RNA polymerases binding to such promoters are well known in the art and include eukaryotic promoters such as, for example, the CMV promoter (from human cytomegalovirus), SV40 promoter (from simian vacuolating virus 40), U6 promoter (from the human small U6 small nuclear promoter), and H1 promoter (from the human polymerase III RNA promoter), as well as prokaryotic promoters such as, for example, the T7 promoter (from T7 bacteriophage), the Sp6 promoter (from Sp6 bacteriophage).

Transcription of a herein described RNA molecule (ptRNA or ptRNA-ribozyme) and/or the transcription of the pRS-encoding sequence that is controlled by a constitutive promoter transcription can be constitutive or inducible. Constitutive transcription can be achieved in particular if the RNA polymerase which catalyzes transcription via said promoter is constitutively expressed in the eukaryotic cell. Alternatively, transcription can be inducible if the RNA polymerase which catalyzes transcription via said promoter is inducibly expressed in the eukaryotic cell, for example under the (direct) control of a TRE. In particular embodiments, wherein expression of the herein described RNA molecule (ptRNA or ptRNA-ribozyme) and/or the transcription of the pRS-encoding sequence is controlled by a constitutive promoter, and is inducible by inducible expression of the RNA polymerase which catalyzes transcription via said promoter, the constitutive promoter is a prokaryotic promoter, in particular a promoter which requires an RNA polymerase that does not naturally occur in eukaryotic cells. Particular examples include the Sp6 promoter and, preferably, the T7 promoter.

The term "T7 promoter" refers to a region of DNA that initiates transcription of a particular gene by a T7 RNA polymerase (17RNAP). According to particular embodiments, the T7 promoter used in the context of the present invention comprises (or consists of) a nucleotide sequence having at least 80%, at least 85%, at least 90%, at least 95%, at least 96%, at least 97%, at least 98%, at least 99% or 100% identity to the sequence set forth in any one of SEQ ID NOs:15-17. In preferred embodiments of invention, the T7 promoter comprises the amino acid sequence of SEQ ID NO:15 or 16.

In preferred embodiments of the invention, where transcription (and thus expression) of one or both of the pRS and the ptRNA or ptRNA-ribozyme, respectively, is controlled by a constitutive promoter, said constitutive promoter is a T7 promoter and preferably comprises (or consists of) the nucleotide sequence of any one of SEQ ID NOs:15-17. In embodiments where a T7 promoter is used, the eukaryotic cell expediently further expresses a T7RNAP. Said T7RNAP may be constitutively expressed or inducibly expressed. e.g. under the (direct) control of a TRE.

A "17 RNA polymerase" (T7RNAP) is a protein that binds to a T7 promoter and catalyzes transcription of sequences downstream of the T7 promoter. The amino acid sequence of the naturally occurring T7RNAP is known in the art, see, e.g., UniProtKB/Swiss-Prot accession no.: P00573.2. According to particular embodiments, the T7RNAP used in the context of the present invention comprises an amino acid sequence having at least 80%, at least 85%, at least 90%, at least 95%, at least 96%, at least 97%, at least 98%, at least 99% or 100% identity to the sequence set forth in SEQ ID NO:18 or the sequence set forth in SEQ ID NO:19 (includes a NES covering amino acid positions 2-17).

To direct its localizations within the eukaryotic cell, the T7RNAP (or other RNA polymerase recombinantly expressed in the eukaryotic cell) may carry a signal peptide, in particular at its N-terminus, e.g., inserted between amino acid positions 1 and 2 of the RNA polymerase. In one embodiment, the T7RNAP may carry a nuclear localization signal (NLS) or a nuclear export signal (NES) each as defined herein above (see section 1). The amino acid sequence of such NES-T7RNAP is set forth in SEQ ID NO:19. In another embodiment, the T7RNAP may not carry such nuclear localization or export tag/signal.

4. dsRNA-Binding Polypeptides

One aspect of the present invention provides eukaryotic cells and methods for preparing a POI as described herein, wherein the eukaryotic cells comprise polynucleotides encoding a ptRNA/pRS pair (wherein the ptRNA can be expressed as ptRNA-ribozyme) and further comprise a polynucleotide encoding a dsRNA-binding polypeptide, and wherein the method for preparing a POI comprises expressing such ptRNA/pRS pair in a eukaryotic cell and expressing a dsRNA-binding polypeptide.

The dsRNA-binding polypeptide used in the present invention is a polypeptide that is capable of binding to a double stranded RNA molecule (dsRNA) having 30 or more, preferably 80 or more base pairs, and wherein the binding is not dependent on the particular nucleotide sequence of the dsRNA. Such binding is conferred by the dsRNA-binding domain of protein kinase R (PKR) which comprises two dsRNA-binding motifs (each containing an α-β-β-β-α fold) flanking a linker region. A preferred dsRNA-binding polypeptide used in the present invention is a polypeptide comprising the amino acid sequence of SEQ ID No 36.

Accordingly, the dsRNA-binding polypeptide used in the present invention comprises, or consists of, an amino acid sequence having at least 80% (such as at least 85%, at least 90%, at least 93%, at least 95%, at least 96%, at least 97%, at least 98%, at least 99% or 100%) identity to the sequence set forth in any one of SEQ ID NOs:37, and 57-59. More preferably, the dsRNA-binding polypeptide used in the present invention comprises, or consists of, an amino acid sequence having at least 80% (such as at least 85%, at least 90%, at least 93%, at least 95%, at least 96%, at least 97%, at least 98%, at least 99% or 100%) identity to the sequence set forth in any one of SEQ ID NOs:38, and 57-59.

Expediently, the dsRNA-binding polypeptide lacks a functional PKR kinase domain and preferably is incapable of phosphorylating eukaryotic initiation factor 2α (eIF-2α).

In the methods of the invention for preparing a POI, the dsRNA-binding polypeptide is expressed at least concomitantly with (i.e. concomitantly with or both prior to and concomitantly with) the expression of the ptRNA/pRS pair.

5. Polynucleotides

The invention also relates to a polynucleotide, or a combination of two or more polynucleotides, comprising:

a nucleotide sequence that encodes an RNA molecule as described herein, wherein said RNA comprises a ptRNA and a ribozyme (ptRNA-ribozyme), and, optionally:

(i) a nucleotide sequence encoding a tetO-binding protein as described herein, or (ii) a nucleotide sequence encoding a pRS as described herein, or (ii) both of (i) and (ii);

and/or (a) nucleotide sequence(s) complementary to said encoding nucleotide sequence(s).

The invention further relates to a polynucleotide, or a combination of two or more polynucleotides, comprising:

a nucleotide sequence that encodes a dsRNA-binding polypeptide as described herein, and:

(i) a nucleotide sequence that encodes a ptRNA or a ptRNA-ribozyme as described herein, or (ii) a nucleotide sequence encoding a pRS as described herein, or (iii) both of (i) and (ii), and, optionally:

a nucleotide sequence encoding a tetO-binding protein as described herein;

and/or (a) nucleotide sequence(s) complementary to said encoding nucleotide sequence(s).

Unless otherwise stated or required by context, the term "polynucleotide", "polynucleotide molecule" or "nucleic acid molecule" as used herein refers to polymers of nucleotides as well as ribonucleotides, i.e. refers to both nucleic acids as well as ribonucleic acids such as single-stranded or double-stranded DNA and RNA molecules, including cDNA and mRNA.

Unless otherwise stated or required by context, the expression "nucleotide sequence encoding [an expression product]" is intended to refer to a sequence directly encoding said expression product and/or to a nucleotide sequence complementary thereto.

The encoding nucleotide sequences which are specified to be comprised by a polynucleotide, or a combination of two or more polynucleotides, of the present invention, can be located on the same polypeptide or can be distributed over two or more different polynucleotides thus resulting in a combination of said different polypeptides (for example each encoding nucleotide sequence can located on a different polypeptide of the combination).

The invention further relates to, in particular recombinant, expression constructs or expression cassettes, containing, under the genetic control of regulatory nucleotide sequences the (specified encoding) nucleotide sequence of the polynucleotide, or combination of polynucleotides, of the invention as described herein.

In one aspect of the invention, the expression cassette of the invention may comprise a nucleotide sequence encoding a ptRNA-ribozyme as described herein. In said aspect of the invention, said expression cassette may optionally further comprise, or may optionally be combined with one or more further expression cassettes comprising:

(i) a nucleotide sequence encoding a tetO-binding protein as described herein, or (ii) a nucleotide sequence encoding a pRS as described herein, or (ii) both of (i) and (ii).

In a further aspect of the invention, the expression cassette of the invention may comprise a nucleotide sequence encoding a dsRNA-binding polypeptide as described herein. In said aspect of the invention, said expression cassette may further comprise, or may optionally be combined with one or more further expression cassettes comprising:

(i) a nucleotide sequence that encodes a ptRNA or a ptRNA-ribozyme as described herein, or (ii) a nucleotide sequence encoding a pRS as described herein, or (iii) both of (i) and (ii).

The invention also relates to, in particular recombinant, vectors, comprising one or more than one of these expression cassettes or combination of expression cassettes (expression vectors).

An expression cassette comprises the nucleotide sequence encoding the expression product is functionally linked to a promoter sequence located 5' (upstream) thereof, and typically a terminator sequence (e.g., a T7 terminator sequence) located 3' (downstream) of said encoding sequence, and optionally further regulatory elements. Examples of such further regulatory elements include, but are not limited to, targeting sequences, enhancers, polyadenylation signals, selectable markers, amplification signals, replication origins and the like. Suitable regulatory sequences are described for example in Goeddel, Gene Expression Technology: Methods in Enzymology 185, Academic Press, San Diego, CA (1990).

A "functional" linkage of elements of polynucleotides (e.g., expression cassettes), such as promotor, encoding sequence, terminator, regulators, etc., means that these elements are arranged such that the encoding sequence can be transcribed and the optional regulatory elements can perform their regulation of said transcription. This can be achieved by a direct linkage of the elements in one and the same nucleic acid molecule. However, such direct linkage is not necessarily required. Genetic control sequences, for example enhancer sequences, can even exert their function on the target sequence from more remote positions or even from other DNA molecules. Arrangements are preferred in which the nucleic acid sequence to be transcribed is positioned downstream (i.e. at the 3'-end of) the promoter sequence, so that the two sequences are joined together covalently. The distance between the promoter sequence and the nucleic acid sequence to be expressed can be smaller than 200 base pairs, or smaller than 100 base pairs or smaller than 50 base pairs.

For expression in a cell, the expression cassette is advantageously inserted into an expression vector. Expression vectors are chosen according to the cell to be used for expression which makes optimal expression of the encoding nucleotide sequences in the cell possible. Vectors are well known by a person skilled in the art and are given for example in "Cloning vectors" (Pouwels P. H. et al., Ed., Elsevier, Amsterdam-New York-Oxford, 1985). Examples of expression vectors include, but are not limited to, plasmids, viral vectors (phages), e.g. SV40, CMV, baculovirus and adenovirus, transposons, IS elements, phasmids, cosmids, and linear or circular DNA. See, e.g., the book "Cloning Vectors" (Eds. Pouwels P. H. et al. Elsevier, Amsterdam-New York-Oxford, 1985, ISBN 0 444 904018). These vectors can be replicated autonomously in the (host) cell or can be replicated chromosomally. Expression vectors comprising one or more than one expression cassette of the present invention represent a further aspect of the invention.

For the expression of a POI in a eukaryotic cell according to the present invention, it is possible, e.g., to introduce a polynucleotide encoding the POI (e.g., an expression vector) into the cell. Alternatively, an existing gene of the cell can be modified so as to comprise selector codons at those amino acid positions where the POI is intended to carry ncAA residues. Methods for introducing (recombinant) polypeptide-encoding nucleic acid molecules into, or for modifying existing genes of, a cell are known in the art.

The term "expression" describes, in the context of the invention, the production of polypeptides encoded by the corresponding nucleotide sequence in a eukaryotic cell. The term "expression" is also used for the production of RNA molecules (ptRNA or ptRNA-ribozyme as described herein) which are encoded by nucleotide sequences in the eukaryotic cell.

The polynucleotides of the invention, including the expression cassettes and expression vectors of the invention can be prepared using common cloning techniques known in the art. Common recombination and cloning techniques are used, as described for example in T. Maniatis, E. F. Fritsch and J. Sambrook, Molecular Cloning: A Laboratory Manual, Cold Spring Harbor Laboratory, Cold Spring Harbor, NY (1989) and in T. J. Silhavy, M. L. Berman and L. W. Enquist, Experiments with Gene Fusions, Cold Spring Harbor Laboratory, Cold Spring Harbor, NY (1984) and in Ausubel, F. M. et al., Current Protocols in Molecular Biology, Greene Publishing Assoc. and Wiley interscience (1987).

The polynucleotides, or combinations of polynucleotides, of the invention, including expression cassettes and expression vectors of the invention, can be isolated, for example by methods known in the art.

An "isolated" polynucleotide or an "isolated" combination of polynucleotides is separated from other polynucleotides that are present in the natural source of the polynucleotide (e.g., the cell), and moreover can be essentially free of other cellular material or culture medium, when it is produced by recombinant techniques, or free of chemical precursors or other chemicals, when it is chemically synthesized.

Polynucleotides according to the invention can be isolated by standard techniques of molecular biology and the sequence information provided according to the invention. For example, cDNA can be isolated from a suitable cDNA-bank, using one of the concretely disclosed complete sequences or a segment thereof as hybridization probe and standard hybridization techniques (as described for example in Sambrook, J., Fritsch, E. F. and Maniatis, T. Molecular Cloning: A Laboratory Manual. 2nd edition, Cold Spring Harbor Laboratory, Cold Spring Harbor Laboratory Press, Cold Spring Harbor, NY, 1989). Moreover, a polynucleotide, comprising one of the disclosed sequences or a segment thereof, can be isolated by polymerase chain reaction, using the oligonucleotide primers that were constructed on the basis of this sequence. The polynucleotide thus amplified can be cloned into a suitable vector and can be characterized by DNA sequence analysis.

6. POIs Having One or More than One ncAA Residue

The present invention provides methods for preparing a POI having one or more than one ncAA residue. The ncAA residues of the POI are encoded by selector codons.

The term "selector codon" as used herein refers to a codon that is recognized (i.e. bound) by the ptRNA in the translation process and is not recognized by endogenous tRNAs of the eukaryotic cell. The term is also used for the corresponding codons in polypeptide-encoding sequences of polynucleotides which are not messenger RNAs (mRNAs), e.g. DNA plasmids. Preferably, the selector codon is a codon of low abundance in naturally occurring eukaryotic cells. Expediently, the anticodon of the ptRNA used in the present invention specifically binds to (hybridizes with) a selector codon within an mRNA and thus incorporates the ncAA residue site-specifically into the growing chain of the polypeptide encoded by said mRNA. The known 64 genetic (triplet) codons code for the 20 canonical amino acid residues and three stop codons. Because only one stop codon is needed for translational termination, the other two can in principle be used to encode non-proteinogenic amino acids. For example, the amber codon, UAG, has been successfully used as a selector codon in in vitro and in vivo translation systems to direct the incorporation of ncAAs. Selector codons utilized in methods of the present invention expand the genetic codon framework of the protein biosynthetic machinery of the translation system used. Specifically, selector codons include, but are not limited to: nonsense codons, such as stop codons, e.g., amber (UAG), ochre (UAA), and opal (UGA) codons; codons consisting of more than three bases (e.g., four base codons); and codons derived from natural or unnatural base pairs. For a given system, a selector codon can also include one of the natural three base codons (i.e. natural triplets), wherein the endogenous translation system does not (or only scarcely) use said natural triplet, e.g., a system that is lacking a tRNA that recognizes the natural triplet or a system wherein the natural triplet is a rare codon.

A recombinant tRNA that alters the reading of an mRNA in a given translation system such that it allows for reading through, e.g., a stop codon, a four base codon, or a rare codon (such as a ptRNA in a eukaryotic cell of the present invention), is termed suppressor tRNA. The suppression efficiency for a stop codon serving as a selector codon (e.g., the amber codon) depends upon the competition between the (aminoacylated) recombinant tRNA (ptRNA) which acts as suppressor tRNA and the release factor (e.g. RF1) which binds to the stop codon and initiates release of the growing polypeptide chain from the ribosome. Suppression efficiency of such stop codon can therefore be increased using a release factor—(e.g. RF1-)deficient strain.

A nucleotide sequence encoding a target polypeptide (also referred to herein as polypeptide of interest or POI) can comprise one or more, e.g., two or more, three or more, etc., codons (e.g. selector codons) which are the reverse complement of the anticodon comprised by the ptRNA. Conventional site-directed mutagenesis can be used to introduce said selector codon(s) at the site of interest into a nucleotide sequence so as to generate a POI-encoding nucleotide sequence.

The abbreviation "ncAA" refers generally to any non-canonical or non-natural amino acid (or amino acid residue) that is not among the 20 naturally occurring "standard" proteinogenic amino acids (R, H, K, D, E, S, T, N, Q, C, G, P, A, V, I, L, M, F, Y, W) and is also not selenocysteine or pyrrolysine. Numerous ncAAs are well known in the art. NcAAs useful in methods and kits of the present invention have been described in the prior art (for review see e.g. Liu et al., Annu Rev Biochem 83:379-408, 2010, Lemke, ChemBioChem 15:1691-1694, 2014).

The term "ncAA" also refers to amino acid analogs, e.g. compounds which differ from amino acids such that the α-amino group is replaced by a hydroxyl group (α-hydroxyl acid) and/or the carboxylic acid function forms an ester. When translationally incorporated into a polypeptide, an α-hydroxyl acid (residue) is coupled through its α-hydroxyl group to carboxylic acid function of the adjacent amino acid (analogue) residue by an ester bond. When ncAAs which are amino acid analogs wherein the carboxylic acid function forms an ester of formula —C(O)—O—R are used for preparing polypeptides in a translation system (such as a eukaryotic cell), it is believed that R is removed in situ, for example enzymatically, in the translation system prior of being incorporated in the POI. Accordingly, R is expediently chosen so as to be compatible with the translation system's ability to convert the ncAA or salt thereof into a form that is recognized and processed by the PylRS of the invention.

Particular preferred ncAAs in the context of the present invention are those which can be post-transitionally further modified. For example, ncAAs may comprise a group (herein referred to as "labeling group") that facilitates reaction with a suitable group (herein referred to as "docking group") of another molecule (herein termed "conjugation partner molecule") so as to covalently attach the conjugation partner molecule to the ncAA. When an ncAA comprising a labeling group is translationally incorporated into a POI, the labeling group becomes part of the POI. Accordingly, a POI prepared according to the method of the present invention can be reacted with one or more than one conjugation partner molecule such that the conjugation partner molecules bind covalently to the (labeling groups of the) non-canonical amino acid (ncAA) residue(s) of the POI. Such conjugation reactions may be used for in situ coupling of POIs within a cell or tissue expressing the POI, or for site-specific conjugation of isolated or partially isolated POIs.

Particular useful choices for combinations of labeling groups and docking groups (of conjugation partner molecules) are those which can react by metal-free click reactions. Such click reactions include strain-promoted inverse-electron-demand Diels-Alder cycloadditions (SPIEDAC; see, e.g., Devaraj et al., Angew Chem Int Ed Engl 2009, 48:7013)) as well as cycloadditions between strained cycloalkynyl groups, or strained cycloalkynyl analog groups having one or more of the ring atoms not bound by the triple bond substituted by amino groups), with azides, nitrile oxides, nitrones and diazocarbonyl reagents (see. e.g., Sanders et al., J Am Chem Soc 2010, 133:949; Agard et al., J Am Chem Soc 2004, 126:15046), for example strain promoted alkyne-azide cycloadditions (SPAAC). Such click reactions allow for ultrafast and biorthogonal covalent site-specific coupling of ncAA labeling groups of POIs with suitable groups of coupling partner molecule.

Pairs of docking and labeling groups which can react via the above-mentioned click reactions are known in the art. Examples of suitable ncAAs comprising docking groups include, but are not limited to, the ncAAs described, e.g., in WO 20121104422 and WO 2015/107064.

Examples of particular suitable pairs of docking groups (comprised by the conjugation partner molecule) and labeling groups (comprised by the ncAA residue(s) of the POI) include but are not limited to:

(a) a docking group comprising (or essentially consisting of) a group selected from an azido group, a nitrile oxide functional group (i.e. a radical of formula, a nitrone functional group or a diazocarbonyl group, combined with a labeling group comprising (or essentially consisting of) an optionally substituted strained alkynyl group (such groups can react covalently in a copper-free strain promoted alkyne-azide cycloaddition (SPAAC));

(b) a docking group comprising (or essentially consisting of) an optionally substituted strained alkynyl group, combined with a labeling group comprising (or essentially consisting of) a group selected from an azido group, a nitrile oxide functional group (i.e. a radical of formula, a nitrone functional group or a diazocarbonyl group (such groups can react covalently in a copper-free strain promoted alkyne-azide cycloaddition (SPAAC));

(c) a docking group comprising (or essentially consisting of) a group selected from optionally substituted strained alkynyl groups, optionally substituted strained alkenyl groups and norbornenyl groups, combined with a labeling group comprising (or essentially consisting of) an optionally substituted tetrazinyl group (such groups can react covalently in a copper-free strain promoted inverse-electron-demand Diels-Alder cycloaddition (SPIEDAC)).

(d) a docking group comprising (or essentially consisting of) an optionally substituted tetrazinyl group, combined with a labeling group comprising (or essentially consisting of) a group selected from optionally substituted strained alkynyl groups, optionally substituted strained alkenyl groups and norbornenyl groups (such groups can react covalently in a copper-free strain promoted inverse-electron-demand Diels-Alder cycloaddition (SPIEDAC)).

Optionally substituted strained alkynyl groups include, but are not limited to, optionally substituted trans-cyclooctenyl groups, such as those described in. Optionally substituted strained alkenyl groups include, but are not limited to, optionally substituted cyclooctynyl groups, such as those described in WO 2012/104422 and WO 2015/107064. Optionally substituted tetrazinyl groups include, but are not limited to, those described in WO 2012/104422 and WO 2015/107064.

An azido group is a radical of formula —$N_3$.

A nitrone functional group is a radical of formula —C($R^x$)=$N^+$($R^y$)—$O^-$, wherein $R^x$ and $R^y$ are organic residues. e.g., residues independently selected from $C_1$-$C_6$-alkyl as described herein.

A diazocarbonyl group is a radical of formula —C(O)—CH=$N_2$.

A nitrile oxide functional group is a radical of formula —C≡$N^+$—$O^-$ or, preferably, of formula —C=$N^+$($R^x$)—O—, wherein $R^x$ is an organic residue, e.g., a residue selected from $C_1$-$C_6$-alkyl as described herein.

"Cyclooctynyl" is an unsaturated cycloaliphatic radical having 8 carbon atoms and one triple bond in the ring structure.

"Trans-cyclooctenyl" is an unsaturated cycloaliphatic radical having 8 carbon atoms and one double bond that is in trans configuration in the ring structure.

"Tetrazinyl" is a 6-membered monocyclic aromatic radical having 4 nitrogen ring atoms and 2 carbon ring atoms.

Unless indicated otherwise, the term "substituted" means that a radical is substituted with 1, 2 or 3, especially 1 or 2, substituent(s). In particular embodiments, these substituents can be selected independently from hydrogen, halogen, $C_1$-$C_4$-alkyl, $(R^aO)_2$P(O)O—$C_1$-$C_4$-alkyl, $(R^bO)_2$P(O)—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, di-($C_1$-$C_4$-alkyl)amino, $C_2$-$C_5$-alkenylamino, N—$C_2$-$C_5$-alkenyl-N—$C_1$-$C_4$-alkyl-amino and di-($C_2$-$C_5$-alkenyl)amino, wherein $R^a$ and $R^b$ $R^a$, $R^b$ are independently hydrogen or $C_2$-$C_5$-alkanoyloxymethyl.

The term halogen denotes in each case a fluorine, bromine, chlorine or iodine radical, in particular a fluorine radical.

$C_1$-$C_4$-Alkyl is a straight-chain or branched alkyl group having from 1 to 4, in particular from 1 to 3 carbon atoms. Examples include methyl and $C_2$-$C_4$-alkyl such as ethyl, n-propyl, iso-propyl, n-butyl, 2-butyl, iso-butyl and tert-butyl.

$C_2$-$C_5$-Alkenyl is a singly unsaturated hydrocarbon radical having 2, 3, 4 or 5 carbon atoms. Examples include vinyl, allyl (2-propen-1-yl), 1-propen-1-yl, 2-propen-2-yl, methallyl (2-methylprop-2-en-1-yl), 1-methylprop-2-en-1-yl, 2-buten-1-yl, 3-buten-1-yl, 2-penten-1-yl, 3-penten-1-yl, 4-penten-1-yl, 1-methylbut-2-en-1-yl and 2-ethylprop-2-en-1-yl.

$C_1$-$C_4$-Alkoxy is a radical of formula R—O—, wherein R is a $C_1$-$C_4$-alkyl group as defined herein.

$C_2$-$C_5$-Alkenoxy is a radical of formula R—O—, wherein R is $C_2$-$C_5$-alkenyl as defined herein.

$C_2$-$C_5$-Alkanoyloxy is a radical of formula R—C(O)—O—, wherein R is $C_1$-$C_4$-alkyl as defined herein.

$C_1$-$C_4$-Alkylaminocarbonyloxy is a radical of formula R—NH—C(O)—O—, wherein R is $C_1$-$C_4$-alkyl as defined herein.

$C_1$-$C_4$-Alkythio is a radical of formula R—S—, wherein R is $C_1$-$C_4$-alkyl as defined herein.

$C_1$-$C_4$-Alkylamino is a radical of formula R—NH—, wherein R is $C_1$-$C_4$-alkyl as defined herein.

Di-($C_1$-$C_4$-alkyl)amino is a radical of formula $R^x$—N($R^y$)—, wherein $R^x$ and $R^y$ are independently $C_1$-$C_4$-alkyl as defined herein.

$C_2$-$C_5$-Alkenylamino is a radical of formula R—NH—, wherein R is $C_2$-$C_5$-alkenyl as defined herein.

N—$C_2$-$C_5$-alkenyl-N—$C_1$-$C_4$-alkyl-amino is a radical of formula $R^x$—N($R^y$)—, wherein $R^x$ is $C_2$-$C_5$-alkenyl as defined herein and $R^y$ is $C_1$-$C_4$-alkyl as defined herein.

Di-($C_2$-$C_5$-alkenyl)amino is a radical of formula $R^x$—N($R^y$)—, wherein $R^x$ and $R^y$ are independently $C_2$-$C_5$-alkenyl as defined herein.

$C_2$-$C_5$-Alkanoyloxymethyl is a radical of formula $R^x$—C(O)—O—$CH_2$—, wherein $R^x$ is $C_1$-$C_4$-alkyl as defined herein.

The ncAAs used in the context of the present invention can be used in the form of their salt. Salts of ncAAs as described herein mean acid or base addition salts, especially addition salts with physiologically tolerated acids or bases. Physiologically tolerated acid addition salts can be formed by treatment of the base form of an ncAA with appropriate organic or inorganic acids. NcAAs containing an acidic proton may be converted into their non-toxic metal or amine addition salt forms by treatment with appropriate organic and inorganic bases. The ncAAs and salts thereof described in the context of the present invention also comprise the hydrates and solvent addition forms thereof, e.g. hydrates, alcoholates and the like.

Physiologically tolerated acids or bases are in particular those which are tolerated by the translation system used for preparation of POI with ncAA residues, e.g. are substantially non-toxic to living eukaryotic cells.

NcAAs, and salts thereof, useful in the context of the present the invention can be prepared by analogy to methods which are well known in the art and are described, e.g., in the various publications cited herein.

The nature of the coupling partner molecule depends on the intended use. For example, the POI may be coupled to a molecule suitable for imaging methods or may be functionalized by coupling to a bioactive molecule. For instance, in addition to the docking group, a coupling partner molecule may comprise a group that selected from, but are not limited to, dyes (e.g. fluorescent, luminescent, or phosphorescent dyes, such as dansyl, coumarin, fluorescein, acridine, rhodamine, silicon-rhodamine, BODIPY, or cyanine dyes), molecules able to emit fluorescence upon contact with a reagent, chromophores (e.g., phytochrome, phycobilin, bilirubin, etc.), radiolabels (e.g. radioactive forms of hydrogen, fluorine, carbon, phosphorous, sulphur, or iodine, such as tritium, $^{18}F$, $^{11}C$, $^{14}C$, $^{32}P$, $^{33}P$, $^{33}S$, $^{35}S$, $^{11}In$, $^{125}I$, $^{123}I$, $^{131}I$, $^{212}B$, $^{90}Y$ or $^{186}Rh$), MRI-sensitive spin labels, affinity tags (e.g. biotin, His-tag, Flag-tag, strep-tag, sugars, lipids, sterols, PEG-linkers, benzylguanines, benzylcytosines, or co-factors), polyethylene glycol groups (e.g., a branched PEG, a linear PEG, PEGs of different molecular weights, etc.), photocrosslinkers (such as p-azidoiodoacetanilide), NMR probes. X-ray probes, pH probes, IR probes, resins, solid supports and bioactive compounds (e.g. synthetic drugs). Suitable bioactive compounds include, but are not limited to, cytotoxic compounds (e.g., cancer chemotherapeutic compounds), antiviral compounds, biological response modifiers (e.g., hormones, chemokines, cytokines, interleukins, etc.), microtubule affecting agents, hormone modulators, and steroidal compounds. Specific examples of useful coupling partner molecules include, but are not limited to, a member of a receptor/ligand pair; a member of an antibody/antigen pair, a member of a lectin/carbohydrate pair, a member of an enzyme/substrate pair; biotin/avidin; biotin/streptavidin and digoxin/antidigoxin.

The ability of certain (labeling groups of) ncAA residues to be coupled covalently in situ to (the docking groups of) conjugation partner molecules, in particular by a click reaction as described herein, can be used for detecting a POI having such ncAA residue(s) within a eukaryotic cell or tissue expressing the POI, and for studying the distribution and fate of the POI. Thus, for example, the method of the present invention for preparing a POI by expression in eukaryotic cells can be combined with super-resolution microscopy (SRM) to detect the POI within the cell or a tissue of such cells. Several SRM methods are known in the art and can be adapted so as to utilize lick chemistry for detecting a POI expressed by a eukaryotic cell of the present invention. Specific examples of such SRM methods include DNA-PAINT (DNA point accumulation for imaging in nanoscale topography; described, e.g., by Jungmann et al., Nat Methods 11:313-318, 2014). dSTORM (direct stochastic optical reconstruction microscopy) and STED (stimulated emission depletion) microscopy.

7. Eukaryotic Cells of the Invention

Eukaryotic cells of the invention can be generated by introducing polynucleotides as described herein, in particular polynucleotide comprising nucleotide sequences encoding a pRS and encoding a ptRNA or ptRNA-ribozyme as described herein. And in one aspect, the polynucleotide(s) introduced into the eukaryotic cell further comprise a nucleotide sequence encoding a dsRNA-binding polypeptide. Optionally, the introduced polynucleotide(s) further comprise nucleotide sequences encoding a tetO binding protein and/or a constitutive RNA polymerase (e.g. a T7RNAP) as described herein. Said nucleotide sequences can be located on the same polynucleotide or distributed over two or more different polynucleotides.

Eukaryotic cells of the present invention can be selected from, but are not limited to, mammalian cells (e.g., human, mouse, rat, cynomolgus monkey cells), avian cells (e.g., chicken cells), insect cells, yeast cells and plant cells. The eukaryotic cells of the invention may be present as individual cells or may be part of a tissue (e.g. a cell in a (cultured) tissue, organ or entire organism).

A POI comprising one or more than one non-canonical amino acid (ncAA) residue in its amino acid sequence can be prepared according to the present invention using a eukaryotic cell, in particular a eukaryotic cell of the present invention. The eukaryotic cell expresses a pRS and a ptRNA which for a pair in that the pRS is capable of acylating the ptRNA. In particular embodiments, the ptRNA is expressed in the form of a ptRNA-ribozyme as described herein. The eukaryotic cell further expresses the POI in the presence of one or more than one ncAA or salt thereof corresponding to the one or more than one ncAA residue of the POI. To this end the eukaryotic cell comprises polynucleotides encoding the to be expressed pRS, ptRNA and POI, and further comprises, e.g. is fed with, said ncAA or salt thereof. Where expression of one of said pRS, ptRNA and/or POI is under the control of a TRE, the eukaryotic cell expediently further expresses a tetO-binding protein that is chosen to match the respective TRE used as described herein, and the eukaryotic cell is contacted with, e.g. cultured in a medium containing, tetracycline, doxycycline, or a functional analogue thereof as described herein.

Recombinant expression in eukaryotic cells, including the induction of TRE-controlled expression, is a standard tool in the art. The skilled person is therefore well able to choose conditions of culturing the eukaryotic cells so as to allow for the (recombinant) expression of expression products of interest (here: at least ptRNA, pRS and POI). Depending on the type of cell, a liquid medium can be used for culturing. Culture can be batchwise, semi-batchwise or continuous. Nutrients can be present at the beginning of the culturing or can be supplied later, semi-continuously or continuously.

For producing a POI (target polypeptide) according to a method of the present invention, the eukaryotic cell is cultured under suitable conditions, preferably in the presence of (e.g., in a culture medium containing) the ncAA or salt thereof, for a time suitable to allow translation at a ribosome of the cell. Depending on the polynucleotide(s) encoding the POI (and optionally the other elements pRS, ptRNA, etc.), it may be required to induce expression by adding a compound inducing transcription, such as, e.g., arabinose, isopropyl β-D-thiogalactoside (IPTG) or, in case of TRE-controlled expression, tetracycline, doxycycline, or a functional analog thereof. mRNA that encodes the POI (and comprises one or more than codon that is the reverse complement of the anticodon comprised by the ptRNA) is bound by the ribosome. Then, the POI is formed by stepwise attachment of amino acids and ncAAs at positions encoded by codons which are recognized (bound) by respective aminoacyl tRNAs. Thus, the ncAA(s) is/are incorporated in the POI at the position(s) encoded by the (selector) codon(s) that is/are the reverse complement of the anticodon comprised by the ptRNA.

The eukaryotic cells used for preparing a POI comprising one or more than one non-canonical amino acid (ncAA) residue as described herein can be prepared by introducing polynucleotides encoding the pRS, the ptRNA, the POI and/or further elements, such as a dsRNA-binding polypeptide and/or a tetO-binding polypeptide as described herein, into a eukaryotic (host) cell. Said nucleotide sequences can be located on separate nucleic acid molecules (vectors) or on the same nucleic acid molecule (e.g., vector), in any combination, and can be introduced into the cell in combination or sequentially.

Preferably common cloning and transfection techniques, known by a person skilled in the art, are used, for example co-precipitation, protoplast fusion, electroporation, virus-mediated gene delivery, lipofection, microinjection or others, for introducing the stated nucleic acid molecules in the respective cell. Suitable techniques are described for example in Current Protocols in Molecular Biology, F. Ausubel et al., Ed., Wiley Interscience, New York 1997, or Sambrook et al. Molecular Cloning: A Laboratory Manual. $2^{nd}$ edition, Cold Spring Harbor Laboratory, Cold Spring Harbor Laboratory Press. Cold Spring Harbor, NY, 1989.

After translation, the POI prepared according to the present invention may optionally be recovered from the eukaryotic cell or, if secreted, from the culture medium, and purified, either partially or substantially to homogeneity, according to procedures generally known in the art. For this purpose, the POI can be recovered and purified, either partially or substantially to homogeneity, according to procedures known to and used by those of skill in the art. Unless the target polypeptide is secreted into the culture medium, recovery usually requires cell disruption. Methods of cell disruption are well known in the art and include physical disruption. e.g., by (ultrasound) sonication, liquid-sheer disruption (e.g., via French press), mechanical methods (such as those utilizing blenders or grinders) or freeze-thaw cycling, as well as chemical lysis using agents which disrupt lipid-lipid, protein-protein and/or protein-lipid interactions (such as detergents), and combinations of physical disruption techniques and chemical lysis. Standard procedures for purifying polypeptides from cell lysates or culture media are also well known in the art and include, e.g., ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. Antibodies made against the polypeptides of the invention can be used as purification reagents, i.e. for affinity-based purification of the polypeptides. A variety of purification/protein folding methods are well known in the art, including, e.g., those set forth in Scopes, Protein Purification, Springer, Berlin (1993); and Deutscher, Methods in Enzymology Vol. 182: Guide to Protein Purification, Academic Press (1990); and the references cited therein.

As noted, those of skill in the art will recognize that, after synthesis, expression and/or purification, polypeptides can possess a conformation different from the desired conformations of the relevant polypeptides. For example, overexpressed polypeptides as well as polypeptides produced by prokaryotic systems often are optimized by exposure to chaotropic agents to achieve proper folding. During purification from, e.g., lysates derived from *E. coli*, the expressed polypeptide is optionally denatured and then renatured. This is accomplished, e.g., by solubilizing the proteins in a chaotropic agent such as guanidine HCl. In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are well known to those of skill in the art. Polypeptides can be refolded in a redox buffer containing, e.g., oxidized glutathione and L-arginine.

The POIs expressed by a method of the present invention can be purified by known techniques, such as, e.g., molecular sieve chromatography (gel filtration), such as Q-sepharose chromatography, ion exchange chromatography and hydrophobic chromatography, and other common protein purification techniques such as ultrafiltration, crystallization, salting-out, dialysis and native gel electrophoresis. Suitable methods are described, for example, in Cooper, T. G., Biochemische Arbeitsmethoden [Biochemical processes], Verlag Walter de Gruyter, Berlin, New York or in Scopes, R., Protein Purification, Springer Verlag, New York. Heidelberg. Berlin.

For isolating a POI, it can be advantageous to link the POI with a tag that can serve for easier purification. This can be achieved by introducing a corresponding tag-encoding sequence into the POI-encoding nucleotide sequence. Suitable tags for protein purification are well known in the art and include, e.g., histidine tags (e.g., $His_6$ tag) and epitopes that can be recognized as antigens of antibodies (described for example in Harlow, E. and Lane, D., 1988, Antibodies: A Laboratory Manual. Cold Spring Harbor (N.Y.) Press). These tags can serve for attaching the proteins to a solid carrier, for example a polymer matrix, which can for example be used as packing in a chromatography column, or can be used on a microtiter plate or on some other carrier.

A tag linked to a POI can also serve for detecting the POI. Tags for protein detection are well known in the art and include, e.g., fluorescent dyes, enzyme markers, which form a detectable reaction product after reaction with a substrate, and others.

Also described are POIs produced by the methods of the invention. Such POIs can be prepared by a method of the invention that makes use of a eukaryotic cell as described herein.

8. Kits

The present invention also provides kits for preparing a POI having one or more than one non-canonical amino acid (ncAA) residue in its amino acid sequence. The kit of the invention comprises one or more than one ncAA, or salt thereof, corresponding to the one or more than one ncAA residue of the POI. The kit may further comprise a polynucleotide, or combination of polynucleotides, of the present invention, and/or a polynucleotide encoding a dsRNA-binding polypeptide as described herein and/or an eukaryotic cell of the present invention. The kit may additionally comprise one or more reporter constructs encoding an easily detectable (e.g. fluorescent) reporter polypeptide. The report construct comprises at least one selector codon that is located in the encoding sequence of the report polypeptide such that successful incorporation of an amino acid or ncAA at the position encoded by said selector codon(s) allows for the translational synthesis of the reporter polypeptide.

The kits of the present invention can be used in methods of the invention for preparing ncAA-residue containing POIs as described herein.

9. Particular Embodiments

The present invention refers to the following particular embodiments:

1. According to a first embodiment the invention relates to an eukaryotic cell comprising:
   - (a) a polynucleotide encoding a prokaryotic aminoacyl tRNA synthetase (pRS),
   - (b) a polynucleotide encoding a prokaryotic tRNA (ptRNA) and one or more than one ribozyme, wherein the pRS is capable of acylating the ptRNA, and wherein the sequences encoding the ptRNA and the ribozyme(s) are linked such that transcription produces an RNA molecule comprising both the ptRNA and the ribozyme(s) (ptRNA-ribozyme).

A second embodiment relates to an eukaryotic cell of embodiment one, wherein the ribozyme is selected from a hammerhead ribozyme, a hairpin ribozyme, a Varkud satellite ribozyme, a glucosamine-6-phosphate synthetase riboswitch and a hepatitis delta virus (HDV) ribozyme.

A third embodiment relates to an eukaryotic cell of embodiment one or embodiment two, wherein the ribozyme is a HDV ribozyme which, in the ptRNA-ribozyme, is directly linked to the 3' end of the ptRNA.

A fourth embodiment relates to an eukaryotic cell of any one of embodiments one to three, wherein:
- (i) transcriptional synthesis of the ptRNA-ribozyme is controlled by a tetracycline-responsive promoter element (TRE), or
- (ii) the ptRNA-ribozyme is transcriptionally synthesized by an RNA polymerase, wherein expression of said RNA polymerase is controlled by a TRE.

A fifth embodiment relates to an eukaryotic cell of any one of embodiments one to four, wherein the transcription of the pRS-encoding sequence is controlled by a tetracycline-responsive promoter element (TRE).

A sixth embodiment relates to an eukaryotic cell of embodiment four or embodiment five, further comprising a polynucleotide encoding a protein which binds to a tetracycline operator (tetO) sequence (tetO-binding protein), wherein the tetO-binding protein is selected from the group consisting of
- (i) a tetracycline repressor (tetR).
- (ii) a tetracycline-controlled transcriptional activator (tTA), and
- (iii) a reverse tTA (rtTA).

A seventh embodiment relates to an eukaryotic cell of any one of embodiments one to six, wherein:
- (i) transcriptional synthesis of the ptRNA-ribozyme is controlled by a T7 promoter, and/or
- (ii) transcription of the pRS-encoding sequence is controlled by a T7 promoter, and wherein the eukaryotic cell further comprises
- (c) a polynucleotide encoding a T7 RNA polymerase (T7RNAP).

An eighth embodiment relates to an eukaryotic cell of embodiment seven, wherein expression of the T7RNAP is controlled by a TRE.

A ninth embodiment relates to an eukaryotic cell of embodiment seven or embodiment eight, wherein the T7RNAP carries
- (i) a nuclear localization signal (NLS), or
- (ii) a nuclear export signal (NES), or
- (iii) none of NES and NLS.

A tenth embodiment relates to an eukaryotic cell of any one of embodiments one to nine further comprising a polynucleotide encoding a dsRNA-binding polypeptide as defined in any one of following embodiments eleven to thirteen.

An eleventh embodiment relates to an eukaryotic cell comprising:
- (a) a polynucleotide encoding a prokaryotic aminoacyl tRNA synthetase (pRS),
- (b) a polynucleotide encoding a prokaryotic tRNA (ptRNA), and
- (c) a polynucleotide encoding a polypeptide that is capable of binding to double-stranded RNA (dsRNA-binding polypeptide) and comprises an amino acid sequence having at least 80%, 85%, 90%, 91%, 92%, 93%, 94%, 95%, 96%, 97%, 98%, or 99% identity to the sequence set forth in any one of SEQ ID NOs:37, and 57-59.

A twelfth embodiment relates to an eukaryotic cell of embodiment eleven, wherein the amino acid sequence comprised by the dsRNA-binding polypeptide has at least 80%, 85%, 90%, 91%, 92%, 93%, 94%, 95%, 96%, 97%, 98%, or 99% identity to the sequence set forth in SEQ ID NO:38.

A thirteenth embodiment relates to an eukaryotic cell of embodiment eleven or embodiment twelve, wherein the dsRNA-binding polypeptide is incapable of phosphorylating eukaryotic initiation factor 2α (eIF-2α).

A fourteenth embodiment relates to an eukaryotic cell of any one of embodiments eleven to thirteen, wherein:

(i) transcriptional synthesis of the ptRNA is controlled by a tetracycline-responsive promoter element (TRE), or (ii) the ptRNA is transcriptionally synthesized by an RNA polymerase, wherein expression of said RNA polymerase is controlled by a TRE.

A fifteenth embodiment relates to an eukaryotic cell of any one of embodiments eleven to fourteen, wherein:

(i) transcription of the pRS-encoding sequence is controlled by a tetracycline-responsive promoter element (TRE), or (ii) transcription of the pRS-encoding sequence is catalyzed by an RNA polymerase, wherein the expression of said RNA polymerase is controlled by a TRE.

A sixteenth embodiment relates to an eukaryotic cell of embodiment fourteen or embodiment fifteen, further comprising a polynucleotide encoding a protein which binds to a tetracycline operator (tetO) sequence (tetO-binding protein), wherein the tetO-binding protein is selected from the group consisting of:

(i) a tetracycline repressor (tetR), (ii) a tetracycline-controlled transcriptional activator (tTA), and (iii) a reverse tTA (rtTA).

A seventeenth embodiment relates to an eukaryotic cell of any one of embodiments eleven to sixteen, wherein:

(i) transcriptional synthesis of the ptRNA is controlled by a T7 promoter, or (ii) transcription of the pRS-encoding sequence is controlled by a T7 promoter, or (iii) both of (i) and (ii);

and wherein the eukaryotic cell further comprises (c) a polynucleotide encoding a T7 RNA polymerase (T7RNAP).

An eighteenth embodiment relates to an eukaryotic cell of embodiment seventeen, wherein expression of the T7RNAP is controlled by a TRE.

A nineteenth embodiment relates to an eukaryotic cell of embodiment seventeen of embodiment eighteen, wherein the T7RNAP carries (i) a nuclear localization signal (NLS), or (ii) a nuclear export signal (NES), or (iii) none of NES and NLS.

A twentieth embodiment relates to an eukaryotic cell of any one of embodiments eleven to thirteen, wherein the eukaryotic cell is a cell of any one of embodiments one to nine.

A twenty-first embodiment relates to a polynucleotide encoding an RNA molecule comprising a ptRNA and one or more than one ribozyme (ptRNA-ribozyme) as defined in any one of embodiments one to four and seven; wherein, more particularly, a) the ribozyme is a HDV ribozyme which, in the ptRNA-ribozyme, is directly linked to the 3' end of the ptRNA; or b) the ptRNA is derived from a *Methanosarcina* species, in particular a pyrrolysyl tRNA of *M. mazei*; or c) wherein a ptRNA molecule is encoded missing the 3'-terminal aminoacyl acceptor stem motif CCA; or d) the ptRNA is encoded by the following nucleotide sequence (SEQ ID NO:60) ggaaacctgatcatgtagatcgaatggactxxxaatccgttcagccgggttagattcccggggtttccg wherein xxx encodes an anticodon;

A twenty-second embodiment relates to a polynucleotide, or combination of two or more polynucleotides, comprising a nucleotide sequence encoding an RNA molecule comprising a ptRNA and one or more than one ribozyme (ptRNA-ribozyme) as defined in any one of embodiments one to four and seven, and:

(i) a nucleotide sequence encoding a tetO-binding protein as defined in embodiment six, or (ii) a nucleotide sequence encoding a pRS as defined in any one of embodiments one, five and seven, or (ii) both of (i) and (ii).

A twenty-third embodiment relates to a method for preparing a polypeptide of interest (POI) having one or more than one non-canonical amino acid (ncAA) residue in its amino acid sequence, wherein the method comprises:

(a) expressing, in a eukaryotic cell:

a prokaryotic aminoacyl tRNA synthetase (pRS) and an RNA molecule comprising a prokaryotic tRNA (ptRNA) and one or more than one ribozyme (ptRNA-ribozyme);

and concomitantly or sequentially (b) expressing the POI in the eukaryotic cell in the presence of one or more than one ncAA or salt thereof corresponding to the one or more than one ncAA residue of the POI; and (c) optionally recovering the expressed POI;

wherein the pRS is capable of acylating the ptRNA with the ncAA or the salt thereof, wherein the POI is encoded by a nucleotide sequence that comprises one or more than one selector codon encoding the one or more than one ncAA residue, and wherein the selector codon is the reverse complement of the anticodon of the ptRNA.

A twenty-fourth embodiment relates to a method of embodiment twenty-three, wherein the ribozyme is selected from a hammerhead ribozyme, a hairpin ribozyme, a Varkud satellite ribozyme, a glucosamine-6-phosphate synthetase riboswitch and a hepatitis delta virus (HDV) ribozyme.

A twenty-fifth embodiment relates to a method of embodiment twenty-three or embodiment twenty-four, wherein the ribozyme is a HDV ribozyme which, in the ptRNA-ribozyme, is directly linked to the 3' end of the ptRNA.

T7-Controlled in General

A twenty-sixth embodiment relates to a method of any one of embodiments twenty-three to twenty-five, wherein the transcriptional synthesis of the ptRNA-ribozyme is controlled by a T7 promoter, and wherein the method further comprises expressing a T7 RNA polymerase (T7RNAP) in the eukaryotic cell prior to or concomitantly with the thereby controlled expression of the ptRNA-ribozyme (i) or the pRS (ii) or both (iii), respectively.

T-REx System (tetR, +tet/dox)

A twenty-seventh embodiment relates to a method of any one of embodiments twenty-three to twenty-five, wherein:

(i) transcriptional synthesis of the ptRNA-ribozyme is controlled by a tetracycline-responsive promoter element (TRE), or (ii) the ptRNA-ribozyme is transcriptionally synthesized by an RNA polymerase, wherein the expression of said RNA polymerase is controlled by a TRE;

wherein the method further comprises expressing a tetracycline repressor (tetR) in the eukaryotic cell at least prior to the expression of the ptRNA-ribozyme, and wherein expression of the ptRNA-ribozyme involves contacting the eukaryotic cell with tetracycline, doxycycline, or a functional analogue thereof, thereby inducing transcriptional synthesis of the ptRNA-ribozyme.

A twenty-eighth embodiment relates to a method of any one of embodiments twenty-three to twenty-five and twenty-seven, wherein:

(i) transcription of the pRS-encoding sequence is controlled by a tetracycline-responsive promoter element (TRE), or (ii) transcription of the pRS-encoding sequence is catalyzed by an RNA polymerase, wherein the expression of said RNA polymerase is controlled by a TRE;

wherein the method further comprises expressing a tetracycline repressor (tetR) in the eukaryotic cell at least prior to the expression of the pRS; and wherein expression of the pRS involves contacting the eukaryotic cell with tetracycline, doxycycline, or afunctional analogue thereof, thereby inducing transcription of the pRS-encoding sequence.

A twenty-ninth embodiment relates to a method of embodiment twenty-seven or embodiment twenty-eight, wherein:

(i) transcriptional synthesis of the ptRNA-ribozyme is controlled by a T7 promoter, or (ii) transcription of the pRS-encoding sequence is controlled by a T7 promoter, or (iii) both of (i) and (ii);

and wherein the method further comprises:

expressing a T7 RNA polymerase (T7RNAP) in the eukaryotic cell prior to or concomitantly with the thereby controlled expression of the ptRNA-ribozyme (i) or the pRS (ii) or both (iii), respectively, wherein expression of the T7RNAP is controlled by a TRE, and expressing a tetR in the eukaryotic cell at least concomitantly with the expression of the T7RNAP;

wherein expression of the T7RNAP involves contacting the eukaryotic cell with tetracycline, doxycycline, or a functional analogue thereof, thereby inducing transcription of the T7RNAP-encoding sequence.

Tet-Off System (TA, −tet/dox)

A thirtieth embodiment relates to a method of any one of embodiments twenty-three to twenty-five, wherein:

(i) transcriptional synthesis of the ptRNA-ribozyme is controlled by a tetracycline-responsive promoter element (TRE), or (ii) the ptRNA-ribozyme is transcriptionally synthesized by an RNA polymerase, wherein expression of said RNA polymerase is controlled by a TRE;

wherein the method further comprises:

(1) expressing a tetracycline-controlled transcriptional activator (tTA) in the eukaryotic cell prior to and concomitantly with the expression of the ptRNA-ribozyme, and (2) keeping the eukaryotic cell prior to the expression of the ptRNA-ribozyme in contact with tetracycline, doxycycline, or a functional analogue thereof, thereby suppressing the transcriptional synthesis of the ptRNA-ribozyme, and then reducing the concentration of, or preferably removing, said tetracycline, doxycycline, or functional analogue thereof so as to induce transcriptional synthesis of the ptRNA-ribozyme.

A thirty-first embodiment relates to a method of any one of embodiments twenty-three to twenty-five and thirty, wherein:

(i) transcription of the pRS-encoding sequence is controlled by a TRE, or (ii) transcription of the pRS-encoding sequence is catalyzed by an RNA polymerase, wherein the expression of said RNA polymerase is controlled by a TRE;

wherein the method further comprises:

(1) expressing a tetracycline-controlled transcriptional activator (tTA) in the eukaryotic cell prior to and concomitantly with the expression of the pRS, and (2) keeping the eukaryotic cell prior to the expression of the pRS in contact with tetracycline, doxycycline, or a functional analogue thereof, thereby suppressing transcription of the pRS-encoding sequence, and then reducing the concentration of, or preferably removing, said tetracycline, doxycycline, or functional analogue thereof so as to induce transcription of the pRS-encoding sequence.

A thirty-second embodiment relates to a method of embodiment thirty or embodiment thirty-one, wherein:

(i) transcriptional synthesis of the ptRNA-ribozyme is controlled by a T7 promoter, or (ii) transcription of the pRS-encoding sequence is controlled by a T7 promoter, or (iii) both of (i) and (ii);

wherein the method further comprises:

(3) expressing a T7 RNA polymerase (T7RNAP) in the eukaryotic cell prior to or concomitantly with the thereby controlled expression of the ptRNA-ribozyme (i) or the pRS (ii) or both (iii), respectively, wherein expression of the T7RNAP is controlled by a TRE, (4) expressing a tTA in the eukaryotic cell prior to and concomitantly with the expression of the T7RNAP, and (5) keeping the eukaryotic cell prior to the expression of the T7RNAP in contact with tetracycline, doxycycline, or a functional analogue thereof, thereby suppressing transcription of the T7RNAP-encoding sequence, and then reducing the concentration of, or preferably removing, said tetracycline, doxycycline, or functional analogue thereof so as to induce transcription of the T7RNAP-encoding sequence.

Tet-On system (rtTA, +dox)

A thirty-third embodiment relates to a method of any one of embodiments twenty-three to twenty-five, wherein:

(i) transcriptional synthesis of the ptRNA-ribozyme is controlled by a tetracycline-responsive promoter element (TRE), or (ii) the ptRNA-ribozyme is transcriptionally synthesized by an RNA polymerase, wherein the expression of said RNA polymerase is controlled by a TRE;

wherein the method further comprises expressing a reverse tTA (rtTA) in the eukaryotic cell at least concomitantly with the expression of the ptRNA, and wherein expression of the ptRNA-ribozyme involves contacting the eukaryotic cell with doxycycline, or a functional analogue thereof, thereby inducing transcriptional synthesis of the ptRNA-ribozyme.

A thirty-fourth embodiment relates to a method of any one of embodiments twenty-three to twenty-five and thirty-three, wherein:

(i) transcription of the pRS-encoding sequence is controlled by a tetracycline-responsive promoter element (TRE), or (ii) transcription of the pRS-encoding sequence is catalyzed by an RNA polymerase, wherein the expression of said RNA polymerase is controlled by a TRE;

wherein the method further comprises expressing a reverse tTA (rtTA) in the eukaryotic cell at least concomitantly with the expression of the pRS; and wherein expression of the pRS involves contacting the eukaryotic cell with doxycycline, or a functional analogue thereof, thereby inducing transcription of the pRS-encoding sequence.

A thirty-fifth embodiment relates to a method of embodiment thirty-three or embodiment thirty-four, wherein:
(i) transcriptional synthesis of the ptRNA-ribozyme is controlled by a T7 promoter, or
(ii) transcription of the pRS-encoding sequence is controlled by a T7 promoter, or
(iii) both of (i) and (ii);
and wherein the method further comprises:
expressing a T7 RNA polymerase (17RNAP) in the eukaryotic cell prior to or concomitantly with the thereby controlled expression of the ptRNA-ribozyme (i) or the pRS (ii) or both (iii), respectively, wherein expression of the T7RNAP is controlled by a TRE, and
expressing a rtTA in the eukaryotic cell at least concomitantly with the expression of the T7RNAP;
wherein expression of the T7RNAP involves contacting the eukaryotic cell with doxycycline, or a functional analogue thereof, thereby inducing transcription of the T7RNAP-encoding sequence.

A thirty-sixth embodiment relates to a method of any one of embodiments twenty-three to twenty-five further comprising:
expressing, in the eukaryotic cell, a dsRNA-binding polypeptide as defined in any one of embodiments eleven to thirteen.

A thirty-seventh embodiment relates to a method for preparing a polypeptide of interest (POI) having one or more than one non-canonical amino acid (ncAA) residue in its amino acid sequence, wherein the method comprises:
(a) expressing, in a eukaryotic cell:
a prokaryotic aminoacyl tRNA synthetase (pRS).
a prokaryotic tRNA (ptRNA) and
a polypeptide capable of binding to double-stranded RNA (dsRNA-binding polypeptide);
and concomitantly or sequentially
(b) expressing the POI in the eukaryotic cell in the presence of one or more than one ncAA or salt thereof corresponding to the one or more than one ncAA residue of the POI; and
(c) optionally recovering the expressed POI;
wherein the pRS is capable of acylating the ptRNA with the ncAA or the salt thereof,
wherein the dsRNA-binding polypeptide comprises an amino acid sequence having at least 80%, 85%, 90%, 91%, 92%, 93%, 94%, 95%, 96%, 97%, 98%, or 99% identity to the sequence set forth in any one of SEQ ID NOs:37, and 57-59;
wherein the POI is encoded by a nucleotide sequence that comprises one or more than one selector codon encoding the one or more than one ncAA residue, and
wherein the selector codon is the reverse complement of the anticodon of the ptRNA.

A thirty-eighth embodiment relates to a method of embodiment thirty-seven, wherein the amino acid sequence comprised by the dsRNA-binding polypeptide has at least 80%, 85%, 90%, 91%, 92%, 93%, 94%, 95%, 96%, 97%, 98%, or 99% identity to the sequence set forth in SEQ ID NO:38.

A thirty-ninth embodiment relates to a method of embodiment thirty-seven or embodiment thirty-eight, wherein the dsRNA-binding polypeptide is incapable of phosphorylating eukaryotic initiation factor 2α (eIF-2α).

T7-Controlled in General

A fortieth embodiment relates to a method of any one of embodiments thirty-seven to thirty-nine, wherein:
(i) transcriptional synthesis of the ptRNA is controlled by a T7 promoter, or
(ii) transcription of the pRS-encoding sequence is controlled by a T7 promoter, or
(iii) both of (i) and (ii);
wherein the method further comprises expressing a T7 RNA polymerase (T7RNAP) in the eukaryotic cell prior to or concomitantly with the thereby controlled expression of the ptRNA (i) or the pRS (ii) or both (iii), respectively.

T-REx System (tetR, +tet/dox)

A forty-first embodiment relates to a method of any one of embodiments thirty-seven to thirty-nine, wherein:
(i) transcriptional synthesis of the ptRNA is controlled by a tetracycline-responsive promoter element (TRE), or
(ii) the ptRNA is transcriptionally synthesized by an RNA polymerase, wherein the expression of said RNA polymerase is controlled by a TRE;
wherein the method further comprises expressing a tetracycline repressor (tetR) in the eukaryotic cell at least prior to the expression of the ptRNA, and
wherein expression of the ptRNA involves contacting the eukaryotic cell with tetracycline, doxycycline, or a functional analogue thereof, thereby inducing transcriptional synthesis of the ptRNA.

A forty-second embodiment relates to a method of any one of embodiments thirty-seven to thirty-nine and forty-one, wherein:
(i) transcription of the pRS-encoding sequence is controlled by a tetracycline-responsive promoter element (TRE), or
(ii) transcription of the pRS-encoding sequence is catalyzed by an RNA polymerase, wherein the expression of said RNA polymerase is controlled by a TRE;
wherein the method further comprises expressing a tetracycline repressor (tetR) in the eukaryotic cell at least prior to the expression of the pRS; and
wherein expression of the pRS involves contacting the eukaryotic cell with tetracycline, doxycycline, or a functional analogue thereof, thereby inducing transcription of the pRS-encoding sequence.

A forty-third embodiment relates to a method of embodiment forty-one or embodiment forty-two, wherein:
(i) transcriptional synthesis of the ptRNA is controlled by a T7 promoter, or
(ii) transcription of the pRS-encoding sequence is controlled by a T7 promoter, or
(iii) both of (i) and (ii);
and wherein the method further comprises:
expressing a T7 RNA polymerase (T7RNAP) in the eukaryotic cell prior to or concomitantly with the thereby controlled expression of the ptRNA (i) or the pRS (ii) or both (iii), respectively, wherein expression of the T7RNAP is controlled by a TRE, and
expressing a tetR in the eukaryotic cell at least concomitantly with the expression of the T7RNAP;
wherein expression of the T7RNAP involves contacting the eukaryotic cell with tetracycline, doxycycline, or a functional analogue thereof, thereby inducing transcription of the T7RNAP-encoding sequence.

Tet-Off System (tTA, −tet/dox)

A forty-fourth embodiment relates to a method of any one of embodiments thirty-seven to thirty-nine, wherein:

(i) transcriptional synthesis of the ptRNA is controlled by a tetracycline-responsive promoter element (TRE), or
(ii) the ptRNA is transcriptionally synthesized by an RNA polymerase, wherein expression of said RNA polymerase is controlled by a TRE;
wherein the method further comprises:
(1) expressing a tetracycline-controlled transcriptional activator (tTA) in the eukaryotic cell prior to and concomitantly with the expression of the ptRNA, and
(2) keeping the eukaryotic cell prior to the expression of the ptRNA in contact with tetracycline, doxycycline, or a functional analogue thereof, thereby suppressing the transcriptional synthesis of the ptRNA, and then reducing the concentration of, or preferably removing, said tetracycline, doxycycline, or functional analogue thereof so as to induce transcriptional synthesis of the ptRNA.

A forty-fifth embodiment relates to a method of any one of embodiments thirty-seven to thirty-nine and forty-four, wherein:
(i) transcription of the pRS-encoding sequence is controlled by a TRE, or
(ii) transcription of the pRS-encoding sequence is catalyzed by an RNA polymerase, wherein the expression of said RNA polymerase is controlled by a TRE;
wherein the method further comprises:
(1) expressing a tetracycline-controlled transcriptional activator (tTA) in the eukaryotic cell prior to and concomitantly with the expression of the pRS, and
(2) keeping the eukaryotic cell prior to the expression of the pRS in contact with tetracycline, doxycycline, or a functional analogue thereof, thereby suppressing transcription of the pRS-encoding sequence, and then reducing the concentration of, or preferably removing, said tetracycline, doxycycline, or functional analogue thereof so as to induce transcription of the pRS-encoding sequence.

A forty-sixth embodiment relates to a method of embodiment forty-four or embodiment forty-five, wherein:
(i) transcriptional synthesis of the ptRNA is controlled by a T7 promoter, or
(ii) transcription of the pRS-encoding sequence is controlled by a T7 promoter, or
(iii) both of (i) and (ii);
wherein the method further comprises:
(3) expressing a T7 RNA polymerase (T7RNAP) in the eukaryotic cell prior to or concomitantly with the thereby controlled expression of the ptRNA (i) or the pRS (ii) or both (iii), respectively,
wherein expression of the T7RNAP is controlled by a TRE,
(4) expressing a tTA in the eukaryotic cell prior to and concomitantly with the expression of the T7RNAP, and
(5) keeping the eukaryotic cell prior to the expression of the T7RNAP in contact with tetracycline, doxycycline, or afunctional analogue thereof, thereby suppressing transcription of the T7RNAP-encoding sequence, and then reducing the concentration of, or preferably removing, said tetracycline, doxycycline, or functional analogue thereof so as to induce transcription of the T7RNAP-encoding sequence.

Tet-On System (rtTA, +dox)

A forty-seventh embodiment of a method of any one of embodiments thirty-seven to thirty-nine, wherein:
(i) transcriptional synthesis of the ptRNA is controlled by a tetracycline-responsive promoter element (TRE), or
(ii) the ptRNA is transcriptionally synthesized by an RNA polymerase, wherein the expression of said RNA polymerase is controlled by a TRE;
wherein the method further comprises expressing a reverse tTA (rtTA) in the eukaryotic cell at least concomitantly with the expression of the ptRNA, and
wherein expression of the ptRNA involves contacting the eukaryotic cell with doxycycline, or a functional analogue thereof, thereby inducing transcriptional synthesis of the ptRNA.

A forty-eighth embodiment of a method of any one of embodiments thirty-seven to thirty-nine and forty-seven, wherein:
(i) transcription of the pRS-encoding sequence is controlled by a tetracycline-responsive promoter element (TRE), or
(ii) transcription of the pRS-encoding sequence is catalyzed by an RNA polymerase, wherein the expression of said RNA polymerase is controlled by a TRE;
wherein the method further comprises expressing a reverse tTA (rtTA) in the eukaryotic cell at least concomitantly with the expression of the pRS; and
wherein expression of the pRS involves contacting the eukaryotic cell with doxycycline, or a functional analogue thereof, thereby inducing transcription of the pRS-encoding sequence.

A forty-ninth embodiment relates to a method of embodiment forty-seven or embodiment forty-eight, wherein:
(i) transcriptional synthesis of the ptRNA is controlled by a T7 promoter, or
(ii) transcription of the pRS-encoding sequence is controlled by a T7 promoter, or
(iii) both of (i) and (ii);
and wherein the method further comprises:
expressing a T7 RNA polymerase (T7RNAP) in the eukaryotic cell prior to or concomitantly with the thereby controlled expression of the ptRNA (i) or the pRS (ii) or both (iii), respectively, wherein expression of the T7RNAP is controlled by a TRE, and
expressing a rtTA in the eukaryotic cell at least concomitantly with the expression of the T7RNAP;
wherein expression of the T7RNAP involves contacting the eukaryotic cell with doxycycline, or a functional analogue thereof, thereby inducing transcription of the T7RNAP-encoding sequence.

A fiftieth embodiment relates to a method of any one of embodiments thirty-seven to forty-nine, wherein the ptRNA is expressed a part of an RNA molecule further comprising one or more than one ribozyme (ptRNA-ribozyme).

A fifty-first embodiment relates to a method of embodiment fifty, wherein the method is a method of any one of embodiments twenty-three to thirty-five.

A fifty-second embodiment relates to a kit for preparing a polypeptide of interest (POI) having one or more than one non-canonical amino acid (ncAA) residue in its amino acid sequence, wherein the kit comprises one or more than one ncAA, or salt thereof, corresponding to the one or more than one ncAA residue of the POI, and:
(a) a polynucleotide of embodiment twenty-one, or
(b) a polynucleotide, or combination of two or more polynucleotides, of embodiment twenty-two, or
(c) a polynucleotide encoding a dsRNA-binding polypeptide as defined in any one of embodiments eleven to thirteen, or
(d) an eukaryotic cell of any one of embodiments one to twenty.

The invention is now explained in more detail by making reference to the particular, non-limiting embodiments of the subsequent experiment section.

EXAMPLES

Material and Methods

Unless stated otherwise, the cloning and expression of recombinant polypeptides was carried out by standard methods, as described for example in Sambrook, J., Fritsch, E. F. and Maniatis, T., Molecular Cloning: A Laboratory Manual, $2^{nd}$ edition, Cold Spring Harbor Laboratory. Cold Spring Harbor Laboratory Press, Cold Spring Harbor, NY, 1989.

A) Cloning

The reporter gene NLS-iRFP-Flag-GFP$^{Y39\rightarrow TAG}$-6His (SEQ ID NO:39) was cloned into a pCI plasmid (Promega) as described in Nikic et al. (Angew Chem Int Ed Engl 2016, 55:16172-16176). NLS-iRFP-Flag-GFP$^{Y39\rightarrow TAG}$-6His contains iRFP fused to a GFP wherein position 39 of the GFP is encoded by the amber stop codon TAG (iRFP-GFP$^{Y39TAG}$).

The coding sequence of T7 RNA polymerase gene with and without a NES signal (NES-T7RNAP or T7RNAP) was inserted into the pcDNA3.1 plasmid or pCAGGS plasmid. The pcDNA3.1 plasmid and pCAGGS plasmid differ in the promoter the pcDNA3.1 plasmid comprises the CMV promoter; the pCAGGS plasmid comprises a CMV enhancer with a chicken actin promoter and an intron (SEQ ID NO: 56). For constitutive expression the T7RNAP- or NES-T7RNAP-encoding sequence was inserted downstream of the CMV promoter (pcDNA3.1 plasmid) or downstream of the chicken actin promoter and intron (pCAGGS plasmid). For inducible expression via T-REx system, the NES-T7RNAP-encoding sequence was inserted downstream of a "T-REx" promoter comprising two tetO sequences (SEQ ID NO:12, ThermoFisher Scientific). For inducible expression via Tet-On system, the NES-T7RNAP-encoding sequence was inserted downstream of a "Tet-On" promoter comprising 8 tetO sequences (SEQ ID NO:10). The expression cassettes for constitutive, "T-REx" and "Tet-On" expression of NES-T7RNAP are set forth in SEQ ID NOs:40-43, respectively.

For constitutive expression the coding sequence for PylRS$^{AF}$ (from *Methanosarcina mazei*) with or without a NES signal (NES-PylRS$^{AF}$ or PylRS$^{AF}$) was inserted into a pcDNA3.1 plasmid (Invitrogen) downstream of the CMV promoter. For inducible expression via T-REx system, the NES-PylRS$^{AF}$-encoding sequence was inserted into the plasmid pDEST downstream of a "T-REx" promoter comprising two tetO sequences (SEQ ID NO:12, ThermoFisher Scientific). For inducible expression via Tet-On system, the NES-PylRS$^{AF}$ encoding sequence was inserted into the pcDNA3.1 plasmid downstream of a "Tet-On" promoter comprising 8 tetO sequences (SEQ ID NO:10). The expression cassettes for constitutive, "T-REx"- and "Tet-On"-expression of NES-PylRS$^{AF}$ are set forth in SEQ ID NO:44-47, respectively.

Figure 1:
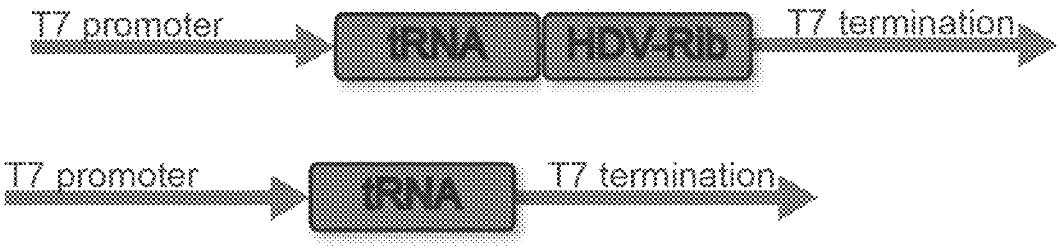
FIG. 1 provides a schematic view (5' to 3' direction) of tRNA expression cassettes for T7RNAP-controlled expression of a tRNA with and without a (HDV) ribozyme ("HDV-Rib.").

A T7 promoter-controlled expression cassette for tRNA$^{Pyl}$ (SEQ ID NO:48) was generated by cloning a T7 promoter sequence upstream of the tRNA$^{Pyl}$ encoding sequence, and a T7 termination signal downstream of the tRNA$^{Pyl}$ encoding sequence, and insertion of this expression cassette into a p2RZ plasmid (Avis et al., Methods Mol Biol. 941:83-98, 2012; (see FIG. 1)). A variant of this expression cassette having a HDV ribozyme (tRNA$^{Pyl}$-HDV) was generated by a combination of restriction cloning, site-directed mutagenesis and restriction-free cloning so as to insert the HDV ribozyme encoding sequence directly downstream of the tRNA$^{Pyl}$ (SEQ ID NO:49, cf. FIG. 1). For inducible expression via T-REx system, two different expression cassettes under the control of tet-inducible promoters were generated by inserting the tRNA$^{Pyl}$-encoding sequence into the plasmids pUC57 (in case of the U6 promoter) and pPBEX (in case of the H1 promoter) downstream of a variant of either a human U6 promoter comprising eight tetO sequences before the U6 [promoter and two tetO sequences after or a human H1 promoter comprising two tetO sequences (SEQ ID NOs:50 and 51).

Expression cassettes for an rtTA or a tetR contained the rtTA-encoding sequence (SEQ ID NO:14) downstream of the CMV promoter and the tetR-encoding sequence (SEQ ID NO:13) downstream of the CMV promoter.

The N-terminal dsRNA-binding domain (residues 2-174) of human protein kinase R ("PKR(2-174)") was cloned into a p1.18 plasmid (U.S. Pat. No. 6,187,759 B1, pUC based plasmid containing a hCMV promoter, intron A, a terminator sequence and a multiple cloning site) for constitutive expression together with an N-terminal HA-tag under the control of the CMV promoter fused to intron A (the biggest intron of the transcribed region of the hCMV major immediate-early (IE1) gene, which enhances expression of protein. The cytomegalovirus (hCMV) is also called human beta-herpes virus 5 (HHV-5); cf. Chapman, B. S. et al NAR, 1991, Vol. 19, N0 14, 2979-3986). The amino acid sequence of HA-PKR(2-174) is set forth in SEQ ID NO:36.

B) Cell Culture and Transfection

HEK293T cells (ATCC CRL-3216) and HEK Flp-In T-REx 293 cells (ThermoFisher Scientific, #R78007) were maintained in Dulbecco's modified Eagle's medium (Life Technologies #41965-039) supplemented with 1% penicillin-streptomycin (Sigma P0781, 10,000 U/ml penicillin, 10 mg/ml streptomycin, 0.9% NaCl), 1% L-glutamine (Sigma #G7513), 1% sodium pyruvate (Life Technologies #11360), and 10% Fetal Bovine Serum (FBS, Sigma #F7524). For HEK Flp-In T-REx 293 cells the medium was supplemented with blasticidin (15 μg/ml) accordingly to the manufacturer's manual. The HEK Flp-In T-REx 293 cell line is derived from HEK293 cells (ATCC CRL-1573) and stably expresses the tet repressor (tetR) gene under the control of the constitutive CMV promoter. See user guide "Growth and Maintenance of the Flp-In™ T-REx™ Cell Line", catalog no. R780-07, document part no. 25-0369, publication no. MAN0000187, revision 2.0, 14 Sep. 2015 by Gibco/Life Technologies.

Cells were cultured at 37° C. in a 5% $CO_2$ atmosphere and passaged every 2-3 days up to 15-20 passages.

Cells were seeded 15-20 hours prior to transfection (~110.000 cells/well) and grown in 24-well plate cell culture plates at 37° C. in a 5% $CO_2$ atmosphere to a confluency of 70-80%. For HEK TetOn-3G cells the cell culture plates had previously been coated with polylysine hydrobromide for 4-10 h. For three and four plasmid transfections 1.2 μg total DNA/well was used. For five or six plasmid transfections 1.5 μg total DNA/well was used. Transfections were done with polyethylenimine (PEI) at a DNA to PEI ratio of 1 to 3.

C) Induction of Expression and Feeding with ncAAs

Four hours after transfection the medium was exchanged for fresh medium. Depending on the experiment and sample, said fresh medium contained 1 μg/ml tetracycline (for induction of expression in T-REx systems, systems with tetR co-expression) or 1 μg/ml doxycycline (for induction of expression in Tet-On systems) and/or 250 μM of the used ncAA (e.g., BOC), or none of these (indicated concentrations=final concentration in the cell culture).

The cells were then incubated at 37° C. in 5% $CO_2$ atmosphere for 2 days and afterwards analyzed as described herein.

D) Analysis by Flow Cytometry Spectroscopy (FCS)

Cells were washed once with 1×PBS and analyzed via flow cytometry spectroscopy. Data acquisition and analysis were performed using a BD LSRFortessa instrument (BD Bioscience) and the FlowJo software (FlowJo). GFP fluorescence was acquired using the 488 nm laser with detection at 530/30 nm, and iRFP fluorescence was acquired using 670 nm laser with detection at 730145 nm. The measured events were gated first in the FSC-A×SSC-A scatter plot for live cells, and then in the FSC-A×SSC-W scatter plot for singlets. In the figures, the events of the singlet gate are shown as a plot of GFP signal vs iRFP signal, which is divided into four areas showing four different species: cell with iRFP fluorescence (lacking GFP) in the top left, cells with both iRFP and GFP fluorescence (expressing the full-length protein iRFP-GFP, called "double positive specimen" or "DPs") in the top right, cells with GFP fluorescence (lacking iRFP) in the lower right, and cells lacking both iRFP and GFP in the lower left.

The reporter NLS-iRFP-Flag-GFP$^{Y39\rightarrow TAG}$-6His is a fusion of iRFP (infrared fluorescent protein) and GFP (green fluorescent protein) wherein amino acid position 39 of the GFP is encoded by the amber (TAG) stop codon. Cells express iRFP (detectable as red fluorescence) if properly transfected and further express GFP (detectable as green fluorescence) only if the amber codon is suppressed to encode the ncAA (here: BOC or SCO). The ratio of green fluorescence (GFP) to red fluorescence (iRFP) in the cells is therefore an indicator of amber suppression efficiency.

Example 1: Amber Suppression Using tRNA$^{Pyl}$ Expressed as RNA-Ribozyme

Amber suppression was examined using the reporter gene NLS-iRFP-Flag-GFP$^{Y39\rightarrow TAG}$-6His, PylRS$^{AF}$, tRNA$^{Pyl}$ and the ncAA SCO in the presence of PKR(2-174). PKR(2-174) was expressed together with an N-terminal HA-tag (SEQ ID NO:36) as HA-PKR(2-174). tRNA$^{Pyl}$ was expressed together with a HDV ribozyme as a tRNA-ribozyme RNA molecule (tRNA$^{Pyl}$-HDV). PylRS$^{AF}$ was expressed under the control of a CMV promoter. The cells further expressed T7 RNA polymerase (T7RNAP).

PylRS$^{AF}$ and T7RNAP were constitutively expressed using HEK293T cells (ATCC CRL-3216).

HEK293T cells were transfected with vectors carrying expression cassettes for the reporter gene NLS-iRFP-Flag-GFP$^{Y39\rightarrow TAG}$-6His, PylRS$^{AF}$ under the control of the CMV promoter, tRNA$^{Pyl}$-HDV under the control of a T7 promoter and T7RNAP under the control of the CMV promoter using the respective constructs and transfection method described in sections A) and B) above.

The controls were prepared identically with the exception that cells were not fed with SCO ("−ncAA") and/or the tRNA$^{Pyl}$ was expressed without the HDV ribozyme.

Figure 3:
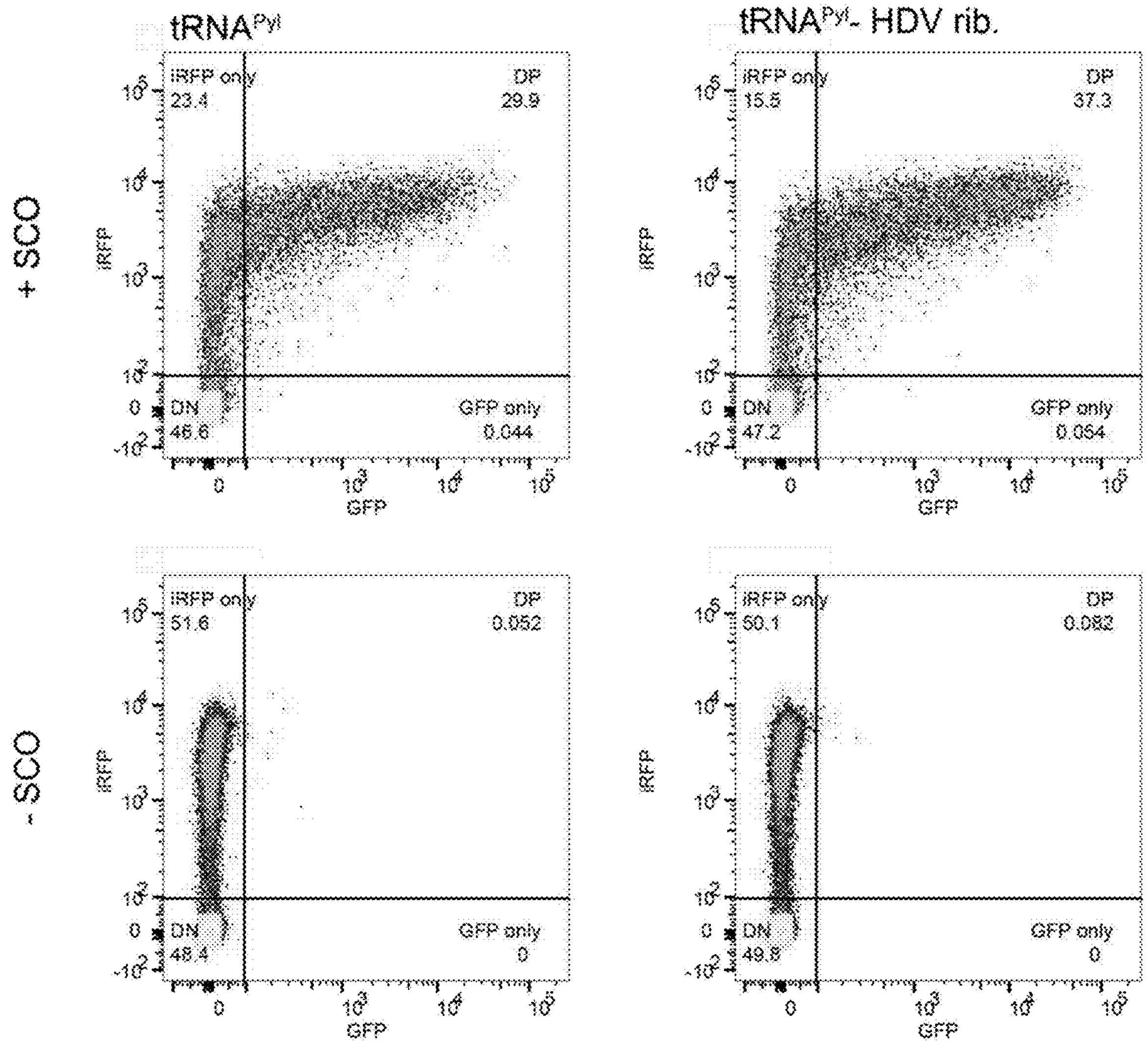
FIG. 3 shows the results of a flow cytometry analysis of HEK293T cells carrying expression cassettes for the NLS-iRFP-Flag-GFP$^{Y39\rightarrow TAG}$-6His amber suppression reporter, T7RNAP and the amber suppression pair tRNA$^{Pyl}$/PylRS$^{AF}$, wherein the tRNA$^{Pyl}$ was either expressed together with a HDV ribozyme ("tRNA$^{Pyl}$-HDV rib.") or without such ribozyme ("tRNA$^{Pyl}$"). The HEK293T cells further carried an expression cassette for HA-tagged human PKR(2-174).

The cells were analyzed by FCS as described in section D) above. The results shown in FIG. 2 (using the pcDNA3.1 plasmid) and FIG. 3 (using the pCAGGS plasmid) indicate that expression of tRNA$^{Pyl}$ together with HDV ribozyme resulted in more efficient amber suppression compared to tRNA$^{Pyl}$ expressed without a ribozyme. Without wishing to be bound by theory it is assumed that this effect results from the ribozyme improving tRNA processing.

Example 2: Amber Suppression Using Different Inducible Expression Systems

Amber suppression was examined using the reporter gene NLS-iRFP-Flag-GFP$^{Y39\rightarrow TAG}$-6His, PylRS$^{AF}$, tRNA$^{Pyl}$ und the ncAA BOC. tRNA$^{Pyl}$ was expressed together with a HDV ribozyme as a tRNA-ribozyme RNA molecule (tRNA$^{Pyl}$-HDV) under the control of a T7 promoter. PylRS$^{AF}$ was expressed together with a NES signal (NES-PylRS$^{AF}$). The cells further expressed T7 RNA polymerase together with a NES signal (NES-T7RNAP).

NES-PylRS$^{AF}$ and NES-T7RNAP were inducibly expressed using either the T-REx system or the Tet-On system.

For the T-REx system. HEK Flp-In T-REx 293 cells were transfected with vectors carrying expression cassettes for the reporter gene NLS-iRFP-Flag-GFP$^{Y39\rightarrow TAG}$-6His, NES-PylRS$^{AF}$ under the control of a "T-REx" promoter, tRNA$^{Pyl}$-HDV under the control of a T7 promoter and NES-T7RNAP under the control of a "T-REx" promoter using the respective constructs and transfection method described in sections A) and B) above. HEK Flp-In T-REx 293 cells stably express the tet repressor (tetR) gene. Expression of NES-T7RNAP (and thereby tRNA$^{Pyl}$-HDV) and NES-PylRS$^{AF}$ was induced by adding tetracycline and the cells were fed with the ncAA BOC as described in section C) above.

For the Tet-On system, HEK293T cells (ATCC CRL-3216) were co-transfected with vectors carrying expression cassettes for the reporter gene NLS-iRFP-Flag-GFP$^{Y39\rightarrow TAG}$-6His, NES-PylRS$^{AF}$ under the control of a "Tet-On" promoter, tRNA$^{Pyl}$-HDV under the control of a T7 promoter, NES-T7RNAP under the control of a "Tet-On" promoter and rtTA using the respective constructs and transfection method described in sections A) and B) above in the presence of PKR(2-174). PKR(2-174) was expressed together with an N-terminal HA-tag (SEQ ID NO:36) as HA-PKR(2-174). Expression of NES-T7RNAP (and thereby tRNA$^{Pyl}$-HDV) and NES-PylRS$^{AF}$ was induced by adding doxycycline and the cells were fed with the ncAA BOC as described in section C) above.

The controls were prepared identically with the exception that neither tetracycline nor doxycycline was added.

The cells were analyzed by FCS as described in section D) above. The results shown in FIG. 4 indicate that amber suppression using BOC together with inducibly expressed tRNA$^{Pyl}$-HDV and NES-PylRS$^{AF}$ worked effectively in both the T-REx system (FIG. 4*a*) and the Tet-On system (FIG. 4*b*).

Example 3: Effect of PKR(2-174) on Amber Suppression in Inducible and Non-Inducible Expression Systems Amber suppression was examined using the reporter gene NLS-iRFP-Flag-GFP$^{Y39\rightarrow TAG}$-6His, PylRS$^{AF}$, tRNA$^{Pyl}$, tetR und the ncAA BOC in the presence or absence of PKR(2-174).

PKR(2-174) was expressed together with an N-terminal TA-tag (SEQ ID NO:36) as HA-PKR(2-174).

One of three different expression cassettes for tRNA$^{Pyl}$ was used: T7-tRNA$^{Pyl}$-HDV wherein tRNA$^{Pyl}$ was expressed together with a HDV ribozyme (located at the 3'-end of tRNA$^{Pyl}$) as a tRNA-ribozyme RNA molecule (tRNA$^{Pyl}$-HDV) under the control of a T7 promoter; 8×tetO- U6-tetO-tRNA$^{Pyl}$ wherein expression of tRNA$^{Pyl}$ is controlled by a tetracycline-inducible variant of the human U6 promoter comprising eight tetO sequences before the U6 promoter and two tetO sequences after the U6 promoter (SEQ ID NO:50); and H1-TetO-tRNA$^{Pyl}$ wherein expression of tRNA$^{Pyl}$ is controlled by a tetracycline-inducible variant of the human H1 promoter comprising two tetO sequences (SEQ ID NO:51).

PylRS$^{AF}$ was expressed together with a NES signal (NES-PylRS$^{AF}$). One of two different expression cassettes for NES-PylRS$^{AF}$ was used: CMV-tetO-NES-PylRS$^{AF}$ wherein expression of NES-PylRS$^{AF}$ is controlled by a tetracycline-inducible variant of the CMV promoter comprising two tetO sequences (SEQ ID NO:46); CMV-NES-PylRS$^{AF}$ wherein expression of NES-PylRS$^{AF}$ is controlled by the (constitutive) CMV promoter (SEQ ID NO:45).

Cells wherein expression of tRNA$^{Pyl}$ was controlled by a T7 promoter (expression cassette T7-tRNA$^{Pyl}$-HDV) further contained one of two different expression cassettes for T7 RNA polymerase to be expressed together with a NES signal (NES-T7RNAP); CMV-tetO-T7RNAP wherein NES-T7RNAP expression is under the control of a tetracycline-inducible variant of the CMV promoter comprising two tetO sequences (SEQ ID NO:12); CMV-NES-T7RNAP wherein NES-T7RNAP expression is under the control of the (constitutive) CMV promoter (SEQ ID NO:43).

HEK293T cells were transfected with vectors carrying the following combinations of expression cassettes (x marks the presence of the respective expression cassette in the combination):

| | combinations | | | | | |
|---|---|---|---|---|---|---|
| expression cassette | 1 | 2 | 3 | 4 | 5 | 6 |
| NLS-iRFP-Flag-GFP$^{Y39\rightarrow TAG}$_6His | X | X | X | X | X | X |
| HA-PKR(2-174) | X | X | X | X | X | X |
| CMV-tetO-NES-PylRS$^{AF}$ | | | X | X | | X |
| CMV-NES-PylRS$^{AF}$ | X | X | | | X | |
| T7-tRNA$^{Pyl}$-HDV | | | | X | X | X |
| 8xtetO-U6-tetO-tRNA$^{Pyl}$ | X | | X | | | |
| H1-tetO-tRNA$^{Pyl}$ | | X | | | | |
| CMV-tetO-T7RNAP | | | | X | X | |
| CMV-NES-T7RNAP | | | | | | X |
| results shown in FIG. | 5a | 5b | 5c | 5d | 5e | 5f |

Controls were prepared in the same manner but without the expression cassette for HA-PKR(2-174).

Tetracycline was added for expression of tet-inducible elements and the cells were fed with the ncAA BOC as described in section C) above. Control samples were prepared identically with the exception that the addition of one or both of tetracycline and Boc was omitted.

The cells were analyzed by FCS as described in section D) above. The results shown in FIG. 5 indicate that co-expression of PKR(2-174) increases the intensity of GFP fluorescence detected in double positive cells, indicating the presence of an increased amount of full-length reporter gene expression product (resulting from successful amber suppression) per cell.

Abbreviations

BCN=2-amino-6-(9-biocyclo[6.1.0]non-4-ynylmethoxy-carbonylamino)hexanoid acid

BOC=2-amino-6-(tert-butoxycarbonylamino)hexanoic acid, in the examples “BOO” specifically designates (2S)-2-amino-6-(tert-butoxycarbonylamino)hexanoic acid=Boc-L-Lys-OH=N-α-tert-butyloxycarbonyl-L-lysine CMV=cytomegalovirus Crm1=chromosomal region maintenance 1, also known as karyopherin exportin 1 dsRNA=double-stranded RNA dSTORM=direct stochastic optical reconstruction microscopy

*E. coli* BL21(DE3)AI=*E. coli* strain B $F^-$ ompT gal dcm lon $hsdS_B(r_B^- m_B^-)$ λ(DE3 [lacl lacUV5-T7p07 ind1 sam7 nin5]) $[malB^+]_{K-12}(\lambda^S)$ araB::T7RNAP-tetA eIF-2α=alpha subunit of eukaryotic initiation factor 2

FBS=fetal bovine serum

FISH=fluorescence in situ hybridization

GCE=genetic code expansion

GFP=green fluorescent protein glmS=glucosamine-6-phosphate synthetase

H1 promoter=human RNA polymerase III promoter

HDV=hepatitis delta virus

IPTG=isopropyl β-D-1-thiogalactopyranoside iRFP=infrared fluorescent protein ncAA=non-canonical amino acid NES=nuclear export signal NLS=nuclear localization signal O-tRNA=orthogonal tRNA O-RS=orthogonal RS PAINT=point accumulation for imaging in nanoscale topography PBS=phosphate buffered saline PKR=protein kinase R; alternative names: dsRNA-dependent protein kinase, interferon-(IFN-)inducible dsRNA-activated serine/threonine-protein kinase, p68 kinase PMSF=phenylmethyAsulfonyl fluoride POI=polypeptide of interest, target polypeptide PrK=2-amino-6-(prop-2-ynoxycarbonylamino)hexanoic acid pRS=prokaryotic RS ptRNA=prokaryotic tRNA ptRNA-ribozyme=prokaryotic RNA molecule comprising a ptRNA and at least one ribozyme PylRS=pyrrolysyl tRNA synthetase PylRS$^{AF}$=mutant *M. mazei* pyrrolysyl tRNA synthetase comprising amino acid substitutions Y306A and Y384F RP-HPLC=reversed phase high-performance liquid chromatography RS=aminoacyl tRNA synthetase RT=room temperature rtTA=reverse tTA SCO=2-amino-6-(cyclooct-2-yn-1-yloxycarbonylamino) hexanoic acid SPAAC=(copper-free) strain promoted alkyne-azide cycloaddition SPIEDAC=(copper-free) strain promoted inverse-electron-demand Diels-Alder cycloaddition SRM=super-resolution microscopy SV40=simian vacuolating virus 40

T7RNAP=T7 RNA polymerase

TCO=2-amino-6[(2E-cyclooct-2-en-1-yl)oxycarbonylamino]hexanoic acid

TCO*=2-amino-6[(2E-cyclooct-2-en-1-yl)oxycarbonylamino]hexanoic acid tetR=tetracycline repressor tetO=tetracycline operator tTA=tetracycline-controlled transcriptional activator TRE=tetracycline-responsive promoter element (also termed tetracycline response element)

tRNA$^{Pyl}$=tRNA that can be acylated with pyrrolysin by a wild-type or modified PylRS and has an anticodon that, for site-specific incorporation of the ncAA into a POI, is preferably the reverse complement of a selector codon. (in the $tRNA^{Pyl}$ used in the examples, the anticodon is CUA.)

U6 promoter=promoter that normally controls expression of the U6 RNA (a small nuclear RNA) in mammalian cells VS=Varkud satellite

| Listing of sequences | | | | |
|---|---|---|---|---|
| SEQ ID NO | Description | Source | Type | Features |
| | | | ribozymes | |
| 1 | hepatitis delta virus (HDV) ribozyme (Avis) | hepatitis delta virus | gcuagc**cauggucccagccuccucgcuggcggcuagugggcaacaugcuucggcauggcgaaugggac** | HOV ribozyme core sequence(7-68) flanking sequence (1-6) (has to be there, but sequence can be different) |
| 2 | hepatitis delta virus (HDV) ribozyme (Schuerer) | hepatitis delta virus | gggtcggcatggcatctccacctcctcgcggtccgacctgggctacttcggtaggctaagggagaag | |
| 3 | hepatitis delta virus (HDV) ribozyme (Akoopie) | hepatitis delta virus | gagggatagtacagagcctccccgtggctcccttggataaccaactgatactgtac | |
| 4 | hammerhead ribozyme | artificial sequence synthetic | ucacguuucc**cugaugaguccgugaggacgaaacgguacccggua**ccguc | HH ribozyme core sequence(11-45) flanking sequences (1-10, 46-50) (have to be there, but sequence can be different) |
| 5 | hairpin ribozyme | artificial sequence synthetic | ggagagagaagucaaccagagaaacacaccaacccauugcacuccggguuggugguauauuaccuggu acgggggaaacuucgugguggccg | [There are other hairpin sequences existing, but this one seems to be the most used one.] |
| 6 | Varkud satel-lite (VS) ribozyme | *Neurospora intermedia* | gggaaagcuugcgaagggcgucgucgccccgagcgguaguaagcagggaacucaccuccaauuucagu acugaaauugucguagcaguugacuacuguuaugugauugguagaggcuaagugacgguauuggcgua agucaguauugcagcacagcacaagcccgcuugcgagaau | |
| 7 | glucosamine-6-phosphate synthetase (glmS) riboswitch (glmS ribozyme) | *Bacillus* spec. | gcgccagaactggcaccauugcacuccggugccaguugacgaggugggguuuaucgagauuucggcgg augacucccgguuguucaucacaaccgcaagcuuuuacuuaaaucauuaaggugacuuaguggacaaa ggugaaagugugauga | |

-continued

| Listing of sequences | | | | |
|---|---|---|---|---|
| SEQ ID NO | Description | Source | Type | Features |
| Elements of the TetOn/Off system | | | | |
| 8 | tetracycline operator (tetO) | artificial sequence synthetic | tccctatcagtgatagaga | |
| 9 | minimal cytomegalovirus (CMV) promoter | artificial sequence derived from CMV promoter | gtaggcgtgtacggtgggaggtctatataagcagagctcgtttagtgaaccgtcagatc | |
| 10 | "Tet-On" promoter comprising 8 tetO sequences | artificial sequence synthetic | caattgctcgagtttac**tccctatcagtgatagaga**acgtatgtcgactttac**tccctatcagtgata**<br>**gaga**acgtatgaagagtttac**tccctatcagtgatagaga**acgtatgcagactttac**tccctatcagt**<br>**gatagaga**acgtataaggagtttac**tccctatcagtgatagaga**acgtatgaccagtttac**tccctat**<br>**cagtgatagaga**acgtatctacagtttac**tccctatcagtgatagaga**acgtatatccagtttac**tcc**<br>**ctatcagtgatagaga**acgtatacgctttaggcgtgtacggtgggcgcctataaaagcagagctcgtt<br>tagtgaaccgtcagatcgcctggagcaattccacaacacttttgtcttataccaactttccgtaccac<br>ttcctaccctcgaaagtccatatggctagcctgcagggatccagatatcaagcttcacc | tetQ sequences (8x, 18-36, 54-72, 90-108, 126-144, 162-180, 198-216, 234-252, 270-288) in CMV promoter |
| 11 | "Tet-On" promoter comprising 7 tetO sequences | artificial sequence synthetic | ctcgactttac**tccctatcagtgatagaga**acgtatgaagagtttac**tccctatcagtgatagaga**ac<br>gtatgcagactttac**tccctatcagtgatagaga**acgtataaggagtttac**tccctatcagtgataga**<br>**ga**acgtatgaccagtttac**tccctatcagtgatagaga**acgtatctacagtttac**tcccatcagtgat**<br>**agaga**acgtatatccagtttac**tccctatcagtgatagaga**acgtatacgctttaggcgtgtacggtg<br>ggcgcctataaaagcagagctcgtttagtgaaccgtcagatcgcctggagcaattccacaacactttt<br>gtcttataccaactttccgtaccacttcctaccctcgaaagtccatatggctagcctgcagggatcca<br>gatatcaagcttcacc | tetO sequences (7x, 12-30, 48-66, 84-102, 120-138, 156-174, 192-210, 228-246) in CMV promoter |
| 12 | "T-REX" promoter comprising two tetO sequences | artificial sequence synthetic | gacattgattattgactagttattaatagtaatcaattacggggtcattagttcatagcccatatatg<br>gagttccgcgttacataacttacggtaaatggcccgcctggctgaccgcccaacgacccccgcccatt<br>gacgtcaataatgacgtatgttcccatagtaacgccaatagggactttccattgacgtcaatgggtgg<br>agtatttacggtaaactgcccacttggcagtacatcaagtgtatcatatgccaagtacgccccctatt<br>gacgtcaatgacggtaaatggcccgcctggcattatgcccagtacatgaccttatgggactttcctac<br>ttggcagtacatctacgtattagtcatcgctattaccatcgtg**gtgcggttttggcagtacatcaatg**<br>**ggcgtggatagcggtttgactcacggggatttccaagtctccaccattgacgtcaatgggagtttgtt**<br>**ttggcaccaaaatcaacgggactttccaaaatgtcgtaacaactccgccccattgacgcaaatgggcg**<br>**gtaggcgtgtacggtgggaggtctatataagcagagctctccctatcagtgatagagatctccctatc**<br>**actgatagaga**tcgtcgacgagctcgtttagtgaaccgtcagatcgcctggagacgccatccacgctg<br>ttttgacctccatagaagacaccgggaccgatccagcctccggactctagcgtttaaacatcacaagt<br>tgtacaaaaaagcaggcgctagcgtttaaacttaagcttcacc | CMV enhancer (1-380)<br>CMV promoter (381-584)<br>tetO sequences (586-604, 607-625) (2x) |

-continued

| Listing of sequences | | | | |
|---|---|---|---|---|
| SEQ ID NO | Description | Source | Type | Features |
| 13 | tetracycline repressor (tetR) UniProtKB/ Swiss-Prot accession no.: P04483.1 | artificial sequence synthetic | MSRLDKSKVINSALELLNEVGIEGLTTRKLAQKLGVEQPTLYWHVKNKRALLDALAIEMLDRHHTH<br>FCPLEGESWQDFLRNNAKSFRCALLSHRDGAKVHLGTRPTEKQYETLENQLAFLCQQGFSLENA<br>LYALSAVGHFTLGCVLEDQEHQVAKEERETPTTDSMPPLLRQAIELFDHQGAEPAFLFGLELIICG<br>LEKQLKCESGS | |
| 14 | rtTA expression cassette | artificial sequence synthetic | DNA:<br>**gttgacattgattattgactagttattaatagtaatcaattacggggtcattagttcatagcccatat**<br>**atggagttccgcgttacataacttacggtaaatggcccgcctggctgaccgcccaacgacccccgccc**<br>**attgacgtcaataatgacgtatgttcccatagtaacgccaatagggactttccattgacgtcaatggg**<br>**tggactatttacggtaaactgcccacttggcagtacatcaagtgtatcatatgccaagtacgccccct**<br>**attgacgtcaatgacggtaaatggcccgcctggcattatgcccagtacatgaccttatgggactttcc**<br>**tacttggcagtacatctacgtattagtcatcgctattaccatggtgatgcggttttggcagtacatca**<br>**atgggcgtggatagcggtttgactcacggggatttccaagtctccaccccattgacgtcaatgggagt**<br>**ttgttttggcaccaaaatcaacgggactttccaaaatgtcgtaacaactccgccccattgacgcaaat**<br>**gggcggtaggggtgtacggtgggaggtctatataagcagagctc**tctggctaactagagaacccactg<br>cttactggcttatcgaaattaatacgactcactatagggagacccaagctggctagcgtttaaactta<br>agcttctcgagcaccatgtctagactggacaagagcaaagtcataaactctgctctggaattactcaa<br>tggagtcggtatcgaaggcctgacgacaaggaaactcgctcaaaagctgggagttgagcagcctaccc<br>tgtatactggcacgtgaagaacaagcgggccctgctcgatgccctgccaatcgagatgctggacaggc<br>atcatacccactcctgccccctggaaggcgagtcatggcaagactttctgcggaacaacgccaagtca<br>taccgctgtgctctcctctcacatcgcgacggggctaaagtgcatctcggcacccgcccaacagagaa<br>acagtacgaaaccctggaaaatcagctcgcgttcctgtgtcagcaaggcttctccctggagaacgcac<br>tgtacgctctgtccgccgtgggccactttacactgggctgcgtattggaggaacaggagcatcaagta<br>gcaaaagaggaaagagagacacctaccaccgattctatgcccccacttctgaaacaagcaattgagct<br>gttcgaccggcagggagccgaacctgccttccttttcggcctggaactaatcatatgtggcctggaga<br>aacagctaaagtgcgaaagcggcgggccgaccgacgcccttgacgattttgacttagacatgctccca<br>gccgatgcccttgacgactttgaccttgatatgctgccgctgacgctcttgacgattttgaccttgac<br>atgctcccccgggtaa | CMV<br>TetOn3G |
| 52 | TetOn3G protein Zhou et al, Nature, 2006 | human immuno-deficiency virus (HIV)-rtTA variant, optimized for TetOn-system | Protein:<br>MSRLDKSKVINSALELLNGVGIEGLTTRKLAQKLGVEQPTLYWHVKNKRALLDALPIEMLDRHHTH<br>SCPLEGESWQDFLRNNAKSYRCALLSHRDGAKVHLGTRPTEKQYETLENQLAFLCQQGFSLENA<br>LYALSAVGHFTLGCVLEEQEHQVAKEERETPTTDSMPPLLKQAIELFDRQGAEPAFLFGLELIICGL<br>EKQLKCESGGPTDALDDFDLDMLPADALDDFDLDMLPADALDDFDLDMLPG* | |

-continued

Listing of sequences

| SEQ ID NO | Description | Source | Type | Features |
| --- | --- | --- | --- | --- |
| | | | T7 promoter/RNA polymerase | |
| 15 | T7 promoter class III (core) | artificial sequence derived from enterobacteria phage T7 promoter | taatacgactcactatag | G at position 18 is preferred nucleotide at the +1 position to promote efficient transcription initiation |
| 16 | T7 promoter class III | artificial sequence derived from enterobacteria phage T7 promoter | taatacgactcactatagg | GG at positions 18 and 19 are preferred nucleotides at the +1 and +2 positions to promote efficient transcription initiation |
| 17 | T7 promoter class II (core) | artificial sequence derived from enterobacteria phage T7 promoter | taatacgactcactatta | A at position 18 is preferred nucleotide at the +1 position of the gene to promote efficient transcription initiation |
| 18 | T7 RNA polymerase | Enterobacteria phage T7 | MNTINIAKNDFSDIELAAIPFNTLADHYGERLAREQLALEHESYEMGEARFRKMFERQLKAGEVAD<br>NAAAKPLITTLLPKMIARINDWFEEVKAKRGKRPTAFQFLQEIKPEAVAYITIKTTLACLTSADNTTV<br>QAVASAIGRAIEDEARFGRIRDLEAKHFKKNVEEQLNKRVGHVYKKAFMQVVEADMLSKGLLGGE<br>AWSSWHKEDSIHVGVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYKAINIAQNTAW<br>KINKKVLAVANVITKWKHCPVEDIPAIEREELPMKPEDIDMNPEALTAWKRAAAAVYRKDKARKSR<br>RISLEFMLEGANKFANHKAIWFPYNMDWRGRVYAVSMFNPQGNDMTKGLLTLAKGKPIGKEGYY<br>WLKIHGANCAGVDKVPFPERIKFIEENHENIMACAKSPLENTWWAEQDSPFCFLAFCFEYAGVQH<br>HGLSYNCSLPLAFDGSCSGIQHFSAMLRDEVGGRAVNLLPSETVQDIYGIVAKKVNEILQADAING<br>TDNEWVTVIDENTGEISEKVKLGTKALAGQWLAYGVTRSVTKRSVMTLAYGSKEFGFRQQVLED<br>TIQPAIDSGKGLMFTQPNQAAGYMAKLIWESVSVTVVAAVEAMNWLKSAAKLLAAEVKDKKTGEI<br>LRKRCAVHWVTPDGFPVWQEYKKPIQTRLNLMFLGQFRLQPTINTNKDSEIDAHKQESGIAPNFV<br>HSQDGSHLRKTVVWAHEKYGIESFALIHDSFGTIPADAANLFKAVRETMVDTYESCDVLADFYDQ<br>FADQLHESQLDKMPALPAKGNLNLRDILESDFAFA | |
| 19 | NES-T7 RNA polymerase | artificial sequence derived from Enterobacteria phage T7 | MCPVPLQLPPLERLTLDNTINIAKNDFSDIELAAIPFNTLADHYGERLAREQLALEHESYEMGEARF<br>RKMFERQLKAGEVADNAAAKPLITTLLPKMIARINDWFEEVKAKRGKRPTAFQFLQEIKPEAVAYIT<br>IKTTLACLTSADNTTVQAVASAIGRAIEDEARFGRIRDLEAKHFKKNVEEQLNKRVGHVYKKAFMQ<br>WVEADMLSKGLLGGEAWSSWHKEDSIHVGVRCIEMLIESTGMVSLHRQNAGVVGQDSETIELAP<br>EYAEAIATRAGALAGISPMFQPCVVPPKPWTGITGGGYWANGRRPLALVRTHSKKALMRYEDVY<br>MPEVYKAINIAQNTAWKINKKVLAVANVITKWKHCPVEDIPAIEREELPMKPEDIDMNPEALTAWK | NES |

-continued

| SEQ ID NO | Description | Source | Type | Features |
|---|---|---|---|---|
| | Listing of sequences | | | |
| | | | RAAAAVYRKDKARKSRRISLEFMLEQANKFANHKAIWFPYNMDWRGRVYAVSMFNPQGNDMTK<br>GLLTLAKGKPIGKEGYYWLKIHGANCAGVDKVPFPERIKFIEENHENIMACAKSPLENTWWAEQD<br>SPFCFLAFCFEYAGVQHHGLSYNCSLPLAFDGSCSGIQHFSAMLRDEVGGRAVNLLPSETVQDIY<br>GIVAKKVNEILQADAINGTDNEVVTVTDENTGEISEKVKLGTKALAGQWLAYGVTRSVTKRSVMTL<br>AYGSKEFGFRQQVLEDTIQPAIDSGKGLMFTQPNQAAGYMAKLIWESVSVTVVAAVEAMNWLKS<br>AAKLLAAEVKDKKTGEILRKRCAVHWVTPDGFPVWQEYKKPIQTRLNLMFLGQFRLQPTINTNKD<br>SEIDAHKQESGIAPNFVHSQDGSHLRKTWWWAHEKYGIESFALIHDSFGTIPADAANLFKAVRETM<br>VDTYESCDVLADFYDQFADQLHESQLDKMPALPAKGNLNLRDILESDFAFA | |
| 20 | NLS consensus | artificial sequence synthetic | $KX^1X^2X^3$ | $X^1$ and $X^3$ are independently selected from K and R, and $X^2$ is any naturally occurring amino acid |
| 21 | NLS of SV40 large T antigen | simian vacuolating virus 40 (SV40) | PKKKRKV | |
| | pRS and ptRNA | | | |
| 22 | *Methanosarcina mazei* PylRS Y306A, Y384F mutant ($PylRS^{AF}$) | artificial sequence synthetic | DNA:<br>**atg**gcgtgcccggtgccgctgcagctgccgccgctggaacgcctgaccctggatgataaaaaaccgct<br>gaataccctgatctctgctactggtctgtggatgagtcgtaccggaaccattcataaaatcaaacacc<br>acgaggttagccgttcgaaaatctatattgagatggcgtgtggcgatcatctggttgtgaacaatagc<br>cgctcttctcgtacagcacgtgcactgcgtcaccacaaatatcgtaaaacctgtaaacgttgccgtgt<br>gtccgatgaggatctgaacaaattcctgacaaaagccaatgaggaccaaacaagcgtgaaagtgaaag<br>tcgttagcgctcctacccgtactaaaaaagcaatgccgaaatccgttgctcgtgcccctaaaccactg<br>gaaaacactgaagcagcacaggcacagccgtctggaagcaaattctctccggccattcctgtttctac<br>ccaggagtccgtttctgttccagcaagtgtgagcaccagcattagcagtattagcaccggtgccaccg<br>ctagcgccctggttaaaggcaataccaatccgattacaagcatgtctgccccggttcaagcatcagct<br>ccagcactgacaaaatcccaaaccgatcgtctggaggttctgctgaatccgasagacgaaatcagcct<br>gaattccggcaaaccgtttcgtgaactggagagcgaactgctgtcacgtcgtaaaaaagacctgcaac<br>aaatctatgccgaagaacgtgagaactatctggggaaactggaacgtgaaatcacccgcttttttcgtg<br>gatcgtggctttctggagatcaaatccccgattctgattcctctggagtatatcgagcgtatgggcat<br>cgacaatgataccgaactgagcaaacaaattttccgtgtggataaaaacttctgtctgcgccctatgc<br>tagcaccaaatctggctaactatctgcgcaaactggaccgtgccctgcctgatcctatcaaaatcttc<br>gagatcggcccgtgttatcgtaaagagtccgacggtaaagaacatctggaggagtttaccatgctgaa<br>cttttgccaaatgggttcaggttgtactcgtgagaacctggaaagcatcatcaccgattttctgaacc<br>acctgggcattgacttcaaaattgtgggcgacagctgtatggtgtttggcgacaccctggatgtcatg<br>cacggcgacctggaactgtctagtgccgttgtgggcccaatcccgctggatcgtgagtggggtatcga<br>caaaccttggatcggtgcgggttttggtctggagcgtctgctgaaagtaaaacacgacttcaagaaca<br>tcaaacgtgctgcacgttcgagtcctattacaatggtatttctactaacctgtaa | ATG ($M^1$) may be missing |

-continued

| Listing of sequences | | | | |
|---|---|---|---|---|
| SEQ ID NO | Description | Source | Type | Features |
| 53 | *Methanosarcina mazei* PylRS Y306A, Y384F mutant (PylRS$^{AF}$)_ amino acid sequence | artificial sequence synthetic | Protein:<br>**M**ACPVPLqLPPLERLTLDDKKPLNTLISATGLWMSRTGTIHKIKHHEVSRSKIYIEMACGDHLVVN<br>NSRSSRTARALRHHKYRKTCKRCRVSDEDLNKFLTKANEDQTSVKVKVVSAPTRTKKAMPKSVA<br>RAPKPLENTEAAQAQPSGSKFSPAIPVSTQESVSVPASVSTSISSISTGATASALVKGNTNPITSM<br>SAPVQASAPALTKSQTDRLEVLLNPKDEISLNSGKPFRELESELLSRRKKDLQQIYAEERENYLGK<br>LEREITRFFVDRGFLEIKSPILIPLEYIERMGIDNDTELSKQIFRVDKNFCLRPMLAPNLANYLRKLDR<br>ALPDPIKIFEIGPCYRKESDGKEHLEEFTMLNFCQMGSGCTRENLESITDFLNHLGIDFKIVGDSC<br>MVFGDTLDVMHGDLELSSAVVGPIPLDREWGIDKPWIGAGFGLERLLKVKHDFKNIKRAARSESY<br>YNGISTNL | M[1] may be missing<br>Y306A, Y384F |
| 23 | *Methanosarcina mazei* PylRS N346A, C348A mutant (PylRS$^{AA}$) | artificial sequence synthetic | DNA:<br>**atg**gcgtgcccggtgccgctgcagctgccgccgctggaacgcctgaccctggatgacaaaaaaccgct<br>gaataccctgatctctgctactggtctgtggatgagtcgtaccggaaccattcataaaatcaaacacc<br>acgaggttagccgttcgaaaatctatattgagatggcgtgtggcgatcatctggttgtgaacaatagc<br>cgctcttctcgtacagcacgtgcactgcgtcaccacaaatatcgtaaaacctgtaaacgttgccgtgt<br>gtccgatgagatctgaaaattcctgacaaaagccaatgaggaagcgtgaaagtgaaagtcgttagcgc<br>tcctacccgtactaaaaaagcaatgccgaaatccgttgctcgtgcccctaaaccactggaaaacactg<br>aagcagcacaggcacagccgtctggaagcaaattctctccggccattcctgtttctacccaggagtcc<br>gtttctgttccagcaagtgtgagcaccagcattagcagtattagcaccggtgccaccgctagcgccct<br>ggttaaaggcaataccaatccgattacaagcatgtctgccccggttcaagcatcagctccagcactga<br>caaaatcccaaaccgatcgtctggggttctgctgaatccgaaagacgaaatcagcctgaattccggca<br>aaccgtttcgtgaactggagagcgaactgctgtcacgtcgtaaaaaagacctgcaacaaatctatgcc<br>gaagaacgtgagaactatctggggaaactggaacgtgaaatcacccgctttttcgtggatcgtggctt<br>tctggagatcaaatccccgattctgattcctctggagtatatcgagcgtatgggcatcgacaatgata<br>ccgaactgagcaaacaaattttccgtgtggataaaaacttctgtctgcgccctatgctggcaccaaat<br>ctgtataactatctgcgcaaactggaccgtgccctgcctgatcctatcaaaatcttcgagatcggccc<br>gtgttatcgtaaagagtccgacggtaaagaacatctggaggagtttaccatgctggcctttgcccaaa<br>tgggttcaggttgtactcgtgagaacctggaaagcatcatcaccgattttctgaaccacctgggcatt<br>gacttcaaaattgtgggcgacagctgtatggtgtatggcgacaccctggatgtcatgcacggcgacct<br>ggaactgtctagtgccgttgttggaccaattccgctggaccgtgagtggggtatcgacaaaccgtgga<br>tcggagcaggattcggtctggaacgcctgctgaaagtgaaacacgacttcaaaaacatcaaacgtgcc<br>gcccgttctgaatcgtattataacgggatctctacgaacctgtaa | ATG (M[1]) may be missing |
| 54 | *Methanosarcina mazei* PylRS N346A, C348A mutant (PylRS$^{AA}$)_ amino acid sequence | artificial sequence synthetic | Protein:<br>**M**ACPVPLqLPPLERLTLDDKKPLNTLISATGLWMSRTGTIHKIKHHEVSRSKIYIEMACGDHLVVN<br>NSRSSRTARALRHHKYRKTCKRCRVSDEDLNKFLTKANEDQTSVKVKVVSAPTRTKKAMPKSVA<br>RAPKPLENTEAAQAQPSGSKFSPAIPVSTQESVSVPASVSTSISSISTGATASALVKGNTNPITSM<br>SAPVQASAPALTKSQTDRLEVLLNPKDEISLNSGKPFRELESELLSRRKKDLQQIYAEERENYLGK<br>LEREITRFFVDRGFLEIKSPILIPLEYIERMGIDNDTELSKQIFRVDKNFCLRPMLAPNLYNYLRKLQR<br>ALPDPIKIFEIGPCYRKESDGKEHLEEFTMLAFAQMGSGCTRENLESIITDFLNHLGIDFKIVGDSC<br>MVYGdTLDVMHGDLELSSAVVGPIPLDREWGIDKPWIGAGFGLERLLKVKHDFKNIKRAARSESY<br>YNGISTNL | M[1] may be missing<br>N346A, C348A |

-continued

Listing of sequences

| SEQ ID NO | Description | Source | Type | Features |
|---|---|---|---|---|
| 24 | *Methanosarcina mazei* PylRS Y306A, N346A, C348A, Y384Fmutant (PylRS$^{AAAF}$) | artificial sequence synthetic | gcgtgcccggtgccgctgcagctgccgccgctggaacgcctgaccctggatgataaaaaaccgctgaa<br>taccctgatctctgctactggtctgtggatgagtcgtaccggaaccattcataaaatcaaacaccacg<br>aggttagccgttcgaaaatctatattgagatggcgtgtggcgatcatctggttgtgaacaatagccgc<br>tcttctcgtacagcacgtgcactgcgtcaccacaaatatcgtaaaacctgtaaacgttgccgtgtgtc<br>cgatgaggatctgaacaaattcctgacaaaagccaatgaggaccaaacaagcgtgaaagtgaaagtcg<br>ttagcgctcctacccgtactaaaaaagcaatgccgaaatccgttgctcgtgcccctaaaccactggaa<br>aacactgaagcagcacaggcacagccgtctggaagcaaattctctccggccattcctgtttctaccca<br>ggagtccgtttctgttccagcaagtgtgagcaccagcattagcagtattagcaccggtgccaccgcta<br>gcgccctggttaaaggcaataccaatccgattacaagcatgtctgccccggttcaagcatcagctcca<br>gcactgacaaaatcccaaaccgatcgtctggaggttctgctgaatccgaaagacgaaatcagcctgaa<br>ttccggcaaaccgtttcgtgaactggagagcgaactgctgtcacgtcgtaaaaaagacctgcaacaaa<br>tctatgccgaagaacgtgagaactatctggggaaactggaacgtgaaatcacccgctttttcgtggat<br>cgtggctttctggagatcaaatccccgattctgattcctctggagtatatcgagcgtatgggcatcga<br>caatgataccgaactgagcaaacaaattttccgtgtggataaaaacttctgtctgcgccctatgctag<br>caccaaatctggctaactatctgcgcaaactggaccgtgccctgcctgatcctatcaaaatcttcgag<br>atcggcccgtgttatcgtaaagagtccgacggtaaagaacatctggaggagtttaccatgctggcctt<br>tgcccaaatgggttcaggttgtactcgtgagaacctggaaagcatcatcaccgattttctgaaccacc<br>tgggcattgacttcaaaattgtcggcgacagctgtatggtgtttggcgacaccctggatgtcatgcac<br>ggcgacctggaactgtctagtgccgttgtgggcccaatcccgctggatcgtgagtggggtatcgacaa<br>accttggatcggtgcgggttttggtctggagcgtctgctgaaagtaaaacacgacttcaagaacatca<br>aacgtgctgcacgttccagtcctattacaatggtatttctactaacctgtaa | |
| 55 | *Methanosarcina mazei* PylRS Y306A, N346A, C348A, Y384Fmutant (PylRS$^{AAA}$) amino acid sequence | artificial sequence synthetic | Protein:<br>ACPVPLQLPPLERLTLDDKKPLNTLISATGLWMSRTGTIHKIKHHEVSRSKIYIEMACGDHLVVNNS<br>RSSRTARALRHHKYRKTCKRCRVSDEDLNKFLTKANEDQTSVKVKVVSAPTRTKKAMPKSVARA<br>PKPLENTEAAQAQPSGSKFSPAIPVSTQESVSVPASVSTSISSISTGATASALVKGNTNPITSMSAP<br>VQASAPALIKSQTDRLEVLLNPKDEISLNSGKPFRELESELLSRRKKDLQQIYAEERENYLGKLER<br>EITRFFVDRGFLEIKSPILIPLEYIERMGIDNDTELSKQIFRVDKNFCLRPMLAPNLANYLRKLDRALP<br>DPIKIFEIGPCYRKESDGKEHLEEFTMLAFAQMGSGCTRENLESIITDFLNHLGIDFKIVGDSCMVF<br>GDTLdVMHGDLELSSAVVGPIPLDREWGIDKPWIGAGFGLERLLKVKHDFKNIKRAARSESYYNG<br>ISTNL | May be optionally extended by a $M^1$ (before first A-amino acid) Y306A, N346A, C348A, Y384F |
| 25 | pyrrolysyl tRNA of *Methanosarcina mazei* for Amber codon (tRNA$^{Pyl,CUA}$) | artificial sequence synthetic | ggaaacctgatcatgtagatcgaatggactctaaatccgttcagccgggttagattcccggggtttccg | Underlined: anticodon (31-33) |
| 26 | pyrrolysyl tRNA of *Methanosarcina mazei* for Opal codon (tRNA$^{Pyl,UCA}$) | artificial sequence synthetic | ggaaacctgatcatgtagatcgaatggacttcaaatccgttcagccgggttagattcccggggtttccg | Underlined: anticodon (31-33) |

-continued

Listing of sequences

| SEQ ID NO | Description | Source | Type | Features |
|---|---|---|---|---|
| 27 | pyrrolysyl IRNA of *Methanosarcina mazel* for Ochre codon ($tRNA^{Pyl,UUA}$) | artificial sequence synthetic | ggaaacctgatcatgtagatcgaatggacttaaatccgttcagccgggttagattcccggggtttccg | Underlined: anticodon (31-33) |
| | | NES | | |
| 28 | NES motif | artificial sequence synthetic | XXXXXX | Underlined: independently selected from Leu, Ile, Val Phe and Met Bold: independently selected from any canonical amino acid |
| 29 | NES motif | artificial sequence synthetic | XXXXXXX | Underlined: independently selected from Leu, Ile, Val Phe and Met Bold: independently selected from any canonical amino acid |
| 30 | NES motif | artificial sequence synthetic | LXXXXXLX*X* | Underlined: independently selected selected from Leu, Ile, Val, Phe and Met Bold: independently selected from any canonical amino acid Italic: independently selected from Leu and Ile |
| 31 | NES motif | artificial sequence synthetic | LXXXXXLX | Underlined: independently selected from Leu, Ile, Val, Phe and Met Bold: independently selected from any canonical amino acid |

-continued

| SEQ ID NO | Description | Source | Type | Features |
|---|---|---|---|---|
| | | | Listing of sequences | |
| 32 | NES motif | artificial sequence synthetic | L**XXXXXXL**X | Underlined: independently selected from Leu, Ile, Val, Phe and Met Bold: independently selected from any canonical amino acid |
| 33 | NES motif | artificial sequence synthetic | L**XXXXXXXL**X*X* | Underlined: Independently selected from Leu, Ile, Val, Phe and Met Bold: independently selected from any canonical amino acid Italic: independently selected from Leu and Ile |
| 34 | NES motif | artificial sequence synthetic | LPPLERLTL | |
| 35 | NES motif | artificial sequence synthetic | ACPVPLQLPPLERLTLD | |
| | | | dsRNA-binding polypeptides | |
| 36 | HA-PKR(2-174) | artificial sequence synthetic | **MYPYDVPDYA**AGDLSAGFFMEELNTYRQKQGVVLKYQELPNSGPPHDRRFTFQVIIDGREFPEG EGRSKKEAKNAAAKLAVEILNKEKKAVSPLLLTTTNSSEGLSMGNYIGLINRIAQKKRLTVNYEQCA SGVHGPEGFHYKCKMGQKEYSIGTGSTKQEAKQLAAKLAYLQILSEETSVKS | HA (2-10) human PKR(2-174) (11-183) |
| 37 | core of dsRNA-binding domain of PKR | artificial sequence synthetic | FMEELNTY**RQK**QGVVLKYQELPNSGPPHDRRFTFQVIIDGREFPEGEGRSKKEAKNAAAKLAVEI LNKEKKAVSPLLLTTTNSSEGLSMGNYIGLINRIAQKKRLTVNYEQCASGVHGPEGFHYKCKMGQ KEYSIGTGSTKQEAKQLAAKLAYLQILSE | conserved; R30, F32, G48, S50, K51, K52, K55, F122, K141, K145 restricted: 1) R9, Q10 ≠ hydrophobic (i.e.: K, R, H, D, E, S, T, N, Q, C, preferably, R9 = R, S, C, Q, H, (K), Q10 = Q, (N) 2) A59, L66, A149 ≠ A59D, L66A, A149D |

-continued

| Listing of sequences | | | | |
|---|---|---|---|---|
| SEQ ID NO | Description | Source | Type | Features |
| | | | | (i.e.: A59 = A, G, I, L, M, V; L66 = L, I, V, M; A149 = A, G, I, L, M, V) |
| 38 | (full) dsRNA-binding domain of PKR-M1 | artificial sequence synthetic | AGDLSAGFFMEELNTYRQKQGVVLKYQELPNSGPPHDRRFTFQVIIDGREFPEGEGRSKKEAKN<br>AAAKLAVEILNKEKKAVSPLLLTTTNSSEGLSMGNYIGLINRIAQKKRLTVNYEQCASGVHGPEGF<br>HYKCKMGQKEYSIGTGSTKQEAKQLAAKLAYLQILSEETSVKS | |
| constructs used in examples | | | | |
| 39 | expression cassette for reporter gene NLS-iRFP-Flag-GFP$^{Y39\rightarrow TAG}$-6His | artificial sequence synthetic | **ggcattgattattgactagttattaatagtaatcaattacggggtcattagttcatagcccatataggagttccgcgttacataactt**<br>**acggtaaatggcccgcctggctgaccgcccaacgacccccgcccattgacgtcaataatgacgtatgttcccatagtaacgc**<br>**caatagggactttccattgacgtcaatgggtggagtatttacggtaaactgcccacttggcagtacatcaagtgtatcatatgcc**<br>**aagtccgccccctattgacgtcaatgacggtaaatggcccgcctggcattatgcccagtacatgaccttacgggactttcctac**<br>**ttggcagtacatctacgtattagtcatcgctattaccatggtgatgcggttttggcagtacaccaatgggcgtggatagcggtttg**<br>**actcacggggatttccaagtctccaccccattgacgtcaatgggagtttgttttggcaccaaaatcaacgggactttccaaaatg**<br>**tcgtaataaccccgccccgttgacgcaaatgggcggtaggcgtgtacggtgggaggtctatataagcagctcgtttagtga**<br>**accgtcagatcactagaagctttattgcggtagtttatcacagttaaattgctaacgcagtcagtgcttctgacacaacagtctcg**<br>**aacttaagctgcagaagttggtcgtgaggcactgggcaggtaagtatcaaggttacaagacaggtttaaggagaccaataga**<br>**aactgggcttgtcgagacagagaagactcttgcgtttctgataggcacctattggtcttactgacatccactttgcctttctctcca**<br>**cag**gtgccactcccagttcaattacagctcttaaggctagagtacttaatacgactcataggctagccaccatgggccgcctggaaa<br>gcaccccgccgaaaaaaaaacgcaaagtggaagatagcgcgagcgcggaaggatccgtcgccaggcagcctgacctcttgacctg<br>cgacgatgagccgatccatatccccggtgccatccaaccgcatggactgctgctcgccctcgccgccgacatgacgatcgttgccggca<br>gcacaaccttcccgaactcaccggactggcgatcggcgccctgatcggccgctctgcggccgatgtcttcgactcggagacgcacaa<br>ccgtctgacgatcgccttggccgagcccggggcggccgtcggagcaccgatcactgtcggcttcacggatgcgaaaggacgcaggcttc<br>atcggctcctggcatcgccatgatcagctcatcttcctcgagctcgagcctccccagcgggacgtcgccgagccgcaggcgttcttccgc<br>cgcaccaacagcgccatccgccgcctgcaggccgccgaaaccttggaaagcgcctgcgccgccgcggcacaagaggtgcggaag<br>attaccggcttcgatcgggtgatgatctatcgcttcgcctccgacttcagcggcgaagtgatcgcagaggatcggtgcgccgaggtcgagt<br>caaaactaggcctgcactatcctgcctcaaccgtgccggcgcaggcccgtcggctctataccatcaacccggtacggatcattcccgata<br>tcaattatcggccggtgccggtcaccccagacctcaatccggtcaccgggcggccgattgatcttagcttcgccatcctgcgcagcgtctc<br>gcccgtccatctggaattcatgcgcaacataggcatgcacggcacgatgtcgatctcgattttgcgcggcgagcgactgtggggattgatc<br>gtttgccatcaccgaacgccgtactacgtcgatctcgatggccgccaagcctgcgagctagtcgcccaggttctggcctggcagatcggc<br>gtgatggaagag**ctggcggaagcggcggccaaagaagcggcggccaaagaagcggcggccaaagaagcggcggcca**<br>**aagcggcggcc**ggtacc**gattacaaagatgatgatgataaa***gtgagcaagggcgaggagctgttcaccggggtggtgcccatcct*<br>*ggtcgagctggacggcgacgtaaacggccacaagttcagcgtgtccggcgagggcgagggcgatgcccacctagggcaagctgacc*<br>*ctgaagttcatctgcaccaccggcaagctgcccgtgccctggcccaccctcgtgaccaccctgacctacggcgtgcagtgcttcagccg*<br>*ctaccccgaccacatgaagcagcacgacttcttcaagtccgccatgcccgaaggctacgtccaggagcgcaccatcttcttcaaggac*<br>*gcaggcaactacaagacccgcgccgaggtgaagttcgagggcgacaccctggtgaaccgcatcgagctgaagggcatcgacttcaa*<br>*ggaggacggcaacatcctggggcacaagctggagtacaatacaacagccacaacgtctatatcatggccgacaagcagaagaac*<br>*ggcatcaaggccaacttcaagatccgccacaacatcgaggacggcagcgtgcagctcgccgaccactaccagcagaacacccccca*<br>*tcggcgacggccccgtgctgctgcccgacaaccatacctgagcacccagtccgccctgagcaaagaccccaacgagaagcgcgat*<br>*cacatggtcctgctggagttcgtgaccgccgccgggatcactctcggcatggacgagctgtacaag***catcaccatcaccatcac**tga | Promoter (1-852)<br>NLS (949-984)<br>IRFP (988-1929)<br>25 Helix (1930-2004)<br>Flag (2011-2034)<br>GFP$^{Y39}$ CDS (2035-2748)<br>Y39-encoding triplet (2149-1251)<br>6His (2749-2766) |

-continued

Listing of sequences

| SEQ ID NO | Description | Source | Type | Features |
|---|---|---|---|---|
| 40 | T7 RNA polymerase expression cassette for constitutive expression via CMV promoter | artificial sequence synthetic | **gttgacattgattattgactagttattaatagtaatcaattacggggtcattagttcatagcccatataggagttccgcgttacataa**<br>**cttacggtaaatggcccgcctggctgaccgcccaacgacccccgcccattgacgtcaataatgacgtatgttcccatagtaac**<br>**gccaatagggactttccattgacgtcaatgggtggactatttacggtaaactgcccacttggcagtacatcaagtgtatcatatg**<br>**ccaagtacgccccctattgacgtcaatgacggtaaatggcccgcctggcattatgcccagtacatgaccttatgggactttcct**<br>**acttggcagtacatctacgtattagtcatcgctattaccatggtgatgcggttttggcagtacatcaatgggcgtggatagcggttt**<br>**gactcacggggatttccaagtctccaccccattgacgtcaatgggagtttgttttggcaccaaaatcaacgggactttccaaaat**<br>**gtcgtaacaactccgccccattgacgcaaatgggcggtaggcgtgtacggtgggaggtctatataagcagagctc**tctggcta<br>actagagaacccactgcttactggcttatcgaaattaatacgactcactatagggagacccaagctggctagcgtttaaacttaagcttca<br>ccatgaacacgattaacatcgctaagaacgacttctctgacatcgaactggctgctatcccgttcaacactctggctgaccattacggtga<br>gcgtttagctcgcgaacagttggcccttgagcatgagtcttacgagatgggtgaaggcacgcttccgcaagatgtttgagcgtcaacttaaa<br>gctggtgaggttgcggataacgctgccaccaagcctctcatcactaccctactccctaagatgattgcacgcatcaacgactggtttgagg<br>aagtgaaagctaagcgcggcaagcgcccgacagccttccagttcctgcaagaaatcaagccggaagccgtagcgtacatcaccatta<br>agaccactctggcttgcctaaccagtgctgacaatacaaccgttcaggctgtagcaagcgcaatcggtcgggccattgaggacgaggct<br>cgcttcggtcgtatccgtgaccttgaagctaagcacttcaagaaaaacgttgaggaacaactcaacaagcgcgtagggcacgtctaca<br>agaaagcatttatgcaagttgtcgaggctgacatgctctctaagggtctactcggtggcgaggcgtggtcttcgtggcataaggaagactc<br>tattcatgtaggagtacgctgcatcgagatgctcattgagtcaaccggaatggttagcttacaccgccaaaatgctggcgtagtaggtcaa<br>gactctgagactatcgaactcgcacctgaatacgctgaggctatcgcaacccgtgcaggtgcgctggctggcatctctccgatgttccaac<br>cttgcgtagttcctcctaagccgtggactggcattactggtggtggctat-<br>tgggctaacggtcgtcgtcctctggcgctggtgcgtactcacag<br>taagaaagcactgatgcgctacgaagacgtttacatgcctgaggtgtacaaagcgattaacattgcgcaaaacaccgcaTggaaaat<br>caacaagaaagtcctagcggtcgccaacgtaatcaccaagtggaagcattgtccggtcgaggacatccctgcgattgagcgtgaaga<br>actcccgatgaaaccggaagacatcgacatgaatcctgaggctctcaccgcgtggaaacgtgctgccgctgctgtgtaccgcaaggac<br>aaggctcgcaagtctcgccgtatcagccttgagttcatgcttgagcaagccaataagtttgctaaccataaggccatctggttcccttacaa<br>catggactggcgcgatcgtatttacgctgtatcaatgttcaacccgcaaggtaacgatatgaccaaaggactgcttacgctggcgaaagg<br>taaaccaatcggtaaggaaggttactactggctgaaaatccacggtgcaaaactgtgcgggtgtcgataaggttccgttccctgagcgat<br>caagttcattgaggaaaaccacgagaacatcatggcttgcgctaagtctccactggagaacacttggtgggtgagcaagattctccgtt<br>ctgcttccttgcattctgctttgagtacgctggggtacagcaccaggcctgagc-<br>tataactgctcccttccgctggcgtttgacgggtcttgct<br>ctggcatccagcacttctccgcgatgctccgagatgaggtaggtggtcgcgcggttaacttgcttcctagtgaaaccgttcaggacatctac<br>gggattgttgctaagaaagtcaacgagattctacaagcagacgcaatcaatgggaccgataacgaagtagttaccgtgaccgatgaga<br>acactggtgaaatctctgagaaagtcaagctgggcactaaggcactggctggtcaatggctggcttacggtgttactcgcagtgtgactaa<br>gcgttcagtcatgacgctggcttacgggtccaaagagttcggcttccgtcaacaagtgctggaagataccattcagccagctattgattccg<br>gcaagggtctgatgttcactcagccgaatcaggctgctggatacatggctaagctgAtttgggaatctgtgagcgtgacggtggtagctgc<br>ggttgaagcaatgaactggcttaagtctgctgctaagctgctggctgctgaggtcaaagataagaagactggagagattcttcgcaagcg<br>ttgcgctgtgcattgggtaactcctgatggtttccctgtgtggcaggaatacaagaagcc-<br>tattcagacgcgcttgaacctgatgttcctcggt<br>cagttccgcttacagcctaccattaacaccaacaaagatagcgagattggatgcacaaacaggagtctggtatcgctcctaactttgtac<br>acagccaagacggtagccaccttcgtaagactgtagtgtgggcacacgagaagtacggaatcgaatcttttgcactgattcacgactcct<br>tcggtaccattccggctgacgctgcgaacctgttcaaagcagtgcgcgaaactatggttgacacatatgagtcttgtgatgtactggctgatt<br>tctacgaccagttcgctgaccagttgcacgagtctcaattggacaaaatgccagcacttccggctaaaggtaacttgaacctccgtgacat<br>cttagagtcggacttcgcgttcgcgtaa | CMV promoter (2-588)<br>CDS (690-3341) |

-continued

Listing of sequences

| SEQ ID NO | Description | Source | Type | Features |
|---|---|---|---|---|
| 41 | NES-T7 RNA polymerase expression cassette containing "T-REx" promoter comprising two tetO sequences | artificial sequence synthetic | **gacattgattattgactagttattaatagtaatcaattacggggtcattagttcatagcccatatatggagttccgcgttacataactt**<br>**acggtaaatggcccgcctggctgaccgcccaacgacccccgcccattgacgtcaataatgacgtatgttcccatagtaacgc**<br>**caatagggactttccattgacgtcaatgggtggagtatttacggtaaactgcccacttggcagtacatcaagtgtatcatatgcc**<br>**aagtacgccccctattgacgtcaatgacggtaaatggcccgcctggcattatgcccagtacatgaccttatgggactttcctact**<br>**tggcagtacatctacgtattagtcatcgctattaccatggtgatgcggttttggcagtacatcaatgggcgtggatagcggtttga**<br>**ctcacggggatttccaagtctccaccccattgacgtcaatgggagtttgttttggcaccaaaatcaacgggactttccaasatgt**<br>**cgtaacaactccgccccattgacgcsaatgggcggtaggcgtgtacggtgggaggtctatataagcagagctctccctatca**<br>**gtgatagaga**tc**tccctatcaqtcatagaga**tcgtcgacgagctcgtttagtgaaccgtcagatcgcctggagacgccatccacgctgt<br>tttgacctccatagaagacaccgggaccgatccagcctccggactctagcgtttaaacatcacaagtttgtacaaaaaagcaggcgcta<br>gcgtttaaacttaagcttcaccatgtgcccggtgccgctgcagctgccgccgctggaacgcctgaccctggataacacgattaacatcgct<br>aagaacgacttctctgacatcgaactggctgctatcccgttcaacactctggctgaccattacggtgagcgtttagctcgcgaacagttggc<br>ccttgagcatgagtcttacgagatgggtgaagcacgcttccgcaagatgtttgagcgtcaacttaaagctggtgaggttgcggataacgct<br>gccgccaagcctctcatcactaccctactccctaagatgattgcacgcatcaacgactggtttgaggaagtgaaagctaagcgcggcaa<br>gcgcccgacagccttccagttcctgcaagaaatcaagccggaagccgtagcgtacatcaccattaagaccactctggcttgcctaacca<br>gtgctgacaatacaaccgttcaggctgtagcaagcgcaatcggtcgggccattgaggacgaggctcgcttcggtcgtatccgtgaccttg<br>aagctaagcacttcaagaaaaacgttgaggaacaactcaacaacgcgtagggcacgtctacaagaagcatttatgcaagttgtcg<br>aggctgacatgctctctaagggtctactcggtggcgaggcgtggtcttcgtggcataaggaagactctattcatgtaggagtacgctgcatc<br>gagatgctcattgagtcaaccggaatggttagcttacaccgccaaaatgctggcgtagtaggtcaagactctgagactatcgaactcgca<br>cctgaatacgctgaggctatcgcaacccgtgcaggtgcgctggctggcatctctccgatgttccaaccttgcgtagttcctcctaagccgtg<br>gactggcattactggtggtggctattgggctaacggtcgtcgtcctctggcgctggtgcgtactcacagtaagaaagcactgatgcgctac<br>gaagacgtttacatgcctgaggtgtgtacaaagcgattaacattgcgcaaaacaccgcaTggaaaatcaacaagaaagtcctagcggtc<br>gccaacgtaatcaccaagtggaagcattgtccggtcgaggacatccctgcgattgagcgtgaagaactcccgatgaaaccggaagac<br>atcgacatgaatcctgaggctctcaccgcgtggaaacgtgctgccgctgctatgtaccgcaaggacaaggctcgcaagtctcgccgtat<br>cagccttgagttvcatgcttgagcaagccaataagtttgctaaccataaggc-<br>catctggttcccttacaacatggactggcgcggtcgtgttta<br>cgctgtgcaatgttcaacccgcaaggtaacgatatgaccaaaggactgcttacgctggcgaaaggtaaaccaatcggtaaggaaggtt<br>actactggctgaaaatccacggtgcaaactgtgcgggtgtcgataaggttccgttccctgagcgcatcaagttcattgaggaaaccacg<br>agaacatcatggcttgcgctaagtctccactggagaacacttggtgggctgagcaagat-<br>tctccgttctgcttccttgcgttctgctttgagtac<br>gctggggtacagcaccacggcctgagctataactgctcccttccgctggcgtttgacgggtcttgctctggcatccagcacttctccgcgat<br>gctccgagatgaggtaggtggtcgcgcggttaacttgcttcctagtgaaaccgttcaggacatctacgggattgttgctaagaaagtcaac<br>gagattctacaagcagacgcaatcaatgggaccgataacgaagtagttaccgtgaccgatgagaacactggtgaaatctcgagaaa<br>gtcaagctgggcactaaggcactggctggtcaatggctggcttacggtgttactcgcagtgtgactaagcgttcagtcatgacgctggctta<br>cgggtccaaagagttcggcttccgtcaacaagtgctggaagataccattcagccagctattgattccggcaagggtctgatgttcactcag<br>ccgaatcaggctgctggatactggctaagctgatttgggaatctgtgagcgtgacggtggtagctgcggttgaagcaatgaactggctta<br>agtctgctgctaagctgctggctgctgaggtcaaagataagaagactggagagattcttcgcaagcgttgcgctgtgcattgggtaactcct<br>gatggtttccctgtgtggcaggaatacaagaagcctattcagacgcgttgaacctgatgttcctcggtcagttccgcttacagcctaccatt<br>aacaccaacaaagatagcgagattgatgcacacaaacaggagtctggtatcgctcctaactttgtacacagccaagacggtagccaccc<br>ttcgtaagactgtagtgtgggcacacgagaagtacggaatcgaatcttttgcactgattcacgactccttcggtaccattccggctgacgct<br>gcgaacctgttcaaagcagtgcgcgaaactatggttgacacatatgagtcttgtgatgtactggctgatttctacgaccagttcgctgacca<br>gttgcacgagtctcaattggacaaaatgccagcacttccggctaaaggtaacttgaacctccgtgactcttagagtcggacttcgcgttcg<br>cgtaa | Promoter (1-584)<br>tetO (586-604; 607-625)<br>NES (798-845)<br>CDS (846-3494) |

-continued

| Listing of sequences | | | | |
|---|---|---|---|---|
| SEQ ID NO | Description | Source | Type | Features |
| 42 | NES-T7 RNA polymerase expression cassette containing "Tet-On" promoter comprising 8 tetO sequences | artificial sequence synthetic | **caattgctcgagtttactccctatcagtgatagagaacgtatgtcgactttactccctatcagtgagaacgtatgaagagttt**<br>**actccctatcagtgatagagaacgtatgcagactttactccctatcactcatagagaacgtataaggagtttactccctatcagtg**<br>**atagagaacgtatgaccagtttactccctatcagtgatagagaacgtatctacagtttactccctatcagtgatagagaacgtata**<br>**tccagtttactccctatcagtgatagagaacgtatacgctttaggcgtgtacggtgggcgcctataaaagcagagctcgtttagt**<br>**gaaccgtcagatcgcctggagcaattccacaacacttttgtcttataccaactttccgtaccacttcctaccctcgaaagtccata**<br>**tggctagcctgcagggatccagatatca**agcttgccaccatgtgcccggtgccgctgcagctgccgccgctggaacgcctgaccctg<br>gataacacgattaacatcgctaagaacgacttctctgacatcgaactggctgctatcccgttcaacactctggctgaccattacggtgagc<br>gtttagctcgcgaacagttggcccttgagcatgagtcttacgagatgggtgaagcacgcttccgcaagatgtttgagcgtcaacttaaagct<br>ggtgaggttgcggataacgctgccgccaagcctctcatcactaccctactccctaagatgattgcacgatcaacgactggtttgaggaa<br>gtgaaagctaagcgcggaagcgcccgacagccttccagttcctgcaagaaatcaagccggaagccgtagcgtacatcaccattaag<br>accactctggcttgcctaaccagtgctgacaatacaaccgttcaggctgtagcaagcgcaatcggtcgggccattgaggacgaggctcg<br>cttcggtcgtatccgtgaccttgaagctaagcacttcaagaaaaacgttgaggaacaactcaacaagcgcgtaggcacgtctacaag<br>aaagcatttatgcaagttgtcaggctgacatgctctaagggtctactcggtggcgaggcgtggtcttcgtggcataaggaagactat<br>tcatgtaggagtacgctgcatcgagatgctcattgagtcaaccggaatggttagcttacaccgccaaaatgctggcgtagtaggtcaaga<br>ctctgagactatcgaactcgcacctgaatacgctgaggctatcgcaacccgtgcaggtgcgctggctggcatctctccgatgttccaacctt<br>gcgtagttcctcctaagccgtggactggcattactggtggtggctattgggctaacggtcgtcgtcctctggcgctggtgcgtactcacagta<br>agaaagcactgatgcgctacgaagacgtttacatgcctgaggtgtacaaagcgattaacattgcgcaaaacaccgcaTggaaaatca<br>acaagaaagtcctagcggtcgccaacgtaatcaccaagtggaagcattgtccggtcgaggacatccctgcgattgagcgtgaagaact<br>cccgatgaaaccggaagacatcgacatgaatcctgaggctctcaccgcgtggaaacgtgctgccgctgctgtgtaccgcaaggacaa<br>ggctcgcaagtctcgccgtatcagccttgagttcatgcttgagcaagccaataagtttgctaaccataaggccatctggttcccttacaacat<br>ggactggcgcggtcgtgtttacgctgtcaatgttcaacccgcaaggtaacgatatgaccaaaggactgcttacgctggcgaaaggtaa<br>accaatcggtaaggaaggttactactggctgaaaatccacggtgcaaactgtgcgggtgcgataaggttccgttccctgagcgcatcaa<br>gttcattgaggaaaaccacgagaacatcatggcttgcgctaagtctccactggagaacacttggtgggctgagcaagattctccgttctgc<br>ttccttgcgttctgctttgagtacgctggggtacagcaccacggcctgagc-<br>tataactgctcccttccgctggcgtttgacgggtcttgctctgg<br>catccagcacttctccgcgatgctccgagatgaggtaggtggtcgcgcggttaacttgcttcctagtgaaaccgttcaggacatctacggg<br>attgttgctaagaaagtcaacgagattctacaagcagacgcaatcaatgggaccgataacgaagtagttaccgtgaccgatgagaaca<br>ctggtgaaatctctgagaaagtcaagctgggcactaaggcactggctggtcaatggctggcttacggtgttactcgcagtgtgactaagca<br>ttcagtcatgacgctggcttacgggtccaaagagttcggcttccgtcaacaagtgctggaagataccattcagccagctattgattccggca<br>agggtctgatgttcactcagccgaatcaggctgctggatacatggctaagctgatttgggaatctgtgagcgtgacggtggtagctgcggtt<br>gaagcaatgaactggcttaagtctgctgctaagctgctggctgctgaggtcaagataagaagactggagagattcttcgcaagcgttgc<br>gctgtgcattgggtaactcctgatggtttccctgtgtggcaggaatacaagaagcctattcagacgcgcttgaactgatgttcctcggtcag<br>ttccgcttacagcctaccattaacaccaacaaagatagcgagattgatgcacacaaacaggagtctggtatcgctcctaactttgtacaca<br>gccaagacggtagccaccttcgtaagactgtagtgtgggcacagagaagtacggaatcgaatcttttgcactgattcacgactccttcg<br>gtaccattccggctgacgctgcgaacctgttcaaagcagtgcgcgaaactatggttgacacatatgagtcttgtgatgtactggctgatttct<br>acgaccagttcgctgaccagttgcacgagtctcaattggacaaaatgccagcacttccggctaaaggctaacttgaacctccgtgactctt<br>agagtcggacttcgcgttcgcgtaa | Promoter (1-458)<br>tetO (18-36; 54-72; 90-108; 126-144; 162-180; 198-216; 234-252: 270-288)<br>NES (473-520)<br>CDS (521-3169) |
| 43 | NES-17 RNA polymerase expression cassette for constitutive expression via CMV promoter | artificial sequence synthetic | **gttgacattgattattgactagttattaatagtaatcaattacggggtcattagttcatagcccatatatggagttccgcgttacataa**<br>**cttacggtaaatggcccgcctggctgaccgcccaacgacccccgcccattgacgtcaataatgacgtatgttcccatagtaac**<br>**gccaatagggactttccattgacgtcaatgggtggactatttacggtaaactgcccacttggcagtacatcaagtgtatcatatg**<br>**ccaagtacgccccctattgacgtcaatgacggtaaatggcccgcctggcattatgcccagtacatgaccttatgggactttcct**<br>**acttggcagtacatctacgtattagtcatcgctattaccatggtgatgcggttttggcagtacatcaatgggcgtggatagcggttt**<br>**gactcacggggatttccaagtctccaccccattgacgtcaatgggagtttgttttggcaccaaaatcaacgggactttccaaaat**<br>**gtcgtaacaactccgccccattgacgcaaatgggcggtaggcgtgtacggtgggaggtctatataagcagagctc**tctggcta<br>actagagaacccactgcttactggcttatcgaaattaatacgactcactatagggagacccaagctggctagcgtttaaacttaagcttca | CMV promoter (1-588)<br>NES (693-740)<br>CDS (741-3389) |

-continued

| Listing of sequences | | | | |
|---|---|---|---|---|
| SEQ ID NO | Description | Source | Type | Features |
| | | | ccatgtgcccggtgccgctgcagctgccgccgctggaacgcctgaccctggataacacgattaacatcgctaagaacgacttctctgac<br>atcgaactggctgctatcccgttcaacactctggctgaccattacggtgagcgtttagctcgcgaacagttggcccttgagcatgagtcttac<br>gagatgggtgaagcacgcttccgcaagatgtttgagcatcaacttaaagctggtgaggttacggataacgctgccgccaagcctctcatc<br>actaccctactccctaagatgattgcacgcatcaacgactggtttgaggaagtgaaagctaagcgcggcaagcgcccgacagccttcc<br>agttcctgcaagaaatcaagccggaagccgtagcgtacatcaccattaagaccactctggcttgcctaaccagtgctgacatacaacc<br>gttcaggctgtagcaagcgcaatcggtcgggccattgaggacgaggctcgcttcggtcgtatccgtgaccttgaagctaagcacttcaag<br>aaaaacgttgaggaacaactcaacaagcgcgtagggcacgtctacaagaaagcatttatgcaagttgtcgaggctgacatgctctctaa<br>gggtctactcggtggcgaggcgtggtcttcgtggcataaggaagactctattcatgtaggagtacgtgcatcgagatgctcattgagtca<br>accggaatggttagcttacaccgccaaaatgctggcgtagtaggtcaagactctgagactatcgaactcgcacctgaatacgctgaggc<br>tatcgcaaccgtgcaggtgcgctggctggcatctctccgatgttccaaccttgcgtagttcctcctaagccgtggactggcattactggtgg<br>tggctattgggctaacggtcgtcgtcctctggcgctggtgcgtactcacagtaagaaagcactgatgcgctacgaagacgtttacatgcct<br>gaggtgtacaaagcgattaacattgcgcaaaacaccgcaTggaaaatcaacaagaagtcctagcggtcgccaacgtaatcaccaa<br>gtggaagcattgtccggtcgaggacatccctgcgattgagcgtgaagaactcccgatgaaaccggaagacatcgacatgaatcctgag<br>gctctcaccgcgtggaaacgtgctgccgctgctgtgtaccgcaaggacaaggctcgcaagtctcgccgtatcagccttgagttcatgcttg<br>agcaagccaataagtttgctaaccataaggccatctggttcccttacaacatggactggcgcggtcgtatttacgctgtgtcaatgttcaacc<br>cgcaaggtaacgatatgaccaaaggactgcttacgctggcgaaaggtaaaccaatcggtaaggaaggttactactggctgaaaatcc<br>acggtgcaaactgtgcgggtgtcgataaggttccggttccctgagcgcatcaagttcattgaggaaaaccacgagaacatcatggcttgcg<br>ctaagtctccactggagaacacttggtgggctgagcaagat-<br>tctccgttctgcttccttgcgttctgctttgagtacgctggggtacagcacca<br>cggcctgagctataactgctcccttccgctggcgtttgacgggtcttgctctggcatccagcacttctccgcgatgctccgagatgaggtagg<br>tggtcgcgcggttaacttgcttcctagtgaaaccgttcaggacatctacgggattgttgctaagaaagtcaacgagattctacaagcagac<br>gcaatcaatgggaccgataacgaagtagttaccgtgaccgatgagaacactggtaaatctctgagaaagtcaagctgggcactaag<br>gcactggctggtcaatggctggcttacggtgttactcgcagtgtgactaagcgttcagtcatgacgctggcttacgggtccaaagagttcgg<br>cttccgtcaacaagtgctggaagataccattcagccagctattgattccggcaagggtctgatgttcactcagccgaatcaggctgctggat<br>acatggctaagctgatttgggaatctgtgagcgtgacggtggtagctgcggttgaagcaatgaactggcttaagtctgctgctaagctgctg<br>gctgctgaggtcaaagataagaagactggagagattcttcgcaagcgttgcgctgtgcattgggtaactcctgatggtttccctgtgtggca<br>ggaatacaagaagcctattcagacgcgcttgaacctgatgttcctcggtcagttccgcttacagcctaccattaacaccaacaaagatag<br>cgagattgatgcacacaaacaggagtctggtatcgctcctaactttgtacacagccaagacggtagccaccttcgtaagactgtagtgtg<br>ggcacacgagaagtacggaatcgaatcttttgcactgattcacgactccttcggtaccattccggctgacgctgcgaacctgttcaaagca<br>gtgcgcgaaactatggttgacacatatgagtcttgtgatgtactggctgatttc-<br>tacgaccagttcgctgaccagttgcacgagtctcaattgg<br>acaaaatgccagcacttccggctaaaggtaacttgaacctccgtgacatcttagagtcggacttcgcgttcgcgtaa | |
| 44 | PylRS$^{AF}$ expression cassette for constitutive expression via CMV promoter | artificial sequence synthetic | **gttgacattgattattgactagttattaatagtaatcaattacggggtcattagttcatagcccatatatggagttccgcgttacataa**<br>**cttacggtaaatggcccgcctggctgaccgcccaacgacccccgcccattgacgtcaataatgacgtatgttcccatagtaac**<br>**gccaatagggactttccattgacgtcaatgggggactatttacggtaaactgcccacttggcagtacatcaagtgtatcatatg**<br>**ccaagtacgccccctattgacgtcaatgacggtaaatggcccgcctggcattatgcccagtacatgaccttatgggactttcct**<br>**acttggcagtacatctacgtattagtcatcgctattaccatggtgatgcggttttggcagtacatcaatgggcgtggatagcggttt**<br>**gactcacggggatttccaagtctccaccccattgacgtcaatgggagtttgttttggcaccaaaatcaacgggactttccaasat**<br>**gtcgtaacaactccgccccattgacgcaaatgggcggtaggcgtgtacggtgggaggtctatataagcagagctctc**tggcta<br>actagagaacccactgcttactggcttatcgaaattaatacgactcactatagggagacccaagctggctagcgtttaaacttaagcttca<br>ccatggataaaaaaccactgaataccctgatctctcctactcgtctatcgatcactcatacccgaaccattcataaaatcaaacaccacg<br>aggttagccgttcgaaaatctatattgagatggcgtgtggcgatcatctggttgtgaacaatagccgctcttctcgtacagcacgtgcactgc<br>gtcaccacaaatatcgtaaaacctgtaaacgttgccgtgtgtccgatgaggatctgaacaaattcctgacaaagccaatgaggaccaa<br>acaagcgtgaaagtgaaagtcgttagcgtcctacccgtactaaaaagcaatgccgaaatccgttgctcgtgcccctaaaccactgga<br>aaacactgaagcagcacaggcacagccgtctggaagcaaattctctccggccattcctgtttctacccaggagtccgtttctgttccagca<br>agtgtgagcaccagcattagcagtattagcaccggtgccaccgctagcgccctggttaaaggcaataccaatccgattacaagcatgtct | CMV promoter (1-588)<br>CDS (690-2054)<br>306A, 384F |

-continued

| SEQ ID NO | Description | Source | Type | Features |
|---|---|---|---|---|
| | | | gccccggttcaagcatcagctccagcactgacaaaatcccaaaccgatcgtctggaggttctgctgaatccgaaagacgaaatcagcc<br>tgaattccggcaaaccgtttcgtgaactggagagcgaactgctgcacgtcgtaaaaaagacctgcaacaaatctatgccgaagaacgt<br>gagaactatctggggaaactggaacgtgaaatcacccgctttttcgtggatcgtggctttctggagatcaaatccccgattctgattcctctg<br>gagtatacgagcgtatgggcatcgacaatgataccgaactgagcaaacaaattttccgtgtggataaaacttctgtctgcgccctatgct<br>agcaccaaatctggctaactatctgcgcaaactggaccgtgccctgcctgatcctatcaaaatcttcgagatcggcccgtgttatcgtaaa<br>gagtccgacggtaaagaacatctggaggaggtttaccatgctgaacttttgccaaatgggttcaggtgtactcgtgagaacctggaaagc<br>atcatcaccgattttctgaaccacctgggcattgacttcaaaattgtgggcgacagctgtatggtgtttggcgacaccctggatgtcatgcac<br>ggcgacctggaactgtctagtgccgttgtgggcccaatcccgctggatcgtgagtggggtatcgacaaaccttggatcggtgcgggttttg<br>gtctggagcgtctgctgaaagtaaaacacgacttcaagaacatcaaacgtgctgcacgttccgagtcctatacaatggtatttctactaac<br>ctgtaa | |
| 45 | NES-PylRS[4F] expression cassette for constitutive expression via CMV promoter | artificial sequence synthetic | **gttgacattgattattgactagttattaatagtaatcaattacggggtcattagttcatagcccatatatggagttccgcgttacataa**<br>**cttacggtaaatggcccgcctggctgaccgcccaacgacccccgcccattgacgtcaataatgacgtatgttcccatagtaac**<br>**gccaatagggactttccattgacgtcaatgggggactatttacggtaaactgcccacttggcagtacatcaagtgtatcatatg**<br>**ccaagtacgccccctattgacgtcaatgacggtaaatggcccgcctggcattatgcccagtacatgaccttatgggactttcct**<br>**acttggcagtacatctacgtattagtcatcgctattaccatggtgatgcggttttggcagtacatcaatgggcgtggatagcggttt**<br>**gactcacggggatttccaagtctccaccccattgacgtcaatgggagtttgttttggcaccaaaatcaacgggactttccaaaat**<br>**gtcgtaacaactccgccccattgacgcaastgggcggtaggcgtgtacggtgggaggtctatataagcagagctc**tctggcta<br>actagagaacccactgcttactggcttatcgaaattaatacgactcactatagggagacccaagctggctagcgtttaaacttaagcttca<br>ccatggcgtgcccggtgccgctgcagctgccgccgctggaacgcctgacctggatgataaaaaaccgctgaataccctgatctcgct<br>actggtctgtggatgagtcgtaccggaaccattcataaaatcaaacaccacgaggttagccgttcgaaaatctatattgagatggcgtgtg<br>gcgatcatctggttgtgaacaatagccgctcttctcgtacagcacgtgcactgcgtcaccacaaatatctaaaacctgtaaacgttgccgt<br>gtgtccgatgaggatctgaacaaattcctgacaaaagccaatgaggaccaaacaagcgtgaaagtgaaagtcgttagcgctcctaccc<br>gtactaaaaaagcaatgccgaaatccgttgctcgtgcccctaaaccactggaaaacactgaagcagcacaggcacagccgtctggaa<br>gcaaattctctccggccattcctgtttctacccaggagtccgtttctgttccagcaagtgtgagcaccagcattagcagtattagcaccggtg<br>ccaccgctagcgccctggttaaaggcaataccaatccgattacaagcatgtctgccccggttcaagcatcagctccagcactgacaaaa<br>tcccaaaccgatcgtctggaggttctgctgaatccgaaagacgaaatcagcctgaattccggcaaaccgtttcgtgaactggagagcga<br>actgctgtcacgtgtaaaaaagacctgcaacaaatctatgccgaagaacgtgagaactatctggggaaactggaacgtgaaatcacc<br>cgctttttcgtggatcgtggctttctggagatcaaatccccgattctgaatcctctg-<br>gagtatatcgagcgtatgggcatcgacaatgataccg<br>aactgagcaaacaaattttccgtgtggataaaaacttctgtctgcgcctatgctagcaccaaatctggctaactactctgcgcaaactgga<br>ccgtgcctgcctgatcctatcaaaatcttcgagatcggcccgtgttatcgtaaagagtccgacggtaaagaacatctggaggagtttacc<br>atgctgaacttttgccaaatgggttcaggttgtactcgtgagaacctggaaagcatcatcaccgattttctgaaccacctgggcattgacttc<br>aaaattgtgggcgacagctgtatggtgtttggcgacaccctggatgtcatgcacggcgacctggaactgtctagtgccgttgtgggccca<br>atcccgctggatcgtgagtggggtatcgacaaaccttggatcggtgcgggttttggtctggagcgtctgctgaaagtaaaacacgacttca<br>agaacatcaaacgtgctgcacgttccgagtcctattacaatggtatttctactaacctgtaa | CMV promoter (1-588)<br>NES (696-743)<br>CDS (744-2105)<br>306A, 384F |
| 46 | NES-PylRS[4F] expression cassette containing "T-REx" promoter comprising two tetO sequences | artificial sequence synthetic | **gacattgattattgactagttattaatagtaatcaattacggggtcattagttcatagcccatatatggagttccgcgttacataactt**<br>**acggtaaatggcccgcctggctgaccgcccaacgacccccgcccattgacgtcaataatgacgtatgttcccatagtaacgc**<br>**caatagggactttccattgacgtcaatgggtggagtatttacggtaaactgcccacttggcagtacatcaagtgtatcatatgcc**<br>**aagtacgccccctattgacgtcaatgacggtaaatggcccgcctggcattatgcccagtacatgaccttatgggactttcctact**<br>**tggcagtacatctacgtattagtcatcgctattaccatggtgatgcggttttggcagtacatcaatgggcgtggatagcggtttga**<br>**ctcacggggatttccaagtctccaccccattgacgtcaatgggagtttgttttggcaccaaaatcaacgggactttccasaatgt**<br>**cgtaacaactccgccccattgacgcaaatgggcggtaggcgtgtacggtgggaggtctatataagcagagctctccctatca**<br>**gtaatacaga**tc**tccctatcagtgatagaga**tcgtcgacgagctcgtttagtgaaccgtcagatcgcctggagacgccatccacgctgt<br>tttgacctccatagaagacaccgggaccgatccagcctccggactctagcgtttaaacatcacaagtttglacaaaaaagcaggcgcta<br>gacaccatggcgtgcccggtgccgctgcagctgccgccgctggaacgcctgaccctggatgataaaaaaccgctgaataccctgatct | Promoter (1-584)<br>tetO (586-604; 607-625)<br>NES (785-832)<br>CDS (833-2194)<br>306A, 384F |

-continued

| Listing of sequences | | | | |
|---|---|---|---|---|
| SEQ ID NO | Description | Source | Type | Features |
| | | | ctgctactggtctgtggatgagtcgtaccggaaccattcataaaatcaaacaccacgaggttagccgttcgaaaatctatattgagatggc<br>gtgtggcgatcatctggttgtgaacaatagccgctcttctcgtacagcacgtgcactgcgtcaccacaaatatcgtaaaacctgtaaacgtt<br>gccgtgtgtccgatgaggatctgaacaaattcctgacaaaagccaatgaggaccaaacaagcgtgaaagtgaaagtcgttagcgctcc<br>tacccgtactaaaaagcaatgccgaatccgttgctcgtgcccctaaaccactggaaaacactgaagcagcacaggcacagccgtc<br>tggaagcaaattctctccggccattcctgtttctacccaggagtccgtttctgttccagcaagtgtgagcaccagcattagtattagcac<br>cggtgccaccgctagcgccctggttaaaggcaataccaatccgattacaagcatgtctgccccggttcaagcatcagctccagcactga<br>caaaatcccaaaccgatcgtctggaggttctgctgaatccgaaagacgaaatcagcctgaattccggcaaaccgtttcgtgaactggag<br>agcgaactgctgtcacgtcgtaaaaaagacctgcaacaaatctatgccgaagaacgtgagaactatctggggaaactggaacgtgaa<br>atcacccgctttttcgtggatcgtggctttctggagatcaaatccccgattctgattcctctggagtatacgagcgtatgggcatcgacaatg<br>ataccgaactgagcaaacaaattttccgtgtggataaaaacttctgtctgcgccctatgctagcaccaaatctggctaactatctgcgcaa<br>actggaccgtgccctgcctgatcctatcaaaatcttgagatcggcccgtgttatcgtaaagagtccgacggtaaagaacatctggagga<br>gtttaccatgctgaacttttgccaaatgggttcaggttgtactcgtgagaacctg-<br>gaaagcatcatcaccgattttctgaaccacctgggcatt<br>gacttcaaaattgtgggcgacagctgtatggtgtttggcgacaccctggatgtcagcacggcgacctggaactgtctagtgccgttgtgg<br>gccaatccgctggatcgtgagtggggtatcgacaaaccttggatcggtgcgggttttggtctggagcgtctgctgaaagtaaaacacg<br>acttcaagaacatcaaacgtgctgcacgttccgagtcctattacaatggtatttctactaacctgtaa | |
| 47 | NES-PyIRSAF expression cassette containing "Tet-On" promoter comprising 8 tetO sequences | artificial sequence synthetic | **caattgctcgagtttactccctatcactcatagagaacgtatgtcgactttactccctatcagtgatagagaacgtatgaagagttt**<br>**actccctatcagtgatagagaacgtatgcagactttactccctatcagtgatagagaacgtataaggagtttactccctatcagtg**<br>**atagagaacgtatgaccagtttactccctatcagtatagagaacgtatctacagtttactccctatcagtcatagagaacgtata**<br>**tccagtttactccctatcagtgatagagaacgtatacgctttaggcgtgtacggggcgcctataaaagcagagctcgtttagt**<br>**gaaccgtcagatcgcctggagcaattccacaacacttttgtcttataccaactttccgtaccacttcctaccctcgaaagtccata**<br>**tggctagcctgcagggatccagatatca**agcttcaccatggcgtgcccggtgccgctgcagctgccgccgctggaacgcctgaccct<br>ggatgataaaaaaccgctgaataccctgatctctgctactggtctgtggatgagtcgtaccggaaccattcataaaatcaaacaccacga<br>ggttagccgttcgaaaatctatattgagatggcgtgtggcgatcatctggttgtgaacaatagccgctcttctgtacagcacgtgcactgcg<br>tcaccacaaatatcgtaaaacctgtaaacgttgccgtgtgtccgatgaggatctgaacaaattcctgacaaaagccaatgaggaccaaa<br>caagcgtgaaagtgaaagtcgttagcgctcctacccgtactaaaaaagcaatgccgaaatccgttgctcgtgcccctaaaccactggaa<br>aacactgaagcagcacaggcacagccgtctggaagcaaattctctccggccattcctgtttctacccaggagtccgtttctgttccagcaa<br>gtgtgagcaccagcattagcagtattagcaccggtgccaccgctagcgccctggttaaaggcaataccaatccgattacaagcatgtctg<br>ccccggttcaagcatcagctccagcactgacaaaatcccaaaccgatcgtcggaggttctgctgaatccgaaagacgaaatcagcct<br>gaattccggcaaaccgtttcgtgaactggagagcgaactgctgtcacgtcgtaaaaaagacctgcaacaatctgccgaagaacgt<br>gagaactatctggggaaactggaacgtgaaatcacccgctttttcgtggatcgtggctttctggagatcaaatccccgattctgattcctctg<br>gagtatatcgagcgtatgggcatcgacaatgataccgaactgagcaaacaaattttccgtgtggataaaaacttctgtctgcgccctatgct<br>agcaccaaatctggctaactatctgcgcaaactggaccgtgccctgcctgatcctatcaaaatcttcgagatcggcccgtgttatcgtaaa<br>gagtccgacggtaaagaacatctggaggagtttaccatgctgaacttttgccaaatgggttcaggttgtactgtgagaacctggaaagc<br>atcatcaccgattttctgaaccacctgggcattgacttcaaaattgtgggcgacgctgtatggtgtttggcgacaccctggatgtcatgcac<br>ggcgacctggaactgtagtgccgttgtgggcccaatcccgctggatcgtgagtggggtatcgacaaacttggatcggtgcgggttttg<br>gtctggagcgtctgctgaaagtaaaacacgacttcaagaacatcaaacgtgctgcacgttccgagtcctattacaatggtatttctactaac<br>ctgtaa | Promoter (1-458)<br>tetO (18-36: 54-72; 90-108; 128-144; 162-180; 198-216; 234-252; 270-288)<br>NES (474-521)<br>CDS (522-1883)<br>306A, 384F |
| 48 | $tRNA^{Pyl}$ expression cassette for expression via T7 promoter | artificial sequence Synthetic | **taatacgactcactata**ggaaacctgatcatgtagatcgaatggactctaaatccgttcagccgggttagattcccggggtttccgtttttgg<br>ccgc**ctgctaacaaagcccgaaaggaagctgagttggctgctgccaccgctgagcaataactagcataaccccttggggcct**<br>**ctaaacgggtcttgaggggttttttgctgaaaggaggaactatatccggat** | T7 promoter (1-17)<br>$tRNA^{Pyl}$ (18-86)<br>T7term (98-226) |

-continued

Listing of sequences

| SEQ ID NO | Description | Source | Type | Features |
|---|---|---|---|---|
| 49 | tRNA$^{Pyl}$-HDV ribozyme expression cassette for expression via T7 promoter | artificial sequence synthetic | taatacgactcactataggaaacctgatcatgtagatcgaatggactctaaatccgttcagccgggttagattcccggggtttccggctag<br>ccatggtcccagcctcctcgctggcggctagtgggcaacatgcttcggcatggcgaatgggactttaaactcgagctgctaacaaagc<br>ccgaaaggaagctgagttggctgctgccaccgctgagcaataactagcataaccccttggggcctctaaacgggtcttgagg<br>ggtttttttgctgaaaggaggaactatatccggat | T7 promoter (1-17)<br>tRNA$^{Pyl}$ (18-86)<br>HDV (87-154)<br>T7term (167-295) |
| 50 | tRNA$^{Pyl}$ expression cassette containing a variant of the human U6 promoter modified to comprise 8 tetO before and two tetO sequences after the U6 promoter | artificial sequence synthetic | gaattccaattgctcgagtttactccctatcagtgatagagaacgtatgtcgactttactccctatcagtgatagagaacgtatgaagag<br>tttactccctatcagtgatagagaacgtatgcagactttactccctatcagtcatagagaacgtataaggagtttactccctatcagtg<br>atagagaacgtatgaccagttactccctatcagtgatagagaacgtatctacgtttactccctatcagtgatagagaacgtatacc<br>agtttactccctatcagtgatagagaacgtgtcgaaggcgtgtacggtcaaggtcgggcaggaagagggcctatttcccatg<br>attccttcatatttgcatatacgatacaaggctgttagagagataattagaattaatttgactgtaaacacaaagatattagtacaaa<br>atacgtgacgtagaaagtaataatttcttgggtagtttgcagttttaaaattatgttttaaaatggactatcatatgcttaccgtaactt<br>gaaagttccctatcagtgatagagattatatatctccctatcagtgatagagaccggaaacctgatcatgtagatcgaatggactctaa<br>atccgttcagcccggttagattccccgggtttccgtttttttagatcc | tetO sequences (24-42; 60-78; 96-114; 132-150; 168-186; 204-222; 276-294; 540-558; 568-586) U6 promoter (337-637)<br>tRNA$^{Pyl}$ (589-657) |
| 51 | tRNA$^{Pyl}$ expression cassette containing a variant of the human H1 promoter modified to comprise 2 tetO sequences | artificial sequence Synthetic | atatttgcatgtcgctatgtgttctgggaaatcaccataaacgtgaaatccctatcactgatagagacttataagttccctatcagt<br>gatagagatcccggaaacctgatcatgtagatcgaaggactctaaatccgttcagccgggttagattcccggggtttccgaagcttttt | tetO sequences (49-67; 77-95)<br>H1 promoter (1-99)<br>tRNA$^{Pyl}$ (100-168) |
| 56 | pCAGGS-T7-RNAP | artificial sequence synthetic | gacattgattattgactagttattaatagtaatcaattacggggtcattagttcatagcccatatatggagttccgcgttacataactt<br>acggtaaatggcccgcctggctgaccgcccaacgacccccgcccattgacgtcaataatgacgtatgttcccatagtaacgc<br>caatagggactttccattgacgtcaatgggtggagtatttacggtaaactgcccacttggcagtacatcaagtgtatcatatgcc<br>aagtacgccccctattgacgtcaatgacggtaaatggcccgcctggcattatgcccagtacatgaccttatgggactttcctact<br>tggcagtacatctacgtattagtcatcgctattaccatggtcgaggtgagccccacgttctgcttcactctccccatctcccccc<br>ctccccacccccaattttgtatttatttattttttaattattttgtgcagcgatgggggcgggggggggggggggcgcgcgcca<br>ggcggggcggggcggggcgaggggcggggcggggcgaggcggagaggtgcggcggcagccaatcagagcggcgc<br>gctccgaaagtttccttttatggcgaggcggcggcggcggcggccctataaaaagcgaagcgcgcggcgggcggggagtc<br>gctgcgacgctgccttcgccccgtgccccgctccgccgccgcctcgcgccgcccgccccggctctgactgaccgcgttactcccacagg<br>tgagcgggcgggacggcccttctcctccgggctgtaattagcgcttggtt-<br>taatgacggcttgtttcttttctgtggctgcgtgaaagccttgag | CMV enhancer (1-380)<br>Chicken b-actin promoter (382-659)<br>Chimeric intron chicken actin (661-1678)<br>T7-RNAP (1789-4437) |

-continued

| Listing of sequences | | | | |
|---|---|---|---|---|
| SEQ ID NO | Description | Source | Type | Features |
| | | | gggctccgggagggccctttgtgcggggggagcggctcggggggtgcgtgcgtgtgtgtgtgcgtggggagcgccgcgtgcggctccg | |
| | | | cgctgcccggcggctgtgagcgctgcgggcgcggcgcgggctttgtgcgtccgcagtgtgcgcgaggggagcgcggccgggggc | |
| | | | ggtgccccgcggtgcgggggggctgcgaggggaacaaaggctgcgtgcggggtggtcgtgggggggtgagcaggggtgtgg | |
| | | | gcgcgtcggtcgggctgcaaccccccctgcacccccctccccgagttgctgagcacggcccggcttcgggtgcggggctccgtacggg | |
| | | | gcgtggcgcggggctcgccgtgccgggcgggggtggcgggcaggtgggggtgccgggcggggcggggccgcctcgggccgggg | |
| | | | agggctcgggggaggggcgcggcggcccccggagcgccggcggctgtcgaggcgcggcgagccgcagccattgccttttatggtaa | |
| | | | tcgtgcgagagggcgcagggacttcctttgtcccaaatctgtgcggagccgaaatctgggaggcgccgccgcaccccctctagcgggc | |
| | | | gcggggcgaagcggtgcggcgccggcaggaaggaaatgggcggggaggccttcgtgcgtcgccgcgccgccgtccccttctccct | |
| | | | ctccagcctcggggctgtccgcgggggggacggctgccttcgggggggacggggcagggcggggttcggcttctggcgtgtgaccggc | |
| | | | ggctctagagcctctgctaaccatgttcatgccttgttctttttccta- | |
| | | | cagctcctgggcaacgtgctggttattgtgctgtctcatcattttg | |
| | | | gcaaagaattcgagctcatcggatccagatctgatccggatttactaactggaagaggcactaaatgaacacgattaacatcgctaagaacga | |
| | | | cttctctgacatcgaactggctgctatcccgttcaacactctggctgaccattacggt- | |
| | | | gagcgtttagcctcgcgaacagttggcccttgagca | |
| | | | tgagtcttacgagatgggtgaagcacgcttccgcaagatgtttgagcgtcaacttaaagctggtgaggttgcggataacgctgccgccaa | |
| | | | gcctctcatcactaccctactccctaagatgattgcacgcatcaacgactggtttgaggaagtgaaagctaagcgcggcaagcgcccga | |
| | | | cagccttccagttcctgcaagaaatcaagccggaagccgtagcgtacatcaccattaagaccactctggcttgcctaaccagtgctgaca | |
| | | | atacaaccgttcaggctgtagcaagcgcaatcggtcgggccattgaggacgaggctgcttcggtcgtatccgtgaccttgaagctaagc | |
| | | | acttcaagaaaaacgttgaggaacaactcaacaagcgcgtagggcacgtctacaagaaagcatttatgcaagttgtcgaggctgacat | |
| | | | gctctctaagggtctactcggtggcgaggcgtggtcttcttcgtggcataaggaagactc- | |
| | | | tattcatgtaggagtacgctgcatcgagatgctca | |
| | | | ttgagtcaaccggaatggttagcttacaccgccaaaatgctggcgtagtaggtcaagactctgagactatcgaactcgcacctgaatacg | |
| | | | ctgaggctatcgcaacccgtgcaggtgcgctggctggcatctccgatgttccaaccttgcgtagttcctcaagccgtggactggcatta | |
| | | | ctggtggtggctattgggctaacggtcgtcgtcctctggcgctggtgcgtactcacagtaagaaagcactgatgcgtacgaagacgttta | |
| | | | catgcctgaggtgtacaaagcgattaacattgcgcaaaacaccgcatggaaaatcaacaagaaagtcctagcggtcgccaacgtaat | |
| | | | caccaagtggaagcattgtccggtcgaggacatccctgcgattgagcgtgaagaactcccgatgaaaccggaagacatcgacatgaa | |
| | | | tcctgaggctctcaccgcgtggaaacgtgctgccgctgctgtaccgcaaggacaaggctcgcaagtctgccgtacagccttgagttc | |
| | | | atgcttgagcaagccaataagttgctaaccataaggccatctggttcccttacaacatggactggcgcggtcgtgtttacgtgtgcaatg | |
| | | | ttcaacccgcaaggtaacgatatgaccaaaggactgcttacgctggcgaaaggtaaaccaatcggtaaggaaggttactacggctga | |
| | | | aaatccacggtgcaaactgtgcgggtgtgataaggttccgttccctgagcgcatcaagttcattgaggaaaaccagagaacatcatg | |
| | | | gcttgcgctaagtctccactggagaacacttggtgggctgagcaagat- | |
| | | | tctccgttctgcttccttgcgttctgctttgagtacgctggggtaca | |
| | | | gcaccacggcctgagctataactgctcccttccgctggcgtttgacgggtcttgctctggcatccagcacttctccgcgargctccgagatg | |
| | | | aggtaggtggtcgcgcggttaacttgcttcctagtgaaaccgttcaggacatctacgggattgttgctaagaaagtcaacgagattctaca | |
| | | | agcagacgcaatcaatgggaccgataacgaagtagttaccgtgaccgatgagaacactggtgaaatctctgagaaagtcaagctggg | |
| | | | cactaaggcactggctggctggtcaatggctggcttacggtgt- | |
| | | | tactcgcagtgtgactaagcgttcagtcatgacgctggcttacgggtccaaa | |
| | | | gagttcggcttccgtcaacaagtgctggaagataccattcagccagctattgattccggcaagggtctgatgttcactcagccgaatcagg | |
| | | | ctgctggatacatggctaagctgatttgggaatctgtgagcgtgacggtggtagctgcggttgaagcaatgaactggcttaagtctgctgct | |
| | | | aagctgctggctgctgaggtcaaagataagaagactggagagattcttcgcaagcgttgcgctgtgcattgggtaactrcctgatggtttccc | |
| | | | tgtgtggcaggaatacaagaagcctattcagacgcgcttgaacctgatgttcctggtcagttccgcttacagcctaccattaacaccaac | |
| | | | aaagatagcgagattgatgcacacaaacaggagtctggtatcgctcctaactttgtacacagccaagacggtagccaccttcgtaagac | |
| | | | tgtagtgggcacacgagaagtacggaatcgaatcttttgcactgattcacgactccttggtaccattccggctgacgctgcgaacctgtt | |
| | | | caaagcagtgcgcgaaactatggttgacacatatgagtcttgtgatgtactggctgatttctacgaccagttcgctgaccagttgcacgagt | |
| | | | ctcaattggacaaaatgccagcacttccggctaaaggtaacttgaacctccgtgacatcttagagtcggacttcgcgttcgcgtaa | |

-continued

| Listing of sequences | | | | |
|---|---|---|---|---|
| SEQ ID NO | Description | Source | Type | Features |
| Further dsRNA-binding polypeptides | | | | |
| 57 | dsRNA-binding polypeptide (https://www.uniprot.org/uniprot/Q03963) | *Mus musculus* | MASDTPGFYMDKLNKYRQMHGVAITYKELSTSGPPHDRRFTFQVLIDEKEFPEAKGRSKQEARN<br>AAAKLAVDILDNENKVDCHTSASEQGLFVGNYIGLVNSFAQKKKLSVNYEQCEPNSELPQRFICK<br>CKIGQTMYGTGSGVTKQEAKQLAAKEAYQKLLKSPPKTAGTSSSVVTSTFSGFSSSSSMTSNGV<br>SQSAPGSFSSENVFTNGLGENKRKSGVKVSPDDVQRNKYTLDARFNSDFEDIEEIGLGGFGQVF<br>KAKHRIDGKRYAIKRVKYNTEKAEHEVQALAELNHVNIVQYHSCWEGVDYDPEHSMSDTSRYKT<br>RCLFIQMEFCDKGTLEQWMRNRNQSKVDKALILDLYEQIVTGVEYIHSKGLIHRDLKPGNIFLVDE<br>RHIKIGDFGLATALENDGKSRTRRTGTLQYMSPEQLFLKHYGKEVDIFALGLILAELLHTCFTESEKI<br>KFFESLRKGDFSNDIFDNKEKSLLKKLLSEKPKDRPETSEILKTLAEWRNISEKKKRNTC | |
| 58 | dsRNA-binding polypeptide (https://www.uniprot.org/uniprot/89UKH7) | *Pan troglodytes* | MAGDLSAGFFMEELNTYRQKQGVVLKYQELPNSGPPHDRRFTFRVIIDGREFPEGEGRSKKEAK<br>NAAAKLAVEILNKEKKAVSPLVLTTTNSSEGLSMGNYIGLINRIAQKKRLTVNYEQCASGVHGPEG<br>FHYKCKMGQKEYSIGTSSTKQEAKQLAAKLAYLQILSEETSVKSDYLSSGSFATTCDSQSNSLVT<br>STLASESSSEGDFSADTSEINSNSDSLNSSSLLMNGLRNNQRKAKRSLAPRFDLPDMKETKYTVD<br>KRFGMDFKEIELIGSGGFGQVFKAKHRIDGKTYVIKRVKYNNEKAEREVKALAKLDHVNIVHYNGC<br>WDGFDYDPETSDDDLESSDYDPENSKNSSRSKTKCLFIQMEFCDKGTLEQWIEDRRGKKLDKVL<br>ALELFEQITKGVDYIHSKKLIHRDLKPSNIFLVDTKQVKIGDFGLVTSLKNDGKRTRSKGTLRYMSP<br>EQISSQDYGKEVDLYALGLILAELLHVCDTAFETSKFFTDLRDGIISDILFDKKEKTLLQKLLSKKPE<br>DRPNTSEILRTLTVWKKSPEKNERHTC | |
| 59 | dsRNA-binding polypeptide (https://www.uniprot.org/uniprot/G3RTN4) | *Gorilla gorilla* | MAGDLSAGFFMEELNTYRQKQGVVLKYQELPNSGPPHDRRFTFRVIIDEREFPEGEGRSKKEAK<br>NAAAKLAVEILNKEKKAVSPLLLTTTNSSEGLSMGNYIGLINRIAQKKRLTVNYEQCASGVHGPEG<br>FHYKCKMGQKEYSIGTGSTKQEAKQLAAKLAYLQIVSEETSVKSDYLSSGSFATTCDSQSNSLVT<br>STLASESSSEGDFSADTSEINSNSDSLNSSSLLMNGLRNNQRKAKRSLAPRFDLPDMKETKYTVD<br>KRFGMDFKEIELIGSGGFGQVFKAKHRIDGKTYVIKRVKYNNEKAEREVKALAKLDHVNIVHYNGC<br>WDGVDYDPETSDDYLESSDYDPENSKNSSRSKTKCLFIQMEFCDKGTLEQWIENRRGEKLDKVL<br>ALELFEQITKGVDYIHSKKLIHRDLKPSNIFLVDTKQVKIGDFGLVTSLKNDGKRTRSKGTLRYMSP<br>EQISSQDYGKEVDLYALGLILAELLHVCDTAFETSKFFTDLRDGIISDIFDKKEKTLLQKLLSKKPED<br>RPNTSEILRTLTVWKKSPEKNERHTC | |
| 60 | pyrrolysyl tRNA of *Methanosarcina mazei* for unidentified codon (tRNA$^{Pyl,rem}$) | Artificial sequence Synthetic cf.: SEQ ID NOs: 25, 26 and 27 | ggaaacctgatcatgtagatcgaatggactnnnaatccgttcagccgggttagattcccggggtttccg | Underlined: unidentified anticodon (31-33) |

The invention claimed is:

1. An isolated eukaryotic cell comprising:

(a) a polynucleotide encoding a prokaryotic aminoacyl tRNA synthetase (pRS), (b) a polynucleotide encoding a prokaryotic tRNA (ptRNA) and one or more than one ribozyme, and (c) a polynucleotide encoding a dsRNA-binding polypeptide, wherein the pRS is capable of acylating the ptRNA, and wherein the sequences encoding the ptRNA and the ribozyme(s) are linked such that transcription produces an RNA molecule comprising both the ptRNA and the ribozyme(s) (ptRNA-ribozyme).

2. The eukaryotic cell of claim 1, wherein the ribozyme is selected from a hammerhead ribozyme, a hairpin ribozyme, a Varkud satellite ribozyme, a glucosamine-6-phosphate synthetase riboswitch and a hepatitis delta virus (HDV) ribozyme.

3. The eukaryotic cell of claim 1, wherein the ribozyme is a HDV ribozyme which, in the ptRNA-ribozyme, is directly linked to the 3' end of the ptRNA.

4. The eukaryotic cell of claim 1, wherein:

(i) transcriptional synthesis of the ptRNA-ribozyme is controlled by a tetracycline-responsive promoter element (TRE), or (ii) the ptRNA-ribozyme is transcriptionally synthesized by an RNA polymerase, wherein expression of said RNA polymerase is controlled by a TRE.

5. The eukaryotic cell of claim 1, wherein the transcription of the pRS-encoding sequence is controlled by a tetracycline-responsive promoter element (TRE).

6. The eukaryotic cell of claim 4, further comprising a polynucleotide encoding a protein which binds to a tetracycline operator (tetO) sequence (tetO-binding protein), wherein the tetO-binding protein is selected from the group consisting of:

(i) a tetracycline repressor (tetR), (ii) a tetracycline-controlled transcriptional activator (tTA), and (iii) a reverse tTA (rtTA).

7. The eukaryotic cell of claim 1, wherein:

(i) transcriptional synthesis of the ptRNA-ribozyme is controlled by a T7 promoter, and/or (ii) transcription of the pRS-encoding sequence is controlled by a T7 promoter, and wherein the eukaryotic cell further comprises (c) a polynucleotide encoding a T7 RNA polymerase (T7RNAP).

8. The eukaryotic cell of claim 7, wherein expression of the T7RNAP is controlled by a TRE.

9. The eukaryotic cell of claim 7, wherein the T7RNAP carries (i) a nuclear localization signal (NLS), or (ii) a nuclear export signal (NES), or (iii) none of NES and NLS.

* * * * *

SEQUENCE LISTING

<160> NUMBER OF SEQ ID NOS: 60

<210> SEQ ID NO 1
<211> LENGTH: 68
<212> TYPE: DNA
<213> ORGANISM: hepatitis delta virus
<220> FEATURE:
<221> NAME/KEY: misc_feature
<223> OTHER INFORMATION: hepatitis delta virus (HDV) ribozyme (Avis)
<220> FEATURE:
<221> NAME/KEY: misc_feature
<222> LOCATION: (1)..(6)
<223> OTHER INFORMATION: flanking sequence
<220> FEATURE:
<221> NAME/KEY: misc_feature
<222> LOCATION: (7)..(68)
<223> OTHER INFORMATION: HDV ribozyme core sequence

<400> SEQUENCE: 1
gcuagccaug gucccagccu ccucgcuggc ggcuaguggg caacaugcuu cggcauggcg 60
aaugggac 68

<210> SEQ ID NO 2
<211> LENGTH: 67
<212> TYPE: DNA
<213> ORGANISM: hepatitis delta virus
<220> FEATURE:
<221> NAME/KEY: misc_feature
<223> OTHER INFORMATION: hepatitis delta virus (HDV) ribozyme (Schuerer)

<400> SEQUENCE: 2
gggtcggcat ggcatctcca cctcctcgcg gtccgacctg ggctacttcg gtaggctaag 60
ggagaag 67

<210> SEQ ID NO 3
<211> LENGTH: 56
<212> TYPE: DNA
<213> ORGANISM: hepatitis delta virus
<220> FEATURE:
<221> NAME/KEY: misc_feature
<223> OTHER INFORMATION: hepatitis delta virus (HDV) ribozyme (Akoopie)

<400> SEQUENCE: 3
gagggatagt acagagcctc cccgtggctc ccttggataa ccaactgata ctgtac 56

<210> SEQ ID NO 4
<211> LENGTH: 50
<212> TYPE: DNA
<213> ORGANISM: Artificial Sequence
<220> FEATURE:
<223> OTHER INFORMATION: hammerhead ribozyme
<220> FEATURE:
<221> NAME/KEY: misc_feature
<222> LOCATION: (1)..(10)
<223> OTHER INFORMATION: flanking sequence
<220> FEATURE:
<221> NAME/KEY: misc_feature
<222> LOCATION: (11)..(45)
<223> OTHER INFORMATION: ribozyme core sequence
<220> FEATURE:
<221> NAME/KEY: misc_feature
<222> LOCATION: (46)..(50)
<223> OTHER INFORMATION: flanking sequence

<400> SEQUENCE: 4
ucagguuucc cugaugaguc cgugaggacg aaacgguacc cgguaccguc 50

<210> SEQ ID NO 5

<211> LENGTH: 92
<212> TYPE: DNA
<213> ORGANISM: Artificial Sequence
<220> FEATURE:
<223> OTHER INFORMATION: hairpin ribozyme

<400> SEQUENCE: 5
ggagagagaa gucaaccaga gaaacacacc aacccauugc acuccggguu ggugguauau 60
uaccugguac gggggaaacu ucguggugge cg 92

<210> SEQ ID NO 6
<211> LENGTH: 176
<212> TYPE: DNA
<213> ORGANISM: Neurospora intermedia
<220> FEATURE:
<221> NAME/KEY: misc_feature
<223> OTHER INFORMATION: Varkud satellite (VS) ribozyme

<400> SEQUENCE: 6
gggaaagcuu gcgaagggcg ucgucgcccc gagcgguagu aagcagggaa cucaccucca 60
auuucaguac ugaaauuguc guagcaguug acuacuguua ugugauuggu agaggcuaag 120
ugacgguauu ggcguaaguc aguauugcag cacagcacaa gcccgcuugc gagaau 176

<210> SEQ ID NO 7
<211> LENGTH: 152
<212> TYPE: DNA
<213> ORGANISM: Bacillus sp.
<220> FEATURE:
<221> NAME/KEY: misc_feature
<223> OTHER INFORMATION: glucosamine-6-phosphate synthetase (glmS)
      riboswitch (glmS ribozyme)

<400> SEQUENCE: 7
gcgccagaac tggcaccauu gcacuccggu gccaguugac gagguggggu uuaucgagau 60
uucggcggau gacucccggu uguucaucac aaccgcaagc uuuuacuuaa aucauuaagg 120
ugacuuagug gacaaaggug aaagugugau ga 152

<210> SEQ ID NO 8
<211> LENGTH: 19
<212> TYPE: DNA
<213> ORGANISM: Artificial Sequence
<220> FEATURE:
<223> OTHER INFORMATION: tetracycline operator (tetO)

<400> SEQUENCE: 8
tccctatcag tgatagaga 19

<210> SEQ ID NO 9
<211> LENGTH: 59
<212> TYPE: DNA
<213> ORGANISM: Artificial Sequence
<220> FEATURE:
<223> OTHER INFORMATION: minimal cytomegalovirus (CMV) promoter

<400> SEQUENCE: 9
gtaggcgtgt acggtgggag gtctatataa gcagagctcg tttagtgaac cgtcagatc 59

<210> SEQ ID NO 10
<211> LENGTH: 467
<212> TYPE: DNA
<213> ORGANISM: Artificial sequence
<220> FEATURE:
<223> OTHER INFORMATION: “Tet-On” promoter comprising 8 tetO sequences
<220> FEATURE:

```
<221> NAME/KEY: misc_feature
<222> LOCATION: (18)..(36)
<223> OTHER INFORMATION: tetO sequence
<220> FEATURE:
<221> NAME/KEY: misc_feature
<222> LOCATION: (54)..(72)
<223> OTHER INFORMATION: tetO sequence
<220> FEATURE:
<221> NAME/KEY: misc_feature
<222> LOCATION: (90)..(208)
<223> OTHER INFORMATION: tetO sequence
<220> FEATURE:
<221> NAME/KEY: misc_feature
<222> LOCATION: (126)..(144)
<223> OTHER INFORMATION: tetO sequence
<220> FEATURE:
<221> NAME/KEY: misc_feature
<222> LOCATION: (162)..(180)
<223> OTHER INFORMATION: tetO sequence
<220> FEATURE:
<221> NAME/KEY: misc_feature
<222> LOCATION: (198)..(216)
<223> OTHER INFORMATION: tetO sequence
<220> FEATURE:
<221> NAME/KEY: misc_feature
<222> LOCATION: (234)..(252)
<223> OTHER INFORMATION: tetO sequence
<220> FEATURE:
<221> NAME/KEY: misc_feature
<222> LOCATION: (270)..(288)
<223> OTHER INFORMATION: tetO sequence

<400> SEQUENCE: 10

caattgctcg agtttactcc ctatcagtga tagagaacgt atgtcgactt tactccctat     60

cagtgataga gaacgtatga agagtttact ccctatcagt gatagagaac gtatgcagac    120

tttactccct atcagtgata gagaacgtat aaggagttta ctccctatca gtgatagaga    180

acgtatgacc agtttactcc ctatcagtga tagagaacgt atctacagtt tactccctat    240

cagtgataga gaacgtatat ccagtttact ccctatcagt gatagagaac gtatacgctt    300

taggcgtgta cggtgggcgc ctataaaagc agagctcgtt tagtgaaccg tcagatcgcc    360

tggagcaatt ccacaacact tttgtcttat accaactttc cgtaccactt cctaccctcg    420

aaagtccata tggctagcct gcagggatcc agatatcaag cttcacc                  467


<210> SEQ ID NO 11
<211> LENGTH: 425
<212> TYPE: DNA
<213> ORGANISM: Artificial sequence
<220> FEATURE:
<223> OTHER INFORMATION: “Tet-On” promoter comprising 7 tetO sequences
<220> FEATURE:
<221> NAME/KEY: misc_feature
<222> LOCATION: (12)..(30)
<223> OTHER INFORMATION: tetO sequences
<220> FEATURE:
<221> NAME/KEY: misc_feature
<222> LOCATION: (48)..(66)
<223> OTHER INFORMATION: tetO sequences
<220> FEATURE:
<221> NAME/KEY: misc_feature
<222> LOCATION: (84)..(102)
<223> OTHER INFORMATION: tetO sequences
<220> FEATURE:
<221> NAME/KEY: misc_feature
<222> LOCATION: (120)..(138)
<223> OTHER INFORMATION: tetO sequences
<220> FEATURE:
<221> NAME/KEY: misc_feature
<222> LOCATION: (156)..(174)
<223> OTHER INFORMATION: tetO sequences
<220> FEATURE:
<221> NAME/KEY: misc_feature
```

<222> LOCATION: (192)..(210)
<223> OTHER INFORMATION: tetO sequences
<220> FEATURE:
<221> NAME/KEY: misc_feature
<222> LOCATION: (228)..(246)
<223> OTHER INFORMATION: tetO sequences

<400> SEQUENCE: 11

```
ctcgacttta ctccctatca gtgatagaga acgtatgaag agtttactcc ctatcagtga     60

tagagaacgt atgcagactt tactccctat cagtgataga gaacgtataa ggagtttact    120

ccctatcagt gatagagaac gtatgaccag tttactccct atcagtgata gagaacgtat    180

ctacagttta ctccctatca gtgatagaga acgtatatcc agtttactcc ctatcagtga    240

tagagaacgt atacgcttta ggcgtgtacg gtgggcgcct ataaaagcag agctcgttta    300

gtgaaccgtc agatcgcctg gagcaattcc acaacacttt tgtcttatac caactttccg    360

taccacttcc taccctcgaa agtccatatg gctagcctgc agggatccag atatcaagct    420

tcacc                                                                425
```

<210> SEQ ID NO 12
<211> LENGTH: 794
<212> TYPE: DNA
<213> ORGANISM: Artificial Sequence
<220> FEATURE:
<223> OTHER INFORMATION: "T-REx" promoter comprising two tetO sequences
<220> FEATURE:
<221> NAME/KEY: misc_feature
<222> LOCATION: (1)..(380)
<223> OTHER INFORMATION: CMV enhancer
<220> FEATURE:
<221> NAME/KEY: misc_feature
<222> LOCATION: (381)..(584)
<223> OTHER INFORMATION: CMV promoter
<220> FEATURE:
<221> NAME/KEY: misc_feature
<222> LOCATION: (586)..(604)
<223> OTHER INFORMATION: tetO sequence
<220> FEATURE:
<221> NAME/KEY: misc_feature
<222> LOCATION: (607)..(625)
<223> OTHER INFORMATION: tetO sequence

<400> SEQUENCE: 12

```
gacattgatt attgactagt tattaatagt aatcaattac ggggtcatta gttcatagcc     60

catatatgga gttccgcgtt acataactta cggtaaatgg cccgcctggc tgaccgccca    120

acgacccccg cccattgacg tcaataatga cgtatgttcc catagtaacg ccaataggga    180

ctttccattg acgtcaatgg gtggagtatt tacggtaaac tgcccacttg gcagtacatc    240

aagtgtatca tatgccaagt acgcccccta ttgacgtcaa tgacggtaaa tggcccgcct    300

ggcattatgc ccagtacatg accttatggg actttcctac ttggcagtac atctacgtat    360

tagtcatcgc tattaccatg gtgatgcggt tttggcagta catcaatggg cgtggatagc    420

ggtttgactc acggggattt ccaagtctcc accccattga cgtcaatggg agtttgtttt    480

ggcaccaaaa tcaacgggac tttccaaaat gtcgtaacaa ctccgcccca ttgacgcaaa    540

tgggcggtag gcgtgtacgg tgggaggtct atataagcag agctctccct atcagtgata    600

gagatctccc tatcagtgat agagatcgtc gacgagctcg tttagtgaac cgtcagatcg    660

cctggagacg ccatccacgc tgttttgacc tccatagaag acaccgggac cgatccagcc    720

tccggactct agcgtttaaa catcacaagt ttgtacaaaa aagcaggcgc tagcgtttaa    780

acttaagctt cacc                                                      794
```

<210> SEQ ID NO 13
<211> LENGTH: 207
<212> TYPE: PRT
<213> ORGANISM: Artificial Sequence
<220> FEATURE:
<223> OTHER INFORMATION: tetracycline repressor (tetR)
UniProtKB/Swiss-Prot accession no.: P04483.1

<400> SEQUENCE: 13

```
Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205
```

<210> SEQ ID NO 14
<211> LENGTH: 1442
<212> TYPE: DNA
<213> ORGANISM: Artificial Sequence
<220> FEATURE:
<223> OTHER INFORMATION: rtTA expression cassette
<220> FEATURE:
<221> NAME/KEY: misc_feature
<222> LOCATION: (1)..(588)
<223> OTHER INFORMATION: CMV
<220> FEATURE:
<221> NAME/KEY: misc_feature
<222> LOCATION: (696)..(1442)
<223> OTHER INFORMATION: TetOn3G

<400> SEQUENCE: 14

```
gttgacattg attattgact agttattaat agtaatcaat tacggggtca ttagttcata     60

gcccatatat ggagttccgc gttacataac ttacggtaaa tggcccgcct ggctgaccgc    120

ccaacgaccc ccgcccattg acgtcaataa tgacgtatgt tcccatagta acgccaatag    180

ggactttcca ttgacgtcaa tgggtggact atttacggta aactgcccac ttggcagtac    240

atcaagtgta tcatatgcca agtacgcccc ctattgacgt caatgacggt aaatggcccg    300

cctggcatta tgcccagtac atgaccttat gggactttcc tacttggcag tacatctacg    360
```

```
tattagtcat cgctattacc atggtgatgc ggttttggca gtacatcaat gggcgtggat    420

agcggtttga ctcacgggga tttccaagtc tccaccccat tgacgtcaat gggagtttgt    480

tttggcacca aaatcaacgg gactttccaa aatgtcgtaa caactccgcc ccattgacgc    540

aaatgggcgg taggcgtgta cggtgggagg tctatataag cagagctctc tggctaacta    600

gagaacccac tgcttactgg cttatcgaaa ttaatacgac tcactatagg gagacccaag    660

ctggctagcg tttaaactta agcttctcga gcaccatgtc tagactggac aagagcaaag    720

tcataaactc tgctctggaa ttactcaatg gagtcggtat cgaaggcctg acgacaagga    780

aactcgctca aaagctggga gttgagcagc ctaccctgta ctggcacgtg aagaacaagc    840

gggccctgct cgatgccctg ccaatcgaga tgctggacag gcatcatacc cactcctgcc    900

ccctggaagg cgagtcatgg caagactttc tgcggaacaa cgccaagtca taccgctgtg    960

ctctcctctc acatcgcgac ggggctaaag tgcatctcgg cacccgccca acagagaaac   1020

agtacgaaac cctggaaaat cagctcgcgt tcctgtgtca gcaaggcttc tccctggaga   1080

acgcactgta cgctctgtcc gccgtgggcc actttacact gggctgcgta ttggaggaac   1140

aggagcatca agtagcaaaa gaggaaagag agacacctac caccgattct atgcccccac   1200

ttctgaaaca agcaattgag ctgttcgacc ggcagggagc cgaacctgcc ttccttttcg   1260

gcctggaact aatcatatgt ggcctggaga aacagctaaa gtgcgaaagc ggcgggccga   1320

ccgacgccct tgacgatttt gacttagaca tgctcccagc cgatgccctt gacgactttg   1380

accttgatat gctgcctgct gacgctcttg acgattttga ccttgacatg ctccccgggt   1440

aa                                                                  1442


<210> SEQ ID NO 15
<211> LENGTH: 18
<212> TYPE: DNA
<213> ORGANISM: Artificial Sequence
<220> FEATURE:
<223> OTHER INFORMATION: T7 promoter class III (core)
<220> FEATURE:
<221> NAME/KEY: misc_feature
<222> LOCATION: (18)..(18)
<223> OTHER INFORMATION: G at position 18 is preferred nucleotide at
      the +1 position to promote efficient transcription initiation

<400> SEQUENCE: 15

taatacgact cactatag                                                   18


<210> SEQ ID NO 16
<211> LENGTH: 19
<212> TYPE: DNA
<213> ORGANISM: Artificial Sequence
<220> FEATURE:
<223> OTHER INFORMATION: T7 promoter class III
<220> FEATURE:
<221> NAME/KEY: misc_feature
<222> LOCATION: (18)..(19)
<223> OTHER INFORMATION: GG at positions 18 and 19 are preferred
      nucleotides at the +1 and +2 positions to promote efficient
      transcription initiation

<400> SEQUENCE: 16

taatacgact cactatagg                                                  19


<210> SEQ ID NO 17
<211> LENGTH: 18
<212> TYPE: DNA
<213> ORGANISM: Artificial Sequence
```

```
<220> FEATURE:
<223> OTHER INFORMATION: T7 promoter class II (core)
<220> FEATURE:
<221> NAME/KEY: misc_feature
<222> LOCATION: (18)..(18)
<223> OTHER INFORMATION: A at position 18 is preferred nucleotide at
      the +1 position of the gene to promote efficient transcription
      initiation

<400> SEQUENCE: 17

taatacgact cactatta                                                  18


<210> SEQ ID NO 18
<211> LENGTH: 883
<212> TYPE: PRT
<213> ORGANISM: Enterobacteria phage T7

<400> SEQUENCE: 18

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
```

```
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735
```

Gln Glu Tyr Lys Lys Pro Ile Gln Thr Arg Leu Asn Leu Met Phe Leu
740 745 750

Gly Gln Phe Arg Leu Gln Pro Thr Ile Asn Thr Asn Lys Asp Ser Glu
755 760 765

Ile Asp Ala His Lys Gln Glu Ser Gly Ile Ala Pro Asn Phe Val His
770 775 780

Ser Gln Asp Gly Ser His Leu Arg Lys Thr Val Val Trp Ala His Glu
785 790 795 800

Lys Tyr Gly Ile Glu Ser Phe Ala Leu Ile His Asp Ser Phe Gly Thr
805 810 815

Ile Pro Ala Asp Ala Ala Asn Leu Phe Lys Ala Val Arg Glu Thr Met
820 825 830

Val Asp Thr Tyr Glu Ser Cys Asp Val Leu Ala Asp Phe Tyr Asp Gln
835 840 845

Phe Ala Asp Gln Leu His Glu Ser Gln Leu Asp Lys Met Pro Ala Leu
850 855 860

Pro Ala Lys Gly Asn Leu Asn Leu Arg Asp Ile Leu Glu Ser Asp Phe
865 870 875 880

Ala Phe Ala

<210> SEQ ID NO 19
<211> LENGTH: 899
<212> TYPE: PRT
<213> ORGANISM: Artificial Sequence
<220> FEATURE:
<223> OTHER INFORMATION: NES-T7 RNA polymerase
<220> FEATURE:
<221> NAME/KEY: MISC_FEATURE
<222> LOCATION: (2)..(17)
<223> OTHER INFORMATION: NES

<400> SEQUENCE: 19

Met Cys Pro Val Pro Leu Gln Leu Pro Pro Leu Glu Arg Leu Thr Leu
1 5 10 15

Asp Asn Thr Ile Asn Ile Ala Lys Asn Asp Phe Ser Asp Ile Glu Leu
20 25 30

Ala Ala Ile Pro Phe Asn Thr Leu Ala Asp His Tyr Gly Glu Arg Leu
35 40 45

Ala Arg Glu Gln Leu Ala Leu Glu His Glu Ser Tyr Glu Met Gly Glu
50 55 60

Ala Arg Phe Arg Lys Met Phe Glu Arg Gln Leu Lys Ala Gly Glu Val
65 70 75 80

Ala Asp Asn Ala Ala Ala Lys Pro Leu Ile Thr Thr Leu Leu Pro Lys
85 90 95

Met Ile Ala Arg Ile Asn Asp Trp Phe Glu Glu Val Lys Ala Lys Arg
100 105 110

Gly Lys Arg Pro Thr Ala Phe Gln Phe Leu Gln Glu Ile Lys Pro Glu
115 120 125

Ala Val Ala Tyr Ile Thr Ile Lys Thr Thr Leu Ala Cys Leu Thr Ser
130 135 140

Ala Asp Asn Thr Thr Val Gln Ala Val Ala Ser Ala Ile Gly Arg Ala
145 150 155 160

Ile Glu Asp Glu Ala Arg Phe Gly Arg Ile Arg Asp Leu Glu Ala Lys
165 170 175

His Phe Lys Lys Asn Val Glu Glu Gln Leu Asn Lys Arg Val Gly His
180 185 190

```
Val Tyr Lys Lys Ala Phe Met Gln Val Val Glu Ala Asp Met Leu Ser
        195                 200                 205

Lys Gly Leu Leu Gly Gly Glu Ala Trp Ser Ser Trp His Lys Glu Asp
    210                 215                 220

Ser Ile His Val Gly Val Arg Cys Ile Glu Met Leu Ile Glu Ser Thr
225                 230                 235                 240

Gly Met Val Ser Leu His Arg Gln Asn Ala Gly Val Val Gly Gln Asp
                245                 250                 255

Ser Glu Thr Ile Glu Leu Ala Pro Glu Tyr Ala Glu Ala Ile Ala Thr
            260                 265                 270

Arg Ala Gly Ala Leu Ala Gly Ile Ser Pro Met Phe Gln Pro Cys Val
        275                 280                 285

Val Pro Pro Lys Pro Trp Thr Gly Ile Thr Gly Gly Gly Tyr Trp Ala
    290                 295                 300

Asn Gly Arg Arg Pro Leu Ala Leu Val Arg Thr His Ser Lys Lys Ala
305                 310                 315                 320

Leu Met Arg Tyr Glu Asp Val Tyr Met Pro Glu Val Tyr Lys Ala Ile
                325                 330                 335

Asn Ile Ala Gln Asn Thr Ala Trp Lys Ile Asn Lys Lys Val Leu Ala
            340                 345                 350

Val Ala Asn Val Ile Thr Lys Trp Lys His Cys Pro Val Glu Asp Ile
        355                 360                 365

Pro Ala Ile Glu Arg Glu Glu Leu Pro Met Lys Pro Glu Asp Ile Asp
    370                 375                 380

Met Asn Pro Glu Ala Leu Thr Ala Trp Lys Arg Ala Ala Ala Ala Val
385                 390                 395                 400

Tyr Arg Lys Asp Lys Ala Arg Lys Ser Arg Arg Ile Ser Leu Glu Phe
                405                 410                 415

Met Leu Glu Gln Ala Asn Lys Phe Ala Asn His Lys Ala Ile Trp Phe
            420                 425                 430

Pro Tyr Asn Met Asp Trp Arg Gly Arg Val Tyr Ala Val Ser Met Phe
        435                 440                 445

Asn Pro Gln Gly Asn Asp Met Thr Lys Gly Leu Leu Thr Leu Ala Lys
    450                 455                 460

Gly Lys Pro Ile Gly Lys Glu Gly Tyr Tyr Trp Leu Lys Ile His Gly
465                 470                 475                 480

Ala Asn Cys Ala Gly Val Asp Lys Val Pro Phe Pro Glu Arg Ile Lys
                485                 490                 495

Phe Ile Glu Glu Asn His Glu Asn Ile Met Ala Cys Ala Lys Ser Pro
            500                 505                 510

Leu Glu Asn Thr Trp Trp Ala Glu Gln Asp Ser Pro Phe Cys Phe Leu
        515                 520                 525

Ala Phe Cys Phe Glu Tyr Ala Gly Val Gln His His Gly Leu Ser Tyr
    530                 535                 540

Asn Cys Ser Leu Pro Leu Ala Phe Asp Gly Ser Cys Ser Gly Ile Gln
545                 550                 555                 560

His Phe Ser Ala Met Leu Arg Asp Glu Val Gly Gly Arg Ala Val Asn
                565                 570                 575

Leu Leu Pro Ser Glu Thr Val Gln Asp Ile Tyr Gly Ile Val Ala Lys
            580                 585                 590

Lys Val Asn Glu Ile Leu Gln Ala Asp Ala Ile Asn Gly Thr Asp Asn
        595                 600                 605
```

Glu Val Val Thr Val Thr Asp Glu Asn Thr Gly Glu Ile Ser Glu Lys
    610                 615                 620

Val Lys Leu Gly Thr Lys Ala Leu Ala Gly Gln Trp Leu Ala Tyr Gly
625                 630                 635                 640

Val Thr Arg Ser Val Thr Lys Arg Ser Val Met Thr Leu Ala Tyr Gly
                645                 650                 655

Ser Lys Glu Phe Gly Phe Arg Gln Gln Val Leu Glu Asp Thr Ile Gln
            660                 665                 670

Pro Ala Ile Asp Ser Gly Lys Gly Leu Met Phe Thr Gln Pro Asn Gln
        675                 680                 685

Ala Ala Gly Tyr Met Ala Lys Leu Ile Trp Glu Ser Val Ser Val Thr
    690                 695                 700

Val Val Ala Ala Val Glu Ala Met Asn Trp Leu Lys Ser Ala Ala Lys
705                 710                 715                 720

Leu Leu Ala Ala Glu Val Lys Asp Lys Lys Thr Gly Glu Ile Leu Arg
                725                 730                 735

Lys Arg Cys Ala Val His Trp Val Thr Pro Asp Gly Phe Pro Val Trp
            740                 745                 750

Gln Glu Tyr Lys Lys Pro Ile Gln Thr Arg Leu Asn Leu Met Phe Leu
        755                 760                 765

Gly Gln Phe Arg Leu Gln Pro Thr Ile Asn Thr Asn Lys Asp Ser Glu
    770                 775                 780

Ile Asp Ala His Lys Gln Glu Ser Gly Ile Ala Pro Asn Phe Val His
785                 790                 795                 800

Ser Gln Asp Gly Ser His Leu Arg Lys Thr Val Val Trp Ala His Glu
                805                 810                 815

Lys Tyr Gly Ile Glu Ser Phe Ala Leu Ile His Asp Ser Phe Gly Thr
            820                 825                 830

Ile Pro Ala Asp Ala Ala Asn Leu Phe Lys Ala Val Arg Glu Thr Met
        835                 840                 845

Val Asp Thr Tyr Glu Ser Cys Asp Val Leu Ala Asp Phe Tyr Asp Gln
    850                 855                 860

Phe Ala Asp Gln Leu His Glu Ser Gln Leu Asp Lys Met Pro Ala Leu
865                 870                 875                 880

Pro Ala Lys Gly Asn Leu Asn Leu Arg Asp Ile Leu Glu Ser Asp Phe
                885                 890                 895

Ala Phe Ala

<210> SEQ ID NO 20

<400> SEQUENCE: 20

000

<210> SEQ ID NO 21
<211> LENGTH: 7
<212> TYPE: PRT
<213> ORGANISM: Simian vacuolating virus 40 (SV40)

<400> SEQUENCE: 21

Pro Lys Lys Lys Arg Lys Val
1               5

<210> SEQ ID NO 22
<211> LENGTH: 1416
<212> TYPE: DNA
<213> ORGANISM: Artificial Sequence
<220> FEATURE:
<223> OTHER INFORMATION: Methanosarcina mazei PylRS Y306A, Y384F mutant
(PylRSAF)
<220> FEATURE:
<221> NAME/KEY: misc_feature
<222> LOCATION: (1)..(3)
<223> OTHER INFORMATION: ATG coding for M may be missing

<400> SEQUENCE: 22
atggcgtgcc cggtgccgct gcagctgccg ccgctggaac gcctgaccct ggatgataaa 60
aaaccgctga ataccctgat ctctgctact ggtctgtgga tgagtcgtac cggaaccatt 120
cataaaatca aacaccacga ggttagccgt tcgaaaatct atattgagat ggcgtgtggc 180
gatcatctgg ttgtgaacaa tagccgctct tctcgtacag cacgtgcact gcgtcaccac 240
aaatatcgta aaacctgtaa acgttgccgt gtgtccgatg aggatctgaa caaattcctg 300
acaaaagcca atgaggacca aacaagcgtg aaagtgaaag tcgttagcgc tcctacccgt 360
actaaaaaag caatgccgaa atccgttgct cgtgccccta aaccactgga aaacactgaa 420
gcagcacagg cacagccgtc tggaagcaaa ttctctccgg ccattcctgt ttctacccag 480
gagtccgttt ctgttccagc aagtgtgagc accagcatta gcagtattag caccggtgcc 540
accgctagcg ccctggttaa aggcaatacc aatccgatta caagcatgtc tgccccggtt 600
caagcatcag ctccagcact gacaaaatcc caaaccgatc gtctggaggt tctgctgaat 660
ccgaaagacg aaatcagcct gaattccggc aaaccgtttc gtgaactgga gagcgaactg 720
ctgtcacgtc gtaaaaaaga cctgcaacaa atctatgccg aagaacgtga gaactatctg 780
gggaaactgg aacgtgaaat cacccgcttt ttcgtggatc gtggctttct ggagatcaaa 840
tccccgattc tgattcctct ggagtatatc gagcgtatgg gcatcgacaa tgataccgaa 900
ctgagcaaac aaattttccg tgtggataaa aacttctgtc tgcgccctat gctagcacca 960
aatctggcta actatctgcg caaactggac cgtgccctgc ctgatcctat caaaatcttc 1020
gagatcggcc cgtgttatcg taaagagtcc gacggtaaag aacatctgga ggagtttacc 1080
atgctgaact tttgccaaat gggttcaggt tgtactcgtg agaacctgga aagcatcatc 1140
accgattttc tgaaccacct gggcattgac ttcaaaattg tgggcgacag ctgtatggtg 1200
tttggcgaca ccctggatgt catgcacggc gacctggaac tgtctagtgc cgttgtgggc 1260
ccaatcccgc tggatcgtga gtggggtatc gacaaacctt ggatcggtgc gggttttggt 1320
ctggagcgtc tgctgaaagt aaaacacgac ttcaagaaca tcaaacgtgc tgcacgttcc 1380
gagtcctatt acaatggtat ttctactaac ctgtaa 1416

<210> SEQ ID NO 23
<211> LENGTH: 1416
<212> TYPE: DNA
<213> ORGANISM: Artificial Sequence
<220> FEATURE:
<223> OTHER INFORMATION: Methanosarcina mazei PylRS N346A, C348A mutant
(PylRSAA)

<400> SEQUENCE: 23
atggcgtgcc cggtgccgct gcagctgccg ccgctggaac gcctgaccct ggatgacaaa 60
aaaccgctga ataccctgat ctctgctact ggtctgtgga tgagtcgtac cggaaccatt 120
cataaaatca aacaccacga ggttagccgt tcgaaaatct atattgagat ggcgtgtggc 180
gatcatctgg ttgtgaacaa tagccgctct tctcgtacag cacgtgcact gcgtcaccac 240
aaatatcgta aaacctgtaa acgttgccgt gtgtccgatg aggatctgaa caaattcctg 300

```
acaaaagcca atgaggacca aacaagcgtg aaagtgaaag tcgttagcgc tcctacccgt    360
actaaaaaag caatgccgaa atccgttgct cgtgccccta aaccactgga aaacactgaa    420
gcagcacagg cacagccgtc tggaagcaaa ttctctccgg ccattcctgt ttctacccag    480
gagtccgttt ctgttccagc aagtgtgagc accagcatta gcagtattag caccggtgcc    540
accgctagcg ccctggttaa aggcaatacc aatccgatta caagcatgtc tgccccggtt    600
caagcatcag ctccagcact gacaaaatcc caaaccgatc gtctggaggt tctgctgaat    660
ccgaaagacg aaatcagcct gaattccggc aaaccgtttc gtgaactgga gagcgaactg    720
ctgtcacgtc gtaaaaaaga cctgcaacaa atctatgccg aagaacgtga gaactatctg    780
gggaaactgg aacgtgaaat cacccgcttt ttcgtggatc gtggctttct ggagatcaaa    840
tccccgattc tgattcctct ggagtatatc gagcgtatgg gcatcgacaa tgataccgaa    900
ctgagcaaac aaattttccg tgtggataaa aacttctgtc tgcgccctat gctggcacca    960
aatctgtata actatctgcg caaactggac cgtgccctgc ctgatcctat caaaatcttc   1020
gagatcggcc cgtgttatcg taaagagtcc gacggtaaag aacatctgga ggagtttacc   1080
atgctggcct ttgcccaaat gggttcaggt tgtactcgtg agaacctgga aagcatcatc   1140
accgatttc tgaaccacct gggcattgac ttcaaaattg tgggcgacag ctgtatggtg   1200
tatggcgaca ccctggatgt catgcacggc gacctggaac tgtctagtgc cgttgttgga   1260
ccaattccgc tggaccgtga gtggggtatc gacaaaccgt ggatcggagc aggattcggt   1320
ctggaacgcc tgctgaaagt gaaacacgac ttcaaaaaca tcaaacgtgc cgcccgttct   1380
gaatcgtatt ataacgggat ctctacgaac ctgtaa                             1416
```

```
<210> SEQ ID NO 24
<211> LENGTH: 1413
<212> TYPE: DNA
<213> ORGANISM: Artificial Sequence
<220> FEATURE:
<223> OTHER INFORMATION: Methanosarcina mazei PylRS Y306A, N346A, C348A,
      Y384Fmutant (PylRSAAAF)

<400> SEQUENCE: 24

gcgtgcccgg tgccgctgca gctgccgccg ctggaacgcc tgaccctgga tgataaaaaa     60
ccgctgaata ccctgatctc tgctactggt ctgtggatga gtcgtaccgg aaccattcat    120
aaaatcaaac accacgaggt tagccgttcg aaaatctata ttgagatggc gtgtggcgat    180
catctggttg tgaacaatag ccgctcttct cgtacagcac gtgcactgcg tcaccacaaa    240
tatcgtaaaa cctgtaaacg ttgccgtgtg tccgatgagg atctgaacaa attcctgaca    300
aaagccaatg aggaccaaac aagcgtgaaa gtgaaagtcg ttagcgctcc tacccgtact    360
aaaaaagcaa tgccgaaatc cgttgctcgt gcccctaaac cactggaaaa cactgaagca    420
gcacaggcac agccgtctgg aagcaaattc tctccggcca ttcctgtttc tacccaggag    480
tccgtttctg ttccagcaag tgtgagcacc agcattagca gtattagcac cggtgccacc    540
gctagcgccc tggttaaagg caataccaat ccgattacaa gcatgtctgc cccggttcaa    600
gcatcagctc cagcactgac aaaatcccaa accgatcgtc tggaggttct gctgaatccg    660
aaagacgaaa tcagcctgaa ttccggcaaa ccgtttcgtg aactggagag cgaactgctg    720
tcacgtcgta aaaaagacct gcaacaaatc tatgccgaag aacgtgagaa ctatctgggg    780
aaactggaac gtgaaatcac ccgctttttc gtggatcgtg gctttctgga gatcaaatcc    840
ccgattctga ttcctctgga gtatatcgag cgtatgggca tcgacaatga taccgaactg    900
```

-continued

```
agcaaacaaa ttttccgtgt ggataaaaac ttctgtctgc gccctatgct agcaccaaat    960

ctggctaact atctgcgcaa actggaccgt gccctgcctg atcctatcaa aatcttcgag   1020

atcggcccgt gttatcgtaa agagtccgac ggtaaagaac atctggagga gtttaccatg   1080

ctggcctttg cccaaatggg ttcaggttgt actcgtgaga acctggaaag catcatcacc   1140

gattttctga accacctggg cattgacttc aaaattgtgg gcgacagctg tatggtgttt   1200

ggcgacaccc tggatgtcat gcacggcgac ctggaactgt ctagtgccgt tgtgggccca   1260

atcccgctgg atcgtgagtg ggtatcgac aaaccttgga tcggtgcggg ttttggtctg   1320

gagcgtctgc tgaaagtaaa acacgacttc aagaacatca aacgtgctgc acgttccgag   1380

tcctattaca atggtatttc tactaacctg taa                                1413
```

```
<210> SEQ ID NO 25
<211> LENGTH: 69
<212> TYPE: DNA
<213> ORGANISM: Artificial Sequence
<220> FEATURE:
<223> OTHER INFORMATION: pyrrolysyl tRNA of Methanosarcina mazei for
      Amber codon (tRNAPyl,CUA)
<220> FEATURE:
<221> NAME/KEY: misc_feature
<222> LOCATION: (31)..(33)
<223> OTHER INFORMATION: anticodon

<400> SEQUENCE: 25

ggaaacctga tcatgtagat cgaatggact ctaaatccgt tcagccgggt tagattcccg     60

gggtttccg                                                             69


<210> SEQ ID NO 26
<211> LENGTH: 69
<212> TYPE: DNA
<213> ORGANISM: Artificial Sequence
<220> FEATURE:
<223> OTHER INFORMATION: pyrrolysyl tRNA of Methanosarcina mazei for
      Opal codon (tRNAPyl,UCA)
<220> FEATURE:
<221> NAME/KEY: misc_feature
<222> LOCATION: (31)..(33)
<223> OTHER INFORMATION: anticodon

<400> SEQUENCE: 26

ggaaacctga tcatgtagat cgaatggact tcaaatccgt tcagccgggt tagattcccg     60

gggtttccg                                                             69


<210> SEQ ID NO 27
<211> LENGTH: 69
<212> TYPE: DNA
<213> ORGANISM: Artificial Sequence
<220> FEATURE:
<223> OTHER INFORMATION: pyrrolysyl tRNA of Methanosarcina mazei for
      Ochre codon (tRNAPyl,UUA)
<220> FEATURE:
<221> NAME/KEY: misc_feature
<222> LOCATION: (31)..(33)
<223> OTHER INFORMATION: anticodon

<400> SEQUENCE: 27

ggaaacctga tcatgtagat cgaatggact ttaaatccgt tcagccgggt tagattcccg     60

gggtttccg                                                             69


<210> SEQ ID NO 28
<211> LENGTH: 6
<212> TYPE: PRT
```

```
<213> ORGANISM: Artificial Sequence
<220> FEATURE:
<223> OTHER INFORMATION: NES motif
<220> FEATURE:
<221> NAME/KEY: MISC_FEATURE
<222> LOCATION: (1)..(1)
<223> OTHER INFORMATION: Xaa is selected from Leu, Ile, Val, Phe and Met
<220> FEATURE:
<221> NAME/KEY: MISC_FEATURE
<222> LOCATION: (2)..(3)
<223> OTHER INFORMATION: Xaa is selected from any canonical amino acid
<220> FEATURE:
<221> NAME/KEY: MISC_FEATURE
<222> LOCATION: (4)..(4)
<223> OTHER INFORMATION: Xaa is selected from Leu, Ile, Val, Phe and Met
<220> FEATURE:
<221> NAME/KEY: MISC_FEATURE
<222> LOCATION: (5)..(5)
<223> OTHER INFORMATION: Xaa is selected from any canonical amino acid
<220> FEATURE:
<221> NAME/KEY: MISC_FEATURE
<222> LOCATION: (6)..(6)
<223> OTHER INFORMATION: Xaa is selected from Leu, Ile, Val, Phe and Met

<400> SEQUENCE: 28

Xaa Xaa Xaa Xaa Xaa Xaa
1               5


<210> SEQ ID NO 29
<211> LENGTH: 7
<212> TYPE: PRT
<213> ORGANISM: Artificial Sequence
<220> FEATURE:
<223> OTHER INFORMATION: NES motif
<220> FEATURE:
<221> NAME/KEY: MISC_FEATURE
<222> LOCATION: (1)..(1)
<223> OTHER INFORMATION: Xaa is selected from Leu, Ile, Val, Phe and Met
<220> FEATURE:
<221> NAME/KEY: MISC_FEATURE
<222> LOCATION: (2)..(4)
<223> OTHER INFORMATION: Xaa is selected from any canonical amino acid
<220> FEATURE:
<221> NAME/KEY: MISC_FEATURE
<222> LOCATION: (5)..(5)
<223> OTHER INFORMATION: Xaa is selected from Leu, Ile, Val, Phe and Met
<220> FEATURE:
<221> NAME/KEY: MISC_FEATURE
<222> LOCATION: (6)..(6)
<223> OTHER INFORMATION: Xaa is selected from any canonical amino acid
<220> FEATURE:
<221> NAME/KEY: MISC_FEATURE
<222> LOCATION: (7)..(7)
<223> OTHER INFORMATION: Xaa is selected from Leu, Ile, Val, Phe and Met

<400> SEQUENCE: 29

Xaa Xaa Xaa Xaa Xaa Xaa Xaa
1               5


<210> SEQ ID NO 30
<211> LENGTH: 9
<212> TYPE: PRT
<213> ORGANISM: Artificial Sequence
<220> FEATURE:
<223> OTHER INFORMATION: NES motif
<220> FEATURE:
<221> NAME/KEY: MISC_FEATURE
<222> LOCATION: (2)..(3)
<223> OTHER INFORMATION: Xaa is selected from any canonical amino acid
<220> FEATURE:
<221> NAME/KEY: MISC_FEATURE
<222> LOCATION: (4)..(4)
<223> OTHER INFORMATION: Xaa is selected from Leu, Ile, Val, Phe and Met
<220> FEATURE:
<221> NAME/KEY: MISC_FEATURE
```

```
<222> LOCATION: (5)..(6)
<223> OTHER INFORMATION: Xaa is selected from any canonical amino acid
<220> FEATURE:
<221> NAME/KEY: MISC_FEATURE
<222> LOCATION: (8)..(8)
<223> OTHER INFORMATION: Xaa is selected from any canonical amino acid
<220> FEATURE:
<221> NAME/KEY: MISC_FEATURE
<222> LOCATION: (9)..(9)
<223> OTHER INFORMATION: Xaa is selected from Leu and Ile

<400> SEQUENCE: 30

Leu Xaa Xaa Xaa Xaa Xaa Leu Xaa Xaa
1               5


<210> SEQ ID NO 31
<211> LENGTH: 8
<212> TYPE: PRT
<213> ORGANISM: Artificial Sequence
<220> FEATURE:
<223> OTHER INFORMATION: NES motif
<220> FEATURE:
<221> NAME/KEY: MISC_FEATURE
<222> LOCATION: (2)..(3)
<223> OTHER INFORMATION: Xaa is selected from any canonical amino acid
<220> FEATURE:
<221> NAME/KEY: MISC_FEATURE
<222> LOCATION: (4)..(4)
<223> OTHER INFORMATION: Xaa is selected from Leu, Ile, Val, Phe and Met
<220> FEATURE:
<221> NAME/KEY: MISC_FEATURE
<222> LOCATION: (5)..(6)
<223> OTHER INFORMATION: Xaa is selected from any canonical amino acid
<220> FEATURE:
<221> NAME/KEY: MISC_FEATURE
<222> LOCATION: (8)..(8)
<223> OTHER INFORMATION: Xaa is selected from any canonical amino acid

<400> SEQUENCE: 31

Leu Xaa Xaa Xaa Xaa Xaa Leu Xaa
1               5


<210> SEQ ID NO 32
<211> LENGTH: 9
<212> TYPE: PRT
<213> ORGANISM: Artificial Sequence
<220> FEATURE:
<223> OTHER INFORMATION: NES motif
<220> FEATURE:
<221> NAME/KEY: MISC_FEATURE
<222> LOCATION: (2)..(3)
<223> OTHER INFORMATION: Xaa is selected from any canonical amino acid
<220> FEATURE:
<221> NAME/KEY: MISC_FEATURE
<222> LOCATION: (4)..(4)
<223> OTHER INFORMATION: Xaa is selected from Leu, Ile, Val, Phe and Met
<220> FEATURE:
<221> NAME/KEY: MISC_FEATURE
<222> LOCATION: (5)..(7)
<223> OTHER INFORMATION: Xaa is selected from any canonical amino acid
<220> FEATURE:
<221> NAME/KEY: MISC_FEATURE
<222> LOCATION: (9)..(9)
<223> OTHER INFORMATION: Xaa is selected from any canonical amino acid

<400> SEQUENCE: 32

Leu Xaa Xaa Xaa Xaa Xaa Xaa Leu Xaa
1               5


<210> SEQ ID NO 33
<211> LENGTH: 11
<212> TYPE: PRT
<213> ORGANISM: Artificial Sequence
```

<220> FEATURE:
<223> OTHER INFORMATION: NES motif
<220> FEATURE:
<221> NAME/KEY: MISC_FEATURE
<222> LOCATION: (2)..(4)
<223> OTHER INFORMATION: Xaa is selected from any canonical amino acid
<220> FEATURE:
<221> NAME/KEY: MISC_FEATURE
<222> LOCATION: (5)..(5)
<223> OTHER INFORMATION: Xaa is selected from Leu, Ile, Val, Phe and Met
<220> FEATURE:
<221> NAME/KEY: MISC_FEATURE
<222> LOCATION: (6)..(8)
<223> OTHER INFORMATION: Xaa is selected from any canonical amino acid
<220> FEATURE:
<221> NAME/KEY: MISC_FEATURE
<222> LOCATION: (10)..(10)
<223> OTHER INFORMATION: Xaa is selected from any canonical amino acid
<220> FEATURE:
<221> NAME/KEY: MISC_FEATURE
<222> LOCATION: (11)..(11)
<223> OTHER INFORMATION: Xaa is selected from Leu and Ile

<400> SEQUENCE: 33

```
Leu Xaa Xaa Xaa Xaa Xaa Xaa Xaa Leu Xaa Xaa
1               5                   10
```

<210> SEQ ID NO 34
<211> LENGTH: 9
<212> TYPE: PRT
<213> ORGANISM: Artificial Sequence
<220> FEATURE:
<223> OTHER INFORMATION: NES motif

<400> SEQUENCE: 34

```
Leu Pro Pro Leu Glu Arg Leu Thr Leu
1               5
```

<210> SEQ ID NO 35
<211> LENGTH: 17
<212> TYPE: PRT
<213> ORGANISM: Artificial Sequence
<220> FEATURE:
<223> OTHER INFORMATION: NES motif

<400> SEQUENCE: 35

```
Ala Cys Pro Val Pro Leu Gln Leu Pro Pro Leu Glu Arg Leu Thr Leu
1               5                   10                  15

Asp
```

<210> SEQ ID NO 36
<211> LENGTH: 183
<212> TYPE: PRT
<213> ORGANISM: Artificial Sequence
<220> FEATURE:
<223> OTHER INFORMATION: HA-PKR(2-174)
<220> FEATURE:
<221> NAME/KEY: MISC_FEATURE
<222> LOCATION: (2)..(10)
<223> OTHER INFORMATION: HA
<220> FEATURE:
<221> NAME/KEY: MISC_FEATURE
<222> LOCATION: (11)..(183)
<223> OTHER INFORMATION: human PKR(2-174)

<400> SEQUENCE: 36

```
Met Tyr Pro Tyr Asp Val Pro Asp Tyr Ala Ala Gly Asp Leu Ser Ala
1               5                   10                  15

Gly Phe Phe Met Glu Glu Leu Asn Thr Tyr Arg Gln Lys Gln Gly Val
            20                  25                  30
```

```
Val Leu Lys Tyr Gln Glu Leu Pro Asn Ser Gly Pro Pro His Asp Arg
        35                  40                  45

Arg Phe Thr Phe Gln Val Ile Ile Asp Gly Arg Glu Phe Pro Glu Gly
    50                  55                  60

Glu Gly Arg Ser Lys Lys Glu Ala Lys Asn Ala Ala Ala Lys Leu Ala
65                  70                  75                  80

Val Glu Ile Leu Asn Lys Glu Lys Lys Ala Val Ser Pro Leu Leu Leu
                85                  90                  95

Thr Thr Thr Asn Ser Ser Glu Gly Leu Ser Met Gly Asn Tyr Ile Gly
            100                 105                 110

Leu Ile Asn Arg Ile Ala Gln Lys Lys Arg Leu Thr Val Asn Tyr Glu
        115                 120                 125

Gln Cys Ala Ser Gly Val His Gly Pro Glu Gly Phe His Tyr Lys Cys
    130                 135                 140

Lys Met Gly Gln Lys Glu Tyr Ser Ile Gly Thr Gly Ser Thr Lys Gln
145                 150                 155                 160

Glu Ala Lys Gln Leu Ala Ala Lys Leu Ala Tyr Leu Gln Ile Leu Ser
                165                 170                 175

Glu Glu Thr Ser Val Lys Ser
            180
```

<210> SEQ ID NO 37
<211> LENGTH: 159
<212> TYPE: PRT
<213> ORGANISM: Artificial Sequence
<220> FEATURE:
<223> OTHER INFORMATION: core of dsRNA-binding domain of PKR
<220> FEATURE:
<221> NAME/KEY: MISC_FEATURE
<222> LOCATION: (9)..(9)
<223> OTHER INFORMATION: restricted; not hydrophobic (i.e. K, R, H, D, E, S, T, N, Q, C, preferably , R, S, C, Q, H, (K))
<220> FEATURE:
<221> NAME/KEY: MISC_FEATURE
<222> LOCATION: (10)..(10)
<223> OTHER INFORMATION: restricted; not hydrophobic (i.e. K, R, H, D, E, S, T, N, Q, C, preferably, Q, (N))
<220> FEATURE:
<221> NAME/KEY: MISC_FEATURE
<222> LOCATION: (30)..(30)
<223> OTHER INFORMATION: conserved
<220> FEATURE:
<221> NAME/KEY: MISC_FEATURE
<222> LOCATION: (32)..(32)
<223> OTHER INFORMATION: conserved
<220> FEATURE:
<221> NAME/KEY: MISC_FEATURE
<222> LOCATION: (48)..(48)
<223> OTHER INFORMATION: conserved
<220> FEATURE:
<221> NAME/KEY: MISC_FEATURE
<222> LOCATION: (50)..(52)
<223> OTHER INFORMATION: conserved
<220> FEATURE:
<221> NAME/KEY: MISC_FEATURE
<222> LOCATION: (55)..(55)
<223> OTHER INFORMATION: conserved
<220> FEATURE:
<221> NAME/KEY: MISC_FEATURE
<222> LOCATION: (59)..(59)
<223> OTHER INFORMATION: restricted; A59 is not D; i.e. A59 is A, G, I, L, M, V
<220> FEATURE:
<221> NAME/KEY: MISC_FEATURE
<222> LOCATION: (66)..(66)
<223> OTHER INFORMATION: restricted; L66 is not A; i.e. L66 is L, I, V, M
<220> FEATURE:

<221> NAME/KEY: MISC_FEATURE
<222> LOCATION: (122)..(122)
<223> OTHER INFORMATION: conserved
<220> FEATURE:
<221> NAME/KEY: MISC_FEATURE
<222> LOCATION: (141)..(141)
<223> OTHER INFORMATION: conserved
<220> FEATURE:
<221> NAME/KEY: MISC_FEATURE
<222> LOCATION: (145)..(145)
<223> OTHER INFORMATION: conserved
<220> FEATURE:
<221> NAME/KEY: MISC_FEATURE
<222> LOCATION: (149)..(149)
<223> OTHER INFORMATION: restricted; A149 is not D; i.e. A149 is A, G, I, L, M, V

<400> SEQUENCE: 37

```
Phe Met Glu Glu Leu Asn Thr Tyr Arg Gln Lys Gln Gly Val Val Leu
1               5                   10                  15

Lys Tyr Gln Glu Leu Pro Asn Ser Gly Pro Pro His Asp Arg Arg Phe
            20                  25                  30

Thr Phe Gln Val Ile Ile Asp Gly Arg Glu Phe Pro Glu Gly Glu Gly
        35                  40                  45

Arg Ser Lys Lys Glu Ala Lys Asn Ala Ala Ala Lys Leu Ala Val Glu
    50                  55                  60

Ile Leu Asn Lys Glu Lys Lys Ala Val Ser Pro Leu Leu Leu Thr Thr
65                  70                  75                  80

Thr Asn Ser Ser Glu Gly Leu Ser Met Gly Asn Tyr Ile Gly Leu Ile
                85                  90                  95

Asn Arg Ile Ala Gln Lys Lys Arg Leu Thr Val Asn Tyr Glu Gln Cys
            100                 105                 110

Ala Ser Gly Val His Gly Pro Glu Gly Phe His Tyr Lys Cys Lys Met
        115                 120                 125

Gly Gln Lys Glu Tyr Ser Ile Gly Thr Gly Ser Thr Lys Gln Glu Ala
    130                 135                 140

Lys Gln Leu Ala Ala Lys Leu Ala Tyr Leu Gln Ile Leu Ser Glu
145                 150                 155
```

<210> SEQ ID NO 38
<211> LENGTH: 173
<212> TYPE: PRT
<213> ORGANISM: Artificial Sequence
<220> FEATURE:
<223> OTHER INFORMATION: (full) dsRNA-binding domain of PKR - M1

<400> SEQUENCE: 38

```
Ala Gly Asp Leu Ser Ala Gly Phe Phe Met Glu Glu Leu Asn Thr Tyr
1               5                   10                  15

Arg Gln Lys Gln Gly Val Val Leu Lys Tyr Gln Glu Leu Pro Asn Ser
            20                  25                  30

Gly Pro Pro His Asp Arg Arg Phe Thr Phe Gln Val Ile Ile Asp Gly
        35                  40                  45

Arg Glu Phe Pro Glu Gly Glu Gly Arg Ser Lys Lys Glu Ala Lys Asn
    50                  55                  60

Ala Ala Ala Lys Leu Ala Val Glu Ile Leu Asn Lys Glu Lys Lys Ala
65                  70                  75                  80

Val Ser Pro Leu Leu Leu Thr Thr Thr Asn Ser Ser Glu Gly Leu Ser
                85                  90                  95

Met Gly Asn Tyr Ile Gly Leu Ile Asn Arg Ile Ala Gln Lys Lys Arg
            100                 105                 110
```

```
Leu Thr Val Asn Tyr Glu Gln Cys Ala Ser Gly Val His Gly Pro Glu
        115                 120                 125

Gly Phe His Tyr Lys Cys Lys Met Gly Gln Lys Glu Tyr Ser Ile Gly
    130                 135                 140

Thr Gly Ser Thr Lys Gln Glu Ala Lys Gln Leu Ala Ala Lys Leu Ala
145                 150                 155                 160

Tyr Leu Gln Ile Leu Ser Glu Glu Thr Ser Val Lys Ser
                165                 170
```

<210> SEQ ID NO 39
<211> LENGTH: 2769
<212> TYPE: DNA
<213> ORGANISM: Artificial Sequence
<220> FEATURE:
<223> OTHER INFORMATION: expression cassette for reporter gene NLS-iRFP-Flag-GFPY39->TAG-6His
<220> FEATURE:
<221> NAME/KEY: misc_feature
<222> LOCATION: (1)..(852)
<223> OTHER INFORMATION: promoter
<220> FEATURE:
<221> NAME/KEY: misc_feature
<222> LOCATION: (949)..(984)
<223> OTHER INFORMATION: NLS
<220> FEATURE:
<221> NAME/KEY: misc_feature
<222> LOCATION: (988)..(1929)
<223> OTHER INFORMATION: iRFP
<220> FEATURE:
<221> NAME/KEY: misc_feature
<222> LOCATION: (1930)..(2004)
<223> OTHER INFORMATION: 25 Helix
<220> FEATURE:
<221> NAME/KEY: misc_feature
<222> LOCATION: (2011)..(2034)
<223> OTHER INFORMATION: Flag
<220> FEATURE:
<221> NAME/KEY: misc_feature
<222> LOCATION: (2035)..(2748)
<223> OTHER INFORMATION: GFPY39 CDS
<220> FEATURE:
<221> NAME/KEY: misc_feature
<222> LOCATION: (2149)..(2151)
<223> OTHER INFORMATION: Y39-encoding triplet
<220> FEATURE:
<221> NAME/KEY: misc_feature
<222> LOCATION: (2749)..(2766)
<223> OTHER INFORMATION: 6His

<400> SEQUENCE: 39

```
ggcattgatt attgactagt tattaatagt aatcaattac ggggtcatta gttcatagcc      60

catatatgga gttccgcgtt acataactta cggtaaatgg cccgcctggc tgaccgccca     120

acgacccccg cccattgacg tcaataatga cgtatgttcc catagtaacg ccaataggga     180

ctttccattg acgtcaatgg gtggagtatt tacggtaaac tgcccacttg gcagtacatc     240

aagtgtatca tatgccaagt ccgcccccta ttgacgtcaa tgacggtaaa tggcccgcct     300

ggcattatgc ccagtacatg accttacggg actttcctac ttggcagtac atctacgtat     360

tagtcatcgc tattaccatg gtgatgcggt tttggcagta caccaatggg cgtggatagc     420

ggtttgactc acggggattt ccaagtctcc accccattga cgtcaatggg agtttgtttt     480

ggcaccaaaa tcaacgggac tttccaaaat gtcgtaataa ccccgccccg ttgacgcaaa     540

tgggcggtag gcgtgtacgg tgggaggtct atataagcag agctcgttta gtgaaccgtc     600

agatcactag aagctttatt gcggtagttt atcacagtta aattgctaac gcagtcagtg     660

cttctgacac aacagtctcg aacttaagct gcagaagttg gtcgtgaggc actgggcagg     720
```

taagtatcaa ggttacaaga caggtttaag gagaccaata gaaactgggc ttgtcgagac 780
agagaagact cttgcgtttc tgataggcac ctattggtct tactgacatc cactttgcct 840
ttctctccac aggtgtccac tcccagttca attacagctc ttaaggctag agtacttaat 900
acgactcact ataggctagc caccatgggc cgcctggaaa gcaccccgcc gaaaaaaaaa 960
cgcaaagtgg aagatagcgc gagcgcggaa ggatccgtcg ccaggcagcc tgacctcttg 1020
acctgcgacg atgagccgat ccatatcccc ggtgccatcc aaccgcatgg actgctgctc 1080
gccctcgccg ccgacatgac gatcgttgcc ggcagcgaca accttcccga actcaccgga 1140
ctggcgatcg gcgccctgat cggccgctct gcggccgatg tcttcgactc ggagacgcac 1200
aaccgtctga cgatcgcctt ggccgagccc ggggcggccg tcggagcacc gatcactgtc 1260
ggcttcacga tgcgaaagga cgcaggcttc atcggctcct ggcatcgcca tgatcagctc 1320
atcttcctcg agctcgagcc tccccagcgg gacgtcgccg agccgcaggc gttcttccgc 1380
cgcaccaaca gcgccatccg ccgcctgcag gccgccgaaa ccttggaaag cgcctgcgcc 1440
gccgcggcgc aagaggtgcg gaagattacc ggcttcgatc gggtgatgat ctatcgcttc 1500
gcctccgact tcagcggcga agtgatcgca gaggatcggt gcgccgaggt cgagtcaaaa 1560
ctaggcctgc actatcctgc ctcaaccgtg ccggcgcagg cccgtcggct ctataccatc 1620
aacccggtac ggatcattcc cgatatcaat tatcggccgg tgccggtcac cccagacctc 1680
aatccggtca ccgggcggcc gattgatctt agcttcgcca tcctgcgcag cgtctcgccc 1740
gtccatctgg aattcatgcg caacataggc atgcacggca cgatgtcgat ctcgattttg 1800
cgcggcgagc gactgtgggg attgatcgtt tgccatcacc gaacgccgta ctacgtcgat 1860
ctcgatggcc gccaagcctg cgagctagtc gcccaggttc tggcctggca gatcggcgtg 1920
atggaagagc tggcggaagc ggcggccaaa gaagcggcgg ccaaagaagc ggcggccaaa 1980
gaagcggcgg ccaaagcggc ggccggtacc gattacaaag atgatgatga taaagtgagc 2040
aagggcgagg agctgttcac cggggtggtg cccatcctgg tcgagctgga cggcgacgta 2100
aacggccaca agttcagcgt gtccggcgag ggcgagggcg atgccaccta gggcaagctg 2160
accctgaagt tcatctgcac caccggcaag ctgcccgtgc cctggcccac cctcgtgacc 2220
accctgacct acggcgtgca gtgcttcagc cgctaccccg accacatgaa gcagcacgac 2280
ttcttcaagt ccgccatgcc cgaaggctac gtccaggagc gcaccatctt cttcaaggac 2340
gacggcaact acaagacccg cgccgaggtg aagttcgagg gcgacaccct ggtgaaccgc 2400
atcgagctga agggcatcga cttcaaggag gacggcaaca tcctggggca caagctggag 2460
tacaactaca acagccacaa cgtctatatc atggccgaca agcagaagaa cggcatcaag 2520
gccaacttca agatccgcca caacatcgag gacggcagcg tgcagctcgc cgaccactac 2580
cagcagaaca cccccatcgg cgacggcccc gtgctgctgc ccgacaacca ctacctgagc 2640
acccagtccg ccctgagcaa agaccccaac gagaagcgcg atcacatggt cctgctggag 2700
ttcgtgaccg ccgccgggat cactctcggc atggacgagc tgtacaagca tcaccatcac 2760
catcactga 2769

<210> SEQ ID NO 40
<211> LENGTH: 3341
<212> TYPE: DNA
<213> ORGANISM: Artificial Sequence
<220> FEATURE:
<223> OTHER INFORMATION: T7 RNA polymerase expression cassette for
      constitutive expression via CMV promoter <220> FEATURE:
<221> NAME/KEY: misc_feature
<222> LOCATION: (1)..(588)
<223> OTHER INFORMATION: CMV promoter
<220> FEATURE:
<221> NAME/KEY: misc_feature
<222> LOCATION: (690)..(3341)
<223> OTHER INFORMATION: CDS

<400> SEQUENCE: 40
gttgacattg attattgact agttattaat agtaatcaat tacggggtca ttagttcata 60
gcccatatat ggagttccgc gttacataac ttacggtaaa tggcccgcct ggctgaccgc 120
ccaacgaccc ccgcccattg acgtcaataa tgacgtatgt tcccatagta acgccaatag 180
ggactttcca ttgacgtcaa tgggtggact atttacggta aactgcccac ttggcagtac 240
atcaagtgta tcatatgcca agtacgcccc ctattgacgt caatgacggt aaatggcccg 300
cctggcatta tgcccagtac atgaccttat gggactttcc tacttggcag tacatctacg 360
tattagtcat cgctattacc atggtgatgc ggttttggca gtacatcaat gggcgtggat 420
agcggtttga ctcacgggga tttccaagtc tccaccccat tgacgtcaat gggagtttgt 480
tttggcacca aaatcaacgg gactttccaa aatgtcgtaa caactccgcc ccattgacgc 540
aaatgggcgg taggcgtgta cggtgggagg tctatataag cagagctctc tggctaacta 600
gagaacccac tgcttactgg cttatcgaaa ttaatacgac tcactatagg gagacccaag 660
ctggctagcg tttaaactta agcttcacca tgaacacgat taacatcgct aagaacgact 720
tctctgacat cgaactggct gctatcccgt tcaacactct ggctgaccat tacggtgagc 780
gtttagctcg cgaacagttg gcccttgagc atgagtctta cgagatgggt gaagcacgct 840
tccgcaagat gtttgagcgt caacttaaag ctggtgaggt tgcggataac gctgccgcca 900
agcctctcat cactacccta ctccctaaga tgattgcacg catcaacgac tggtttgagg 960
aagtgaaagc taagcgcggc aagcgcccga cagccttcca gttcctgcaa gaaatcaagc 1020
cggaagccgt agcgtacatc accattaaga ccactctggc ttgcctaacc agtgctgaca 1080
atacaaccgt tcaggctgta gcaagcgcaa tcggtcgggc cattgaggac gaggctcgct 1140
tcggtcgtat ccgtgacctt gaagctaagc acttcaagaa aaacgttgag gaacaactca 1200
acaagcgcgt agggcacgtc tacaagaaag catttatgca agttgtcgag gctgacatgc 1260
tctctaaggg tctactcggt ggcgaggcgt ggtcttcgtg gcataaggaa gactctattc 1320
atgtaggagt acgctgcatc gagatgctca ttgagtcaac cggaatggtt agcttacacc 1380
gccaaaatgc tggcgtagta ggtcaagact ctgagactat cgaactcgca cctgaatacg 1440
ctgaggctat cgcaacccgt gcaggtgcgc tggctggcat ctctccgatg ttccaacctt 1500
gcgtagttcc tcctaagccg tggactggca ttactggtgg tggctattgg gctaacggtc 1560
gtcgtcctct ggcgctggtg cgtactcaca gtaagaaagc actgatgcgc tacgaagacg 1620
tttacatgcc tgaggtgtac aaagcgatta acattgcgca aaacaccgca tggaaaatca 1680
acaagaaagt cctagcggtc gccaacgtaa tcaccaagtg gaagcattgt ccggtcgagg 1740
acatccctgc gattgagcgt gaagaactcc cgatgaaacc ggaagacatc gacatgaatc 1800
ctgaggctct caccgcgtgg aaacgtgctg ccgctgctgt gtaccgcaag gacaaggctc 1860
gcaagtctcg ccgtatcagc cttgagttca tgcttgagca agccaataag tttgctaacc 1920
ataaggccat ctggttccct tacaacatgg actggcgcgg tcgtgtttac gctgtgtcaa 1980
tgttcaaccc gcaaggtaac gatatgacca aaggactgct tacgctggcg aaaggtaaac 2040
caatcggtaa ggaaggttac tactggctga aaatccacgg tgcaaactgt gcgggtgtcg 2100
ataaggttcc gttccctgag cgcatcaagt tcattgagga aaaccacgag aacatcatgg 2160
cttgcgctaa gtctccactg gagaacactt ggtgggctga gcaagattct ccgttctgct 2220
tccttgcgtt ctgctttgag tacgctgggg tacagcacca cggcctgagc tataactgct 2280
cccttccgct ggcgtttgac gggtcttgct ctggcatcca gcacttctcc gcgatgctcc 2340
gagatgaggt aggtggtcgc gcggttaact tgcttcctag tgaaaccgtt caggacatct 2400
acgggattgt tgctaagaaa gtcaacgaga ttctacaagc agacgcaatc aatgggaccg 2460
ataacgaagt agttaccgtg accgatgaga acactggtga aatctctgag aaagtcaagc 2520
tgggcactaa ggcactggct ggtcaatggc tggcttacgg tgttactcgc agtgtgacta 2580
agcgttcagt catgacgctg gcttacgggt ccaaagagtt cggcttccgt caacaagtgc 2640
tggaagatac cattcagcca gctattgatt ccggcaaggg tctgatgttc actcagccga 2700
atcaggctgc tggatacatg gctaagctga tttgggaatc tgtgagcgtg acggtggtag 2760
ctgcggttga agcaatgaac tggcttaagt ctgctgctaa gctgctggct gctgaggtca 2820
aagataagaa gactggagag attcttcgca agcgttgcgc tgtgcattgg gtaactcctg 2880
atggtttccc tgtgtggcag gaatacaaga agcctattca gacgcgcttg aacctgatgt 2940
tcctcggtca gttccgctta cagcctacca ttaacaccaa caaagatagc gagattgatg 3000
cacacaaaca ggagtctggt atcgctccta actttgtaca cagccaagac ggtagccacc 3060
ttcgtaagac tgtagtgtgg gcacacgaga agtacggaat cgaatctttt gcactgattc 3120
acgactcctt cggtaccatt ccggctgacg ctgcgaacct gttcaaagca gtgcgcgaaa 3180
ctatggttga cacatatgag tcttgtgatg tactggctga tttctacgac cagttcgctg 3240
accagttgca cgagtctcaa ttggacaaaa tgccagcact tccggctaaa ggtaacttga 3300
acctccgtga catcttagag tcggacttcg cgttcgcgta a 3341

<210> SEQ ID NO 41
<211> LENGTH: 3494
<212> TYPE: DNA
<213> ORGANISM: Artificial Sequence
<220> FEATURE:
<223> OTHER INFORMATION: NES-T7 RNA polymerase expression cassette
containing “T-REx” promoter comprising two tetO sequences
<220> FEATURE:
<221> NAME/KEY: misc_feature
<222> LOCATION: (1)..(584)
<223> OTHER INFORMATION: promoter
<220> FEATURE:
<221> NAME/KEY: misc_feature
<222> LOCATION: (586)..(604)
<223> OTHER INFORMATION: tetO
<220> FEATURE:
<221> NAME/KEY: misc_feature
<222> LOCATION: (607)..(625)
<223> OTHER INFORMATION: tetO
<220> FEATURE:
<221> NAME/KEY: misc_feature
<222> LOCATION: (798)..(845)
<223> OTHER INFORMATION: NES
<220> FEATURE:
<221> NAME/KEY: misc_feature
<222> LOCATION: (846)..(3494)
<223> OTHER INFORMATION: CDS

<400> SEQUENCE: 41
gacattgatt attgactagt tattaatagt aatcaattac ggggtcatta gttcatagcc 60
catatatgga gttccgcgtt acataactta cggtaaatgg cccgcctggc tgaccgccca 120

-continued

```
acgacccccg cccattgacg tcaataatga cgtatgttcc catagtaacg ccaataggga    180
ctttccattg acgtcaatgg gtggagtatt tacggtaaac tgcccacttg gcagtacatc    240
aagtgtatca tatgccaagt acgcccccta ttgacgtcaa tgacggtaaa tggcccgcct    300
ggcattatgc ccagtacatg accttatggg actttcctac ttggcagtac atctacgtat    360
tagtcatcgc tattaccatg gtgatgcggt tttggcagta catcaatggg cgtggatagc    420
ggtttgactc acggggattt ccaagtctcc accccattga cgtcaatggg agtttgtttt    480
ggcaccaaaa tcaacgggac tttccaaaat gtcgtaacaa ctccgcccca ttgacgcaaa    540
tgggcggtag gcgtgtacgg tgggaggtct atataagcag agctctccct atcagtgata    600
gagatctccc tatcagtgat agagatcgtc gacgagctcg tttagtgaac cgtcagatcg    660
cctggagacg ccatccacgc tgttttgacc tccatagaag acaccgggac cgatccagcc    720
tccggactct agcgtttaaa catcacaagt ttgtacaaaa aagcaggcgc tagcgtttaa    780
acttaagctt caccatgtgc ccggtgccgc tgcagctgcc gccgctggaa cgcctgaccc    840
tggataacac gattaacatc gctaagaacg acttctctga catcgaactg gctgctatcc    900
cgttcaacac tctggctgac cattacggtg agcgtttagc tcgcgaacag ttggcccttg    960
agcatgagtc ttacgagatg ggtgaagcac gcttccgcaa gatgtttgag cgtcaactta   1020
aagctggtga ggttgcggat aacgctgccg ccaagcctct catcactacc ctactcccta   1080
agatgattgc acgcatcaac gactggtttg aggaagtgaa agctaagcgc ggcaagcgcc   1140
cgacagcctt ccagttcctg caagaaatca agccggaagc cgtagcgtac atcaccatta   1200
agaccactct ggcttgccta accagtgctg acaatacaac cgttcaggct gtagcaagcg   1260
caatcggtcg ggccattgag gacgaggctc gcttcggtcg tatccgtgac cttgaagcta   1320
agcacttcaa gaaaaacgtt gaggaacaac tcaacaagcg cgtagggcac gtctacaaga   1380
aagcatttat gcaagttgtc gaggctgaca tgctctctaa gggtctactc ggtggcgagg   1440
cgtggtcttc gtggcataag gaagactcta ttcatgtagg agtacgctgc atcgagatgc   1500
tcattgagtc aaccggaatg gttagcttac accgccaaaa tgctggcgta gtaggtcaag   1560
actctgagac tatcgaactc gcacctgaat acgctgaggc tatcgcaacc cgtgcaggtg   1620
cgctggctgg catctctccg atgttccaac cttgcgtagt tcctcctaag ccgtggactg   1680
gcattactgg tggtggctat tgggctaacg gtcgtcgtcc tctggcgctg gtgcgtactc   1740
acagtaagaa agcactgatg cgctacgaag acgtttacat gcctgaggtg tacaaagcga   1800
ttaacattgc gcaaaacacc gcatggaaaa tcaacaagaa agtcctagcg gtcgccaacg   1860
taatcaccaa gtggaagcat tgtccggtcg aggacatccc tgcgattgag cgtgaagaac   1920
tcccgatgaa accggaagac atcgacatga atcctgaggc tctcaccgcg tggaaacgtg   1980
ctgccgctgc tgtgtaccgc aaggacaagg ctcgcaagtc tcgccgtatc agccttgagt   2040
tcatgcttga gcaagccaat aagtttgcta accataaggc catctggttc ccttacaaca   2100
tggactggcg cggtcgtgtt tacgctgtgt caatgttcaa cccgcaaggt aacgatatga   2160
ccaaaggact gcttacgctg gcgaaaggta aaccaatcgg taaggaaggt tactactggc   2220
tgaaaatcca cggtgcaaac tgtgcgggtg tcgataaggt tccgttccct gagcgcatca   2280
agttcattga ggaaaaccac gagaacatca tggcttgcgc taagtctcca ctggagaaca   2340
cttggtgggc tgagcaagat tctccgttct gcttccttgc gttctgcttt gagtacgctg   2400
ggtacagca ccacggcctg agctataact gctcccttcc gctggcgttt gacgggtctt   2460
gctctggcat ccagcacttc tccgcgatgc tccgagatga ggtaggtggt cgcgcggtta   2520
```

acttgcttcc tagtgaaacc gttcaggaca tctacgggat tgttgctaag aaagtcaacg 2580
agattctaca agcagacgca atcaatggga ccgataacga agtagttacc gtgaccgatg 2640
agaacactgg tgaaatctct gagaaagtca agctgggcac taaggcactg gctggtcaat 2700
ggctggctta cggtgttact cgcagtgtga ctaagcgttc agtcatgacg ctggcttacg 2760
ggtccaaaga gttcggcttc cgtcaacaag tgctggaaga taccattcag ccagctattg 2820
attccggcaa gggtctgatg ttcactcagc cgaatcaggc tgctggatac atggctaagc 2880
tgatttggga atctgtgagc gtgacggtgg tagctgcggt tgaagcaatg aactggctta 2940
agtctgctgc taagctgctg gctgctgagg tcaaagataa gaagactgga gagattcttc 3000
gcaagcgttg cgctgtgcat tgggtaactc ctgatggttt ccctgtgtgg caggaataca 3060
agaagcctat tcagacgcgc ttgaacctga tgttcctcgg tcagttccgc ttacagccta 3120
ccattaacac caacaaagat agcgagattg atgcacacaa acaggagtct ggtatcgctc 3180
ctaactttgt acacagccaa gacggtagcc accttcgtaa gactgtagtg tgggcacacg 3240
agaagtacgg aatcgaatct tttgcactga ttcacgactc cttcggtacc attccggctg 3300
acgctgcgaa cctgttcaaa gcagtgcgcg aaactatggt tgacacatat gagtcttgtg 3360
atgtactggc tgatttctac gaccagttcg ctgaccagtt gcacgagtct caattggaca 3420
aaatgccagc acttccggct aaaggtaact tgaacctccg tgacatctta gagtcggact 3480
tcgcgttcgc gtaa 3494

<210> SEQ ID NO 42
<211> LENGTH: 3169
<212> TYPE: DNA
<213> ORGANISM: Artificial Sequence
<220> FEATURE:
<223> OTHER INFORMATION: NES-T7 RNA polymerase expression cassette
containing “Tet-On” promoter comprising 8 tetO sequences
<220> FEATURE:
<221> NAME/KEY: misc_feature
<222> LOCATION: (1)..(458)
<223> OTHER INFORMATION: promoter
<220> FEATURE:
<221> NAME/KEY: misc_feature
<222> LOCATION: (18)..(36)
<223> OTHER INFORMATION: tetO
<220> FEATURE:
<221> NAME/KEY: misc_feature
<222> LOCATION: (54)..(72)
<223> OTHER INFORMATION: tetO
<220> FEATURE:
<221> NAME/KEY: misc_feature
<222> LOCATION: (90)..(108)
<223> OTHER INFORMATION: tetO
<220> FEATURE:
<221> NAME/KEY: misc_feature
<222> LOCATION: (126)..(144)
<223> OTHER INFORMATION: tetO
<220> FEATURE:
<221> NAME/KEY: misc_feature
<222> LOCATION: (162)..(180)
<223> OTHER INFORMATION: tetO
<220> FEATURE:
<221> NAME/KEY: misc_feature
<222> LOCATION: (198)..(216)
<223> OTHER INFORMATION: tetO
<220> FEATURE:
<221> NAME/KEY: misc_feature
<222> LOCATION: (234)..(252)
<223> OTHER INFORMATION: tetO
<220> FEATURE:
<221> NAME/KEY: misc_feature
<222> LOCATION: (270)..(288)
<223> OTHER INFORMATION: tetO
<220> FEATURE:
<221> NAME/KEY: misc_feature
<222> LOCATION: (473)..(520)
<223> OTHER INFORMATION: NES
<220> FEATURE:
<221> NAME/KEY: misc_feature
<222> LOCATION: (521)..(3169)
<223> OTHER INFORMATION: CDS

<400> SEQUENCE: 42

```
caattgctcg agtttactcc ctatcagtga tagagaacgt atgtcgactt tactccctat     60

cagtgataga gaacgtatga agagtttact ccctatcagt gatagagaac gtatgcagac    120

tttactccct atcagtgata gagaacgtat aaggagttta ctccctatca gtgatagaga    180

acgtatgacc agtttactcc ctatcagtga tagagaacgt atctacagtt tactccctat    240

cagtgataga gaacgtatat ccagtttact ccctatcagt gatagagaac gtatacgctt    300

taggcgtgta cggtgggcgc ctataaaagc agagctcgtt tagtgaaccg tcagatcgcc    360

tggagcaatt ccacaacact tttgtcttat accaactttc cgtaccactt cctaccctcg    420

aaagtccata tggctagcct gcagggatcc agatatcaag cttgccacca tgtgcccggt    480

gccgctgcag ctgccgccgc tggaacgcct gaccctggat aacacgatta acatcgctaa    540

gaacgacttc tctgacatcg aactggctgc tatcccgttc aacactctgg ctgaccatta    600

cggtgagcgt ttagctcgcg aacagttggc ccttgagcat gagtcttacg agatgggtga    660

agcacgcttc cgcaagatgt ttgagcgtca acttaaagct ggtgaggttg cggataacgc    720

tgccgccaag cctctcatca ctaccctact ccctaagatg attgcacgca tcaacgactg    780

gtttgaggaa gtgaaagcta agcgcggcaa gcgcccgaca gccttccagt tcctgcaaga    840

aatcaagccg gaagccgtag cgtacatcac cattaagacc actctggctt gcctaaccag    900

tgctgacaat acaaccgttc aggctgtagc aagcgcaatc ggtcgggcca ttgaggacga    960

ggctcgcttc ggtcgtatcc gtgaccttga agctaagcac ttcaagaaaa acgttgagga   1020

acaactcaac aagcgcgtag ggcacgtcta caagaaagca tttatgcaag ttgtcgaggc   1080

tgacatgctc tctaagggtc tactcggtgg cgaggcgtgg tcttcgtggc ataaggaaga   1140

ctctattcat gtaggagtac gctgcatcga gatgctcatt gagtcaaccg gaatggttag   1200

cttacaccgc caaaatgctg gcgtagtagg tcaagactct gagactatcg aactcgcacc   1260

tgaatacgct gaggctatcg caacccgtgc aggtgcgctg gctggcatct ctccgatgtt   1320

ccaaccttgc gtagttcctc ctaagccgtg gactggcatt actggtggtg gctattgggc   1380

taacggtcgt cgtcctctgg cgctggtgcg tactcacagt aagaaagcac tgatgcgcta   1440

cgaagacgtt tacatgcctg aggtgtacaa agcgattaac attgcgcaaa acaccgcatg   1500

gaaaatcaac aagaaagtcc tagcggtcgc caacgtaatc accaagtgga agcattgtcc   1560

ggtcgaggac atccctgcga ttgagcgtga agaactcccg atgaaaccgg aagacatcga   1620

catgaatcct gaggctctca ccgcgtggaa acgtgctgcc gctgctgtgt accgcaagga   1680

caaggctcgc aagtctcgcc gtatcagcct tgagttcatg cttgagcaag ccaataagtt   1740

tgctaaccat aaggccatct ggttccctta caacatggac tggcgcggtc gtgtttacgc   1800

tgtgtcaatg ttcaacccgc aaggtaacga tatgaccaaa ggactgctta cgctggcgaa   1860

aggtaaacca atcggtaagg aaggttacta ctggctgaaa atccacggtg caaactgtgc   1920

gggtgtcgat aaggttccgt tccctgagcg catcaagttc attgaggaaa accacgagaa   1980

catcatggct tgcgctaagt ctccactgga gaacacttgg tgggctgagc aagattctcc   2040
```

gttctgcttc cttgcgttct gctttgagta cgctggggta cagcaccacg gcctgagcta 2100
taactgctcc cttccgctgg cgtttgacgg gtcttgctct ggcatccagc acttctccgc 2160
gatgctccga gatgaggtag gtggtcgcgc ggttaacttg cttcctagtg aaaccgttca 2220
ggacatctac gggattgttg ctaagaaagt caacgagatt ctacaagcag acgcaatcaa 2280
tgggaccgat aacgaagtag ttaccgtgac cgatgagaac actggtgaaa tctctgagaa 2340
agtcaagctg ggcactaagg cactggctgg tcaatggctg gcttacggtg ttactcgcag 2400
tgtgactaag cgttcagtca tgacgctggc ttacgggtcc aaagagttcg gcttccgtca 2460
acaagtgctg gaagatacca ttcagccagc tattgattcc ggcaagggtc tgatgttcac 2520
tcagccgaat caggctgctg gatacatggc taagctgatt tgggaatctg tgagcgtgac 2580
ggtggtagct gcggttgaag caatgaactg gcttaagtct gctgctaagc tgctggctgc 2640
tgaggtcaaa gataagaaga ctggagagat tcttcgcaag cgttgcgctg tgcattgggt 2700
aactcctgat ggtttccctg tgtggcagga atacaagaag cctattcaga cgcgcttgaa 2760
cctgatgttc ctcggtcagt tccgcttaca gcctaccatt aacaccaaca aagatagcga 2820
gattgatgca cacaaacagg agtctggtat cgctcctaac tttgtacaca gccaagacgg 2880
tagccacctt cgtaagactg tagtgtgggc acacgagaag tacggaatcg aatcttttgc 2940
actgattcac gactccttcg gtaccattcc ggctgacgct gcgaacctgt tcaaagcagt 3000
gcgcgaaact atggttgaca catatgagtc ttgtgatgta ctggctgatt tctacgacca 3060
gttcgctgac cagttgcacg agtctcaatt ggacaaaatg ccagcacttc cggctaaagg 3120
taacttgaac ctccgtgaca tcttagagtc ggacttcgcg ttcgcgtaa 3169

<210> SEQ ID NO 43
<211> LENGTH: 3389
<212> TYPE: DNA
<213> ORGANISM: Artificial Sequence
<220> FEATURE:
<223> OTHER INFORMATION: NES-T7 RNA polymerase expression cassette for constitutive expression via CMV promoter
<220> FEATURE:
<221> NAME/KEY: misc_feature
<222> LOCATION: (1)..(588)
<223> OTHER INFORMATION: CMV promoter
<220> FEATURE:
<221> NAME/KEY: misc_feature
<222> LOCATION: (693)..(740)
<223> OTHER INFORMATION: NES
<220> FEATURE:
<221> NAME/KEY: misc_feature
<222> LOCATION: (741)..(3389)
<223> OTHER INFORMATION: CDS

<400> SEQUENCE: 43
gttgacattg attattgact agttattaat agtaatcaat tacggggtca ttagttcata 60
gcccatatat ggagttccgc gttacataac ttacggtaaa tggcccgcct ggctgaccgc 120
ccaacgaccc ccgcccattg acgtcaataa tgacgtatgt tcccatagta acgccaatag 180
ggactttcca ttgacgtcaa tgggtggact atttacggta aactgcccac ttggcagtac 240
atcaagtgta tcatatgcca agtacgcccc ctattgacgt caatgacggt aaatggcccg 300
cctggcatta tgcccagtac atgaccttat gggactttcc tacttggcag tacatctacg 360
tattagtcat cgctattacc atggtgatgc ggttttggca gtacatcaat gggcgtggat 420
agcggtttga ctcacgggga tttccaagtc tccaccccat tgacgtcaat gggagtttgt 480
tttggcacca aaatcaacgg gactttccaa aatgtcgtaa caactccgcc ccattgacgc 540

```
aaatgggcgg taggcgtgta cggtgggagg tctatataag cagagctctc tggctaacta    600
gagaacccac tgcttactgg cttatcgaaa ttaatacgac tcactatagg gagacccaag    660
ctggctagcg tttaaactta agcttcacca tgtgcccggt gccgctgcag ctgccgccgc    720
tggaacgcct gaccctggat aacacgatta acatcgctaa gaacgacttc tctgacatcg    780
aactggctgc tatcccgttc aacactctgg ctgaccatta cggtgagcgt ttagctcgcg    840
aacagttggc ccttgagcat gagtcttacg agatgggtga agcacgcttc cgcaagatgt    900
ttgagcgtca acttaaagct ggtgaggttg cggataacgc tgccgccaag cctctcatca    960
ctaccctact ccctaagatg attgcacgca tcaacgactg gtttgaggaa gtgaaagcta   1020
agcgcggcaa gcgcccgaca gccttccagt tcctgcaaga aatcaagccg gaagccgtag   1080
cgtacatcac cattaagacc actctggctt gcctaaccag tgctgacaat acaaccgttc   1140
aggctgtagc aagcgcaatc ggtcgggcca ttgaggacga ggctcgcttc ggtcgtatcc   1200
gtgaccttga agctaagcac ttcaagaaaa acgttgagga acaactcaac aagcgcgtag   1260
ggcacgtcta caagaaagca tttatgcaag ttgtcgaggc tgacatgctc tctaagggtc   1320
tactcggtgg cgaggcgtgg tcttcgtggc ataaggaaga ctctattcat gtaggagtac   1380
gctgcatcga gatgctcatt gagtcaaccg gaatggttag cttacaccgc caaaatgctg   1440
gcgtagtagg tcaagactct gagactatcg aactcgcacc tgaatacgct gaggctatcg   1500
caacccgtgc aggtgcgctg gctggcatct ctccgatgtt ccaaccttgc gtagttcctc   1560
ctaagccgtg gactggcatt actggtggtg gctattgggc taacggtcgt cgtcctctgg   1620
cgctggtgcg tactcacagt aagaaagcac tgatgcgcta cgaagacgtt tacatgcctg   1680
aggtgtacaa agcgattaac attgcgcaaa acaccgcatg gaaaatcaac aagaaagtcc   1740
tagcggtcgc caacgtaatc accaagtgga agcattgtcc ggtcgaggac atccctgcga   1800
ttgagcgtga agaactcccg atgaaaccgg aagacatcga catgaatcct gaggctctca   1860
ccgcgtggaa acgtgctgcc gctgctgtgt accgcaagga caaggctcgc aagtctcgcc   1920
gtatcagcct tgagttcatg cttgagcaag ccaataagtt tgctaaccat aaggccatct   1980
ggttccctta caacatggac tggcgcggtc gtgtttacgc tgtgtcaatg ttcaacccgc   2040
aaggtaacga tatgaccaaa ggactgctta cgctggcgaa aggtaaacca atcggtaagg   2100
aaggttacta ctggctgaaa atccacggtg caaactgtgc gggtgtcgat aaggttccgt   2160
tccctgagcg catcaagttc attgaggaaa accacgagaa catcatggct tgcgctaagt   2220
ctccactgga gaacacttgg tgggctgagc aagattctcc gttctgcttc cttgcgttct   2280
gctttgagta cgctggggta cagcaccacg gcctgagcta taactgctcc cttccgctgg   2340
cgtttgacgg gtcttgctct ggcatccagc acttctccgc gatgctccga gatgaggtag   2400
gtggtcgcgc ggttaacttg cttcctagtg aaaccgttca ggacatctac gggattgttg   2460
ctaagaaagt caacgagatt ctacaagcag acgcaatcaa tgggaccgat aacgaagtag   2520
ttaccgtgac cgatgagaac actggtgaaa tctctgagaa agtcaagctg ggcactaagg   2580
cactggctgg tcaatggctg gcttacggtg ttactcgcag tgtgactaag cgttcagtca   2640
tgacgctggc ttacgggtcc aaagagttcg gcttccgtca acaagtgctg gaagatacca   2700
ttcagccagc tattgattcc ggcaagggtc tgatgttcac tcagccgaat caggctgctg   2760
gatacatggc taagctgatt tgggaatctg tgagcgtgac ggtggtagct gcggttgaag   2820
caatgaactg gcttaagtct gctgctaagc tgctggctgc tgaggtcaaa gataagaaga   2880
ctggagagat tcttcgcaag cgttgcgctg tgcattgggt aactcctgat ggtttccctg   2940
```

tgtggcagga atacaagaag cctattcaga cgcgcttgaa cctgatgttc ctcggtcagt 3000
tccgcttaca gcctaccatt aacaccaaca aagatagcga gattgatgca cacaaacagg 3060
agtctggtat cgctcctaac tttgtacaca gccaagacgg tagccacctt cgtaagactg 3120
tagtgtgggc acacgagaag tacggaatcg aatcttttgc actgattcac gactccttcg 3180
gtaccattcc ggctgacgct gcgaacctgt tcaaagcagt gcgcgaaact atggttgaca 3240
catatgagtc ttgtgatgta ctggctgatt tctacgacca gttcgctgac cagttgcacg 3300
agtctcaatt ggacaaaatg ccagcacttc cggctaaagg taacttgaac ctccgtgaca 3360
tcttagagtc ggacttcgcg ttcgcgtaa 3389

<210> SEQ ID NO 44
<211> LENGTH: 2054
<212> TYPE: DNA
<213> ORGANISM: Artificial Sequence
<220> FEATURE:
<223> OTHER INFORMATION: PylRSAF expression cassette for constitutive expression via CMV promoter
<220> FEATURE:
<221> NAME/KEY: misc_feature
<222> LOCATION: (1)..(588)
<223> OTHER INFORMATION: CMV promoter
<220> FEATURE:
<221> NAME/KEY: misc_feature
<222> LOCATION: (690)..(2054)
<223> OTHER INFORMATION: CDS

<400> SEQUENCE: 44
gttgacattg attattgact agttattaat agtaatcaat tacggggtca ttagttcata 60
gcccatatat ggagttccgc gttacataac ttacggtaaa tggcccgcct ggctgaccgc 120
ccaacgaccc ccgcccattg acgtcaataa tgacgtatgt tcccatagta acgccaatag 180
ggactttcca ttgacgtcaa tgggtggact atttacggta aactgcccac ttggcagtac 240
atcaagtgta tcatatgcca agtacgcccc ctattgacgt caatgacggt aaatggcccg 300
cctggcatta tgcccagtac atgaccttat gggactttcc tacttggcag tacatctacg 360
tattagtcat cgctattacc atggtgatgc ggttttggca gtacatcaat gggcgtggat 420
agcggtttga ctcacgggga tttccaagtc tccaccccat tgacgtcaat gggagtttgt 480
tttggcacca aaatcaacgg gactttccaa aatgtcgtaa caactccgcc ccattgacgc 540
aaatgggcgg taggcgtgta cggtgggagg tctatataag cagagctctc tggctaacta 600
gagaacccac tgcttactgg cttatcgaaa ttaatacgac tcactatagg gagacccaag 660
ctggctagcg tttaaactta agcttcacca tggataaaaa accgctgaat accctgatct 720
ctgctactgg tctgtggatg agtcgtaccg gaaccattca taaaatcaaa caccacgagg 780
ttagccgttc gaaaatctat attgagatgg cgtgtggcga tcatctggtt gtgaacaata 840
gccgctcttc tcgtacagca cgtgcactgc gtcaccacaa atatcgtaaa acctgtaaac 900
gttgccgtgt gtccgatgag gatctgaaca aattcctgac aaaagccaat gaggaccaaa 960
caagcgtgaa agtgaaagtc gttagcgctc ctacccgtac taaaaaagca atgccgaaat 1020
ccgttgctcg tgcccctaaa ccactggaaa acactgaagc agcacaggca cagccgtctg 1080
gaagcaaatt ctctccggcc attcctgttt ctacccagga gtccgtttct gttccagcaa 1140
gtgtgagcac cagcattagc agtattagca ccggtgccac cgctagcgcc ctggttaaag 1200
gcaataccaa tccgattaca agcatgtctg ccccggttca agcatcagct ccagcactga 1260
caaaatccca aaccgatcgt ctggaggttc tgctgaatcc gaaagacgaa atcagcctga 1320
attccggcaa accgtttcgt gaactggaga gcgaactgct gtcacgtcgt aaaaaagacc 1380
tgcaacaaat ctatgccgaa gaacgtgaga actatctggg gaaactggaa cgtgaaatca 1440
cccgcttttt cgtggatcgt ggctttctgg agatcaaatc cccgattctg attcctctgg 1500
agtatatcga gcgtatgggc atcgacaatg ataccgaact gagcaaacaa attttccgtg 1560
tggataaaaa cttctgtctg cgccctatgc tagcaccaaa tctggctaac tatctgcgca 1620
aactggaccg tgccctgcct gatcctatca aaatcttcga gatcggcccg tgttatcgta 1680
aagagtccga cggtaaagaa catctggagg agtttaccat gctgaacttt tgccaaatgg 1740
gttcaggttg tactcgtgag aacctggaaa gcatcatcac cgatttttctg aaccacctgg 1800
gcattgactt caaaattgtg ggcgacagct gtatggtgtt tggcgacacc ctggatgtca 1860
tgcacggcga cctggaactg tctagtgccg ttgtgggccc aatcccgctg gatcgtgagt 1920
ggggtatcga caaaccttgg atcggtgcgg gttttggtct ggagcgtctg ctgaaagtaa 1980
aacacgactt caagaacatc aaacgtgctg cacgttccga gtcctattac aatggtattt 2040
ctactaacct gtaa 2054

<210> SEQ ID NO 45
<211> LENGTH: 2105
<212> TYPE: DNA
<213> ORGANISM: Artificial Sequence
<220> FEATURE:
<223> OTHER INFORMATION: NES-PylRSAF expression cassette for
constitutive expression via CMV promoter
<220> FEATURE:
<221> NAME/KEY: misc_feature
<222> LOCATION: (1)..(588)
<223> OTHER INFORMATION: CMV promoter
<220> FEATURE:
<221> NAME/KEY: misc_feature
<222> LOCATION: (696)..(743)
<223> OTHER INFORMATION: NES
<220> FEATURE:
<221> NAME/KEY: misc_feature
<222> LOCATION: (744)..(2105)
<223> OTHER INFORMATION: CDS

<400> SEQUENCE: 45
gttgacattg attattgact agttattaat agtaatcaat tacggggtca ttagttcata 60
gcccatatat ggagttccgc gttacataac ttacggtaaa tggcccgcct ggctgaccgc 120
ccaacgaccc ccgcccattg acgtcaataa tgacgtatgt tcccatagta acgccaatag 180
ggactttcca ttgacgtcaa tgggtggact atttacggta aactgcccac ttggcagtac 240
atcaagtgta tcatatgcca agtacgcccc ctattgacgt caatgacggt aaatggcccg 300
cctggcatta tgcccagtac atgaccttat gggactttcc tacttggcag tacatctacg 360
tattagtcat cgctattacc atggtgatgc ggttttggca gtacatcaat gggcgtggat 420
agcggtttga ctcacgggga tttccaagtc tccaccccat tgacgtcaat gggagtttgt 480
tttggcacca aaatcaacgg gactttccaa aatgtcgtaa caactccgcc ccattgacgc 540
aaatgggcgg taggcgtgta cggtgggagg tctatataag cagagctctc tggctaacta 600
gagaacccac tgcttactgg cttatcgaaa ttaatacgac tcactatagg gagacccaag 660
ctggctagcg tttaaactta agcttcacca tggcgtgccc ggtgccgctg cagctgccgc 720
cgctggaacg cctgaccctg gatgataaaa aaccgctgaa taccctgatc tctgctactg 780
gtctgtggat gagtcgtacc ggaaccattc ataaaatcaa acaccacgag gttagccgtt 840
cgaaaatcta tattgagatg gcgtgtggcg atcatctggt tgtgaacaat agccgctctt 900
ctcgtacagc acgtgcactg cgtcaccaca aatatcgtaa aacctgtaaa cgttgccgtg 960
tgtccgatga ggatctgaac aaattcctga caaaagccaa tgaggaccaa acaagcgtga 1020
aagtgaaagt cgttagcgct cctacccgta ctaaaaaagc aatgccgaaa tccgttgctc 1080
gtgcccctaa accactggaa aacactgaag cagcacaggc acagccgtct ggaagcaaat 1140
tctctccggc cattcctgtt tctacccagg agtccgtttc tgttccagca agtgtgagca 1200
ccagcattag cagtattagc accggtgcca ccgctagcgc cctggttaaa ggcaatacca 1260
atccgattac aagcatgtct gccccggttc aagcatcagc tccagcactg acaaaatccc 1320
aaaccgatcg tctggaggtt ctgctgaatc cgaaagacga aatcagcctg aattccggca 1380
aaccgtttcg tgaactggag agcgaactgc tgtcacgtcg taaaaaagac ctgcaacaaa 1440
tctatgccga agaacgtgag aactatctgg ggaaactgga acgtgaaatc acccgctttt 1500
tcgtggatcg tggctttctg gagatcaaat ccccgattct gattcctctg gagtatatcg 1560
agcgtatggg catcgacaat gataccgaac tgagcaaaca aattttccgt gtggataaaa 1620
acttctgtct gcgccctatg ctagcaccaa atctggctaa ctatctgcgc aaactggacc 1680
gtgccctgcc tgatcctatc aaaatcttcg agatcggccc gtgttatcgt aaagagtccg 1740
acggtaaaga acatctggag gagtttacca tgctgaactt ttgccaaatg ggttcaggtt 1800
gtactcgtga gaacctggaa agcatcatca ccgattttct gaaccacctg ggcattgact 1860
tcaaaattgt gggcgacagc tgtatggtgt ttggcgacac cctggatgtc atgcacggcg 1920
acctggaact gtctagtgcc gttgtgggcc caatcccgct ggatcgtgag tggggtatcg 1980
acaaaccttg gatcggtgcg ggttttggtc tggagcgtct gctgaaagta aaacacgact 2040
tcaagaacat caaacgtgct gcacgttccg agtcctatta caatggtatt tctactaacc 2100
tgtaa 2105

<210> SEQ ID NO 46
<211> LENGTH: 2194
<212> TYPE: DNA
<213> ORGANISM: Artificial Sequence
<220> FEATURE:
<223> OTHER INFORMATION: NES-PylRSAF expression cassette containing
"T-REx" promoter comprising two tetO sequences
<220> FEATURE:
<221> NAME/KEY: misc_feature
<222> LOCATION: (1)..(584)
<223> OTHER INFORMATION: promoter
<220> FEATURE:
<221> NAME/KEY: misc_feature
<222> LOCATION: (586)..(604)
<223> OTHER INFORMATION: tetO
<220> FEATURE:
<221> NAME/KEY: misc_feature
<222> LOCATION: (607)..(625)
<223> OTHER INFORMATION: tetO
<220> FEATURE:
<221> NAME/KEY: misc_feature
<222> LOCATION: (785)..(832)
<223> OTHER INFORMATION: NES
<220> FEATURE:
<221> NAME/KEY: misc_feature
<222> LOCATION: (833)..(2194)
<223> OTHER INFORMATION: CDS

<400> SEQUENCE: 46
gacattgatt attgactagt tattaatagt aatcaattac ggggtcatta gttcatagcc 60
catatatgga gttccgcgtt acataactta cggtaaatgg cccgcctggc tgaccgccca 120
acgacccccg cccattgacg tcaataatga cgtatgttcc catagtaacg ccaataggga 180
ctttccattg acgtcaatgg gtggagtatt tacggtaaac tgcccacttg gcagtacatc 240
aagtgtatca tatgccaagt acgcccccta ttgacgtcaa tgacggtaaa tggcccgcct 300
ggcattatgc ccagtacatg accttatggg actttcctac ttggcagtac atctacgtat 360
tagtcatcgc tattaccatg gtgatgcggt tttggcagta catcaatggg cgtggatagc 420
ggtttgactc acggggattt ccaagtctcc accccattga cgtcaatggg agtttgtttt 480
ggcaccaaaa tcaacgggac tttccaaaat gtcgtaacaa ctccgcccca ttgacgcaaa 540
tgggcggtag gcgtgtacgg tgggaggtct atataagcag agctctccct atcagtgata 600
gagatctccc tatcagtgat agagatcgtc gacgagctcg tttagtgaac cgtcagatcg 660
cctggagacg ccatccacgc tgttttgacc tccatagaag acaccgggac cgatccagcc 720
tccggactct agcgtttaaa catcacaagt ttgtacaaaa aagcaggcgc tagacaccat 780
ggcgtgcccg gtgccgctgc agctgccgcc gctggaacgc ctgaccctgg atgataaaaa 840
accgctgaat accctgatct ctgctactgg tctgtggatg agtcgtaccg gaaccattca 900
taaaatcaaa caccacgagg ttagccgttc gaaaatctat attgagatgg cgtgtggcga 960
tcatctggtt gtgaacaata gccgctcttc tcgtacagca cgtgcactgc gtcaccacaa 1020
atatcgtaaa acctgtaaac gttgccgtgt gtccgatgag gatctgaaca aattcctgac 1080
aaaagccaat gaggaccaaa caagcgtgaa agtgaaagtc gttagcgctc ctacccgtac 1140
taaaaaagca atgccgaaat ccgttgctcg tgcccctaaa ccactggaaa acactgaagc 1200
agcacaggca cagccgtctg gaagcaaatt ctctccggcc attcctgttt ctacccagga 1260
gtccgtttct gttccagcaa gtgtgagcac cagcattagc agtattagca ccggtgccac 1320
cgctagcgcc ctggttaaag gcaataccaa tccgattaca agcatgtctg ccccggttca 1380
agcatcagct ccagcactga caaaatccca aaccgatcgt ctggaggttc tgctgaatcc 1440
gaaagacgaa atcagcctga attccggcaa accgtttcgt gaactggaga gcgaactgct 1500
gtcacgtcgt aaaaaagacc tgcaacaaat ctatgccgaa gaacgtgaga actatctggg 1560
gaaactggaa cgtgaaatca cccgcttttt cgtggatcgt ggctttctgg agatcaaatc 1620
cccgattctg attcctctgg agtatatcga gcgtatgggc atcgacaatg ataccgaact 1680
gagcaaacaa attttccgtg tggataaaaa cttctgtctg cgccctatgc tagcaccaaa 1740
tctggctaac tatctgcgca aactggaccg tgccctgcct gatcctatca aaatcttcga 1800
gatcggcccg tgttatcgta aagagtccga cggtaaagaa catctggagg agtttaccat 1860
gctgaacttt tgccaaatgg gttcaggttg tactcgtgag aacctggaaa gcatcatcac 1920
cgattttctg aaccacctgg gcattgactt caaaattgtg ggcgacagct gtatggtgtt 1980
tggcgacacc ctggatgtca tgcacggcga cctggaactg tctagtgccg ttgtgggccc 2040
aatcccgctg gatcgtgagt ggggtatcga caaaccttgg atcggtgcgg gttttggtct 2100
ggagcgtctg ctgaaagtaa aacacgactt caagaacatc aaacgtgctg cacgttccga 2160
gtcctattac aatggtattt ctactaacct gtaa 2194

<210> SEQ ID NO 47
<211> LENGTH: 1883
<212> TYPE: DNA
<213> ORGANISM: Artificial Sequence
<220> FEATURE:
<223> OTHER INFORMATION: NES-PylRSAF expression cassette containing
“Tet-On” promoter comprising 8 tetO sequences
<220> FEATURE:
<221> NAME/KEY: misc_feature
<222> LOCATION: (1)..(458)
<223> OTHER INFORMATION: promoter
<220> FEATURE:
<221> NAME/KEY: misc_feature
<222> LOCATION: (18)..(36)
<223> OTHER INFORMATION: tetO
<220> FEATURE:
<221> NAME/KEY: misc_feature
<222> LOCATION: (54)..(72)
<223> OTHER INFORMATION: tetO
<220> FEATURE:
<221> NAME/KEY: misc_feature
<222> LOCATION: (90)..(108)
<223> OTHER INFORMATION: tetO
<220> FEATURE:
<221> NAME/KEY: misc_feature
<222> LOCATION: (126)..(144)
<223> OTHER INFORMATION: tetO
<220> FEATURE:
<221> NAME/KEY: misc_feature
<222> LOCATION: (162)..(180)
<223> OTHER INFORMATION: tetO
<220> FEATURE:
<221> NAME/KEY: misc_feature
<222> LOCATION: (198)..(216)
<223> OTHER INFORMATION: tetO
<220> FEATURE:
<221> NAME/KEY: misc_feature
<222> LOCATION: (234)..(252)
<223> OTHER INFORMATION: tetO
<220> FEATURE:
<221> NAME/KEY: misc_feature
<222> LOCATION: (270)..(288)
<223> OTHER INFORMATION: tetO
<220> FEATURE:
<221> NAME/KEY: misc_feature
<222> LOCATION: (474)..(521)
<223> OTHER INFORMATION: NES
<220> FEATURE:
<221> NAME/KEY: misc_feature
<222> LOCATION: (522)..(1883)
<223> OTHER INFORMATION: CDS

<400> SEQUENCE: 47
caattgctcg agtttactcc ctatcagtga tagagaacgt atgtcgactt tactccctat 60
cagtgataga gaacgtatga agagtttact ccctatcagt gatagagaac gtatgcagac 120
tttactccct atcagtgata gagaacgtat aaggagttta ctccctatca gtgatagaga 180
acgtatgacc agtttactcc ctatcagtga tagagaacgt atctacagtt tactccctat 240
cagtgataga gaacgtatat ccagtttact ccctatcagt gatagagaac gtatacgctt 300
taggcgtgta cggtgggcgc ctataaaagc agagctcgtt tagtgaaccg tcagatcgcc 360
tggagcaatt ccacaacact tttgtcttat accaactttc cgtaccactt cctaccctcg 420
aaagtccata tggctagcct gcagggatcc agatatcaag cttcaccatg gcgtgcccgg 480
tgccgctgca gctgccgccg ctggaacgcc tgaccctgga tgataaaaaa ccgctgaata 540
ccctgatctc tgctactggt ctgtggatga gtcgtaccgg aaccattcat aaaatcaaac 600
accacgaggt tagccgttcg aaaatctata ttgagatggc gtgtggcgat catctggttg 660
tgaacaatag ccgctcttct cgtacagcac gtgcactgcg tcaccacaaa tatcgtaaaa 720
cctgtaaacg ttgccgtgtg tccgatgagg atctgaacaa attcctgaca aaagccaatg 780
aggaccaaac aagcgtgaaa gtgaaagtcg ttagcgctcc tacccgtact aaaaaagcaa 840
tgccgaaatc cgttgctcgt gcccctaaac cactggaaaa cactgaagca gcacaggcac 900
agccgtctgg aagcaaattc tctccggcca ttcctgtttc tacccaggag tccgtttctg 960
ttccagcaag tgtgagcacc agcattagca gtattagcac cggtgccacc gctagcgccc 1020

```
tggttaaagg caataccaat ccgattacaa gcatgtctgc cccggttcaa gcatcagctc   1080

cagcactgac aaaatcccaa accgatcgtc tggaggttct gctgaatccg aaagacgaaa   1140

tcagcctgaa ttccggcaaa ccgtttcgtg aactggagag cgaactgctg tcacgtcgta   1200

aaaaagacct gcaacaaatc tatgccgaag aacgtgagaa ctatctgggg aaactggaac   1260

gtgaaatcac ccgctttttc gtggatcgtg gctttctgga gatcaaatcc ccgattctga   1320

ttcctctgga gtatatcgag cgtatgggca tcgacaatga taccgaactg agcaaacaaa   1380

ttttccgtgt ggataaaaac ttctgtctgc gccctatgct agcaccaaat ctggctaact   1440

atctgcgcaa actggaccgt gccctgcctg atcctatcaa aatcttcgag atcggcccgt   1500

gttatcgtaa agagtccgac ggtaaagaac atctggagga gtttaccatg ctgaactttt   1560

gccaaatggg ttcaggttgt actcgtgaga acctggaaag catcatcacc gattttctga   1620

accacctggg cattgacttc aaaattgtgg gcgacagctg tatggtgttt ggcgacaccc   1680

tggatgtcat gcacggcgac ctggaactgt ctagtgccgt tgtgggccca atcccgctgg   1740

atcgtgagtg gggtatcgac aaaccttgga tcggtgcggg ttttggtctg gagcgtctgc   1800

tgaaagtaaa acacgacttc aagaacatca aacgtgctgc acgttccgag tcctattaca   1860

atggtatttc tactaacctg taa                                           1883
```

<210> SEQ ID NO 48
<211> LENGTH: 226
<212> TYPE: DNA
<213> ORGANISM: Artificial Sequence
<220> FEATURE:
<223> OTHER INFORMATION: tRNAPyl expression cassette for expression via T7 promoter
<220> FEATURE:
<221> NAME/KEY: misc_feature
<222> LOCATION: (1)..(17)
<223> OTHER INFORMATION: T7 promoter
<220> FEATURE:
<221> NAME/KEY: misc_feature
<222> LOCATION: (18)..(86)
<223> OTHER INFORMATION: tRNA(Pyl)
<220> FEATURE:
<221> NAME/KEY: misc_feature
<222> LOCATION: (98)..(226)
<223> OTHER INFORMATION: T7term

<400> SEQUENCE: 48

```
taatacgact cactatagga aacctgatca tgtagatcga atggactcta aatccgttca     60

gccgggttag attcccgggg tttccgtttt tggccgcctg ctaacaaagc ccgaaaggaa    120

gctgagttgg ctgctgccac cgctgagcaa taactagcat aaccccttgg ggcctctaaa    180

cgggtcttga ggggtttttt gctgaaagga ggaactatat ccggat                   226
```

<210> SEQ ID NO 49
<211> LENGTH: 295
<212> TYPE: DNA
<213> ORGANISM: Artificial Sequence
<220> FEATURE:
<223> OTHER INFORMATION: tRNAPyl-HDV ribozyme expression cassette for expression via T7 promoter
<220> FEATURE:
<221> NAME/KEY: misc_feature
<222> LOCATION: (1)..(17)
<223> OTHER INFORMATION: T7 promoter
<220> FEATURE:
<221> NAME/KEY: misc_feature
<222> LOCATION: (18)..(86)
<223> OTHER INFORMATION: tRNA(Pyl)
<220> FEATURE:
<221> NAME/KEY: misc_feature
<222> LOCATION: (87)..(154)
<223> OTHER INFORMATION: HDV
<220> FEATURE:
<221> NAME/KEY: misc_feature
<222> LOCATION: (167)..(295)
<223> OTHER INFORMATION: T7term

<400> SEQUENCE: 49
taatacgact cactatagga aacctgatca tgtagatcga atggactcta aatccgttca 60
gccgggttag attcccgggg tttccggcta gccatggtcc cagcctcctc gctggcggct 120
agtgggcaac atgcttcggc atggcgaatg ggactttaaa ctcgagctgc taacaaagcc 180
cgaaaggaag ctgagttggc tgctgccacc gctgagcaat aactagcata accccttggg 240
gcctctaaac gggtcttgag gggttttttg ctgaaaggag gaactatatc cggat 295

<210> SEQ ID NO 50
<211> LENGTH: 669
<212> TYPE: DNA
<213> ORGANISM: Artificial Sequence
<220> FEATURE:
<223> OTHER INFORMATION: tRNAPyl expression cassette containing a variant of the human U6 promoter modified to comprise 8 tetO before and two tetO sequences after the U6 promoter
<220> FEATURE:
<221> NAME/KEY: misc_feature
<222> LOCATION: (24)..(42)
<223> OTHER INFORMATION: tetO
<220> FEATURE:
<221> NAME/KEY: misc_feature
<222> LOCATION: (60)..(78)
<223> OTHER INFORMATION: tetO
<220> FEATURE:
<221> NAME/KEY: misc_feature
<222> LOCATION: (96)..(114)
<223> OTHER INFORMATION: tetO
<220> FEATURE:
<221> NAME/KEY: misc_feature
<222> LOCATION: (132)..(150)
<223> OTHER INFORMATION: tetO
<220> FEATURE:
<221> NAME/KEY: misc_feature
<222> LOCATION: (168)..(186)
<223> OTHER INFORMATION: tetO
<220> FEATURE:
<221> NAME/KEY: misc_feature
<222> LOCATION: (204)..(222)
<223> OTHER INFORMATION: tetO
<220> FEATURE:
<221> NAME/KEY: misc_feature
<222> LOCATION: (240)..(285)
<223> OTHER INFORMATION: tetO
<220> FEATURE:
<221> NAME/KEY: misc_feature
<222> LOCATION: (276)..(294)
<223> OTHER INFORMATION: tetO
<220> FEATURE:
<221> NAME/KEY: misc_feature
<222> LOCATION: (337)..(537)
<223> OTHER INFORMATION: U6 promoter
<220> FEATURE:
<221> NAME/KEY: misc_feature
<222> LOCATION: (540)..(558)
<223> OTHER INFORMATION: tetO
<220> FEATURE:
<221> NAME/KEY: misc_feature
<222> LOCATION: (568)..(586)
<223> OTHER INFORMATION: tetO
<220> FEATURE:
<221> NAME/KEY: misc_feature
<222> LOCATION: (589)..(657)
<223> OTHER INFORMATION: tRNA(Pyl)

<400> SEQUENCE: 50

```
gaattccaat tgctcgagtt tactccctat cagtgataga gaacgtatgt cgactttact     60

ccctatcagt gatagagaac gtatgaagag tttactccct atcagtgata gagaacgtat    120

gcagacttta ctccctatca gtgatagaga acgtataagg agtttactcc ctatcagtga    180

tagagaacgt atgaccagtt tactccctat cagtgataga gaacgtatct acagtttact    240

ccctatcagt gatagagaac gtatatccag tttactccct atcagtgata gagaacgtat    300

gtcgaggtag gcgtgtacgg tcaaggtcgg gcaggaagag ggcctatttc ccatgattcc    360

ttcatatttg catatacgat acaaggctgt tagagagata attagaatta atttgactgt    420

aaacacaaag atattagtac aaaatacgtg acgtagaaag taataatttc ttgggtagtt    480

tgcagtttta aaattatgtt ttaaaatgga ctatcatatg cttaccgtaa cttgaaagtt    540

ccctatcagt gatagagatt atatatctcc ctatcagtga tagagaccgg aaacctgatc    600

atgtagatcg aatggactct aaatccgttc agccgggtta gattcccggg gtttccgttt    660

tttggatcc                                                            669
```

```
<210> SEQ ID NO 51
<211> LENGTH: 178
<212> TYPE: DNA
<213> ORGANISM: Artificial Sequence
<220> FEATURE:
<223> OTHER INFORMATION: tRNAPyl expression cassette containing a
      variant of the human H1 promoter modified to comprise 2 tetO
      sequences
<220> FEATURE:
<221> NAME/KEY: misc_feature
<222> LOCATION: (1)..(99)
<223> OTHER INFORMATION: H1 promoter
<220> FEATURE:
<221> NAME/KEY: misc_feature
<222> LOCATION: (49)..(67)
<223> OTHER INFORMATION: tetO
<220> FEATURE:
<221> NAME/KEY: misc_feature
<222> LOCATION: (77)..(95)
<223> OTHER INFORMATION: tetO
<220> FEATURE:
<221> NAME/KEY: misc_feature
<222> LOCATION: (100)..(168)
<223> OTHER INFORMATION: tRNA(Pyl)

<400> SEQUENCE: 51

atatttgcat gtcgctatgt gttctgggaa atcaccataa acgtgaaatc cctatcagtg     60

atagagactt ataagttccc tatcagtgat agagatcccg gaaacctgat catgtagatc    120

gaatggactc taaatccgtt cagccgggtt agattcccgg ggtttccgaa gctttttt      178
```

```
<210> SEQ ID NO 52
<211> LENGTH: 248
<212> TYPE: PRT
<213> ORGANISM: Artificial Sequence
<220> FEATURE:
<223> OTHER INFORMATION: TetOn3G protein
<220> FEATURE:
<221> NAME/KEY: MISC_FEATURE
<223> OTHER INFORMATION: TetOn3G protein

<400> SEQUENCE: 52

Met Ser Arg Leu Asp Lys Ser Lys Val Ile Asn Ser Ala Leu Glu Leu
1               5                   10                  15

Leu Asn Gly Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45
```

```
Arg Ala Leu Leu Asp Ala Leu Pro Ile Glu Met Leu Asp Arg His His
    50                  55                  60

Thr His Ser Cys Pro Leu Glu Gly Glu Ser Trp Gln Asp Phe Leu Arg
65                  70                  75                  80

Asn Asn Ala Lys Ser Tyr Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Glu Gln Glu His Gln Val Ala Lys Glu Glu Arg Glu Thr
145                 150                 155                 160

Pro Thr Thr Asp Ser Met Pro Pro Leu Leu Lys Gln Ala Ile Glu Leu
                165                 170                 175

Phe Asp Arg Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
        195                 200                 205

Thr Asp Ala Leu Asp Asp Phe Asp Leu Asp Met Leu Pro Ala Asp Ala
    210                 215                 220

Leu Asp Asp Phe Asp Leu Asp Met Leu Pro Ala Asp Ala Leu Asp Asp
225                 230                 235                 240

Phe Asp Leu Asp Met Leu Pro Gly
                245
```

<210> SEQ ID NO 53
<211> LENGTH: 471
<212> TYPE: PRT
<213> ORGANISM: Artificial Sequence
<220> FEATURE:
<223> OTHER INFORMATION: Methanosarcina mazei PylRS Y306A, Y384F mutant (PylRSAF)_amino acid sequence

<400> SEQUENCE: 53

```
Met Ala Cys Pro Val Pro Leu Gln Leu Pro Pro Leu Glu Arg Leu Thr
1               5                   10                  15

Leu Asp Asp Lys Lys Pro Leu Asn Thr Leu Ile Ser Ala Thr Gly Leu
            20                  25                  30

Trp Met Ser Arg Thr Gly Thr Ile His Lys Ile Lys His His Glu Val
        35                  40                  45

Ser Arg Ser Lys Ile Tyr Ile Glu Met Ala Cys Gly Asp His Leu Val
    50                  55                  60

Val Asn Asn Ser Arg Ser Ser Arg Thr Ala Arg Ala Leu Arg His His
65                  70                  75                  80

Lys Tyr Arg Lys Thr Cys Lys Arg Cys Arg Val Ser Asp Glu Asp Leu
                85                  90                  95

Asn Lys Phe Leu Thr Lys Ala Asn Glu Asp Gln Thr Ser Val Lys Val
            100                 105                 110

Lys Val Val Ser Ala Pro Thr Arg Thr Lys Lys Ala Met Pro Lys Ser
        115                 120                 125

Val Ala Arg Ala Pro Lys Pro Leu Glu Asn Thr Glu Ala Ala Gln Ala
    130                 135                 140

Gln Pro Ser Gly Ser Lys Phe Ser Pro Ala Ile Pro Val Ser Thr Gln
```

```
145                 150                 155                 160

Glu Ser Val Ser Val Pro Ala Ser Val Ser Thr Ser Ile Ser Ser Ile
                165                 170                 175

Ser Thr Gly Ala Thr Ala Ser Ala Leu Val Lys Gly Asn Thr Asn Pro
            180                 185                 190

Ile Thr Ser Met Ser Ala Pro Val Gln Ala Ser Ala Pro Ala Leu Thr
        195                 200                 205

Lys Ser Gln Thr Asp Arg Leu Glu Val Leu Leu Asn Pro Lys Asp Glu
    210                 215                 220

Ile Ser Leu Asn Ser Gly Lys Pro Phe Arg Glu Leu Glu Ser Glu Leu
225                 230                 235                 240

Leu Ser Arg Arg Lys Lys Asp Leu Gln Gln Ile Tyr Ala Glu Glu Arg
                245                 250                 255

Glu Asn Tyr Leu Gly Lys Leu Glu Arg Glu Ile Thr Arg Phe Phe Val
            260                 265                 270

Asp Arg Gly Phe Leu Glu Ile Lys Ser Pro Ile Leu Ile Pro Leu Glu
        275                 280                 285

Tyr Ile Glu Arg Met Gly Ile Asp Asn Asp Thr Glu Leu Ser Lys Gln
    290                 295                 300

Ile Phe Arg Val Asp Lys Asn Phe Cys Leu Arg Pro Met Leu Ala Pro
305                 310                 315                 320

Asn Leu Ala Asn Tyr Leu Arg Lys Leu Asp Arg Ala Leu Pro Asp Pro
                325                 330                 335

Ile Lys Ile Phe Glu Ile Gly Pro Cys Tyr Arg Lys Glu Ser Asp Gly
            340                 345                 350

Lys Glu His Leu Glu Glu Phe Thr Met Leu Asn Phe Cys Gln Met Gly
        355                 360                 365

Ser Gly Cys Thr Arg Glu Asn Leu Glu Ser Ile Ile Thr Asp Phe Leu
    370                 375                 380

Asn His Leu Gly Ile Asp Phe Lys Ile Val Gly Asp Ser Cys Met Val
385                 390                 395                 400

Phe Gly Asp Thr Leu Asp Val Met His Gly Asp Leu Glu Leu Ser Ser
                405                 410                 415

Ala Val Val Gly Pro Ile Pro Leu Asp Arg Glu Trp Gly Ile Asp Lys
            420                 425                 430

Pro Trp Ile Gly Ala Gly Phe Gly Leu Glu Arg Leu Leu Lys Val Lys
        435                 440                 445

His Asp Phe Lys Asn Ile Lys Arg Ala Ala Arg Ser Glu Ser Tyr Tyr
    450                 455                 460

Asn Gly Ile Ser Thr Asn Leu
465                 470


<210> SEQ ID NO 54
<211> LENGTH: 471
<212> TYPE: PRT
<213> ORGANISM: Artificial Sequence
<220> FEATURE:
<223> OTHER INFORMATION: Methanosarcina mazei PylRS N346A, C348A mutant
      (PylRSAA)_amino acid sequence

<400> SEQUENCE: 54

Met Ala Cys Pro Val Pro Leu Gln Leu Pro Pro Leu Glu Arg Leu Thr
1               5                   10                  15

Leu Asp Asp Lys Lys Pro Leu Asn Thr Leu Ile Ser Ala Thr Gly Leu
            20                  25                  30
```

```
Trp Met Ser Arg Thr Gly Thr Ile His Lys Ile Lys His His Glu Val
        35                  40                  45

Ser Arg Ser Lys Ile Tyr Ile Glu Met Ala Cys Gly Asp His Leu Val
    50                  55                  60

Val Asn Asn Ser Arg Ser Ser Arg Thr Ala Arg Ala Leu Arg His His
65                  70                  75                  80

Lys Tyr Arg Lys Thr Cys Lys Arg Cys Arg Val Ser Asp Glu Asp Leu
                85                  90                  95

Asn Lys Phe Leu Thr Lys Ala Asn Glu Asp Gln Thr Ser Val Lys Val
            100                 105                 110

Lys Val Val Ser Ala Pro Thr Arg Thr Lys Lys Ala Met Pro Lys Ser
        115                 120                 125

Val Ala Arg Ala Pro Lys Pro Leu Glu Asn Thr Glu Ala Ala Gln Ala
    130                 135                 140

Gln Pro Ser Gly Ser Lys Phe Ser Pro Ala Ile Pro Val Ser Thr Gln
145                 150                 155                 160

Glu Ser Val Ser Val Pro Ala Ser Val Ser Thr Ser Ile Ser Ser Ile
                165                 170                 175

Ser Thr Gly Ala Thr Ala Ser Ala Leu Val Lys Gly Asn Thr Asn Pro
            180                 185                 190

Ile Thr Ser Met Ser Ala Pro Val Gln Ala Ser Ala Pro Ala Leu Thr
        195                 200                 205

Lys Ser Gln Thr Asp Arg Leu Glu Val Leu Leu Asn Pro Lys Asp Glu
    210                 215                 220

Ile Ser Leu Asn Ser Gly Lys Pro Phe Arg Glu Leu Glu Ser Glu Leu
225                 230                 235                 240

Leu Ser Arg Arg Lys Lys Asp Leu Gln Gln Ile Tyr Ala Glu Glu Arg
                245                 250                 255

Glu Asn Tyr Leu Gly Lys Leu Glu Arg Glu Ile Thr Arg Phe Phe Val
            260                 265                 270

Asp Arg Gly Phe Leu Glu Ile Lys Ser Pro Ile Leu Ile Pro Leu Glu
        275                 280                 285

Tyr Ile Glu Arg Met Gly Ile Asp Asn Asp Thr Glu Leu Ser Lys Gln
    290                 295                 300

Ile Phe Arg Val Asp Lys Asn Phe Cys Leu Arg Pro Met Leu Ala Pro
305                 310                 315                 320

Asn Leu Tyr Asn Tyr Leu Arg Lys Leu Asp Arg Ala Leu Pro Asp Pro
                325                 330                 335

Ile Lys Ile Phe Glu Ile Gly Pro Cys Tyr Arg Lys Glu Ser Asp Gly
            340                 345                 350

Lys Glu His Leu Glu Glu Phe Thr Met Leu Ala Phe Ala Gln Met Gly
        355                 360                 365

Ser Gly Cys Thr Arg Glu Asn Leu Glu Ser Ile Ile Thr Asp Phe Leu
    370                 375                 380

Asn His Leu Gly Ile Asp Phe Lys Ile Val Gly Asp Ser Cys Met Val
385                 390                 395                 400

Tyr Gly Asp Thr Leu Asp Val Met His Gly Asp Leu Glu Leu Ser Ser
                405                 410                 415

Ala Val Val Gly Pro Ile Pro Leu Asp Arg Glu Trp Gly Ile Asp Lys
            420                 425                 430

Pro Trp Ile Gly Ala Gly Phe Gly Leu Glu Arg Leu Leu Lys Val Lys
        435                 440                 445

His Asp Phe Lys Asn Ile Lys Arg Ala Ala Arg Ser Glu Ser Tyr Tyr
```

```
    450                 455                 460

Asn Gly Ile Ser Thr Asn Leu
465                 470


<210> SEQ ID NO 55
<211> LENGTH: 470
<212> TYPE: PRT
<213> ORGANISM: Artificial Sequence
<220> FEATURE:
<223> OTHER INFORMATION: Methanosarcina mazei PylRS Y306A, N346A, C348A,
      Y384Fmutant (PylRSAAAF)_amino acid sequence

<400> SEQUENCE: 55

Ala Cys Pro Val Pro Leu Gln Leu Pro Pro Leu Glu Arg Leu Thr Leu
1               5                   10                  15

Asp Asp Lys Lys Pro Leu Asn Thr Leu Ile Ser Ala Thr Gly Leu Trp
            20                  25                  30

Met Ser Arg Thr Gly Thr Ile His Lys Ile Lys His His Glu Val Ser
        35                  40                  45

Arg Ser Lys Ile Tyr Ile Glu Met Ala Cys Gly Asp His Leu Val Val
    50                  55                  60

Asn Asn Ser Arg Ser Ser Arg Thr Ala Arg Ala Leu Arg His His Lys
65                  70                  75                  80

Tyr Arg Lys Thr Cys Lys Arg Cys Arg Val Ser Asp Glu Asp Leu Asn
                85                  90                  95

Lys Phe Leu Thr Lys Ala Asn Glu Asp Gln Thr Ser Val Lys Val Lys
            100                 105                 110

Val Val Ser Ala Pro Thr Arg Thr Lys Lys Ala Met Pro Lys Ser Val
        115                 120                 125

Ala Arg Ala Pro Lys Pro Leu Glu Asn Thr Glu Ala Ala Gln Ala Gln
    130                 135                 140

Pro Ser Gly Ser Lys Phe Ser Pro Ala Ile Pro Val Ser Thr Gln Glu
145                 150                 155                 160

Ser Val Ser Val Pro Ala Ser Val Ser Thr Ser Ile Ser Ser Ile Ser
                165                 170                 175

Thr Gly Ala Thr Ala Ser Ala Leu Val Lys Gly Asn Thr Asn Pro Ile
            180                 185                 190

Thr Ser Met Ser Ala Pro Val Gln Ala Ser Ala Pro Ala Leu Thr Lys
        195                 200                 205

Ser Gln Thr Asp Arg Leu Glu Val Leu Leu Asn Pro Lys Asp Glu Ile
    210                 215                 220

Ser Leu Asn Ser Gly Lys Pro Phe Arg Glu Leu Glu Ser Glu Leu Leu
225                 230                 235                 240

Ser Arg Arg Lys Lys Asp Leu Gln Gln Ile Tyr Ala Glu Glu Arg Glu
                245                 250                 255

Asn Tyr Leu Gly Lys Leu Glu Arg Glu Ile Thr Arg Phe Phe Val Asp
            260                 265                 270

Arg Gly Phe Leu Glu Ile Lys Ser Pro Ile Leu Ile Pro Leu Glu Tyr
        275                 280                 285

Ile Glu Arg Met Gly Ile Asp Asn Asp Thr Glu Leu Ser Lys Gln Ile
    290                 295                 300

Phe Arg Val Asp Lys Asn Phe Cys Leu Arg Pro Met Leu Ala Pro Asn
305                 310                 315                 320

Leu Ala Asn Tyr Leu Arg Lys Leu Asp Arg Ala Leu Pro Asp Pro Ile
                325                 330                 335
```

```
Lys Ile Phe Glu Ile Gly Pro Cys Tyr Arg Lys Glu Ser Asp Gly Lys
            340                 345                 350

Glu His Leu Glu Glu Phe Thr Met Leu Ala Phe Ala Gln Met Gly Ser
        355                 360                 365

Gly Cys Thr Arg Glu Asn Leu Glu Ser Ile Ile Thr Asp Phe Leu Asn
    370                 375                 380

His Leu Gly Ile Asp Phe Lys Ile Val Gly Asp Ser Cys Met Val Phe
385                 390                 395                 400

Gly Asp Thr Leu Asp Val Met His Gly Asp Leu Glu Leu Ser Ser Ala
                405                 410                 415

Val Val Gly Pro Ile Pro Leu Asp Arg Glu Trp Gly Ile Asp Lys Pro
            420                 425                 430

Trp Ile Gly Ala Gly Phe Gly Leu Glu Arg Leu Leu Lys Val Lys His
        435                 440                 445

Asp Phe Lys Asn Ile Lys Arg Ala Ala Arg Ser Glu Ser Tyr Tyr Asn
    450                 455                 460

Gly Ile Ser Thr Asn Leu
465                 470
```

<210> SEQ ID NO 56
<211> LENGTH: 4437
<212> TYPE: DNA
<213> ORGANISM: Artificial Sequence
<220> FEATURE:
<223> OTHER INFORMATION: pCAGGS-T7-RNAP
<220> FEATURE:
<221> NAME/KEY: misc_feature
<222> LOCATION: (1)..(380)
<223> OTHER INFORMATION: CMV enhancer
<220> FEATURE:
<221> NAME/KEY: misc_feature
<222> LOCATION: (382)..(659)
<223> OTHER INFORMATION: Chicken b-actin promoter
<220> FEATURE:
<221> NAME/KEY: misc_feature
<222> LOCATION: (661)..(1678)
<223> OTHER INFORMATION: Chimeric intron chicken actin
<220> FEATURE:
<221> NAME/KEY: misc_feature
<222> LOCATION: (1789)..(4437)
<223> OTHER INFORMATION: T7-RNAP

<400> SEQUENCE: 56

```
gacattgatt attgactagt tattaatagt aatcaattac ggggtcatta gttcatagcc     60

catatatgga gttccgcgtt acataactta cggtaaatgg cccgcctggc tgaccgccca    120

acgacccccg cccattgacg tcaataatga cgtatgttcc catagtaacg ccaataggga    180

ctttccattg acgtcaatgg gtggagtatt tacggtaaac tgcccacttg gcagtacatc    240

aagtgtatca tatgccaagt acgcccccta ttgacgtcaa tgacggtaaa tggcccgcct    300

ggcattatgc ccagtacatg accttatggg actttcctac ttggcagtac atctacgtat    360

tagtcatcgc tattaccatg gtcgaggtga gccccacgtt ctgcttcact ctccccatct    420

cccccccctc cccaccccca attttgtatt tatttatttt ttaattattt tgtgcagcga    480

tgggggcggg gggggggggg gggcgcgcgc caggcggggc ggggcggggc gaggggcggg    540

gcggggcgag gcggagaggt gcggcggcag ccaatcagag cggcgcgctc cgaaagtttc    600

cttttatggc gaggcggcgg cggcggcggc cctataaaaa gcgaagcgcg cggcgggcgg    660

ggagtcgctg cgacgctgcc ttcgccccgt gccccgctcc gccgccgcct cgcgccgccc    720

gccccggctc tgactgaccg cgttactccc acaggtgagc gggcgggacg gcccttctcc    780
```

-continued

```
tccgggctgt aattagcgct tggtttaatg acggcttgtt tcttttctgt ggctgcgtga    840
aagccttgag gggctccggg agggcccttt gtgcgggggg agcggctcgg ggggtgcgtg    900
cgtgtgtgtg tgcgtgggga gcgccgcgtg cggctccgcg ctgcccggcg gctgtgagcg    960
ctgcgggcgc ggcgcggggc tttgtgcgct ccgcagtgtg cgcgagggga gcgcggccgg   1020
gggcggtgcc ccgcggtgcg gggggggctg cgaggggaac aaaggctgcg tgcggggtgt   1080
gtgcgtgggg gggtgagcag ggggtgtggg cgcgtcggtc gggctgcaac ccccccctgca  1140
ccccccctccc cgagttgctg agcacggccc ggcttcgggt gcggggctcc gtacggggcg  1200
tggcgcgggg ctcgccgtgc cgggcggggg gtggcggcag gtgggggtgc cgggcggggc   1260
ggggccgcct cgggccgggg agggctcggg ggaggggcgc ggcggccccc ggagcgccgg   1320
cggctgtcga ggcgcggcga gccgcagcca ttgcctttta tggtaatcgt gcgagagggc   1380
gcagggactt cctttgtccc aaatctgtgc ggagccgaaa tctgggaggc gccgccgcac   1440
cccctctagc gggcgcgggg cgaagcggtg cggcgccggc aggaaggaaa tgggcgggga   1500
gggccttcgt gcgtcgccgc gccgccgtcc ccttctccct ctccagcctc ggggctgtcc   1560
gcggggggac ggctgccttc ggggggggacg gggcagggcg gggttcggct tctggcgtgt  1620
gaccggcggc tctagagcct ctgctaacca tgttcatgcc ttcttctttt tcctacagct   1680
cctgggcaac gtgctggtta ttgtgctgtc tcatcatttt ggcaaagaat tcgagctcat   1740
cggatccaga tctgatccgg atttactaac tggaagaggc actaaatgaa cacgattaac   1800
atcgctaaga acgacttctc tgacatcgaa ctggctgcta tcccgttcaa cactctggct   1860
gaccattacg gtgagcgttt agctcgcgaa cagttggccc ttgagcatga gtcttacgag   1920
atgggtgaag cacgcttccg caagatgttt gagcgtcaac ttaaagctgg tgaggttgcg   1980
gataacgctg ccgccaagcc tctcatcact accctactcc ctaagatgat tgcacgcatc   2040
aacgactggt ttgaggaagt gaaagctaag cgcggcaagc gcccgacagc cttccagttc   2100
ctgcaagaaa tcaagccgga agccgtagcg tacatcacca ttaagaccac tctggcttgc   2160
ctaaccagtg ctgacaatac aaccgttcag gctgtagcaa gcgcaatcgg tcgggccatt   2220
gaggacgagg ctcgcttcgg tcgtatccgt gaccttgaag ctaagcactt caagaaaaac   2280
gttgaggaac aactcaacaa gcgcgtaggg cacgtctaca agaaagcatt tatgcaagtt   2340
gtcgaggctg acatgctctc taagggtcta ctcggtggcg aggcgtggtc ttcgtggcat   2400
aaggaagact ctattcatgt aggagtacgc tgcatcgaga tgctcattga gtcaaccgga   2460
atggttagct tacaccgcca aaatgctggc gtagtaggtc aagactctga gactatcgaa   2520
ctcgcacctg aatacgctga ggctatcgca acccgtgcag gtgcgctggc tggcatctct   2580
ccgatgttcc aaccttgcgt agttcctcct aagccgtgga ctggcattac tggtggtggc   2640
tattgggcta acggtcgtcg tcctctggcg ctggtgcgta ctcacagtaa gaaagcactg   2700
atgcgctacg aagacgttta catgcctgag gtgtacaaag cgattaacat tgcgcaaaac   2760
accgcatgga aaatcaacaa gaaagtccta gcggtcgcca acgtaatcac caagtggaag   2820
cattgtccgg tcgaggacat ccctgcgatt gagcgtgaag aactcccgat gaaaccggaa   2880
gacatcgaca tgaatcctga ggctctcacc gcgtggaaac gtgctgccgc tgctgtgtac   2940
cgcaaggaca aggctcgcaa gtctcgccgt atcagccttg agttcatgct tgagcaagcc   3000
aataagtttg ctaaccataa ggccatctgg ttcccttaca acatggactg gcgcggtcgt   3060
gtttacgctg tgtcaatgtt caacccgcaa ggtaacgata tgaccaaagg actgcttacg   3120
ctggcgaaag gtaaaccaat cggtaaggaa ggttactact ggctgaaaat ccacggtgca   3180
```

```
aactgtgcgg gtgtcgataa ggttccgttc cctgagcgca tcaagttcat tgaggaaaac   3240

cacgagaaca tcatggcttg cgctaagtct ccactggaga acacttggtg ggctgagcaa   3300

gattctccgt tctgcttcct tgcgttctgc tttgagtacg ctggggtaca gcaccacggc   3360

ctgagctata actgctccct tccgctggcg tttgacgggt cttgctctgg catccagcac   3420

ttctccgcga tgctccgaga tgaggtaggt ggtcgcgcgg ttaacttgct tcctagtgaa   3480

accgttcagg acatctacgg gattgttgct aagaaagtca acgagattct acaagcagac   3540

gcaatcaatg ggaccgataa cgaagtagtt accgtgaccg atgagaacac tggtgaaatc   3600

tctgagaaag tcaagctggg cactaaggca ctggctggtc aatggctggc ttacggtgtt   3660

actcgcagtg tgactaagcg ttcagtcatg acgctggctt acgggtccaa agagttcggc   3720

ttccgtcaac aagtgctgga agataccatt cagccagcta ttgattccgg caagggtctg   3780

atgttcactc agccgaatca ggctgctgga tacatggcta agctgatttg ggaatctgtg   3840

agcgtgacgg tggtagctgc ggttgaagca atgaactggc ttaagtctgc tgctaagctg   3900

ctggctgctg aggtcaaaga taagaagact ggagagattc ttcgcaagcg ttgcgctgtg   3960

cattgggtaa ctcctgatgg tttccctgtg tggcaggaat acaagaagcc tattcagacg   4020

cgcttgaacc tgatgttcct cggtcagttc cgcttacagc ctaccattaa caccaacaaa   4080

gatagcgaga ttgatgcaca caaacaggag tctggtatcg ctcctaactt tgtacacagc   4140

caagacggta gccaccttcg taagactgta gtgtgggcac acgagaagta cggaatcgaa   4200

tcttttgcac tgattcacga ctccttcggt accattccgg ctgacgctgc gaacctgttc   4260

aaagcagtgc gcgaaactat ggttgacaca tatgagtctt gtgatgtact ggctgatttc   4320

tacgaccagt tcgctgacca gttgcacgag tctcaattgg acaaaatgcc agcacttccg   4380

gctaaaggta acttgaacct ccgtgacatc ttagagtcgg acttcgcgtt cgcgtaa      4437
```

<210> SEQ ID NO 57
<211> LENGTH: 515
<212> TYPE: PRT
<213> ORGANISM: Mus musculus
<220> FEATURE:
<221> NAME/KEY: MISC_FEATURE
<222> LOCATION: (1)..(515)
<223> OTHER INFORMATION: dsRNA-binding polypeptide (uniprot: Q03963)

<400> SEQUENCE: 57

```
Met Ala Ser Asp Thr Pro Gly Phe Tyr Met Asp Lys Leu Asn Lys Tyr
1               5                   10                  15

Arg Gln Met His Gly Val Ala Ile Thr Tyr Lys Glu Leu Ser Thr Ser
            20                  25                  30

Gly Pro Pro His Asp Arg Arg Phe Thr Phe Gln Val Leu Ile Asp Glu
        35                  40                  45

Lys Glu Phe Pro Glu Ala Lys Gly Arg Ser Lys Gln Glu Ala Arg Asn
    50                  55                  60

Ala Ala Ala Lys Leu Ala Val Asp Ile Leu Asp Asn Glu Asn Lys Val
65                  70                  75                  80

Asp Cys His Thr Ser Ala Ser Glu Gln Gly Leu Phe Val Gly Asn Tyr
                85                  90                  95

Ile Gly Leu Val Asn Ser Phe Ala Gln Lys Lys Lys Leu Ser Val Asn
            100                 105                 110

Tyr Glu Gln Cys Glu Pro Asn Ser Glu Leu Pro Gln Arg Phe Ile Cys
        115                 120                 125
```

```
Lys Cys Lys Ile Gly Gln Thr Met Tyr Gly Thr Gly Ser Gly Val Thr
    130                 135                 140

Lys Gln Glu Ala Lys Gln Leu Ala Ala Lys Glu Ala Tyr Gln Lys Leu
145                 150                 155                 160

Leu Lys Ser Pro Pro Lys Thr Ala Gly Thr Ser Ser Ser Val Val Thr
                165                 170                 175

Ser Thr Phe Ser Gly Phe Ser Ser Ser Ser Ser Met Thr Ser Asn Gly
            180                 185                 190

Val Ser Gln Ser Ala Pro Gly Ser Phe Ser Ser Glu Asn Val Phe Thr
        195                 200                 205

Asn Gly Leu Gly Glu Asn Lys Arg Lys Ser Gly Val Lys Val Ser Pro
    210                 215                 220

Asp Asp Val Gln Arg Asn Lys Tyr Thr Leu Asp Ala Arg Phe Asn Ser
225                 230                 235                 240

Asp Phe Glu Asp Ile Glu Glu Ile Gly Leu Gly Gly Phe Gly Gln Val
                245                 250                 255

Phe Lys Ala Lys His Arg Ile Asp Gly Lys Arg Tyr Ala Ile Lys Arg
            260                 265                 270

Val Lys Tyr Asn Thr Glu Lys Ala Glu His Glu Val Gln Ala Leu Ala
        275                 280                 285

Glu Leu Asn His Val Asn Ile Val Gln Tyr His Ser Cys Trp Glu Gly
    290                 295                 300

Val Asp Tyr Asp Pro Glu His Ser Met Ser Asp Thr Ser Arg Tyr Lys
305                 310                 315                 320

Thr Arg Cys Leu Phe Ile Gln Met Glu Phe Cys Asp Lys Gly Thr Leu
                325                 330                 335

Glu Gln Trp Met Arg Asn Arg Asn Gln Ser Lys Val Asp Lys Ala Leu
            340                 345                 350

Ile Leu Asp Leu Tyr Glu Gln Ile Val Thr Gly Val Glu Tyr Ile His
        355                 360                 365

Ser Lys Gly Leu Ile His Arg Asp Leu Lys Pro Gly Asn Ile Phe Leu
    370                 375                 380

Val Asp Glu Arg His Ile Lys Ile Gly Asp Phe Gly Leu Ala Thr Ala
385                 390                 395                 400

Leu Glu Asn Asp Gly Lys Ser Arg Thr Arg Arg Thr Gly Thr Leu Gln
                405                 410                 415

Tyr Met Ser Pro Glu Gln Leu Phe Leu Lys His Tyr Gly Lys Glu Val
            420                 425                 430

Asp Ile Phe Ala Leu Gly Leu Ile Leu Ala Glu Leu Leu His Thr Cys
        435                 440                 445

Phe Thr Glu Ser Glu Lys Ile Lys Phe Phe Glu Ser Leu Arg Lys Gly
    450                 455                 460

Asp Phe Ser Asn Asp Ile Phe Asp Asn Lys Glu Lys Ser Leu Leu Lys
465                 470                 475                 480

Lys Leu Leu Ser Glu Lys Pro Lys Asp Arg Pro Glu Thr Ser Glu Ile
                485                 490                 495

Leu Lys Thr Leu Ala Glu Trp Arg Asn Ile Ser Glu Lys Lys Lys Arg
            500                 505                 510

Asn Thr Cys
        515
```

<210> SEQ ID NO 58
<211> LENGTH: 552
<212> TYPE: PRT

<213> ORGANISM: Pan troglodytes
<220> FEATURE:
<221> NAME/KEY: MISC_FEATURE
<222> LOCATION: (1)..(552)
<223> OTHER INFORMATION: dsRNA-binding polypeptide (uniprot: B9UKH7)

<400> SEQUENCE: 58

```
Met Ala Gly Asp Leu Ser Ala Gly Phe Phe Met Glu Glu Leu Asn Thr
1               5                   10                  15

Tyr Arg Gln Lys Gln Gly Val Val Leu Lys Tyr Gln Glu Leu Pro Asn
            20                  25                  30

Ser Gly Pro Pro His Asp Arg Arg Phe Thr Phe Arg Val Ile Ile Asp
        35                  40                  45

Gly Arg Glu Phe Pro Glu Gly Glu Gly Arg Ser Lys Lys Glu Ala Lys
    50                  55                  60

Asn Ala Ala Ala Lys Leu Ala Val Glu Ile Leu Asn Lys Glu Lys Lys
65                  70                  75                  80

Ala Val Ser Pro Leu Val Leu Thr Thr Thr Asn Ser Ser Glu Gly Leu
                85                  90                  95

Ser Met Gly Asn Tyr Ile Gly Leu Ile Asn Arg Ile Ala Gln Lys Lys
            100                 105                 110

Arg Leu Thr Val Asn Tyr Glu Gln Cys Ala Ser Gly Val His Gly Pro
        115                 120                 125

Glu Gly Phe His Tyr Lys Cys Lys Met Gly Gln Lys Glu Tyr Ser Ile
    130                 135                 140

Gly Thr Ser Ser Thr Lys Gln Glu Ala Lys Gln Leu Ala Ala Lys Leu
145                 150                 155                 160

Ala Tyr Leu Gln Ile Leu Ser Glu Glu Thr Ser Val Lys Ser Asp Tyr
                165                 170                 175

Leu Ser Ser Gly Ser Phe Ala Thr Thr Cys Asp Ser Gln Ser Asn Ser
            180                 185                 190

Leu Val Thr Ser Thr Leu Ala Ser Glu Ser Ser Ser Glu Gly Asp Phe
        195                 200                 205

Ser Ala Asp Thr Ser Glu Ile Asn Ser Asn Ser Asp Ser Leu Asn Ser
    210                 215                 220

Ser Ser Leu Leu Met Asn Gly Leu Arg Asn Asn Gln Arg Lys Ala Lys
225                 230                 235                 240

Arg Ser Leu Ala Pro Arg Phe Asp Leu Pro Asp Met Lys Glu Thr Lys
                245                 250                 255

Tyr Thr Val Asp Lys Arg Phe Gly Met Asp Phe Lys Glu Ile Glu Leu
            260                 265                 270

Ile Gly Ser Gly Gly Phe Gly Gln Val Phe Lys Ala Lys His Arg Ile
        275                 280                 285

Asp Gly Lys Thr Tyr Val Ile Lys Arg Val Lys Tyr Asn Asn Glu Lys
    290                 295                 300

Ala Glu Arg Glu Val Lys Ala Leu Ala Lys Leu Asp His Val Asn Ile
305                 310                 315                 320

Val His Tyr Asn Gly Cys Trp Asp Gly Phe Asp Tyr Asp Pro Glu Thr
                325                 330                 335

Ser Asp Asp Asp Leu Glu Ser Ser Asp Tyr Asp Pro Glu Asn Ser Lys
            340                 345                 350

Asn Ser Ser Arg Ser Lys Thr Lys Cys Leu Phe Ile Gln Met Glu Phe
        355                 360                 365

Cys Asp Lys Gly Thr Leu Glu Gln Trp Ile Glu Asp Arg Arg Gly Lys
    370                 375                 380
```

```
Lys Leu Asp Lys Val Leu Ala Leu Glu Leu Phe Glu Gln Ile Thr Lys
385                 390                 395                 400

Gly Val Asp Tyr Ile His Ser Lys Lys Leu Ile His Arg Asp Leu Lys
                405                 410                 415

Pro Ser Asn Ile Phe Leu Val Asp Thr Lys Gln Val Lys Ile Gly Asp
            420                 425                 430

Phe Gly Leu Val Thr Ser Leu Lys Asn Asp Gly Lys Arg Thr Arg Ser
        435                 440                 445

Lys Gly Thr Leu Arg Tyr Met Ser Pro Glu Gln Ile Ser Ser Gln Asp
    450                 455                 460

Tyr Gly Lys Glu Val Asp Leu Tyr Ala Leu Gly Leu Ile Leu Ala Glu
465                 470                 475                 480

Leu Leu His Val Cys Asp Thr Ala Phe Glu Thr Ser Lys Phe Phe Thr
                485                 490                 495

Asp Leu Arg Asp Gly Ile Ile Ser Asp Ile Leu Phe Asp Lys Lys Glu
            500                 505                 510

Lys Thr Leu Leu Gln Lys Leu Leu Ser Lys Lys Pro Glu Asp Arg Pro
        515                 520                 525

Asn Thr Ser Glu Ile Leu Arg Thr Leu Thr Val Trp Lys Lys Ser Pro
    530                 535                 540

Glu Lys Asn Glu Arg His Thr Cys
545                 550
```

<210> SEQ ID NO 59
<211> LENGTH: 551
<212> TYPE: PRT
<213> ORGANISM: Gorilla gorilla
<220> FEATURE:
<221> NAME/KEY: MISC_FEATURE
<222> LOCATION: (1)..(551)
<223> OTHER INFORMATION: dsRNA-binding polypeptide (uniprot: G3RTN4)

<400> SEQUENCE: 59

```
Met Ala Gly Asp Leu Ser Ala Gly Phe Phe Met Glu Glu Leu Asn Thr
1               5                   10                  15

Tyr Arg Gln Lys Gln Gly Val Val Leu Lys Tyr Gln Glu Leu Pro Asn
            20                  25                  30

Ser Gly Pro Pro His Asp Arg Arg Phe Thr Phe Arg Val Ile Ile Asp
        35                  40                  45

Glu Arg Glu Phe Pro Glu Gly Glu Gly Arg Ser Lys Lys Glu Ala Lys
    50                  55                  60

Asn Ala Ala Ala Lys Leu Ala Val Glu Ile Leu Asn Lys Glu Lys Lys
65                  70                  75                  80

Ala Val Ser Pro Leu Leu Leu Thr Thr Thr Asn Ser Ser Glu Gly Leu
                85                  90                  95

Ser Met Gly Asn Tyr Ile Gly Leu Ile Asn Arg Ile Ala Gln Lys Lys
            100                 105                 110

Arg Leu Thr Val Asn Tyr Glu Gln Cys Ala Ser Gly Val His Gly Pro
        115                 120                 125

Glu Gly Phe His Tyr Lys Cys Lys Met Gly Gln Lys Glu Tyr Ser Ile
    130                 135                 140

Gly Thr Gly Ser Thr Lys Gln Glu Ala Lys Gln Leu Ala Ala Lys Leu
145                 150                 155                 160

Ala Tyr Leu Gln Ile Val Ser Glu Glu Thr Ser Val Lys Ser Asp Tyr
                165                 170                 175
```

```
Leu Ser Ser Gly Ser Phe Ala Thr Thr Cys Asp Ser Gln Ser Asn Ser
            180                 185                 190

Leu Val Thr Ser Thr Leu Ala Ser Glu Ser Ser Ser Glu Gly Asp Phe
        195                 200                 205

Ser Ala Asp Thr Ser Glu Ile Asn Ser Asn Ser Asp Ser Leu Asn Ser
    210                 215                 220

Ser Ser Leu Leu Met Asn Gly Leu Arg Asn Asn Gln Arg Lys Ala Lys
225                 230                 235                 240

Arg Ser Leu Ala Pro Arg Phe Asp Leu Pro Asp Met Lys Glu Thr Lys
                245                 250                 255

Tyr Thr Val Asp Lys Arg Phe Gly Met Asp Phe Lys Glu Ile Glu Leu
            260                 265                 270

Ile Gly Ser Gly Gly Phe Gly Gln Val Phe Lys Ala Lys His Arg Ile
        275                 280                 285

Asp Gly Lys Thr Tyr Val Ile Lys Arg Val Lys Tyr Asn Asn Glu Lys
    290                 295                 300

Ala Glu Arg Glu Val Lys Ala Leu Ala Lys Leu Asp His Val Asn Ile
305                 310                 315                 320

Val His Tyr Asn Gly Cys Trp Asp Gly Val Asp Tyr Asp Pro Glu Thr
                325                 330                 335

Ser Asp Asp Tyr Leu Glu Ser Ser Asp Tyr Asp Pro Glu Asn Ser Lys
            340                 345                 350

Asn Ser Ser Arg Ser Lys Thr Lys Cys Leu Phe Ile Gln Met Glu Phe
        355                 360                 365

Cys Asp Lys Gly Thr Leu Glu Gln Trp Ile Glu Asn Arg Arg Gly Glu
    370                 375                 380

Lys Leu Asp Lys Val Leu Ala Leu Glu Leu Phe Glu Gln Ile Thr Lys
385                 390                 395                 400

Gly Val Asp Tyr Ile His Ser Lys Lys Leu Ile His Arg Asp Leu Lys
                405                 410                 415

Pro Ser Asn Ile Phe Leu Val Asp Thr Lys Gln Val Lys Ile Gly Asp
            420                 425                 430

Phe Gly Leu Val Thr Ser Leu Lys Asn Asp Gly Lys Arg Thr Arg Ser
        435                 440                 445

Lys Gly Thr Leu Arg Tyr Met Ser Pro Glu Gln Ile Ser Ser Gln Asp
    450                 455                 460

Tyr Gly Lys Glu Val Asp Leu Tyr Ala Leu Gly Leu Ile Leu Ala Glu
465                 470                 475                 480

Leu Leu His Val Cys Asp Thr Ala Phe Glu Thr Ser Lys Phe Phe Thr
                485                 490                 495

Asp Leu Arg Asp Gly Ile Ile Ser Asp Ile Phe Asp Lys Lys Glu Lys
            500                 505                 510

Thr Leu Leu Gln Lys Leu Leu Ser Lys Lys Pro Glu Asp Arg Pro Asn
        515                 520                 525

Thr Ser Glu Ile Leu Arg Thr Leu Thr Val Trp Lys Lys Ser Pro Glu
    530                 535                 540

Lys Asn Glu Arg His Thr Cys
545                 550
```

<210> SEQ ID NO 60
<211> LENGTH: 69
<212> TYPE: DNA
<213> ORGANISM: Artificial Sequence
<220> FEATURE:
<223> OTHER INFORMATION: pyrrolysyl tRNA of Methanosarcina mazei for -continued

```
     unidentified codon (tRNAPyl, nnn)
<220> FEATURE:
<221> NAME/KEY: misc_feature
<222> LOCATION: (31)..(33)
<223> OTHER INFORMATION: n can be a,t,g or c

<400> SEQUENCE: 60

ggaaacctga tcatgtagat cgaatggact nnnaatccgt tcagccgggt tagattcccg     60

gggtttccg                                                             69
```